(12) United States Patent
Gobbi et al.

(10) Patent No.: US 7,829,563 B2
(45) Date of Patent: Nov. 9, 2010

(54) AMINOAMIDES AS OREXIN ANTAGONISTS

(75) Inventors: Luca Gobbi, Oberwil BL (CH); Henner Knust, Rheinfelden (DE); Parichehr Malherbe, Muttenz (CH); Matthias Nettekoven, Grenzach-Wyhlen (DE); Emmanuel Pinard, Linsdorf (FR); Olivier Roche, Folgensbourg (FR); Mark Rogers-Evans, Oberwil BL (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 270 days.

(21) Appl. No.: 12/037,975

(22) Filed: Feb. 27, 2008

(65) Prior Publication Data

US 2008/0221166 A1 Sep. 11, 2008

(30) Foreign Application Priority Data

Mar. 5, 2007 (EP) ................................ 07103521

(51) Int. Cl.
| | |
|---|---|
| A61K 31/50 | (2006.01) |
| A61K 31/501 | (2006.01) |
| A61K 31/497 | (2006.01) |
| A01N 43/54 | (2006.01) |
| C07D 239/42 | (2006.01) |
| C07D 401/04 | (2006.01) |
| A01N 43/40 | (2006.01) |
| A61K 31/435 | (2006.01) |
| A01N 43/78 | (2006.01) |
| A61K 31/425 | (2006.01) |
| A01N 43/50 | (2006.01) |
| A61K 31/415 | (2006.01) |
| A01N 43/56 | (2006.01) |
| A01N 43/08 | (2006.01) |
| A61K 31/34 | (2006.01) |
| C07D 279/00 | (2006.01) |
| C07D 285/00 | (2006.01) |
| C07D 401/00 | (2006.01) |
| C07D 421/00 | (2006.01) |
| C07D 419/00 | (2006.01) |
| C07D 277/04 | (2006.01) |
| C07D 277/08 | (2006.01) |
| C07D 409/00 | (2006.01) |
| C07D 335/00 | (2006.01) |
| C07D 333/02 | (2006.01) |
| C07D 321/00 | (2006.01) |
| C07D 307/00 | (2006.01) |
| C07D 317/00 | (2006.01) |
| C07D 323/02 | (2006.01) |

(52) U.S. Cl. ............................ 514/252.01; 514/252.1; 514/256; 514/277; 514/365; 514/461; 540/467; 540/470; 544/2; 544/3; 544/224; 544/238; 544/336; 546/268.1; 546/268.4; 548/146; 548/206; 548/215; 548/240; 548/400; 549/13; 549/29; 549/200; 549/429

(58) Field of Classification Search ............ 514/252.01, 514/252.1, 256, 277, 365, 385, 403, 461; 540/467, 470; 544/2, 3, 238, 242, 224, 336; 546/268.1, 268.4; 548/146, 206, 215, 240, 548/262.4, 300.1, 356.1, 400; 549/13, 29, 549/200, 429; 564/124

See application file for complete search history.

(56) References Cited

U.S. PATENT DOCUMENTS

| 5,290,799 A | 3/1994 | Misra et al. |
| 7,078,565 B2 * | 7/2006 | Chan et al. .................. 564/158 |
| 2003/0144215 A1 | 7/2003 | Ksander et al. |

FOREIGN PATENT DOCUMENTS

WO    WO 2007/025709    3/2007

\* cited by examiner

*Primary Examiner*—Sreeni Padmanabhan
*Assistant Examiner*—Sarah Pihonak
(74) *Attorney, Agent, or Firm*—George W. Johnston; Patricia S. Rocha-Tramaloni; Kimberly J. Prior

(57) ABSTRACT

The present invention relates to compounds of formula I

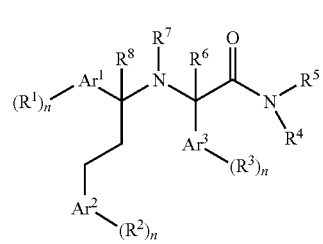

wherein $Ar^1$, $Ar^2$, $Ar^3$, n, and
$R^1$ to $R^8$ are as defined herein and to pharmaceutically suitable acid addition salts, optically pure enantiomers, racemates or diastereomeric mixtures thereof. These compounds are orexin receptor antagonists and may be useful in the treatment of disorders, in which orexin pathways are involved, like sleep disorders.

28 Claims, No Drawings

AMINOAMIDES AS OREXIN ANTAGONISTS

PRIORITY TO RELATED APPLICATION(S)

This application claims the benefit of European Patent Application No. 07103521.6, filed Mar. 5, 2007, which is hereby incorporated by reference in its entirety.

BACKGROUND OF THE INVENTION

Orexins (hypocretins), a family of hypothalamic neuropeptides, play an important role in modulating feeding behavior, energy homeostasis and the sleep-wake cycle (Siegel, Annu. Rev. Psychol., 55, 125-148, 2004). The orexin-A/hypocretin1 (OX-A, 33 amino acids) and orexin-B/hypocretin2 (OX-B, 28 amino acids) are derived from the same precursor by proteolytic processing of 130 amino acids prepro-orexin (de Lecea et al., Proc Natl Acad Sci USA, 95, 322-327, 1998; Sakurai T. et al., Cell, 92, 573-585, 1998). The orexin levels show a diurnal variation being highest during the active cycle. Two receptor subtypes termed orexin-1 receptor ($OX_1R$) and orexin-2 receptor ($OX_2R$) have been identified. The characterization of both receptors in binding and functional assays demonstrated that $OX_2R$ is a non-selective receptor for both OX-A and -B, whereas $OX_1R$ is selective for OX-A, conversely OX-A is a non-selective neuropeptide and binds with similar affinities to $OX_1R$ and $OX_2R$, while OX-B is selective and has a higher affinity for $OX_2R$ (Sakurai T. et al., Cell, 92, 573-585, 1998). Both receptors belong to the class A family of G-protein-coupled receptors (GPCRs) that couple via $G_{q/11}$ to the activation of phospholipase C leading to phosphoinositide (PI) hydrolysis and elevation of intracellular $Ca^{2+}$ levels. However, it has been shown that OX2R could also couple via $G_{i/o}$ to cAMP pathway (Sakurai, Regulatory Peptides, 126, 3-10, 2005). Northern blot analysis of adult rat tissues showed that the prepro-orexin mRNA is detected exclusively in the brain (except for a small amount in the testis) and that the $OX_1R$ and $OX_2R$ transcripts are also exclusively detected in the brain (Sakurai T. et al., Cell, 92, 573-585, 1998). Similar results were obtained using human multiple tissue Northern blot. Distribution studies in rat brain using in situ hybridization and immunohistochemistry have shown that orexin neurons are found only in the lateral hypothalamic area with their projections to the entire CNS (Peyron et al., J Neurosci, 18, 9996-10015, 1998; Nambu et al., Brain Res., 827, 243-60, 1999). In addition, both $OX_1$ and $OX_2$ receptors are present in brain regions important for the regulation of sleep/wakefulness.

A disrupted orexin system is suggested to be the cause of narcolepsy based on following lines of evidence: (a) Prepro-orexin knockout mice possessed a phenotype with characteristics remarkably similar to narcolepsy (Chemelli et al., Cell, 98, 437-451, 1999), (b) a mutation (canarc-1), which disrupts the gene encoding $OX_2R$, was found to be responsible for canine narcolepsy (Lin et al., Cell, 98, 365-376, 1999), (c) lack of OX-A and OX-B was observed in human narcoleptic patients (Nishino et al., Lancet, 355, 39-40, 2000; Peyron et al., Nature Medicine, 6, 991-997, 2000), (d) it has been shown that Modafinil, an anti-narcoleptic drug with unknown mechanism of action, activates orexin neurons (Mignot et al., Sleep, 11, 1012-1020, 1997; Chemelli et al., Cell, 98, 437-451, 1999). The intracerebroventricular (icv) administration of OX-A dose-dependently increases wakefulness in rat and also reduces total REM sleep by 84% (Piper et al., Eur. J. Neuroscience, 12, 726-730, 2000). Taken together, these observations are consistent with a crucial role of the orexin system in the modulation of sleep/wake cycle.

Orexin plays an important role in stress and anxiety via its interaction with the corticotropin-releasing factor (CRF) system in hypothalamus (Sakamoto et al., Regul Pept., 118, 183-91, 2004). The icv injection of OX-A induces grooming (stress-response) which is blocked in part by a CRF antagonist (Ida et al., Biochem. Biophys. Res. Comm., 270, 318-323, 2000). $OX_2R$ is highly expressed in adrenal medulla, whereas $OX_1R$ is high in adrenal cortex. Both OX-A and OX-B stimulate corticosterone release in plasma and induce c-Fos in paraventricular nucleus (PVN) in the hypothalamus (Kuru et al., Neuroreport, 11, 1977-1980, 2000). Furthermore, orexin neurons projecting to CRF neurons express mainly the $OX_2R$ (Winsky-Sommerer et al., J. Neuroscience, 24, 11439-11448, 2004). Therefore, $OX_2R$ stimulation activates the hypothalamo-pituitary-adrenal (HPA) axis. Interestingly, in this context, the orexin A-induced increases in plasma ACTH has been reported to be attenuated by a selective antagonist to OX-2R(N-{(1S)-1-(6,7-dimethoxy-3,4-dihydro-2(1H)-isoquinolinyl)carbonyl}-2,2-dimethylpropyl)-N-{4-pyridinylmethyl}amine (Chang et al., Neurosci Res., 21 Dec. 2006). A recent preclinical report (Suzuki et al., Brain Research, 1044, 116-121, 2005) has suggested an anxiogenic effect of OX-A. The icv injection of OX-A caused an anxiety-like behavior in mice. Effects were similar to those of corticotropin-releasing factor (CRF) that was tested at the same time for comparison. A recent study has also demonstrated the presence of functional OX1 and OX2 receptors in human adipose tissue and their roles in adipose tissue metabolism and adipogenesis (Digby et al., J. Endocrinol., 191, 129-36, 2006).

In summary, considering the very diverse functions played by orexin system in arousal, sleep/wakefulness, appetite regulation and their roles in anxiety and stress response, etc., one expects that the drugs (or compounds) targeting orexin system will have beneficial therapeutic effects for the treatments of diseases like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, headache pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome, extrapyramidal symptoms induced by antipsychotics and other diseases related to general orexin system dysfunction.

Numerous documents describe the current knowledge on orexin pathway, for example the following documents:

Expert Opin. Ther. Patents (2006), 16(5), 631-646

Current Opinion in Drug Discovery & Development, 2006, 9(5), 551-559

J. Neurosci (2000), 20(20), 7760-7765

Neurosci Lett, (2003), 341(3), 256-258

SUMMARY OF THE INVENTION

The present invention provides compounds of formula I

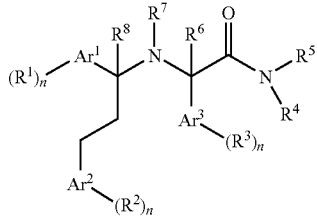

wherein $Ar^1$, $Ar^2$ and $Ar^3$ are each independently unsubstituted or substituted aryl or heteroaryl;

$R^1$, $R^2$ and $R^3$ are each independently hydroxy, halogen, lower alkyl, lower alkyl substituted by halogen, lower alkoxy, lower alkoxy substituted by halogen, cyano, 3-hydroxy-oxetan-3-yl, $SO_2$-lower alkyl or di-lower alkyl amino;

$R^4$ and $R^5$ are each independently hydrogen, lower alkyl, lower alkyl substituted by halogen, lower alkyl substituted by hydroxy, —$(CH_2)_o$—O-lower alkyl, —$(CH_2)_o$—N-(lower alkyl)$_2$, $(CH_2)_p$-cycloalkyl, $(CH_2)_p$-aryl, which aryl ring is optionally substituted by halogen, or $R^4$ and $R^5$ together with the N-atom to which they are attached form a heterocyclic ring, optionally containing further ring-heteroatoms selected from N, O and S;

$R^6$ is hydrogen or lower alkyl;

$R^7$ is hydrogen or lower alkyl;

$R^8$ is hydrogen or cyano;

n is 0, 1, 2 or 3;

o is 1, 2 or 3; and p is 0, 1 or 2;

or pharmaceutically suitable acid addition salts, optically pure enantiomers, racemates or diastereomeric mixtures thereof.

Compounds of formula I are orexin receptor antagonists and the related compounds may be useful in the treatment of disorders, in which orexin pathways are involved like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, headache pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome, extrapyramidal symptoms induced by antipsychotics and other diseases related to general orexin system dysfunction.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "alkyl" denotes a straight- or branched-chain hydrocarbon group containing from 1-7 carbon atoms. The term "lower alkyl" denotes a straight- or branched-chain hydrocarbon group containing from 1-4 carbon atoms, for example, methyl, ethyl, propyl, isopropyl, n-butyl, i-butyl, t-butyl and the like.

The term "lower alkoxy" denotes an alkyl group as defined above, which is attached via an oxygen atom.

The term "halogen" denotes chlorine, iodine, fluorine and bromine.

The term "cycloalkyl" denotes a saturated carbocyclic group, containing 3-6 carbon atoms.

The term "aryl" means the monovalent cyclic aromatic hydrocarbon group consisting of one or more fused rings in which at least one ring is aromatic in nature. Examples of aryl radicals include, but are not limited to, phenyl, naphthyl, 5,6,7,8-tetrahydro-naphthalenyl, biphenyl, indanyl, anthraquinolyl, and the like.

"Heteroaryl" means a cyclic group having one or more rings, wherein at least one ring is aromatic in nature, incorporating one, two, or three heteroatoms within the ring (chosen from nitrogen, oxygen, or sulfur). Examples of heteroaryl radicals include, but are not limited to, imidazolyl, oxazolyl, isoxazolyl, thiazolyl, thiophenyl, furanyl, pyrazolyl, pyridinyl, pyrazinyl, pyrimidinyl, pyridazinyl, quinolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, chromanyl, naphtyridinyl, 2,3-dihydro-benzofuranyl, 3,4-dihydro-2H-benzo[b][1.4]dioxepinyl, 3,4-dihydro-2H-benzo[1.4]oxazinyl, indanyl, benzo[1.3]dioxol, 2,3-dihydro-benzo[1.4]dioxinyl, and the like.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

As used herein, the term "lower alkoxy substituted by halogen" denotes an alkoxy group as defined above, wherein at least one hydrogen atom is replaced by halogen, for example $OCF_3$, $OCHF_2$, $OCH_2F$, $OCH_2CF_3$, $OCH_2CH_2CF_3$, $OCH_2CF_2CF_3$ and the like. As used herein, the term "lower alkyl substituted by hydroxy" denotes an alkyl group as defined above, wherein at least one hydrogen atom is replaced by a hydroxy group.

As used herein, the term "di loweralkyl amino denotes the group $NH_2$, wherein each hydrogen atom is independently replaced by a lower alkyl group as defined above.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of formula I are those of formula I-1

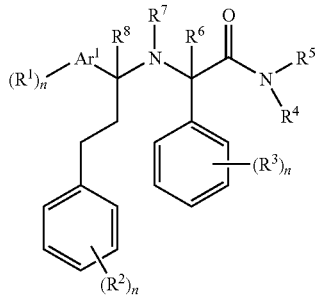

wherein
Ar$^1$ is heteroaryl;
R$^1$, R$^2$ and R$^3$ are each independently hydroxy, halogen, lower alkyl, lower alkyl substituted by halogen, lower alkoxy, lower alkoxy substituted by halogen, cyano, 3-hydroxy-oxetan-3-yl, SO$_2$-lower alkyl or di-lower alkyl amino;
R$^4$ and R$^5$ are each independently hydrogen, lower alkyl, lower alkyl substituted by halogen, lower alkyl substituted by hydroxy, —(CH$_2$)$_o$—O-lower alkyl, —(CH$_2$)$_o$—N-(lower alkyl)$_2$, (CH$_2$)$_p$-cycloalkyl, (CH$_2$)$_p$-aryl, which aryl ring is optionally substituted by halogen, or
R$^4$ and R$^5$ together with the N-atom to which they are attached form a heterocyclic ring, optionally containing further ring-heteroatoms selected from N, O and S;
R$^6$ is hydrogen or lower alkyl;
R$^7$ is hydrogen or lower alkyl;
R$^8$ is hydrogen or cyano;
n is 0, 1, 2 or 3;
o is 1, 2 or 3; and
p is 0, 1 or 2;

or pharmaceutically suitable acid addition salts, optically pure enantiomers, racemates or diastereomeric mixtures thereof.

Preferred compounds from formula I-1 are those, wherein one of R$^1$ or R$^2$ is hydrogen and the other is lower alkyl, for example (S,R)-2-[(R,S)-3-(4-chloro-phenyl)-1-(2,3-dihydro-benzofuran-5-yl)-propylamino]-N-methyl-2-phenyl-acetamide,
(S,R)—N-methyl-2-[(R,S) 1-(4-methyl-3,4-dihydro-2H-benzo[1,4]oxazin-7-yl)-3-(4-trifluoromethyl-phenyl)-propylamino]-2-phenyl-acetamide,
2-[1-(2,4-dimethyl-thiazol-5-yl)-3-(4-trifluoromethyl-phenyl)-propylamino]-2-(4-fluoro-phenyl)-N-methyl-acetamide,
2-[1-(3-isopropyl-isoxazol-5-yl)-3-(4-trifluoromethyl-phenyl)-propylamino]-N-methyl-2-phenyl-acetamide,
2-[1-(2,4-dimethyl-thiazol-5-yl)-3-(4-trifluoromethyl-phenyl)-propylamino]-N-methyl-2-phenyl-acetamide,
(R)-2-[(S)-3-(4-chloro-phenyl)-1-(2,3-dihydro-benzofuran-5-yl)-propylamino]-N-methyl-2-phenyl-acetamide,
(R)-2-[(S)-1-chroman-6-yl-3-(4-trifluoromethyl-phenyl)-propylamino]-N-methyl-2-phenyl-acetamide,
(R)—N-methyl-2-[(S)-1-(4-methyl-3,4-dihydro-2H-benzo[1,4]oxazin-7-yl)-3-(4-trifluoromethyl-phenyl)-propylamino]-2-phenyl-acetamide,
(R)-2-[(S)-1-(2,4-dimethyl-thiazol-5-yl)-3-(4-trifluoromethyl-phenyl)-propylamino]-2-(4-fluoro-phenyl)-N-methyl-acetamide,
(S,R)-2-[(R,S)-3-(4-methoxy-phenyl)-1-(2-methoxy-pyridin-3-yl)-propylamino]-N-methyl-2-phenyl-acetamide,
(S,R)-2-[(R,S)-1-(2-methoxy-pyridin-3-yl)-3-(4-trifluoromethyl-phenyl)-propylamino]-N-methyl-2-phenyl-acetamide,
(S,R)—N-methyl-2-[(R,S)-1-(6-methyl-pyridin-2-yl)-3-(4-trifluoromethyl-phenyl)-propylamino]-2-phenyl-acetamide,
(S,R)-2-[(R,S)-1-(4-methoxy-pyridin-2-yl)-3-(4-trifluoromethyl-phenyl)-propylamino]-N-methyl-2-phenyl-acetamide,
(S,R)—N-methyl-2-[(S,R)-1-(5-methyl-isoxazol-3-yl)-3-(4-trifluoromethyl-phenyl)-propylamino]-2-phenyl-acetamide and
(S,R)—N-methyl-2-[(R,S)-1-(5-methyl-isoxazol-3-yl)-3-(4-trifluoromethyl-phenyl)-propylamino]-2-phenyl-acetamide.

Preferred compounds of formula I are further those of formula I-2

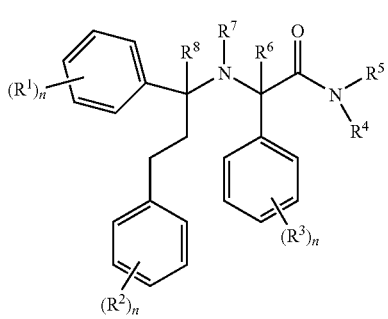

wherein
R$^1$, R$^2$ and R$^3$ are each independently hydroxy, halogen, lower alkyl, lower alkyl substituted by halogen, lower alkoxy, lower alkoxy substituted by halogen, cyano, 3-hydroxy-oxetan-3-yl, SO$_2$-lower alkyl or di-lower alkyl amino;
R$^4$ and R$^5$ are each independently hydrogen, lower alkyl, lower alkyl substituted by halogen, lower alkyl substituted by hydroxy, —(CH$_2$)$_o$—O-lower alkyl, —(CH$_2$)$_o$—N-(lower alkyl)$_2$, (CH$_2$)$_p$-cycloalkyl, (CH$_2$)$_p$-aryl, which aryl ring is optionally substituted by halogen, or
R$^4$ and R$^5$ together with the N-atom to which they are attached form a heterocyclic ring, optionally containing further ring-heteroatoms selected from N, O and S;
R$^6$ is hydrogen or lower alkyl;
R$^7$ is hydrogen or lower alkyl;
R$^8$ is hydrogen or cyano;
n is 0, 1, 2 or 3;
o is 1, 2 or 3; and
p is 0, 1 or 2;

or pharmaceutically suitable acid addition salts, optically pure enantiomers, racemates or diastereomeric mixtures thereof.

Preferred compounds from formula I-2 are those, wherein one of $R^1$ or $R^2$ is hydrogen and the other is lower alkyl, for example (R)-2-[(S or R)-1-(3,4-dimethoxy-phenyl)-3-(4-trifluoromethyl-phenyl)-propylamino]-N-methyl-2-phenyl-acetamide, (R)-2-[(S or R)-1-(3,4-dimethoxy-phenyl)-3-(4-trifluoromethyl-phenyl)-propylamino]-N-methyl-2-phenyl-acetamide, (R)-2-[(R or S)-1-(3,4-dimethoxy-phenyl)-3-(4-trifluoromethyl-phenyl)-propylamino]-N-ethyl-2-phenyl-acetamide, (S,R)-2-[(R,S)-1-(3,4-dimethoxy-phenyl)-3-(4-trifluoromethyl-phenyl)-propylamino]-N-methyl-2-phenyl-propionamide (diastereoisomer 1), (S,R)-2-(4-chloro-phenyl)-2-[(S,R)-1-(3,4-dimethoxy-phenyl)-3-(4-trifluoromethyl-phenyl)-propylamino]-N-methyl-acetamide, (S,R)-2-[(R,S)-1-(3,4-dimethoxy-phenyl)-3-(4-trifluoromethyl-phenyl)-propylamino]-2-(4-fluoro-phenyl)-N-methyl-acetamide, (S,R)-2-[(R,S)-1-(2-chloro-3,4-dimethoxy-phenyl)-3-(4-chloro-phenyl)-propylamino]-N-methyl-2-phenyl-acetamide, (S,R)-2-[(S,R)-1-(2-chloro-3,4-dimethoxy-phenyl)-3-(4-chloro-phenyl)-propylamino]-N-methyl-2-phenyl-acetamide, (R)-2-(4-chloro-phenyl)-2-[(S)-1-(3,4-dimethoxy-phenyl)-3-(4-trifluoromethyl-phenyl)-propylamino]-N-methyl-acetamide, (R)-2-[(S)-1-(3,4-dimethoxy-phenyl)-3-(4-trifluoromethyl-phenyl)-propylamino]-2-(4-fluoro-phenyl)-N-methyl-acetamide, (R)-2-[(S)-1-(2-chloro-3,4-dimethoxy-phenyl)-3-(4-chloro-phenyl)-propylamino]-N-methyl-2-phenyl-acetamide, (R)-2-[(S)-1-(2-fluoro-5-methyl-phenyl)-3-(4-trifluoromethyl-phenyl)-propylamino]-N-methyl-2-phenyl-acetamide, (R)-2-[(S)-1-(2-fluoro-5-methyl-phenyl)-3-(4-trifluoromethyl-phenyl)-propylamino]-2-(4-fluoro-phenyl)-N-methyl-acetamide, (S,R)-2-[(R,S)-3-(4-chloro-phenyl)-1-(3,4-dimethoxy-phenyl)-propylamino]-N-methyl-2-phenyl-acetamide, (S,R)-2-[(S,R)-1-(3,4-dimethoxy-phenyl)-3-(4-trifluoromethyl-phenyl)-propylamino]-N-methyl-2-phenyl-acetamide, (S,R)-2-[(R,S)-1-(3,4-dimethoxy-phenyl)-3-(4-trifluoromethyl-phenyl)-propylamino]-N-methyl-2-phenyl-acetamide, (S,R)-2-[(R,S)-1-(3,4-dimethoxy-phenyl)-3-(4-fluoro-phenyl)-propylamino]-N-methyl-2-phenyl-acetamide, (S,R)-2-[(R,S)-1-(3,4-dimethoxy-phenyl)-3-(4-methoxy-phenyl)-propylamino]-N-methyl-2-phenyl-acetamide, (R)-2-[(S)-3-(4-chloro-phenyl)-1-(3,4-dimethoxy-phenyl)-propylamino]-N-methyl-2-phenyl-acetamide, (S,R)-2-[(S,R)-1-(4-chloro-3-methoxy-phenyl)-3-(4-trifluoromethyl-phenyl)-propylamino]-N-methyl-2-phenyl-acetamide, (S,R)-2-[(R,S)-1-(4-chloro-3-methoxy-phenyl)-3-(4-trifluoromethyl-phenyl)-propylamino]-N-methyl-2-phenyl-acetamide, (R)-2-[(S)-1-(3,4-dimethoxy-phenyl)-3-(6-trifluoromethyl-pyridin-3-yl)-propylamino]-N-methyl-2-phenyl-acetamide hydrochloride, (S,R)-2-[(R,S)-1-(3,4-dimethoxy-phenyl)-3-p-tolyl-propylamino]-N-methyl-2-phenyl-acetamide, (R)-2-[(S)-1-(3-methoxy-phenyl)-3-(4-trifluoromethyl-phenyl)-propylamino]-N-methyl-2-phenyl-acetamide hydrochloride, (S)-2-[(R)-1-(3-methoxy-phenyl)-3-(4-trifluoromethyl-phenyl)-propylamino]-N-methyl-2-phenyl-acetamide hydrochloride, (S,R)-2-[(R,S)-1-(3,4-bis-difluoromethoxy-phenyl)-3-(4-trifluoromethyl-phenyl)-propylamino]-N-methyl-2-phenyl-acetamide, (R)-2-[(S)-1-(3,4-dimethoxy-phenyl)-3-phenyl-propylamino]-N-methyl-2-phenyl-acetamide, (R,S)-2-(4-chloro-phenyl)-2-[(S,R)-3-(4-chloro-phenyl)-1-(3,4-dimethoxy-phenyl)-propylamino]-N-methyl-acetamide, (R,S)-2-[(R,S)-1-(3,4-dimethoxy-phenyl)-3-(3-trifluoromethyl-phenyl)-propylamino]-N-methyl-2-phenyl-acetamide, (R,S)-2-[(S,R)-1-(3,4-dimethoxy-phenyl)-3-(3-trifluoromethyl-phenyl)-propylamino]-N-methyl-2-phenyl-acetamide, (R,S)-2-[(S,R)-1-(4-fluoro-3-methyl-phenyl)-3-p-tolyl-propylamino]-N-methyl-2-phenyl-acetamide, (R)-2-[(S)-1-(3-difluoromethoxy-phenyl)-3-(4-trifluoromethyl-phenyl)-propylamino]-N-methyl-2-phenyl-acetamide, (R)-2-[(S)-1-(3-difluoromethoxy-phenyl)-3-(4-trifluoromethyl-phenyl)-propylamino]-N-methyl-2-p-tolyl-acetamide, (R)-2-[(S)-3-(4-chloro-phenyl)-1-(4-fluoro-3-methyl-phenyl)-propylamino]-N-methyl-2-phenyl-acetamide and (R)-2-[(S)-1-(4-fluoro-3-methyl-phenyl)-3-p-tolyl-propylamino]-N-methyl-2-phenyl-acetamide.

Preferred compounds from formula I-2 are further those, wherein one of $R^1$ or $R^2$ is hydrogen and the other is $(CH_2)_p$-cycloalkyl, for example (R)—N-cyclopropylmethyl-2-[(R or S)-1-(3,4-dimethoxy-phenyl)-3-(4-trifluoromethyl-phenyl)-propylamino]-2-phenyl-acetamide.

Preferred compounds of formula I are further those of formula I-3

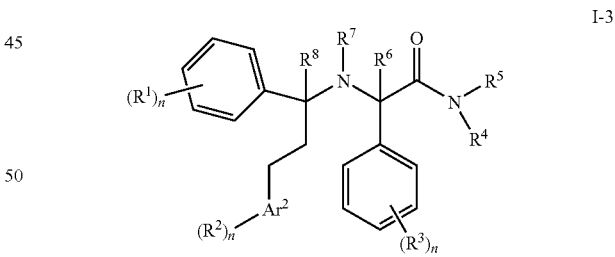

I-3 wherein
$Ar^2$ is heteroaryl;
$R^1$, $R^2$ and $R^3$ are each independently hydroxy, halogen, lower alkyl, lower alkyl substituted by halogen, lower alkoxy, lower alkoxy substituted by halogen, cyano, 3-hydroxy-oxetan-3-yl, $SO_2$-lower alkyl or di-lower alkyl amino;
$R^4$ and $R^5$ are each independently hydrogen, lower alkyl, lower alkyl substituted by halogen, lower alkyl substituted by hydroxy, —$(CH_2)_o$—O-lower alkyl, —$(CH_2)_o$—N-(lower alkyl)$_2$, $(CH_2)_p$-cycloalkyl, $(CH_2)_p$-aryl, which aryl ring is optionally substituted by halogen, or R⁴ and R⁵ together with the N-atom to which they are attached form a heterocyclic ring, optionally containing further ring-heteroatoms selected from N, O and S;
R⁶ is hydrogen or lower alkyl;
R⁷ is hydrogen or lower alkyl;
R⁸ is hydrogen or cyano;
n is 0, 1, 2 or 3;
o is 1, 2 or 3; and
p is 0, 1 or 2;

or pharmaceutically suitable acid addition salts, optically pure enantiomers, racemates or diastereomeric mixtures thereof.

Preferred compounds from formula I-3 are those, wherein one of R¹ or R² is hydrogen and the other is lower alkyl, for example
(R)-2-[(S)-1-(5-chloro-2-methoxy-phenyl)-3-(6-trifluoromethyl-pyridin-3-yl)-propylamino]-2-(4-fluoro-phenyl)-N-methyl-acetamide,
(R)-2-[(S)-1-(2-fluoro-5-methyl-phenyl)-3-(6-trifluoromethyl-pyridin-3-yl)-propylamino]-2-(4-fluoro-phenyl)-N-methyl-acetamide,
(S,R)-2-[(R,S)-1-(3,4-dimethoxy-phenyl)-3-(6-trifluoromethyl-pyridin-3-yl)-propylamino]-N-methyl-2-phenyl-acetamide,
(S,R)-2-[(S,R)-1-(4-chloro-3-methoxy-phenyl)-3-(6-trifluoromethyl-pyridin-3-yl)-propylamino]-N-methyl-2-phenyl-acetamide,
(S,R)-2-[(R,S)-1-(4-chloro-3-methoxy-phenyl)-3-(6-trifluoromethyl-pyridin-3-yl)-propylamino]-N-methyl-2-phenyl-acetamide,
(S,R)-2-[(R,S)-1-(4-chloro-3-methoxy-phenyl)-3-(6-trifluoromethyl-pyridin-3-yl)-propylamino]-2-(4-chloro-phenyl)-N-methyl-acetamide,
(S,R)-2-[(S,R)-1-(4-chloro-3-methoxy-phenyl)-3-(6-trifluoromethyl-pyridin-3-yl)-propylamino]-2-(4-fluoro-phenyl)-N-methyl-acetamide,
(S,R)-2-[(R,S)-1-(4-chloro-3-methoxy-phenyl)-3-(6-trifluoromethyl-pyridin-3-yl)-propylamino]-2-(4-fluoro-phenyl)-N-methyl-acetamide,
(S,R)-2-[(R,S)-1-(3-difluoromethoxy-phenyl)-3-(6-trifluoromethyl-pyridin-3-yl)-propylamino]-N-methyl-2-phenyl-acetamide,
(S,R)—N-methyl-2-phenyl-2-[(S,R)-1-(3-trifluoromethoxyphenyl)-3-(6-trifluoromethyl-pyridin-3-yl)-propylamino]-acetamide,
(S,R)-2-[(R,S)-1-(4-Fluoro-3-methyl-phenyl)-3-(6-trifluoromethyl-pyridin-3-yl)-propylamino]-N-methyl-2-phenyl-acetamide,
(S,R)-2-(4-chloro-phenyl)-2-[(R,S)-1-(4-fluoro-3-methoxyphenyl)-3-(6-trifluoromethyl-pyridin-3-yl)-propylamino]-N-methyl-acetamide,
(S,R)-2-[(R,S)-1-(4-fluoro-3-methoxy-phenyl)-3-(6-trifluoromethyl-pyridin-3-yl)-propylamino]-N-methyl-2-phenyl-acetamide,
(S,R)-2-(4-chloro-phenyl)-2-[(R,S)-1-(4-difluoromethoxy-3-methoxy-phenyl)-3-(6-trifluoromethyl-pyridin-3-yl)-propylamino]-N-methyl-acetamide,
(S,R)-2-[(R,S)-1-(3-chloro-4-methyl-phenyl)-3-(6-trifluoromethyl-pyridin-3-yl)-propylamino]-N-methyl-2-phenyl-acetamide,
(S,R)-2-[(R,S)-1-(4-fluoro-3-methoxy-phenyl)-3-(6-trifluoromethyl-pyridin-3-yl)-propylamino]-2-(4-fluoro-phenyl)-N-methyl-acetamide,
(S,R)-2-[(S,R)-1-(4-chloro-3-methyl-phenyl)-3-(6-trifluoromethyl-pyridin-3-yl)-propylamino]-N-methyl-2-phenyl-acetamide, (S,R)-2-[(R,S)-1-(4-chloro-3-methyl-phenyl)-3-(6-trifluoromethyl-pyridin-3-yl)-propylamino]-N-methyl-2-phenyl-acetamide,
(S,R)-2-[(R,S)-1-(3,4-dimethyl-phenyl)-3-(6-trifluoromethyl-pyridin-3-yl)-propylamino]-N-methyl-2-phenyl-acetamide,
(S,R)-2-[(S,R)-1-(3-methoxy-4-methyl-phenyl)-3-(6-trifluoromethyl-pyridin-3-yl)-propylamino]-N-methyl-2-phenyl-acetamide,
(S,R)-2-[(R,S)-1-(3-methoxy-4-methyl-phenyl)-3-(6-trifluoromethyl-pyridin-3-yl)-propylamino]-N-methyl-2-phenyl-acetamide,
2-[1-(4-fluoro-3-methyl-phenyl)-3-(6-methyl-pyridin-3-yl)-propylamino]-N-methyl-2-phenyl-acetamide,
(R)-2-[(S)-1-(4-Fluoro-3-methyl-phenyl)-3-(6-methyl-pyridin-3-yl)-propylamino]-N-methyl-2-phenyl-acetamide,
2-[1-(3,4-bis-difluoromethoxy-phenyl)-3-(6-trifluoromethyl-pyridin-3-yl)-propylamino]-N-methyl-2-phenyl-acetamide,
(S,R)-2-[(R,S)-3-(6-chloro-pyridin-3-yl)-1-(4-fluoro-3-methyl-phenyl)-propylamino]-N-methyl-2-phenyl-acetamide,
(S,R)-2-[(R,S)-1-(3,4-bis-difluoromethoxy-phenyl)-3-(6-chloro-pyridin-3-yl)-propylamino]-N-methyl-2-phenyl-acetamide,
(S,R)-2-[(R,S)-1-(3,4-bis-difluoromethoxy-phenyl)-3-(5-chloro-pyrazin-2-yl)-propylamino]-N-methyl-2-phenyl-acetamide,
(S,R)-2-[(R,S)-1-(3,4-bis-difluoromethoxy-phenyl)-3-(5-chloro-pyridin-2-yl)-propylamino]-N-methyl-2-phenyl-acetamide,
(R,S)-2-[(S,R)-1-(4-fluoro-3-methyl-phenyl)-3-(6-trifluoromethyl-pyridin-3-yl)-propylamino]-N-methyl-2-p-tolyl-acetamide,
(R,S)—N-ethyl-2-[(S,R)-1-(4-fluoro-3-methyl-phenyl)-3-(6-trifluoromethyl-pyridin-3-yl)-propylamino]-2-phenyl-acetamide,
(R,S)-2-[(S,R)-1-(4-fluoro-3-methyl-phenyl)-3-(6-trifluoromethyl-pyridin-3-yl)-propylamino]-2-(4-methoxy-phenyl)-N-methyl-acetamide and
(R)-2-[(S)-1-(4-fluoro-3-methyl-phenyl)-3-(6-trifluoromethyl-pyridin-3-yl)-propylamino]-2-phenyl-acetamide.

Preferred compounds from formula I-3 are further those, wherein one of R¹ or R² is hydrogen and the other is lower alkyl substituted by hydroxy, for example
(R,S)-2-[(S,R)-1-(4-fluoro-3-methyl-phenyl)-3-(6-trifluoromethyl-pyridin-3-yl)-propylamino]-N-(2-hydroxyethyl)-2-phenyl-acetamide Preferred compounds of formula I are further those of formula I-4

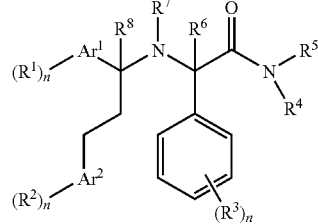

I-4 wherein
Ar¹ and Ar² are heteroaryl;

$R^1$, $R^2$ and $R^3$ are each independently hydroxy, halogen, lower alkyl, lower alkyl substituted by halogen, lower alkoxy, lower alkoxy substituted by halogen, cyano, 3-hydroxy-oxetan-3-yl, $SO_2$-lower alkyl or di-lower alkyl amino;

$R^4$ and $R^5$ are each independently hydrogen, lower alkyl, lower alkyl substituted by halogen, lower alkyl substituted by hydroxy, —$(CH_2)_o$—O-lower alkyl, —$(CH_2)_o$—N-(lower alkyl)$_2$, $(CH_2)_p$-cycloalkyl, $(CH_2)_p$-aryl, which aryl ring is optionally substituted by halogen, or $R^4$ and $R^5$ together with the N-atom to which they are attached form a heterocyclic ring, optionally containing further ring-heteroatoms selected from N, O and S;

$R^6$ is hydrogen or lower alkyl;
$R^7$ is hydrogen or lower alkyl;
$R^8$ is hydrogen or cyano;
n is 0, 1, 2 or 3;
o is 1, 2 or 3; and
p is 0, 1 or 2;

or pharmaceutically suitable acid addition salts, optically pure enantiomers, racemates or diastereomeric mixtures thereof.

Preferred compounds from formula I-4 are those, wherein one of $R^1$ or $R^2$ is hydrogen and the other is lower alkyl, for example (S,R)-2-(4-fluoro-phenyl)-N-methyl-2-[(R,S)-1-(5,6,7,8-tetrahydro-naphthalen-2-yl)-3-(6-trifluoromethyl-pyridin-3-yl)-propylamino]-acetamide and (R)-2-(4-fluoro-phenyl)-N-methyl-2-[(S)-1-(5,6,7,8-tetrahydro-naphthalen-2-yl)-3-(6-trifluoromethyl-pyridin-3-yl)-propylamino]-acetamide.

One embodiment of the present invention are compounds of formula I-A

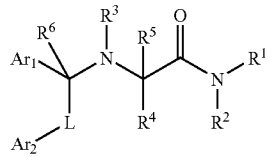

I-A wherein
$R^1$ and $R^2$ are each independently hydrogen, lower alkyl, lower alkyl substituted by halogen, —$(CH_2)_o$—O-lower alkyl, —$(CH_2)_o$—N-(lower alkyl)$_2$, $(CH_2)_p$-cycloalkyl, $(CH_2)_p$-heterocycloalkyl, $(CH_2)_p$-aryl, $(CH_2)_p$-heteroaryl, which rings is optionally substituted by R, or $R^1$ and $R^2$ together with the N-atom to which they are attached form a heterocyclic ring, optionally containing further ring-heteroatoms selected from N, O and S;

R is lower alkyl, lower alkoxy, halogen or lower alkyl substituted by halogen;

$R^3$ is hydrogen, lower alkyl or cycloalkyl;

$Ar^1$ and $Ar^2$ are unsubstituted or substituted aryl or heteroaryl and wherein the aryl and the heteroaryl groups are optionally substituted by one or more substituents selected from the group consisting of hydroxy, halogen, lower alkyl, lower alkyl substituted by halogen, lower alkoxy, lower alkoxy substituted with halogen, nitro, cyano, $SO_2$-lower alkyl and —$NR^1R^2$;

$R^4$ is lower alkyl, lower alkyl substituted by halogen, cycloalkyl, heterocycloalkyl, unsubstituted or substituted aryl or heteroaryl and wherein the aryl and the heteroaryl groups are optionally substituted by one or more substituents selected from the group consisting of hydroxy, halogen, lower alkyl, lower alkyl substituted by halogen, lower alkoxy, lower alkoxy substituted with halogen, nitro, cyano, $SO_2$-lower alkyl and —$NR^1R^2$;

L is —$(CR^7R^8)_n$—;
$R^5$ and $R^6$ are each independently hydrogen, lower alkyl;
$R^7$ and $R^8$ are each independently hydrogen, lower alkyl;
n is 0, 1, 2 or 3
o is 2 or 3; and
p is 0, 1 or 2;

or pharmaceutically suitable acid addition salts, optically pure enantiomers, racemates or diastereomeric mixtures thereof.

The present compounds of formula I and their pharmaceutically acceptable salts can be prepared by methods known in the art, for example, by process described below, which process comprises cleaving off the ester group in a compound of formula

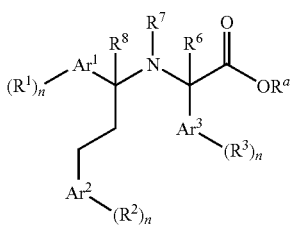

VI wherein $R^a$ is lower alkyl under aqueous basic conditions and converting the corresponding acid with an amine of formula $NHR^4R^5$ under coupling conditions to the aminoamide of formula

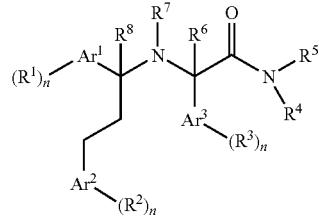

I wherein the substituents are as described above, and if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

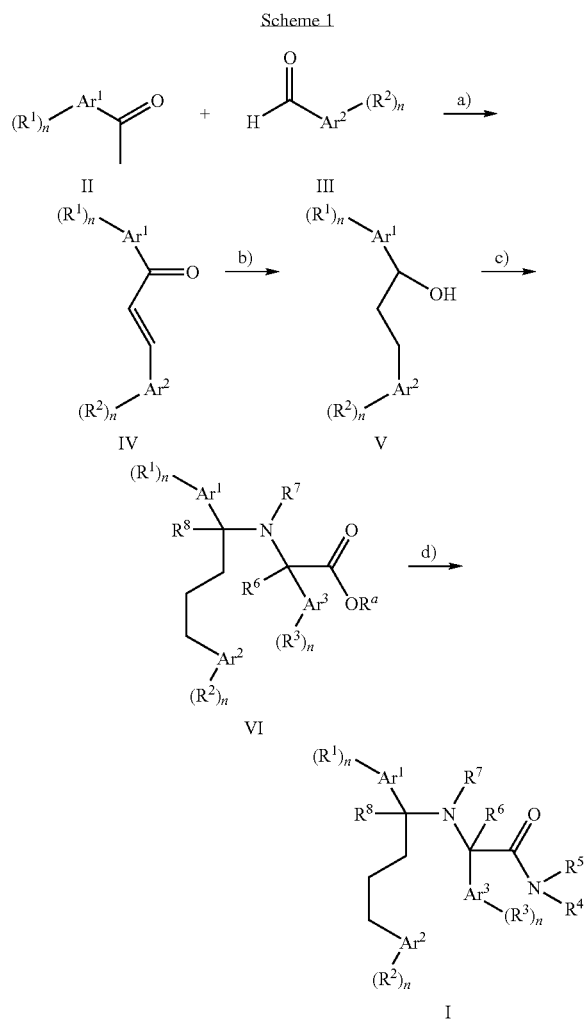

Scheme 1

$R^a$ is lower alkyl, $R^6$ is hydrogen and the remaining substituents are as described above.

Step a)

Acetophenone derivatives II and aldehyde derivatives III are commercially available or can be accessed by methods described in literature. Reaction of acetophenone derivatives II with aldehyde derivatives III can be achieved by various methods as described in literature (for reaction conditions described in literature affecting such reactions see for example: Comprehensive Organic Transformations: A Guide to Functional Group Preparations, 2nd Edition, Richard C. Larock. John Wiley & Sons, New York, N.Y. 1999). However, it is convenient to react acetophenone derivative II with aldehyde derivative III in the presence of a base and a solvent. We find it convenient to carry out the reaction in a solvent like methanol, however, there is no particular restriction on the nature of the solvent to be employed, provided that it has no adverse effect on the reaction or the reagents involved and that it can dissolve the reagents, at least to some extent. Examples for other suitable solvents include: dioxane, THF, and the like. There is no particular restriction on the nature of the base used in this stage, and any base commonly used in this type of reaction may equally be employed here. Examples of such bases include potassium hydroxide and sodium hydroxide, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield unsaturated ketone derivatives IV.

Step b)

Unsaturated ketones like compounds IV can be transformed to their respective hydroxy derivatives V by several methods as described in literature. For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). However, it is convenient to reduce the unsaturated ketone with hydrogen in the presence of a solvent with a suitable catalyst. We find it convenient to carry out the reaction in a solvent like ethyl acetate, however, there is no particular restriction on the nature of the solvent to be employed, provided that it has no adverse effect on the reaction or the reagents involved and that it can dissolve the reagents, at least to some extent. Examples for other suitable solvents include: dioxane, THF, and the like. There is no particular restriction on the nature of the catalyst used in this stage, and any catalyst commonly used in this type of reaction may equally be employed here. Examples of such catalysts include $PtO_2$, and the like. The reaction can take place over a wide range of hydrogen pressure which is not critical to the invention, however, pressures ranging from atmospheric to several bar are usually employed. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of 0.5 h to several days will usually suffice to yield hydroxy derivatives V.

Step c)

Hydroxy derivatives V can be transformed to the respective aminoacid ester derivatives VI by several methods as referred to in literature. However we find it convenient to activate the free hydroxy group in V by transforming it into a leaving group and subsequently reacting the intermediate with an aminoacid ester. However, we find it convenient to react hydroxy derivative V with methanesulfonylchloride to the respective intermediately built mesylate which can conveniently react with an amino acid ester (commercially available or prepared from commercially available starting materials, as appropriate) in a solvent and in the presence of a base. We find it convenient to carry out the reaction in a solvent like diethyl ether or THF, however, there is no particular restriction on the nature of the solvent to be employed, provided that it has no adverse effect on the reaction or the reagents involved and that it can dissolve the reagents, at least to some extent. Examples for other suitable solvents include: dioxane, and the like. There is no particular restriction on the nature of the base used in this stage, and any base commonly used in this type of reaction may equally be employed here. Examples of such bases include NEt₃ and DIPEA, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of 0.5 h to several days will usually suffice to yield amino acid ester derivatives VI.

Step d)

Transformation of amino acid ester derivative VI into the final aminoamide derivatives I can be done according to procedures described in literature. However, we find it convenient to employ a two step reaction sequence in which the ester functionality in VI is cleaved under aqueous basic conditions and the liberated acid functionality converted with the respective amines under coupling conditions to the aminoamide derivatives I. The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). The intermediately built acid can conveniently be transformed to the respective amide through coupling with an amine (either commercially available or accessible by methods described in references or by methods known in the art; as appropriate) by employing the usage of coupling reagents. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. We find it convenient to carry out the reaction in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of 0.5 h to several days will usually suffice to yield aminoamide derivatives I.

However, the synthesis of compounds of general formula I is not restricted to the synthetic pathway described above. Alternative pathways are shown in schemes 2-7.

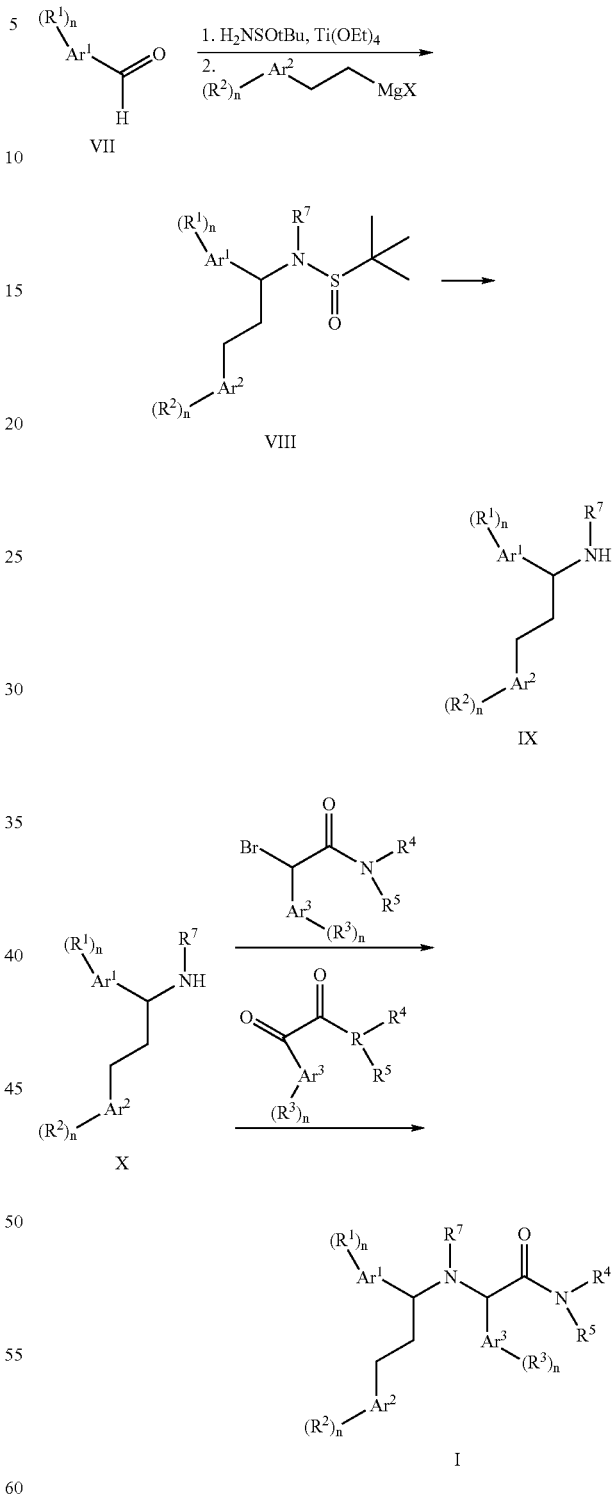

A further possible way for preparation of compounds of formula I is according to Ellmann-alkylation or reductive amination:

R⁸ in scheme 2 is hydrogen, and the other substituents are as described above.

Scheme 3

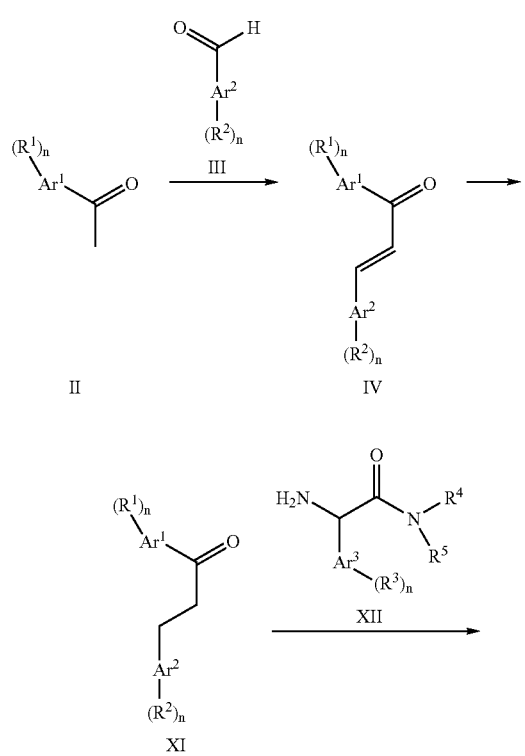

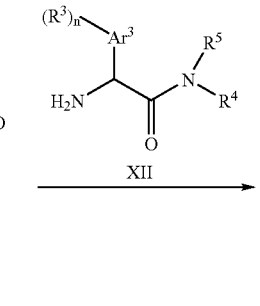

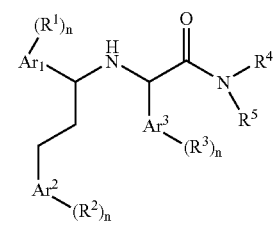

Compounds of formula I may also be prepared according to phosphonate reductive amination:

$R^7$ and $R^8$ in scheme 4 are hydrogen, and the other substituents are as described above.

Furthermore, compounds of formula I may be prepared according to boronic acid reductive amination:

Scheme 5

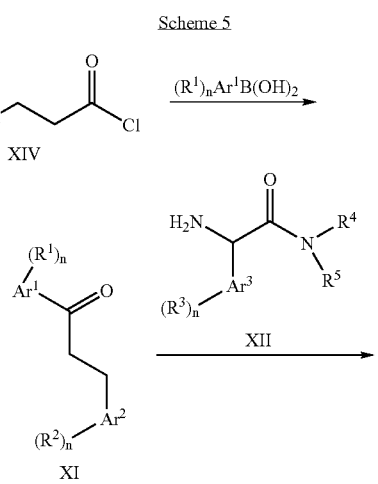

Scheme 3 describes an alternative preparation of compounds of formula I via Aldol-Reductive amination.

$R^7$ and $R^8$ in scheme 3 are hydrogen, and the other substituents are as described above.

Scheme 4

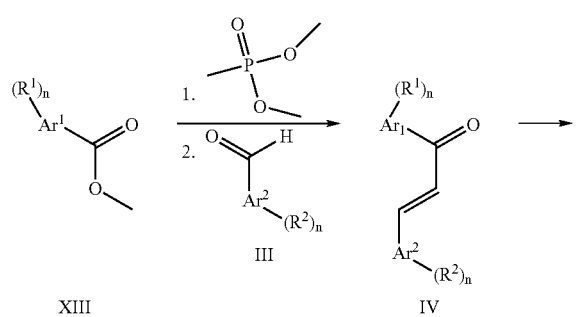

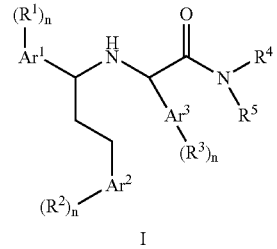

$R^7$ and $R^8$ in scheme 5 are hydrogen, and the other substituents are as described above.

Compounds of formula I may be prepared according to Weinreb reductive amination, as described in scheme 6.

Scheme 6

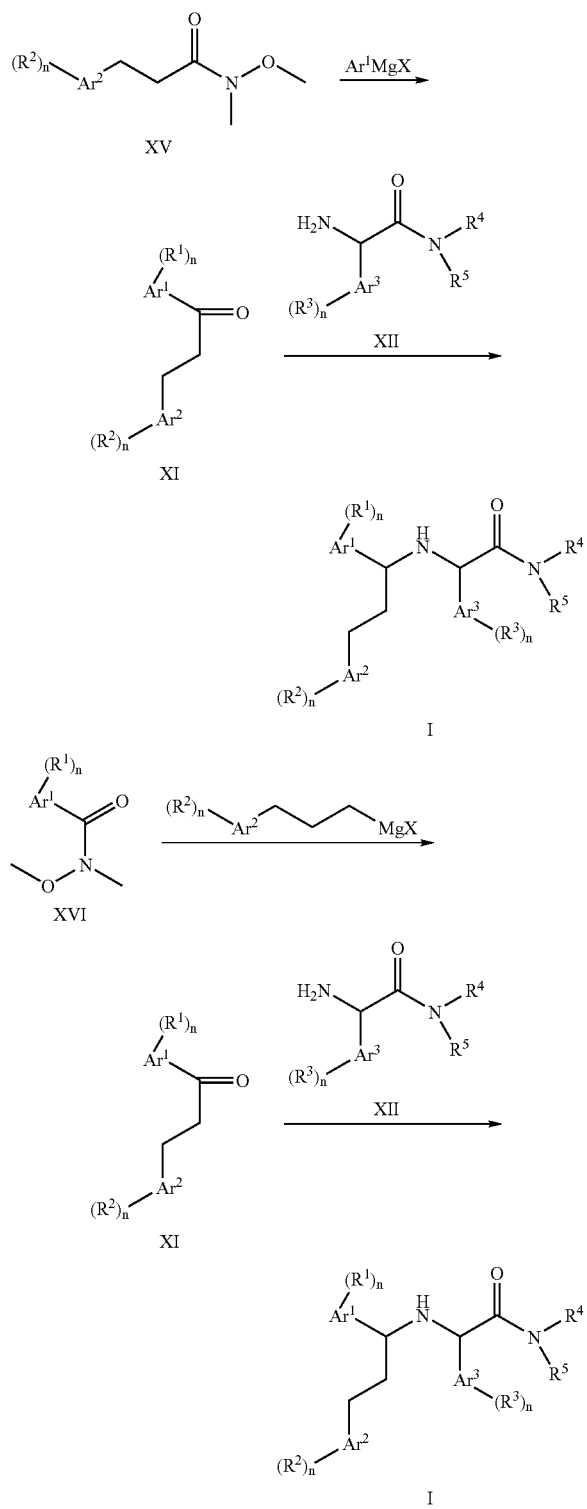

$R^7$ and $R^8$ in scheme 5 are hydrogen, and the other substituents are as described above.

Compounds of formula I may also be prepared according to transamination-reduction:

Scheme 7

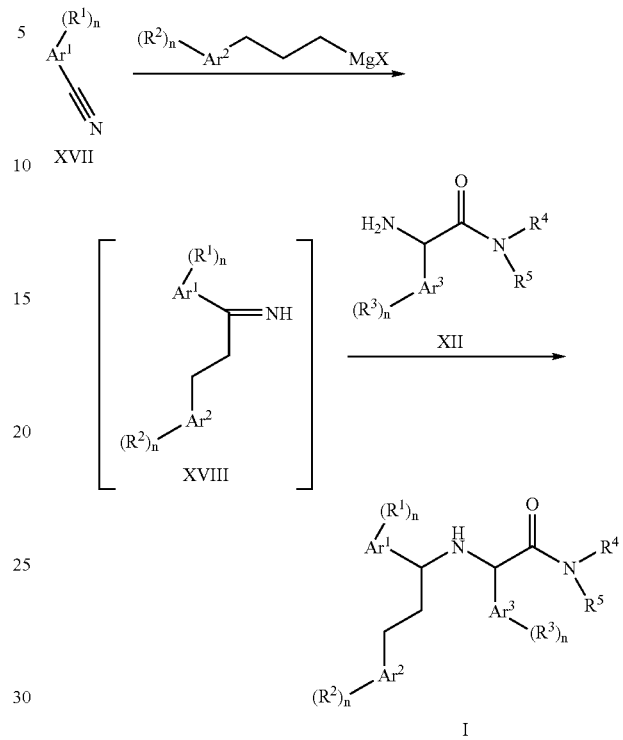

$R^7$ and $R^8$ in scheme 5 are hydrogen, and the other substituents are as described above The compounds were investigated in accordance with the test given hereinafter.

Intracellular $Ca^{2+}$ Mobilization Assay

The Chinese Hamster Ovary (dHFr−) mutant cell line stably expressing human orexin-1 (hOX1) or human orexin-2 (hOX2) receptors were maintained in Dulbecco's Modified Eagle Medium (1×) with GlutaMax™ 1, 4500 mg/L D-Glucose and Sodium Pyruvate (Catalog No. 31966-021, Invitrogen, Carlsbad, Calif.), 5% dialyzed fetal calf serum (Catalog No. 26400-044), 100 µg/ml penicillin and 100 µg/ml streptomycin. The cells were seeded at $5 \times 10^4$ cells/well in the poly-D-lysine treated, 96-well, black/clear-bottomed plates (Catalog No. BD356640, BD Biosciences, Palo Alto, Calif.). 24 h later, the cells were loaded for 1 h at 37° C. with 4 µM Flou-4 acetoxymethyl ester (Catalog No. F-14202, Molecular Probes, Eugene, Oreg.) in FLIPR buffer (1×HBSS, 20 mM HEPES, 2.5 mM Probenecid). Hanks' Balanced Salt Solution (HBSS) (10×) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with FLIPR buffer to remove excess dye and intracellular calcium mobilization, $[Ca^{2+}]_i$ were measured using a Fluorometric Imaging Plate Reader (FLIPR-96, Molecular Devices, Menlo Park, Calif.) as described previously (Malherbe et al., *Mol. Pharmacol.*, 64, 823-832, 2003). Orexin A (catalog No. 1455, Toris Cookson Ltd, Bristol, UK) was used as agonist. Orexin A (50 mM stock solution in DMSO) was diluted in FLIPR buffer+0.1% BSA. The $EC_{50}$ and $EC_{80}$ values of orexin-A were measured daily from standard agonist concentration-response curves in CHO(dHFr−)-OX1R and —OX2R cell lines. All compounds were dissolved in 100% DMSO. Inhibition curves were determined by addition of 11 concentrations (0.0001-10 μM) of inhibitory compounds and using $EC_{80}$ value of orexin-A as agonist (a concentration which gave 80% of max agonist response, determined daily). The antagonists were applied 25 min (incubation at 37° C.) before the application of the agonist. Responses were measured as peak increase in fluorescence minus basal, normalized to the maximal stimulatory effect induced by $EC_{80}$ value of orexin-A or orexin-B. Inhibition curves were fitted according to the Hill equation: $y=100/(1+(x/IC_{50})^{nH})$, where $n_H$=slope factor using Excel-fit 4 software (Microsoft). $K_b$ values were calculated according to the following equation $K_b=IC_{50}/(1+[A]/EC_{50})$ where A is the concentration of agonist added which is very close to agonist $EC_{80}$ value, and $IC_{50}$ and EC50 values were derived from the antagonist inhibition and orexin-A or B agonist curves, respectively.

Representative compounds show a $K_b$ value (μM) in human on orexin receptor as shown in the table below.

| Example | $K_b$ (μM) OX2R (human) |
|---|---|
| 6 | 0.0017 |
| 7 | 0.0142 |
| 13 | 0.0026 |
| 16 | 0.0142 |
| 29 | 0.0184 |
| 33 | 0.009 |
| 34 | 0.0049 |
| 38 | 0.0096 |
| 40 | 0.0068 |
| 41 | 0.0167 |
| 57 | 0.0093 |
| 78 | 0.0127 |
| 80 | 0.0192 |
| 92 | 0.007 |
| 93 | 0.017 |
| 94 | 0.0051 |
| 95 | 0.0086 |
| 96 | 0.0018 |
| 98 | 0.0014 |
| 102 | 0.0114 |
| 104 | 0.0148 |
| 107 | 0.0124 |
| 113 | 0.0089 |
| 115 | 0.0114 |
| 116 | 0.0061 |
| 123 | 0.0129 |
| 124 | 0.0123 |
| 135 | 0.0155 |
| 140 | 0.0014 |
| 141 | 0.0168 |
| 142 | 0.003 |
| 144 | 0.0097 |
| 146 | 0.0132 |
| 163 | 0.0011 |
| 171 | 0.005 |
| 176 | 0.0086 |
| 177 | 0.0099 |
| 179 | 0.0081 |
| 200 | 0.0028 |
| 207 | 0.0079 |
| 209 | 0.0024 |
| 210 | 0.0096 |
| 215 | 0.008 |
| 216 | 0.0073 |
| 220 | 0.0015 |
| 221 | 0.0026 |
| 222 | 0.0171 |
| 223 | 0.0171 |
| 224 | 0.0057 |
| 225 | 0.0144 |
| 226 | 0.0195 |

-continued

| Example | $K_b$ (μM) OX2R (human) |
|---|---|
| 228 | 0.0035 |
| 230 | 0.0117 |
| 232 | 0.0085 |
| 234 | 0.013 |
| 238 | 0.0196 |
| 240 | 0.0107 |
| 243 | 0.0122 |
| 244 | 0.0145 |
| 251 | 0.0022 |
| 252 | 0.0024 |
| 253 | 0.0034 |
| 258 | 0.0172 |
| 262 | 0.0173 |
| 263 | 0.0102 |
| 266 | 0.0175 |
| 290 | 0.0536 |
| 296 | 0.013 |
| 297 | 0.0153 |
| 301 | 0.0116 |
| 302 | 0.0161 |
| 306 | 0.0063 |
| 314 | 0.0067 |
| 319 | 0.0086 |
| 320 | 0.0021 |
| 321 | 0.0028 |
| 334 | 0.01 |
| 340 | 0.0178 |
| 350 | 0.0164 |
| 353 | 0.0057 |
| 356 | 0.0044 |
| 365 | 0.0124 |
| 387 | 0.008 |
| 389 | 0.0048 |
| 391 | 0.0141 |
| 392 | 0.0059 |
| 397 | 0.0042 |

The present invention also provides pharmaceutical compositions containing compounds of the invention, for example compounds of formula (I) and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| | | Tablet Formulation (Wet Granulation) mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | | Capsule Formulation mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Example 1

(S)-2-[(S or R)-1-(3,4-Dimethoxy-phenyl)-3-(4-trifluoromethyl-phenyl)-propylamino]-N-(2-methoxy-ethyl)-2-phenyl-acetamide

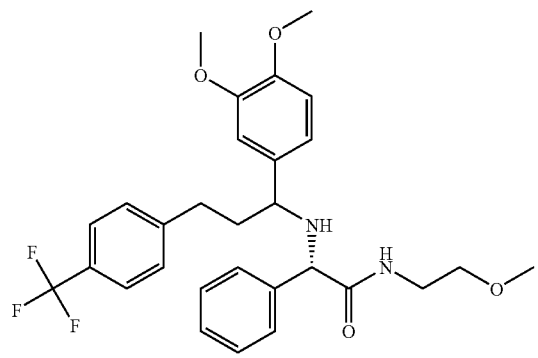

a) Step 1

(E)-1-(3,4-Dimethoxy-phenyl)-3-(4-trifluoromethyl-phenyl)-propenone

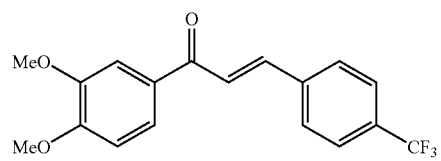

A mixture of 4 g (22 mmol) 1-(3,4-dimethoxy-phenyl)-ethanone, 3.86 g (22 mmol) 4-trifluoromethyl-benzaldehyde and 1.37 g (24 mmol) potassium hydroxide in 100 mL methanol was heated to 50° C. for 4 h. After evaporation to dryness the residue was taken up in ethyl acetate and washed with water. The aqueous phase was extracted with ethyl acetate and the combined organic phases were dried with MgSO$_4$ and evaporated to dryness. The residue was purified with flash column chromatography on silica eluting with a gradient formed from ethyl acetate and heptane. The product containing fractions were evaporated to yield 5.89 g (79%) of the title compound as yellow oil.

b) Step 2

1-(3,4-Dimethoxy-phenyl)-3-(4-trifluoromethyl-phenyl)-propan-1-ol

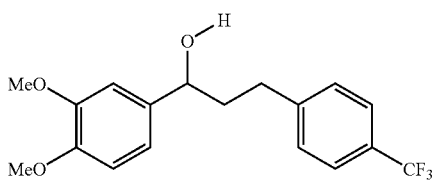

5.65 g (16.8 mmol) (E)-1-(3,4-Dimethoxy-phenyl)-3-(4-trifluoromethyl-phenyl)-propenone was hydrogenated at room temperature for 16 h with atmospheric pressure of hydrogen in 50 mL ethyl acetate over PtO₂ (hydrate). The catalyst was filtered off and the filtrate evaporated to dryness to yield the title compound which was used without further purification. MS (m/e): 323.3 (MH$^+$-(H$_2$O)).

c) Step 3

(S)-[(S or R)-1-(3,4-Dimethoxy-phenyl)-3-(4-trifluoromethyl-phenyl)-propylamino]-phenyl-acetic acid methyl ester and (S)-[(R or S)-1-(3,4-Dimethoxy-phenyl)-3-(4-trifluoromethyl-phenyl)-propylamino]-phenyl-acetic acid methyl ester

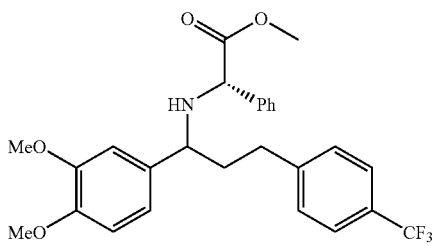

A mixture of 2.74 g (80 mmol) 1-(3,4-dimethoxy-phenyl)-3-(4-trifluoromethyl-phenyl)-propan-1-ol, 1.1 g (9.6 mmol) methanesulfonylchloride and 2.44 g (24 mmol) NEt₃ in 60 mL diethyl ether was stirred at 0° C. for 1 h. 3.25 g (16 mmol) (S)-2-phenylglycine methyl ester hydrochloride, and 2.44 g (24 mmol) NEt₃ and 30 mL THF was added. The mixture was stirred at 0° C. for 1 h and 16 h at room temperature. Water was added and the mixture was extracted with ethyl acetate. The combined organic fractions were washed with water, dried with MgSO4 and evaporated to dryness. The residue was purified by flash column chromatography on silica eluting with a gradient formed from ethyl acetate and heptane. The product containing fractions were evaporated to dryness to yield 0.97 g (S)-[(S or R)-1-(3,4-dimethoxy-phenyl)-3-(4-trifluoromethyl-phenyl)-propylamino]-phenyl-acetic acid methyl ester (MS (m/e): 488.0 (MH$^+$)) as yellow oil and 0.91 g (S)-[(R or S)-1-(3,4-Dimethoxy-phenyl)-3-(4-trifluorom- ethyl-phenyl)-propylamino]-phenyl-acetic acid methyl ester (MS (m/e): 488.0 (MH$^+$)) as yellow oil.

d) Step 4

(S)-[(S or R)-1-(3,4-Dimethoxy-phenyl)-3-(4-trifluoromethyl-phenyl)-propylamino]-phenyl-acetic acid, hydrochloride (intermediate 1)

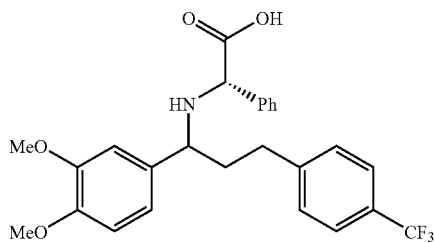

A mixture of 0.97 g (2 mmol) (S)-[(S or R)-1-(3,4-dimethoxy-phenyl)-3-(4-trifluoromethyl-phenyl)-propylamino]-phenyl-acetic acid methyl ester, 1.2 mL 5N KOH aq. in 2 mL methanol and 4 mL THF was stirred at room temperature for 2 h. Organic solvents were removed under reduced pressure and 4N HCl aq. was added. The mixture was extracted with ethyl acetate and the combined organic phases were washed with NaCl sat. aq., dried with MgSO₄ and evaporated to dryness to yield 0.94 g of the title compound as orange solid which was used without further purification. MS (m/e): 496.0 (M−HCl+Na$^+$).

e) Step 5

A mixture of 37.8 mg (0.074 mmol) (S)-[(S or R)-1-(3,4-dimethoxy-phenyl)-3-(4-trifluoromethyl-phenyl)-propylamino]-phenyl-acetic acid, hydrochloride (intermediate 1), 9 mg (0.12 mmol) 2-Methoxy-ethylamine, 33.4 mg (0.104 mmol) TBTU and 31 mg (0.24 mmol) DIPEA in 1 mL DMF was shaken at room temperature for 16 h. Formic acid was added and the mixture was subjected to preparative HPLC purification on reversed phase eluting with a gradient formed from acetonitrile, water and formic acid. The product containing fractions were evaporated to yield 8.5 mg (22%) of the title compound. MS (m/e): 530.8 (MH$^+$).

Intermediate 2

(S)-[(R or S)-1-(3,4-Dimethoxy-phenyl)-3-(4-trifluoromethyl-phenyl)-propylamino]-phenyl-acetic acid, hydrochloride

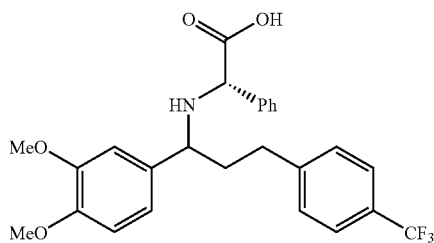

In analogy to the procedure described for the synthesis of intermediate 1 the title compound was prepared from (S)-[(R or S)-1-(3,4-Dimethoxy-phenyl)-3-(4-trifluoromethyl-phenyl)-propylamino]-phenyl-acetic acid methyl ester through KOH mediated ester cleavage and acidic work-up. MS (m/e): 496.0 (M−HCl+Na$^+$).

Intermediate 3

(R)-[(S or R)-1-(3,4-Dimethoxy-phenyl)-3-(4-trifluoromethyl-phenyl)-propylamino]-phenyl-acetic acid, hydrochloride

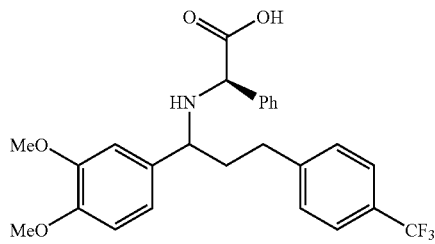

In analogy to the procedure described for the synthesis of intermediate 1 the title compound was prepared from (R)-[(S or R)-1-(3,4-Dimethoxy-phenyl)-3-(4-trifluoromethyl-phenyl)-propylamino]-phenyl-acetic acid methyl ester (accessed according to the procedure described for example 1, step 3 from 1-(3,4-dimethoxy-phenyl)-3-(4-trifluoromethyl-phenyl)-propan-1-ol and (R)-2-phenylglycine methyl ester hydrochloride) through KOH mediated ester cleavage and acidic work-up. MS (m/e): 496.1 (M−HCl+Na$^+$).

Intermediate 4

(R)-[(R or S)-1-(3,4-Dimethoxy-phenyl)-3-(4-trifluoromethyl-phenyl)-propylamino]-phenyl-acetic acid, hydrochloride

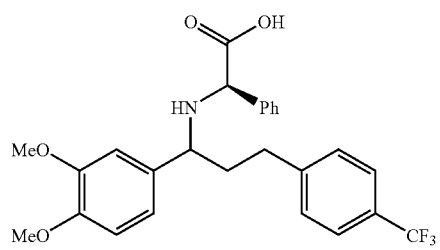

In analogy to the procedure described for the synthesis of intermediate 1 the title compound was prepared from (R)-[(R or S)-1-(3,4-dimethoxy-phenyl)-3-(4-trifluoromethyl-phenyl)-propylamino]-phenyl-acetic acid methyl ester (accessed according to the procedure described for example 1, step 3 from 1-(3,4-Dimethoxy-phenyl)-3-(4-trifluoromethyl-phenyl)-propan-1-ol and (R)-2-phenylglycine methyl ester hydrochloride) through KOH mediated ester cleavage and acidic work-up. MS (m/e): 474.1 (MH$^+$).

In analogy to the procedure described for the synthesis of example 1 further derivatives have been synthesised from their respective starting materials mentioned in table 1. Table 1 comprises example 2 to example 20.

TABLE 1

| No | Structure | MW | Name | Starting materials | MW MH+ found |
|----|-----------|-----|------|-------------------|--------------|
| 1 | 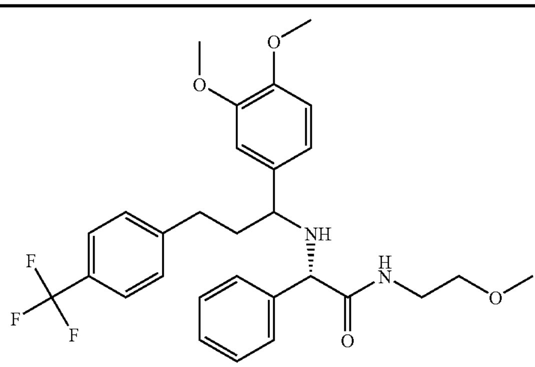 | 530.6 | (S)-2-[(S or R)-1-(3,4-Dimethoxy-phenyl)-3-(4-trifluoromethyl-phenyl)-propylamino]-N-(2-methoxy-ethyl)-2-phenyl-acetamide | (S)-[(S or R)-1-(3,4-Dimethoxy-phenyl)-3-(4-trifluoromethyl-phenyl)-propylamino]-phenyl-acetic acid, hydrochloride (intermediate 1) and 2-Methoxy-ethylamine (commercially available) | 530.8 |
| 2 | 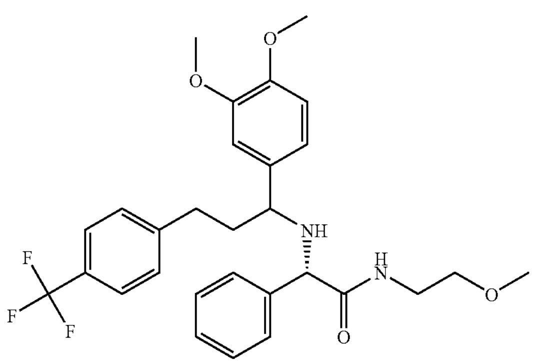 | 530.6 | (S)-2-[(R or S)-1-(3,4-Dimethoxy-phenyl)-3-(4-trifluoromethyl-phenyl)-propylamino]-N-(2-methoxy-ethyl)-2-phenyl-acetamide | (S)-[(R or S)-1-(3,4-Dimethoxy-phenyl)-3-(4-trifluoromethyl-phenyl)-propylamino]-phenyl-acetic acid, hydrochloride (intermediate 2) and 2-Methoxy-ethylamine (commercially available) | 531.2 |

TABLE 1-continued

| No | Structure | MW | Name | Starting materials | MW MH+ found |
|---|---|---|---|---|---|
| 3 | 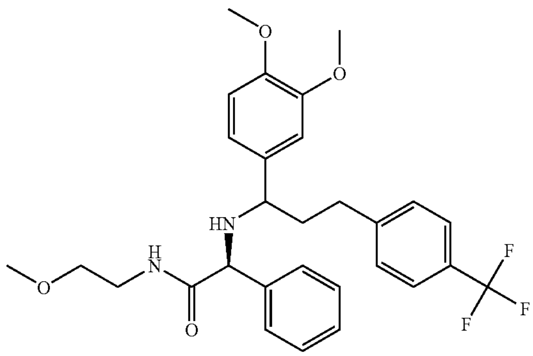 | 530.6 | (R)-2-[(S or R)-1-(3,4-Dimethoxy-phenyl)-3-(4-trifluoromethyl-phenyl)-propylamino]-N-(2-methoxy-ethyl)-2-phenyl-acetamide | (R)-[(S or R)-1-(3,4-Dimethoxy-phenyl)-3-(4-trifluoromethyl-phenyl)-propylamino]-phenyl-acetic acid, hydrochloride (intermediate 3) and 2-Methoxy-ethylamine (commercially available) | 530.584 |
| 4 | 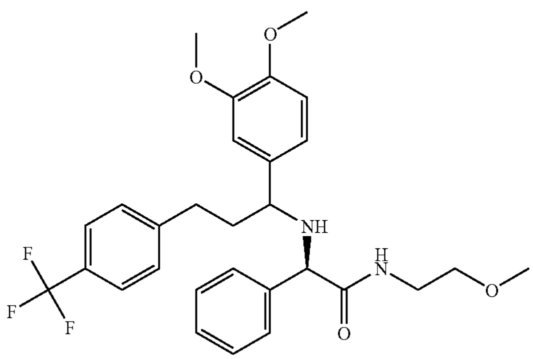 | 530.6 | (R)-2-[(R or S)-1-(3,4-Dimethoxy-phenyl)-3-(4-trifluoromethyl-phenyl)-propylamino]-N-(2-methoxy-ethyl)-2-phenyl-acetamide | (R)-[(R or S)-1-(3,4-Dimethoxy-phenyl)-3-(4-trifluoromethyl-phenyl)-propylamino]-phenyl-acetic acid, hydrochloride (intermediate 4) and 2-Methoxy-ethylamine (commercially available) | 531 |
| 5 | 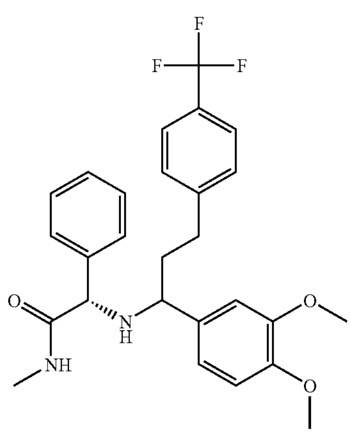 | 486.5 | (S)-2-[(R or S)-1-(3,4-Dimethoxy-phenyl)-3-(4-trifluoromethyl-phenyl)-propylamino]-N-methyl-2-phenyl-acetamide | (S)-[(R or S)-1-(3,4-Dimethoxy-phenyl)-3-(4-trifluoromethyl-phenyl)-propylamino]-phenyl-acetic acid, hydrochloride (intermediate 2) and methylamine (commercially available) | 487.4 |
| 6 | 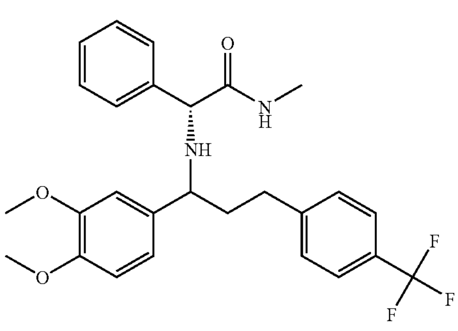 | 486.5 | (R)-2-[(S or R)-1-(3,4-Dimethoxy-phenyl)-3-(4-trifluoromethyl-phenyl)-propylamino]-N-methyl-2-phenyl-acetamide | (R)-[(R or S)-1-(3,4-Dimethoxy-phenyl)-3-(4-trifluoromethyl-phenyl)-propylamino]-phenyl-acetic acid, hydrochloride (intermediate 4) and methylamine (commercially available) | 487.4 |

TABLE 1-continued

| No | Structure | MW | Name | Starting materials | MW MH+ found |
|---|---|---|---|---|---|
| 7 | 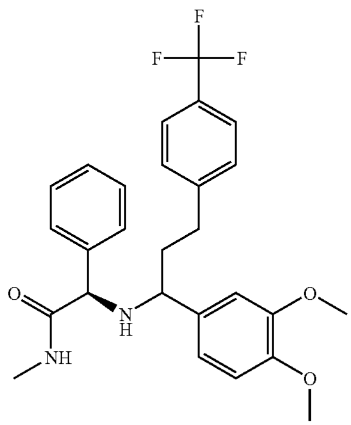 | 486.5 | (R)-2-[(S or R)-1-(3,4-Dimethoxy-phenyl)-3-(4-trifluoromethyl-phenyl)-propylamino]-N-methyl-2-phenyl-acetamide | (R)-[(S or R)-1-(3,4-Dimethoxy-phenyl)-3-(4-trifluoromethyl-phenyl)-propylamino]-phenyl-acetic acid, hydrochloride (intermediate 3) and methylamine (commercially available) | 487.4 |
| 8 | 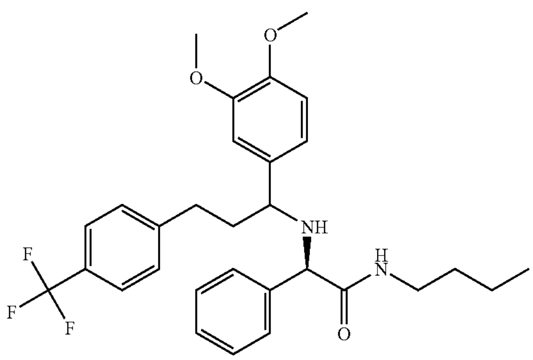 | 528.6 | (R)-N-Butyl-2-[(S or R)-1-(3,4-dimethoxy-phenyl)-3-(4-trifluoromethyl-phenyl)-propylamino]-2-phenyl-acetamide | (R)-[(S or R)-1-(3,4-Dimethoxy-phenyl)-3-(4-trifluoromethyl-phenyl)-propylamino]-phenyl-acetic acid, hydrochloride (intermediate 3) and butylamine (commercially available) | 529 |
| 9 | 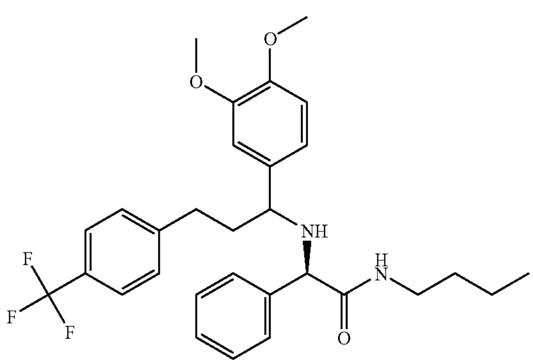 | 528.6 | (R)-N-Butyl-2-[(R or S)-1-(3,4-dimethoxy-phenyl)-3-(4-trifluoromethyl-phenyl)-propylamino]-2-phenyl-acetamide | (R)-[(R or S)-1-(3,4-Dimethoxy-phenyl)-3-(4-trifluoromethyl-phenyl)-propylamino]-phenyl-acetic acid, hydrochloride (intermediate 4) and butylamine (commercially available) | 528.8 |

TABLE 1-continued

| No | Structure | MW | Name | Starting materials | MW MH+ found |
|---|---|---|---|---|---|
| 10 | 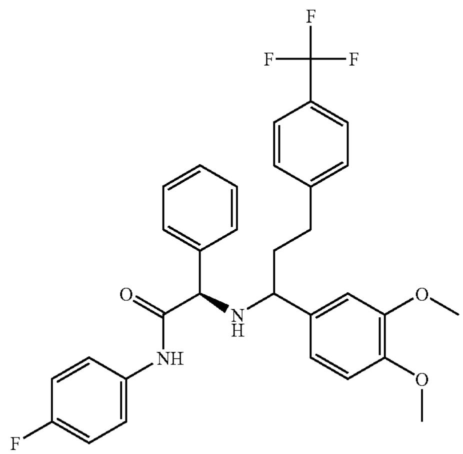 | 566.6 | (R)-2-[(S or R)-1-(3,4-Dimethoxy-phenyl)-3-(4-trifluoromethyl-phenyl)-propylamino]-N-(4-fluoro-phenyl)-2-phenyl-acetamide | (R)-[(S or R)-1-(3,4-Dimethoxy-phenyl)-3-(4-trifluoromethyl-phenyl)-propylamino]-phenyl-acetic acid, hydrochloride (intermediate 3) and 4-Fluoro-phenylamine (commercially available) | 567 |
| 11 | 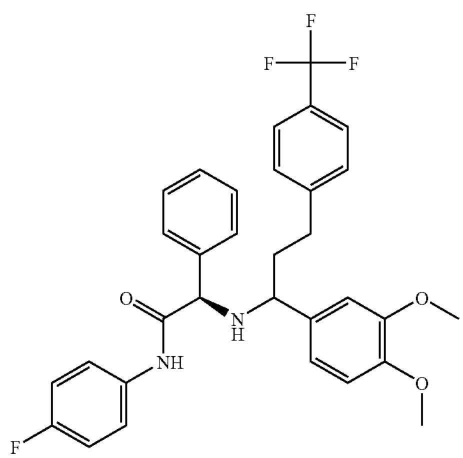 | 566.6 | (R)-2-[(R or S)-1-(3,4-Dimethoxy-phenyl)-3-(4-trifluoromethyl-phenyl)-propylamino]-N-(4-fluoro-phenyl)-2-phenyl-acetamide | (R)-[(R or S)-1-(3,4-Dimethoxy-phenyl)-3-(4-trifluoromethyl-phenyl)-propylamino]-phenyl-acetic acid, hydrochloride (intermediate 4) and 4-Fluoro-phenylamine (commercially available) | 566.8 |
| 12 | 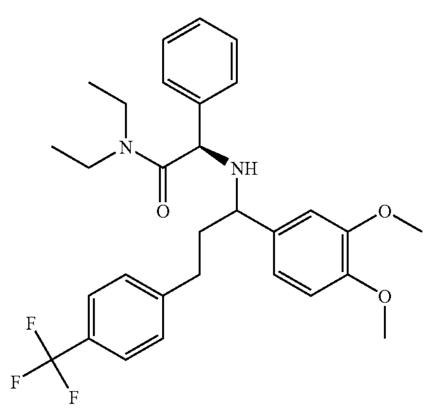 | 528.6 | (R)-2-[(R or S)-1-(3,4-Dimethoxy-phenyl)-3-(4-trifluoromethyl-phenyl)-propylamino]-N,N-diethyl-2-phenyl-acetamide | (R)-[(R or S)-1-(3,4-Dimethoxy-phenyl)-3-(4-trifluoromethyl-phenyl)-propylamino]-phenyl-acetic acid, hydrochloride (intermediate 4) and diethylamine (commercially available) | 529 |

TABLE 1-continued

| No | Structure | MW | Name | Starting materials | MW MH+ found |
|---|---|---|---|---|---|
| 13 | 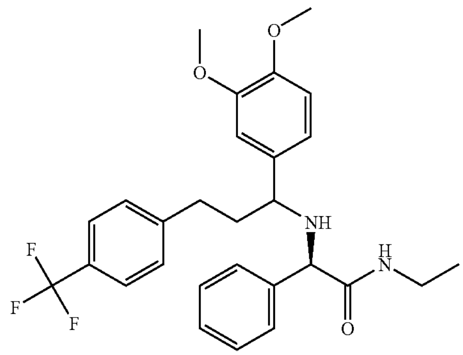 | 500.6 | (R)-2-[(R or S)-1-(3,4-Dimethoxy-phenyl)-3-(4-trifluoromethyl-phenyl)-propylamino]-N-ethyl-2-phenyl-acetamide | (R)-[(R or S)-1-(3,4-Dimethoxy-phenyl)-3-(4-trifluoromethyl-phenyl)-propylamino]-phenyl-acetic acid, hydrochloride (intermediate 4) and ethylamine (commercially available) | 501.2 |
| 14 | 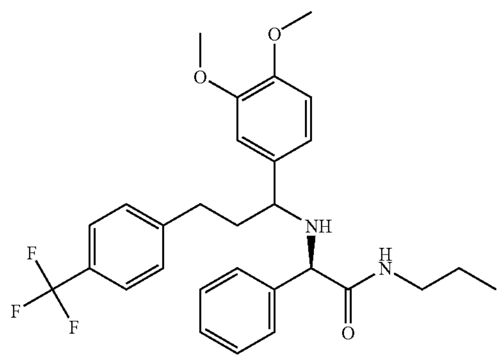 | 514.6 | (R)-2-[(R or S)-1-(3,4-Dimethoxy-phenyl)-3-(4-trifluoromethyl-phenyl)-propylamino]-2-phenyl-N-propyl-acetamide | (R)-[(R or S)-1-(3,4-Dimethoxy-phenyl)-3-(4-trifluoromethyl-phenyl)-propylamino]-phenyl-acetic acid, hydrochloride (intermediate 4) and propylamine (commercially available) | 515.2 |
| 15 | 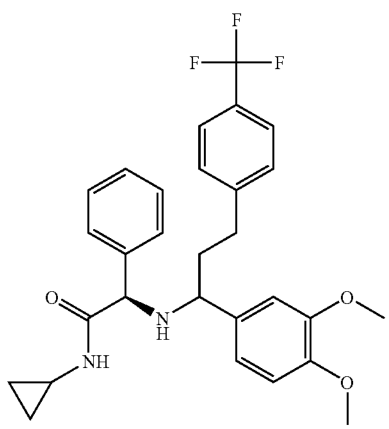 | 512.6 | (R)-N-Cyclopropyl-2-[(R or S)-1-(3,4-dimethoxy-phenyl)-3-(4-trifluoromethyl-phenyl)-propylamino]-2-phenyl-acetamide | (R)-[(R or S)-1-(3,4-Dimethoxy-phenyl)-3-(4-trifluoromethyl-phenyl)-propylamino]-phenyl-acetic acid, hydrochloride (intermediate 4) and cyclopropylamine (commercially available) | 513.2 |
| 16 | 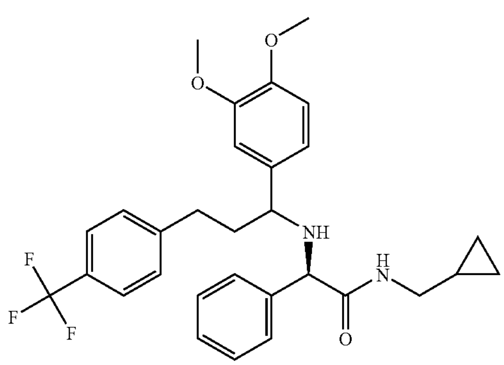 | 526.6 | (R)-N-Cyclopropylmethyl-2-[(R or S)-1-(3,4-dimethoxy-phenyl)-3-(4-trifluoromethyl-phenyl)-propylamino]-2-phenyl-acetamide | (R)-[(R or S)-1-(3,4-Dimethoxy-phenyl)-3-(4-trifluoromethyl-phenyl)-propylamino]-phenyl-acetic acid, hydrochloride (intermediate 4) and cyclopropylmethylamine (commercially available) | 527.2 |

TABLE 1-continued

| No | Structure | MW | Name | Starting materials | MW MH+ found |
|---|---|---|---|---|---|
| 17 | 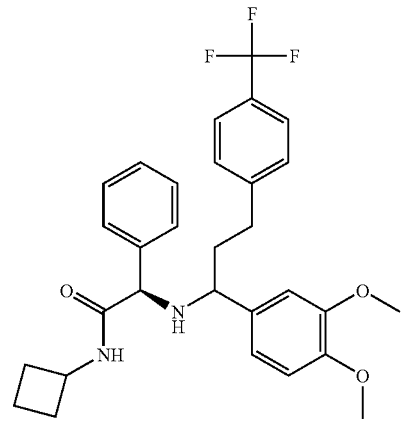 | 526.6 | (R)-N-Cyclobutyl-2-[1(R or S)-(3,4-dimethoxy-phenyl)-3-(4-trifluoromethyl-phenyl)-propylamino]-2-phenyl-acetamide | (R)-[(R or S)-1-(3,4-Dimethoxy-phenyl)-3-(4-trifluoromethyl-phenyl)-propylamino]-phenyl-acetic acid, hydrochloride (intermediate 4) and cyclobutylamine (commercially available) | 527.2 |
| 18 | 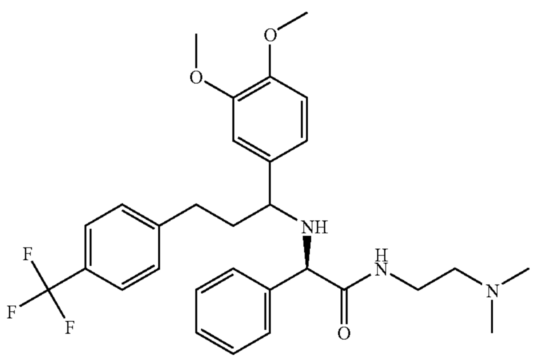 | 543.6 | (R)-2-[(R or S)-1-(3,4-Dimethoxy-phenyl)-3-(4-trifluoromethyl-phenyl)-propylamino]-N-(2-dimethylamino-ethyl)-2-phenyl-acetamide | (R)-[(R or S)-1-(3,4-Dimethoxy-phenyl)-3-(4-trifluoromethyl-phenyl)-propylamino]-phenyl-acetic acid, hydrochloride (intermediate 4) and 2-dimethylamino-ethyl amine (commercially available) | 544.2 |
| 19 | 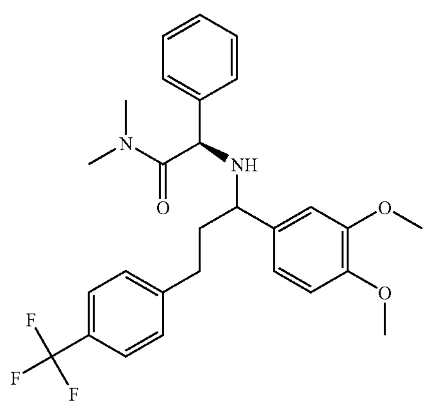 | 500.6 | (R)-2-[(R or S)-1-(3,4-Dimethoxy-phenyl)-3-(4-trifluoromethyl-phenyl)-propylamino]-N,N-dimethyl-2-phenyl-acetamide | (R)-[(R or S)-1-(3,4-Dimethoxy-phenyl)-3-(4-trifluoromethyl-phenyl)-propylamino]-phenyl-acetic acid, hydrochloride (intermediate 4) and dimethyl amine (commercially available) | 501.2 |
| 20 | 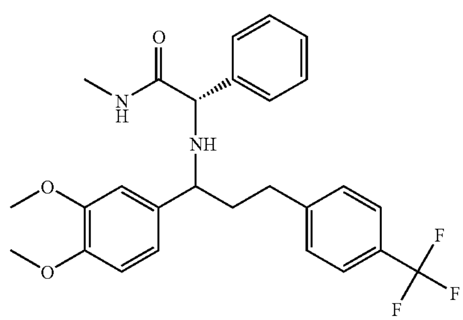 | 500.6 | (S)-2-[(R or S)-1-(3,4-Dimethoxy-phenyl)-3-(4-trifluoromethyl-phenyl)-propylamino]-N-methyl-2-phenyl-acetamide | (S)-[(R or S)-1-(3,4-Dimethoxy-phenyl)-3-(4-trifluoromethyl-phenyl)-propylamino]-phenyl-acetic acid, hydrochloride and methylamine (commercially available) | 487.3 |

Example 21

(R)-2-[(S or R) 1-(4-Methoxy-phenyl)-3-(4-trifluoromethyl-phenyl)-propylamino]-N-methyl-2-phenyl-acetamide and

Example 22

(R)-2-[(R or S)1-(4-Methoxy-phenyl)-3-(4-trifluoromethyl-phenyl)-propylamino]-N-methyl-2-phenyl-acetamide

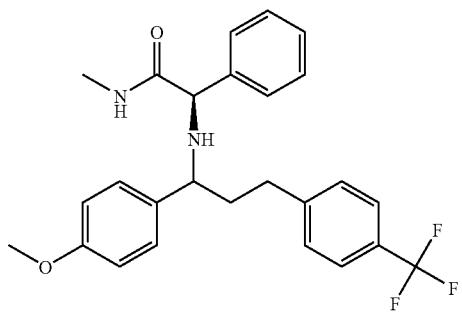

a) Step 1

(E)-1-(4-Methoxy-phenyl)-3-(4-trifluoromethyl-phenyl)-propenone

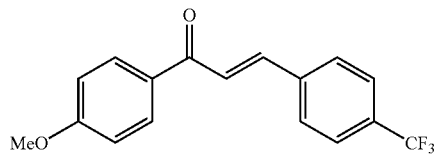

In analogy to the procedure described for the synthesis of (E)-1-(3,4-dimethoxy-phenyl)-3-(4-trifluoromethyl-phenyl)-propenone (example 1, step 1) the title compound was prepared from 4-methoxyacetophenone (commercially available) and 4-trifluoromethylbenzaldehyde (commercially available).

b) Step 2

1-(4-Methoxy-phenyl)-3-(4-trifluoromethyl-phenyl)-propan-1-ol

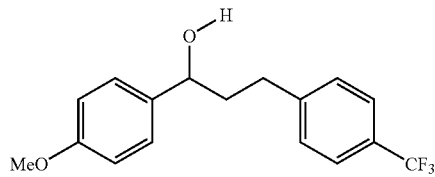

In analogy to the procedure described for the synthesis of 1-(3,4-dimethoxy-phenyl)-3-(4-trifluoromethyl-phenyl)-propan-1-ol (example 1, step 2) the title compound was prepared from (E)-1-(4-methoxy-phenyl)-3-(4-trifluoromethyl-phenyl)-propenone through reduction with NaBH$_4$ and NiCl$_2$.6H$_2$O. MS (m/e): 293.1 (M−OH)$^+$ c) Step 3

In analogy to the procedure described for the synthesis of (S)-[(S or R)-1-(3,4-dimethoxy-phenyl)-3-(4-trifluoromethyl-phenyl)-propylamino]-phenyl-acetic acid methyl ester and (S)-[(R or S)-1-(3,4-dimethoxy-phenyl)-3-(4-trifluoromethyl-phenyl)-propylamino]-phenyl-acetic acid methyl ester (Example 1, step 3) the title compounds were prepared from 1-(4-methoxy-phenyl)-3-(4-trifluoromethyl-phenyl)-propan-1-ol through mesylation with trifluoromethylsulfonyl chloride and subsequent reaction with (R)-2-amino-N-methyl-2-phenyl-acetamide and subsequent separation on silica. Example 21: (R)-2-[(S or R)1-(4-methoxy-phenyl)-3-(4-trifluoromethyl-phenyl)-propylamino]-N-methyl-2-phenyl-acetamide, MS (m/e): 457.5 and example 22: (R)-2-[(R or S)1-(4-methoxy-phenyl)-3-(4-trifluoromethyl-phenyl)-propylamino]-N-methyl-2-phenyl-acetamide, MS (m/e): 457.3.

Example 23

(R)-2-[(S or R)-1-(3-Fluoro-4-methoxy-phenyl)-3-(4-trifluoromethyl-phenyl)-propylamino]-N-methyl-2-phenyl-acetamide and

Example 24

(R)-2-[(R or S)-1-(3-Fluoro-4-methoxy-phenyl)-3-(4-trifluoromethyl-phenyl)-propylamino]-N-methyl-2-phenyl-acetamide

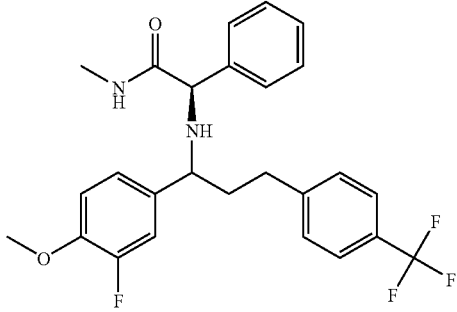

a) Step 1

(E)-1-(3-Fluoro-4-methoxy-phenyl)-3-(4-trifluoromethyl-phenyl)-propenone

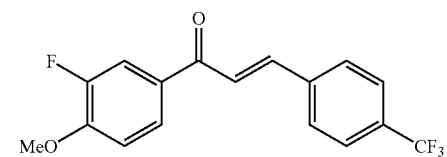

In analogy to the procedure described for the synthesis of (E)-1-(3,4-dimethoxy-phenyl)-3-(4-trifluoromethyl-phenyl)-propenone (example 1, step 1) the title compound was prepared from 1-(3-fluoro-4-methoxy-phenyl)-ethanone (commercially available) and 4-trifluoromethyl-benzaldehyde (commercially available).

b) Step 2

1-(3-Fluoro-4-methoxy-phenyl)-3-(4-trifluoromethyl-phenyl)-propan-1-ol

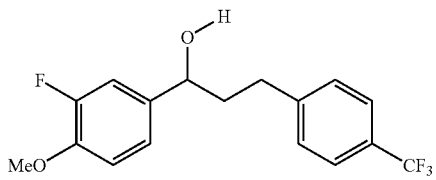

In analogy to the procedure described for the synthesis of 1-(3,4-dimethoxy-phenyl)-3-(4-trifluoromethyl-phenyl)-propan-1-ol (example 1, step 2) the title compound was prepared from (E)-1-(3-fluoro-4-methoxy-phenyl)-3-(4-trifluoromethyl-phenyl)-propenone through reduction with $NaBH_4$ and $NiCl_2.6H_2O$. MS (m/e): 387.1 $(M+OAc)^+$ c) Step 3

In analogy to the procedure described for the synthesis of (S)-[(S or R)-1-(3,4-dimethoxy-phenyl)-3-(4-trifluoromethyl-phenyl)-propylamino]-phenyl-acetic acid methyl ester and (S)-[(R or S)-1-(3,4-dimethoxy-phenyl)-3-(4-trifluoromethyl-phenyl)-propylamino]-phenyl-acetic acid methyl ester (Example 1, step 3) the title compounds were prepared from 1-(3-fluoro-4-methoxy-phenyl)-3-(4-trifluoromethyl-phenyl)-propan-1-ol through mesylation with trifluoromethylsulfonyl chloride and subsequent reaction with (R)-2-amino-N-methyl-2-phenyl-acetamide and subsequent separation on silica. Example 23: (R)-2-[(S or R)-1-(3-fluoro-4-methoxy-phenyl)-3-(4-trifluoromethyl-phenyl)-propylamino]-N-methyl-2-phenyl-acetamide, MS (m/e): 475.0 and example 24 (R)-2-[(R or S)-1-(3-fluoro-4-methoxy-phenyl)-3-(4-trifluoromethyl-phenyl)-propylamino]-N-methyl-2-phenyl-acetamide, MS (m/e): 475.3.

Example 25

2-[3-(3,4-Dimethoxy-phenyl)-1-(5-fluoro-2-hydroxy-phenyl)-propylamino]-2-phenyl-acetamide

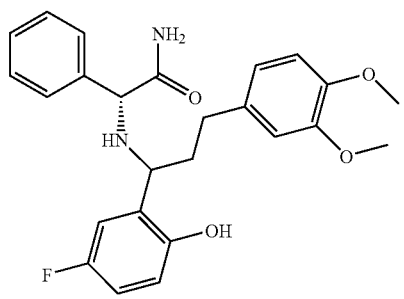

a) Step 1

(E)-3-(3,4-Dimethoxy-phenyl)-1-(5-fluoro-2-hydroxy-phenyl)-propenone

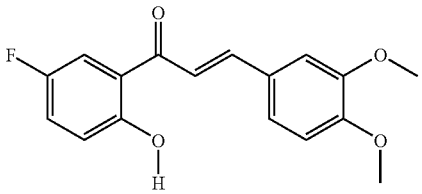

In analogy to the procedure described for the synthesis of (E)-1-(3,4-dimethoxy-phenyl)-3-(4-trifluoromethyl-phenyl)-propenone (example 1, step 1) the title compound was prepared from 1-(5-fluoro-2-hydroxy-phenyl)-ethanone (commercially available) and 3,4-dimethoxy-benzaldehyde (commercially available). MS (m/e): 303.0 $(MH^+)$.

b) Step 2

3-(3,4-Dimethoxy-phenyl)-1-(5-fluoro-2-hydroxy-phenyl)-propan-1-one

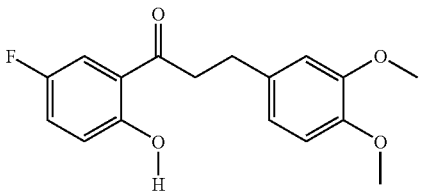

In analogy to the procedure described for the synthesis of 1-(3,4-dimethoxy-phenyl)-3-(4-trifluoromethyl-phenyl)-propan-1-ol (example 1, step 2) the title compound was prepared from (E)-3-(3,4-dimethoxy-phenyl)-1-(5-fluoro-2-hydroxy-phenyl)-propenone through reduction with $H_2$ over $PtO_2$.

c) Step 3

2-[3-(3,4-Dimethoxy-phenyl)-1-imino-propyl]-4-fluoro-phenol

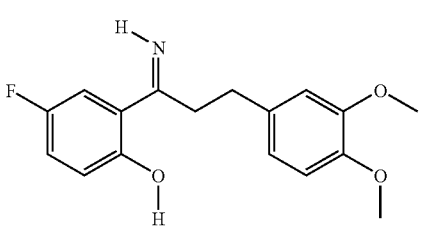

A mixture of 1.72 g (5.6 mmol) 3-(3,4-dimethoxy-phenyl)-1-(5-fluoro-2-hydroxy-phenyl)-propan-1-one and 24 mL $NH_3$ (7N) in methanol was heated to 60° C. for 16 h in a sealed tube. The mixture was concentrated and purified on silica eluting with a gradient formed from heptane and ethyl acetate. The product containing fractions were evaporated to yield 0.693 g (32%) of the title compound. MS (m/e): 304.1 $(MH^+)$.

d) Step 4

[3-(3,4-Dimethoxy-phenyl)-1-(5-fluoro-2-hydroxy-phenyl)-propylamino]-phenyl-acetic acid methyl ester

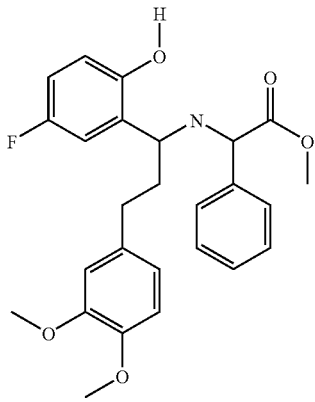

A mixture of 0.28 g (0.92 mmol) 2-[3-(3,4-dimethoxy-phenyl)-1-imino-propyl]-4-fluoro-phenol, 0.2 g (1 mmol) R-phenylglycine methyl ester, hydrochloride in 8 mL DCM was stirred at room temperature for 16 h. The mixture was washed with 1N HCl aq. and the organic layer was dried with $MgSO_4$ and evaporated to dryness. The residue was taken up in 20 mL THF and 0.35 g (1.6 mmol) sodium triacetoxyborohydride was added. The mixture was stirred at room temperature for 5 h, diluted with 1N HCl aq. and extracted with DCM. The combined organic layers were dried with $MgSO_4$ and evaporated to dryness. The residue was purified by preparative HPLC on reversed phase eluting with a gradient formed from acetonitrile, water and formic acid. The product containing fractions were evaporated to yield 0.182 g (48%) of the title compound. MS (m/e): 454.2 ($MH^+$).

e) Step 5

A mixture of 36 mg (0.08 mmol) [3-(3,4-dimethoxy-phenyl)-1-(5-fluoro-2-hydroxy-phenyl)-propylamino]-phenyl-acetic acid methyl ester was suspended in $NH_3$ aq. and heated to 50° C. for 2 h in a sealed tube. The mixture was concentrated and purified by preparative HPLC on reversed phase eluting with a gradient formed from acetonitrile, water and formic acid. The product containing fractions were evaporated to yield 0.3 mg (1%) of the title compound. MS (m/e): 440.1 ($MH^+$).

Example 26

2-[3-(3,4-Dimethoxy-phenyl)-1-(5-fluoro-2-hydroxy-phenyl)-propylamino]-N-methyl-2-phenyl-acetamide

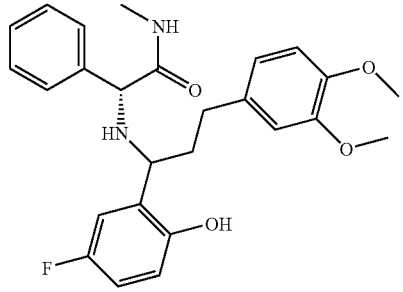

In analogy to the procedure described for the synthesis of 2-[3-(3,4-dimethoxy-phenyl)-1-(5-fluoro-2-hydroxy-phenyl)-propylamino]-2-phenyl-acetamide (example 25) the title compound was prepared from [3-(3,4-dimethoxy-phenyl)-1-(5-fluoro-2-hydroxy-phenyl)-propylamino]-phenyl-acetic acid methyl ester and methylamine. MS (m/e): 452.2 ($MH^+$).

Example 27

2-[3-(3,4-Dimethoxy-phenyl)-1-(5-fluoro-2-hydroxy-phenyl)-propylamino]-N,N-dimethyl-2-phenyl-acetamide

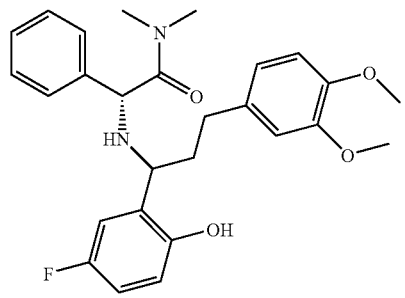

A mixture of 36.2 mg (0.8 mmol) [3-(3,4-dimethoxy-phenyl)-1-(5-fluoro-2-hydroxy-phenyl)-propylamino]-phenyl-acetic acid methyl ester and 0.32 mmol NaOH aq. in ethanol was evaporated to dryness and dissolved in DMF. TBTU (0.24 mmol) and dimethylamine (0.24 mmol) was added and the mixture was stirred for 1 h at room temperature. The mixtures was evaporated and purified by preparative HPLC on reversed phase eluting with a gradient formed from acetonitrile, water and formic acid. The product containing fractions were evaporated to yield 9.8 mg (26%) of the title compound. MS (m/e): 467.2 ($MH^+$).

Example 28

2-[3-(3,4-Dimethoxy-phenyl)-1-(5-fluoro-2-hydroxy-phenyl)-propylamino]-2-phenyl-1-pyrrolidin-1-yl-ethanone

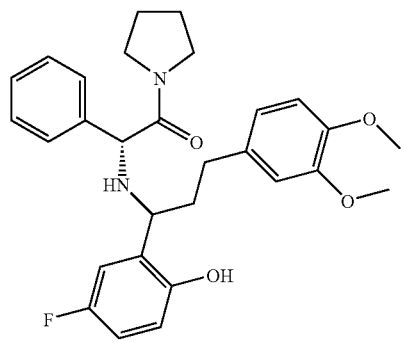

In analogy to the procedure described for the synthesis of 2-[3-(3,4-dimethoxy-phenyl)-1-(5-fluoro-2-hydroxy-phenyl)-propylamino]-N,N-dimethyl-2-phenyl-acetamide (example 27) the title compound was prepared from [3-(3,4-dimethoxy-phenyl)-1-(5-fluoro-2-hydroxy-phenyl)- propylamino]-phenyl-acetic acid methyl ester and pyrrolidine. MS (m/e): 493.2 (MH⁺).

Example 29

(S,R)-2-[(R,S)-1-(3,4-Dimethoxy-phenyl)-3-(4-trifluoromethyl-phenyl)-propylamino]-N-methyl-2-phenyl-propionamide (diastereoisomer 1)

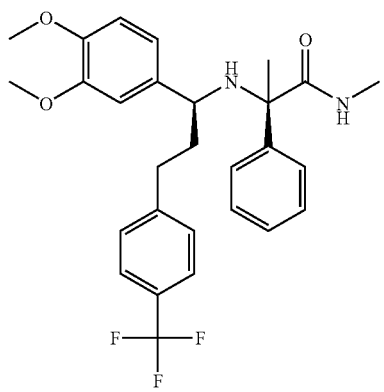

and

Example 30

(S,R)-2-[(S,R)-1-(3,4-Dimethoxy-phenyl)-3-(4-trifluoromethyl-phenyl)-propylamino]-N-methyl-2-phenyl-propionamide (diastereoisomer 2)

a) Step 1

1-(3,4-Dimethoxy-phenyl)-3-(4-trifluoromethyl-phenyl)-propan-1-one

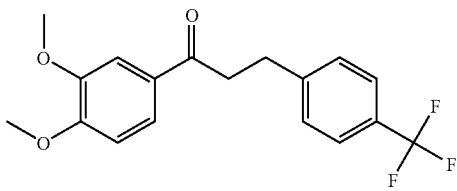

In analogy to the procedure described for the synthesis of 1-(3,4-dimethoxy-phenyl)-3-(4-trifluoromethyl-phenyl)-propan-1-ol (example 1, step 2) the title compound was prepared from (E)-1-(3,4-dimethoxy-phenyl)-3-(4-trifluoromethyl-phenyl)-propenone through reduction with H₂ over Pd/C. MS (m/e): 339.1 (MH⁺).

b) Step 2

A mixture of 0.3 g (0.887 mmol) 1-(3,4-dimethoxy-phenyl)-3-(4-trifluoromethyl-phenyl)-propan-1-one, 0.158 g (0.887 mmol) 2-amino-N-methyl-2-phenyl-propionamide (prepared from 2-amino-2-phenyl-propionic acid methyl ester and methylamine (both commercially available) and 0.21 g (0.887 mmol) Ti(OEt)₄ in 3 mL toluene was heated to reflux for 6 h. The mixture was evaporated and the residue was taken up in 3 mL DCM and 0.05 mL acetic acid and 0.28 g (1.3 mmol) sodium triacetoxyborohydride was added and stirred at room temperature over night. DCM was added and the mixture was washed with NaHCO₃ aq., and water. The organic layer was dried with MgSO₄ and evaporated to dryness. The residue was purified by preparative HPLC on reversed phase eluting with a gradient formed from acetonitrile, water and formic acid and subsequently by preparative TLC on silica to yield 6.4 mg of the diastereoisomer 1, MS (m/e): 501.1 (MH⁺) (example 29) and 1.6 mg of the diastereoisomer 2 MS (m/e): 501.3 (MH⁺). (example 30).

Example 31

(S,R)-2-[(R,S)-1-(3,4-Dimethoxy-phenyl)-3-(4-trifluoromethyl-phenyl)-propylamino]-N-methyl-3-phenyl-propionamide

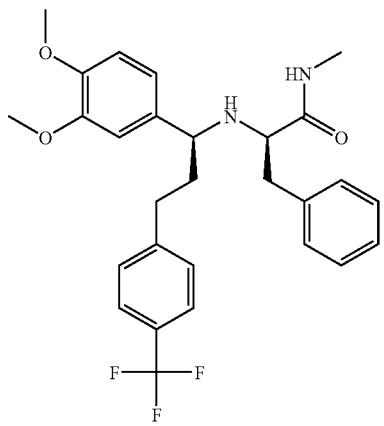

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(3,4-dimethoxy-phenyl)-3-(4-trifluoromethyl-phenyl)-propan-1-one through reductive amination with 2-amino-N-methyl-3-phenyl-propionamide. MS (m/e): 535.3 (MH⁺).

Example 32

(S,R)-2-(4-Chloro-phenyl)-2-[(R,S)-1-(3,4-dimethoxy-phenyl)-3-(4-trifluoromethyl-phenyl)-propylamino]-N-methyl-acetamide

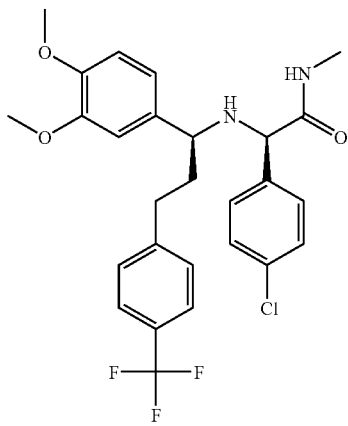

and

Example 33

(S,R)-2-(4-Chloro-phenyl)-2-[(S,R)-1-(3,4-dimethoxy-phenyl)-3-(4-trifluoromethyl-phenyl)-propylamino]-N-methyl-acetamide

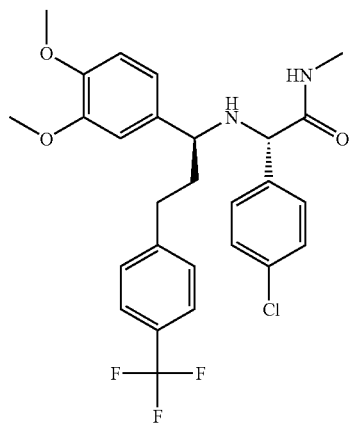

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(3,4-dimethoxy-phenyl)-3-(4-trifluoromethyl-phenyl)-propan-1-one through reductive amination with 2-amino-2-(4-chloro-phenyl)-N-methyl-acetamide. Example 32: MS (m/e): 521.3 (MH$^+$) and Example 33: MS (m/e): 521.3 (MH$^+$).

Example 34

(S,R)-2-[(R,S)-1-(3,4-Dimethoxy-phenyl)-3-(4-trifluoromethyl-phenyl)-propylamino]-2-(4-fluoro-phenyl)-N-methyl-acetamide

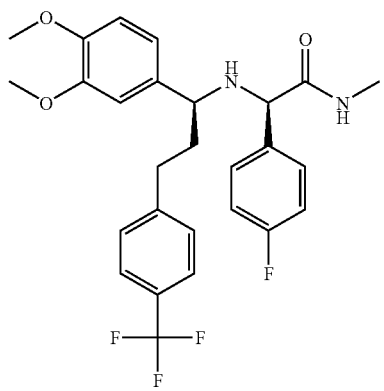

and

Example 35

(S,R)-2-[(S,R)-1-(3,4-Dimethoxy-phenyl)-3-(4-trifluoromethyl-phenyl)-propylamino]-2-(4-fluoro-phenyl)-N-methyl-acetamide

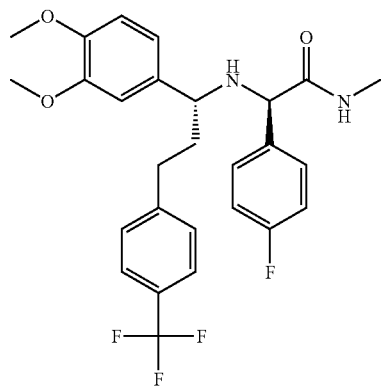

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(3,4-dimethoxy-phenyl)-3-(4-trifluoromethyl-phenyl)-propan-1-one through reductive amination with 2-amino-2-(4-fluoro-phenyl)-N-methyl-acetamide. Example 34: MS (m/e): 505.3 (MH$^+$) and Example 35: MS (m/e): 505.3 (MH$^+$).

Example 36

(S,R)-2-[(R,S)-3-(4-Chloro-phenyl) 1-(1H-indol-5-yl)-propylamino]-N-methyl-2-phenyl-acetamide

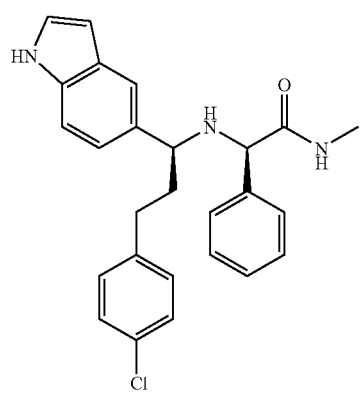

and

Example 37

(S,R)-2-[(S,R)-3-(4-Chloro-phenyl)-1-(1H-indol-5-yl)-propylamino]-N-methyl-2-phenyl-acetamide

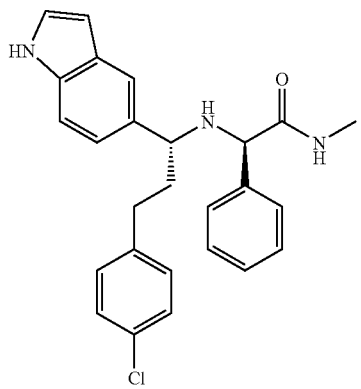

a) Step 1

1H-Indole-5-carboxylic acid methoxy-methyl-amide

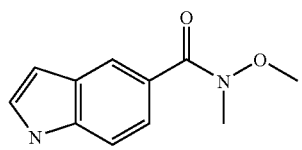

A mixture of 0.483 g (3 mmol) 1H-Indole-5-carboxylic acid, 0.351 mg (3.6 mmol) N,O-dimethylhydroxylamine, 1.155 g (3.6 mmol) TBTU and 1.163 g (9 mmol) DIPEA in 15 mL DMF was stirred at room temperature for 2 h and evaporated. NaHCO$_3$ aq. was added and the mixture was extracted with DCM. The combined organic layers were dried with MgSO$_4$, evaporated and the title compound was used crude in the subsequent reaction.

b) Step 2

3-(4-Chloro-phenyl)-1-(1H-indol-5-yl)-propan-1-one

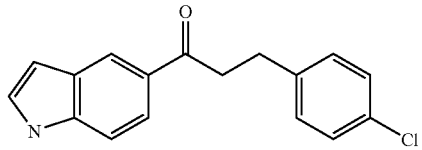

To a solution of 0.6 g (3 mmol) 1H-indole-5-carboxylic acid methoxy-methyl-amide in 5 mL THF was added 15 mL (7.5 mmol) 3-(4-Chloro-phenyl)-1-(1H-indol-5-yl)-propan-1-one in THF (0.5M) and stirred at 45° C. for 16 h. Cold 1N HCl aq. was added and the mixture was extracted with DCM. The combined organic layers were absorbed on Isolute and purified by column chromatography on silica eluting with a gradient formed from heptane and ethyl acetate to yield after evaporation of the product containing fractions 0.64 g (75%) of the title compound. MS (m/e): 284.0 (MH$^+$).

c) Step 3

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 3-(4-chloro-phenyl)-1-(1H-indol-5-yl)-propan-1-one through reductive amination with 2-Amino-N-methyl-2-phenyl-acetamide. Example 36: MS (m/e): 432.4 (MH$^+$) and Example 37: MS (m/e): 432.4 (MH$^+$).

Example 38

(S,R)-2-[(R,S)-3-(4-Chloro-phenyl)-1-(2,3-dihydro-benzofuran-5-yl)-propylamino]-N-methyl-2-phenyl-acetamide

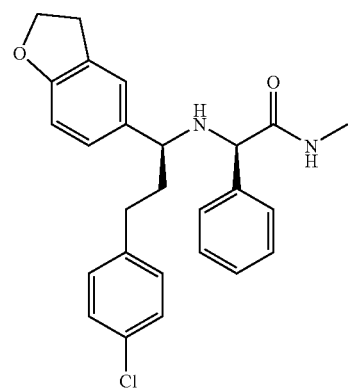

Example 39

(S,R)-2-[(S,R)-3-(4-Chloro-phenyl)-1-(2,3-dihydro-benzofuran-5-yl)-propylamino]-N-methyl-2-phenyl-acetamide

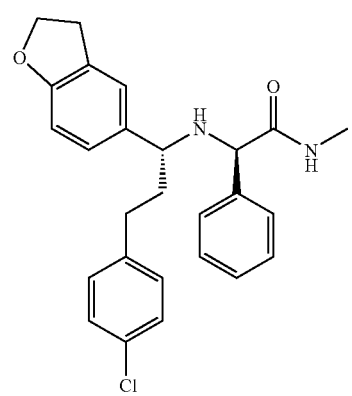

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 3-(4-chloro-phenyl)-1-(2,3-dihydro-benzofuran-5-yl)-propan-1-one (prepared from 2,3-dihydro-benzofuran-5-carboxylic acid, N,O-dimethylhydroxylamine and 4-chlorophenethylmagnesium bromide in analogy to the procedure described in example 37 step 1 & 2) through reductive amination with 2-amino-N-methyl-2-phenyl-acetamide. Example 38: MS (m/e): 435.3 (MH$^+$) and Example 39: MS (m/e): 435.3 (MH$^+$).

Example 40

(S,R)-2-[(R,S)-1-(2-Chloro-3,4-dimethoxy-phenyl)-3-(4-chloro-phenyl)-propylamino]-N-methyl-2-phenyl-acetamide

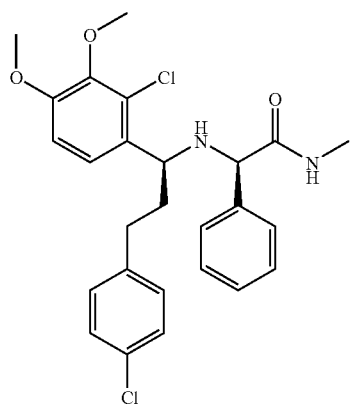

and

Example 41

(S,R)-2-[(S,R)-1-(2-Chloro-3,4-dimethoxy-phenyl)-3-(4-chloro-phenyl)-propylamino]-N-methyl-2-phenyl-acetamide

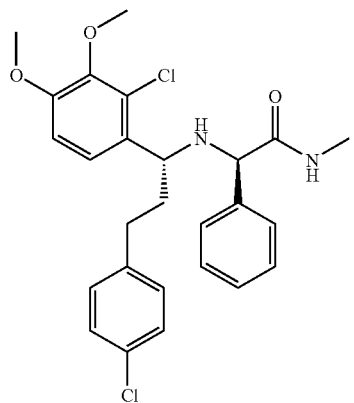

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(2-chloro-3,4-dimethoxy-phenyl)-3-(4-chloro-phenyl)-propan-1-one (prepared from 2-chloro-3,4-dimethoxy-benzoic acid, N,O-dimethylhydroxylamine and 4-chlorophenethylmagnesium bromide in analogy to the procedure described in example 37 step 1 & 2) through reductive amination with 2-Amino-N-methyl-2-phenyl-acetamide. Example 40: MS (m/e): 487.3 (MH$^+$) and Example 41: MS (m/e): 487.3 (MH$^+$).

Example 42

(S,R)-2-[(R,S)-3-(4-Chloro-phenyl)-1-(2,4-dichloro-phenyl)-propylamino]-N-methyl-2-phenyl-acetamide

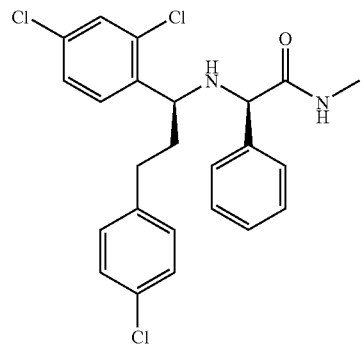

and

Example 43

(S,R)-2-[(S,R)-3-(4-Chloro-phenyl)-1-(2,4-dichloro-phenyl)-propylamino]-N-methyl-2-phenyl-acetamide

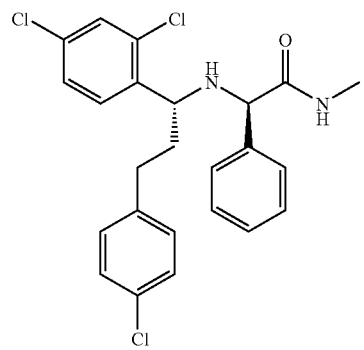

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 3-(4-chloro-phenyl)-1-(2,4-dichloro-phenyl)-propan-1-one (prepared from 2,4-dichloro-benzoic acid, N,O-dimethylhydroxylamine and 4-chlorophenethylmagnesium bromide in analogy to the procedure described in example 37 step 1 & 2) through reductive amination with 2-Amino-N-methyl-2-phenyl-acetamide. Example 42: MS (m/e): 461.1 (MH$^+$) and Example 43: MS (m/e): 461.2 (MH$^+$).

Example 44

2-[1-(3,5-Difluoro-4-methoxy-phenyl)-3-(6-trifluoromethyl-pyridin-3-yl)-propylamino]-N-methyl-2-phenyl-acetamide

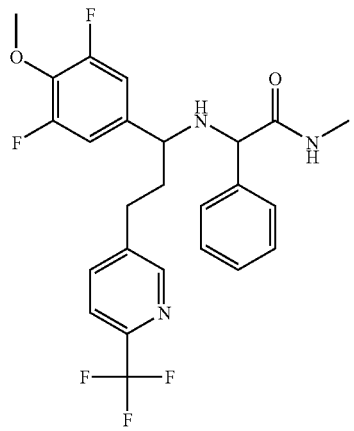

a) Step 1

(E)-1-(3,5-Difluoro-4-methoxy-phenyl)-3-(6-trifluoromethyl-pyridin-3-yl)-propenone

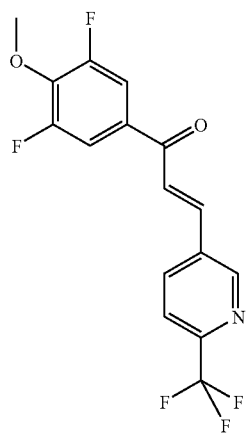

A mixture of 531 mg (2.855 mmol) 1-(3,5-difluoro-4-methoxy-phenyl)-ethanone, 499 mg (2.855 mmol) 6-trifluoromethyl-pyridine-3-carbaldehyde and 920 mg dry MgO in 8 mL toluene was heated to 135° C. for 16 h. The mixture was filtered, the MgO washed with toluene and the combined organic layers evaporated. The residue was purified by preparative HPLC on reversed phase eluting with a gradient formed from acetonitrile, water and formic acid to yield 571 mg of the title compound.

b) Step 2

1-(3,5-Difluoro-4-methoxy-phenyl)-3-(6-trifluoromethyl-pyridin-3-yl)-propan-1-one

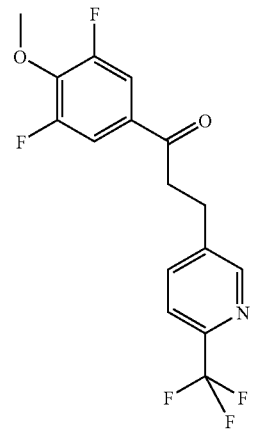

In analogy to the procedure described for the synthesis of 1-(3,4-dimethoxy-phenyl)-3-(4-trifluoromethyl-phenyl)-propan-1-ol (example 1, step 2) the title compound was prepared from (E)-1-(3,5-difluoro-4-methoxy-phenyl)-3-(6-trifluoromethyl-pyridin-3-yl)-propenone through reduction with $H_2$ over $PtO_2$.

c) Step 3

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(3,5-difluoro-4-methoxy-phenyl)-3-(6-trifluoromethyl-pyridin-3-yl)-propan-1-one and 2-Amino-N-methyl-2-phenyl-acetamide. MS (m/e): 494.3 (MH$^+$).

Example 45

(S,R)-2-[(R,S)—(4-Cyano-phenyl)-3-(6-trifluoromethyl-pyridin-3-yl)-propylamino]-N-methyl-2-phenyl-acetamide

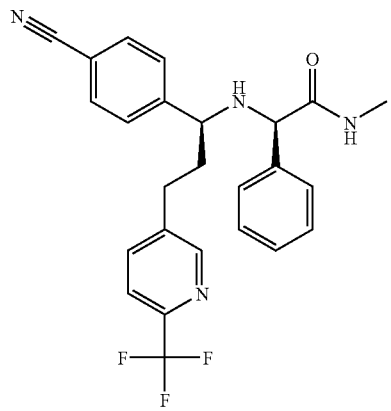

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-

1-(3,4-dimethoxy-phenyl)-3-(4-yl-phenyl)-propylamino]-N-methyl-2-phenyl-propionamide (diastereoisomer 2) (example 30) the title compound was prepared from 3-(4-chloro-phenyl)-1-(2,3-dihydro-benzofuran-5-yl)-propan-1-one (prepared from 4-acetyl-benzonitrile, 6-trifluoromethyl-pyridine-3-carbaldehyde with subsequent reduction in analogy to the procedure described in example 44 step 1&2) through reductive amination with 2-amino-N-methyl-2-phenyl-acetamide. MS (m/e): 453 (MH$^+$).

Example 46

2-[1-(4-Fluoro-2-methoxy-phenyl)-3-(6-trifluoromethyl-pyridin-3-yl)-propylamino]-2-(4-fluoro-phenyl)-N-methyl-acetamide

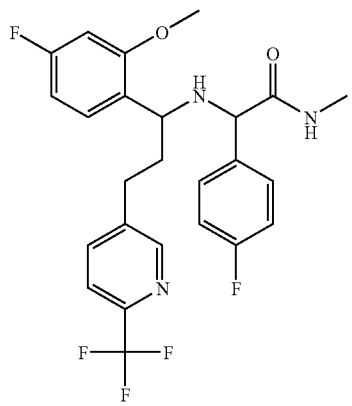

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(4-fluoro-2-methoxy-phenyl)-3-(6-trifluoromethyl-pyridin-3-yl)-propan-1-one (prepared from 1-(4-fluoro-2-methoxy-phenyl)-ethanone, 6-trifluoromethyl-pyridine-3-carbaldehyde with subsequent reduction in analogy to the procedure described in example 44 step 1&2) through reductive amination with 2-amino-2-(4-fluoro-phenyl)-N-methyl-acetamide. MS (m/e): 494.3 (MH$^+$).

Example 47

2-[1-(2-Chloro-pyridin-4-yl)-3-(6-trifluoromethyl-pyridin-3-yl)-propylamino]-2-(4-fluoro-phenyl)-N-methyl-acetamide

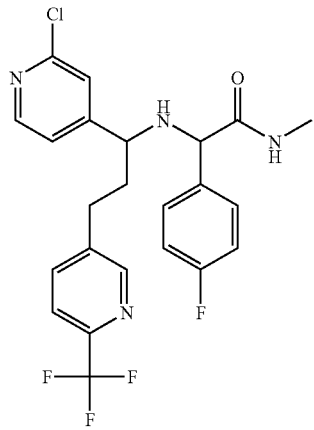

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(2-chloro-pyridin-4-yl)-3-(6-trifluoromethyl-pyridin-3-yl)-propan-1-one (prepared from 1-(2-chloro-pyridin-4-yl)-ethanone, 6-trifluoromethyl-pyridine-3-carbaldehyde with subsequent reduction in analogy to the procedure described in example 44 step 1&2) through reductive amination with 2-amino-2-(4-fluoro-phenyl)-N-methyl-acetamide. MS (m/e): 481.3 (MH$^+$).

Example 48

(S,R)-2-[(R,S)-1-(2-Fluoro-4-methoxy-phenyl)-3-(6-trifluoromethyl-pyridin-3-yl)-propylamino]-2-(4-fluoro-phenyl)-N-methyl-acetamide

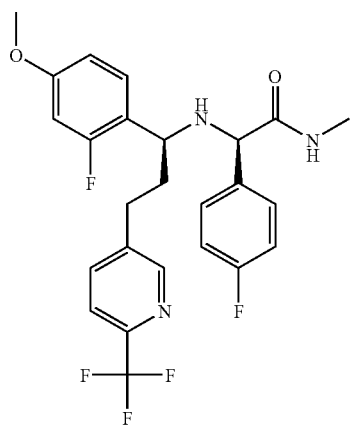

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(2-fluoro-4-methoxy-phenyl)-3-(6-trifluoromethyl-pyridin-3-yl)-propan-1-one (prepared from 1-(2-fluoro-4-methoxy-phenyl)-ethanone, 6-trifluoromethyl-pyridine-3-carbaldehyde with subsequent reduction in analogy to the procedure described in example 44 step 1&2) through reductive amination with 2-amino-2-(4-fluoro-phenyl)-N-methyl-acetamide. MS (m/e): 494.6 (MH$^+$).

Example 49

2-(4-Fluoro-phenyl)-2-[1-indan-5-yl-3-(6-trifluorom-ethyl-pyridin-3-yl)-propylamino]-N-methyl-acetamide

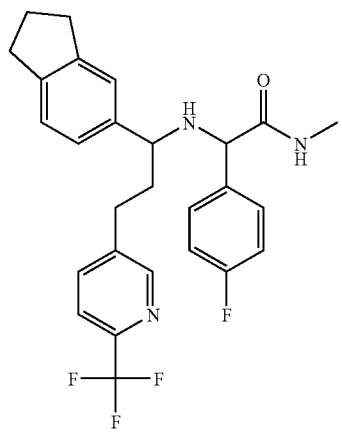

In analogy to the procedure described for the synthesis of (S,R)-2-[(R,S)-1-(3,4-dimethoxy-phenyl)-3-(4-trifluorom-ethyl-phenyl)-propylamino]-N-methyl-2-phenyl-propiona-mide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-indan-5-yl-3-(6-trifluoromethyl-pyridin-3-yl)-propan-1-one (pre-pared from 1-Indan-5-yl-ethanone, 6-trifluoromethyl-pyri-dine-3-carbaldehyde with subsequent reduction in analogy to the procedure described in example 44 step 1&2) through reductive amination with 2-amino-2-(4-fluoro-phenyl)-N-methyl-acetamide. MS (m/e): 486.1 (MH$^+$).

Example 50

(S,R)-2-[(R,S)-1-(3-Cyano-phenyl)-3-(6-trifluorom-ethyl-pyridin-3-yl)-propylamino]-2-(4-fluoro-phe-nyl)-N-methyl-acetamide

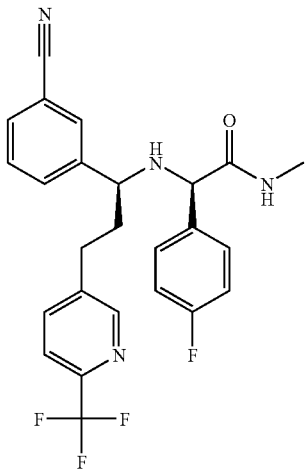

and

Example 51

(S,R)-2-[(S,R)-1-(3-Cyano-phenyl)-3-(6-trifluorom-ethyl-pyridin-3-yl)-propylamino]-2-(4-fluoro-phe-nyl)-N-methyl-acetamide

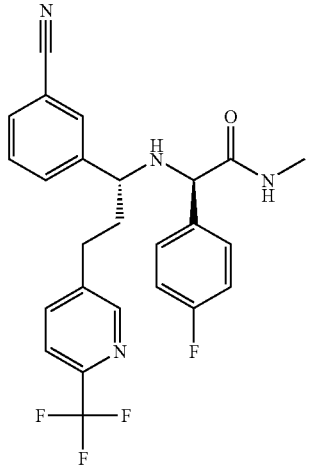

In analogy to the procedure described for the synthesis of (S,R)-2-[(R,S)-1-(3,4-dimethoxy-phenyl)-3-(4-trifluorom-ethyl-phenyl)-propylamino]-N-methyl-2-phenyl-propiona-mide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 3-[3-(6-trifluoromethyl-pyridin-3-yl)-propionyl]-benzonitrile (pre-pared from 3-acetyl-benzonitrile, 6-trifluoromethyl-pyri-dine-3-carbaldehyde with subsequent reduction in analogy to the procedure described in example 44 step 1&2) through reductive amination with 2-amino-2-(4-fluoro-phenyl)-N-methyl-acetamide. Example 50: MS (m/e): 471.0 (MH$^+$). Example 51: MS (m/e): 471.0 (MH$^+$).

Example 52

(S,R)-2-[(R,S)-1-(2,3-Dihydro-benzofuran-5-yl)-3-(6-trifluoromethyl-pyridin-3-yl)-propylamino]-2-(4-fluoro-phenyl)-N-methyl-acetamide

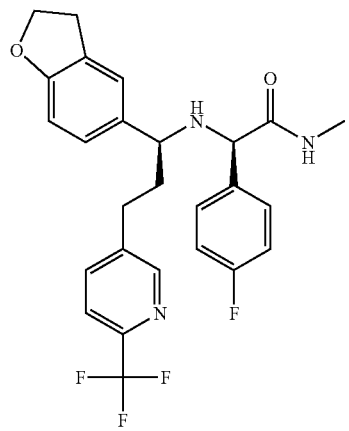

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(2,3-dihydro-benzofuran-5-yl)-3-(6-trifluoromethyl-pyridin-3-yl)-propan-1-one (prepared from 1-(2,3-dihydro-benzofuran-5-yl)-ethanone, 6-trifluoromethyl-pyridine-3-carbaldehyde with subsequent reduction in analogy to the procedure described in example 44 step 1&2) through reductive amination with 2-amino-2-(4-fluoro-phenyl)-N-methyl-acetamide. MS (m/e): 488.4 (MH$^+$).

Example 53

(S,R)-2-[(R,S)-1-(3,4-Dichloro-phenyl)-3-(6-trifluoromethyl-pyridin-3-yl)-propylamino]-2-(4-fluoro-phenyl)-N-methyl-acetamide

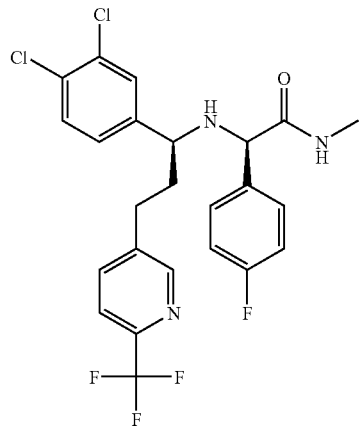

and

Example 54

(S,R)-2-[(S,R)-1-(3,4-Dichloro-phenyl)-3-(6-trifluoromethyl-pyridin-3-yl)-propylamino]-2-(4-fluoro-phenyl)-N-methyl-acetamide

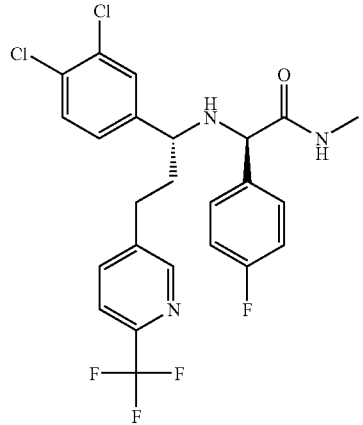

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(3,4-dichloro-phenyl)-3-(6-trifluoromethyl-pyridin-3-yl)-propan-1-one (prepared from 1-(3,4-dichloro-phenyl)-ethanone, 6-Trifluoromethyl-pyridine-3-carbaldehyde with subsequent reduction in analogy to the procedure described in example 44 step 1&2) through reductive amination with 2-amino-2-(4-fluoro-phenyl)-N-methyl-acetamide. Example 53: MS (m/e): 514.3 (MH$^+$). Example 54: MS (m/e): 514.3 (MH$^+$).

Example 55

(S,R)-2-[(R,S)-1-(3,4-Dihydro-2H-benzo[b][1,4]dioxepin-7-yl)-3-(6-trifluoromethyl-pyridin-3-yl)-propylamino]-2-(4-fluoro-phenyl)-N-methyl-acetamide

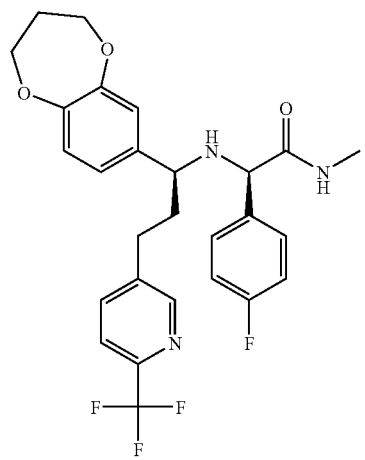

and

Example 56

(S,R)-2-[(S,R)-1-(3,4-Dihydro-2H-benzo[b][1,4]dioxepin-7-yl)-3-(6-trifluoromethyl-pyridin-3-yl)-propylamino]-2-(4-fluoro-phenyl)-N-methyl-acetamide

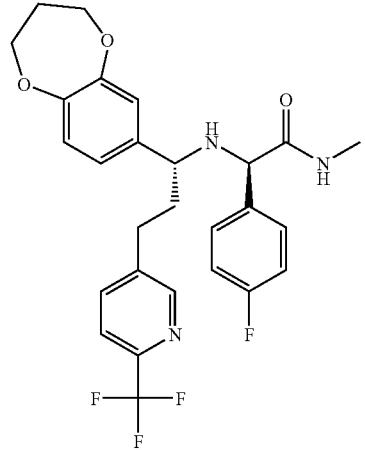

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2)

(example 30) the title compound was prepared from 1-(3,4-dihydro-2H-benzo[b][1,4]dioxepin-7-yl)-3-(6-trifluoromethyl-pyridin-3-yl)-propan-1-one (prepared from 1-(3,4-Dihydro-2H-benzo[b][1,4]dioxepin-7-yl)-ethanone, 6-trifluoromethyl-pyridine-3-carbaldehyde with subsequent reduction in analogy to the procedure described in example 44 step 1&2) through reductive amination with 2-amino-2-(4-fluoro-phenyl)-N-methyl-acetamide. Example 55: MS (m/e): 518.4 (MH+). Example 56: MS (m/e): 518.4 (MH+).

Example 57

(S,R)-2-(4-Fluoro-phenyl)-N-methyl-2-[(R,S)-1-(5,6,7,8-tetrahydro-naphthalen-2-yl)-3-(6-trifluoromethyl-pyridin-3-yl)-propylamino]-acetamide

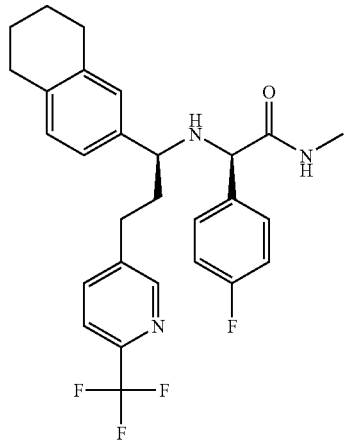

and

Example 58

(S,R)-2-(4-Fluoro-phenyl)-N-methyl-2-[(S,R)-1-(5,6,7,8-tetrahydro-naphthalen-2-yl)-3-(6-trifluoromethyl-pyridin-3-yl)-propylamino]-acetamide

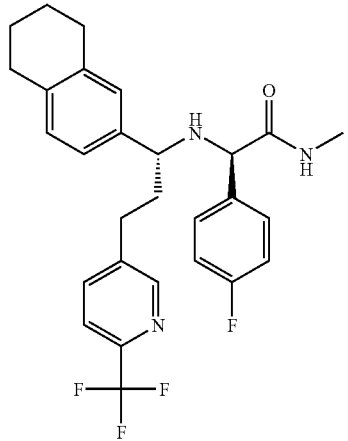

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(5,6,7,8-tetrahydro-naphthalen-2-yl)-3-(6-trifluoromethyl-pyridin-3-yl)-propan-1-one (prepared from 1-(5,6,7,8-tetrahydro-naphthalen-2-yl)-ethanone, 6-trifluoromethyl-pyridine-3-carbaldehyde with subsequent reduction in analogy to the procedure described in example 44 step 1&2) through reductive amination with 2-amino-2-(4-fluoro-phenyl)-N-methyl-acetamide. Example 57: MS (m/e): 500.4 (MH+). Example 58: MS (m/e): 500.4 (MH+).

Example 59

(S,R)-2-(4-Fluoro-phenyl)-N-methyl-2-[(R,S)-1-(5,5,8,8-tetramethyl-5,6,7,8-tetrahydro-naphthalen-2-yl)-3-(6-trifluoromethyl-pyridin-3-yl)-propylamino]-acetamide

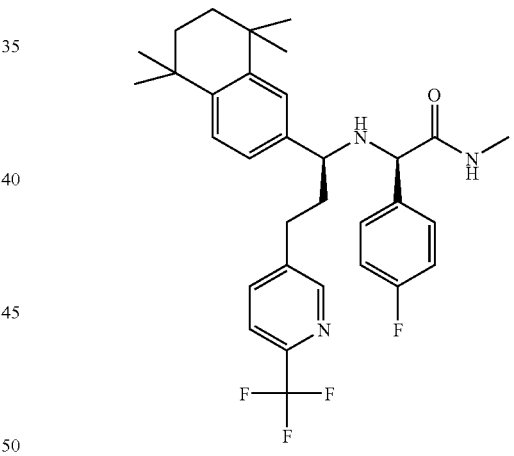

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(5,5,8,8-tetramethyl-5,6,7,8-tetrahydro-naphthalen-2-yl)-3-(6-trifluoromethyl-pyridin-3-yl)-propan-1-one (prepared from 1-(5,5,8,8-tetramethyl-5,6,7,8-tetrahydro-naphthalen-2-yl)-ethanone, 6-trifluoromethyl-pyridine-3-carbaldehyde with subsequent reduction in analogy to the procedure described in example 44 step 1 & 2) through reductive amination with 2-amino-2-(4-fluoro-phenyl)-N-methyl-acetamide. MS (m/e): 556.5 (MH+).

Example 60

(S,R)-2-(4-Fluoro-phenyl)-2-[(R,S)-1-(3-fluoro-phenyl)-3-(6-trifluoromethyl-pyridin-3-yl)-propylamino]-N-methyl-acetamide

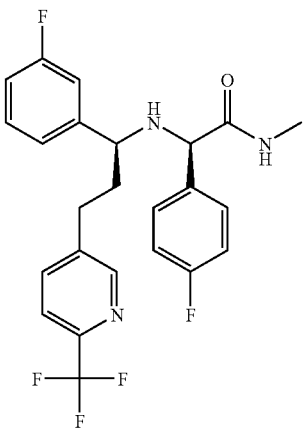

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(3-fluoro-phenyl)-3-(6-trifluoromethyl-pyridin-3-yl)-propan-1-one (prepared from 1-(3-fluoro-phenyl)-ethanone, 6-trifluoromethyl-pyridine-3-carbaldehyde with subsequent reduction in analogy to the procedure described in example 44 step 1 & 2) through reductive amination with 2-amino-2-(4-fluoro-phenyl)-N-methyl-acetamide. MS (m/e): 464.3 (MH$^+$).

Example 61

(S,R)-2-(4-Fluoro-phenyl)-2-[(R,S)-1-(4-fluoro-3-trifluoromethoxy-phenyl)-3-(6-trifluoromethyl-pyridin-3-yl)-propylamino]-N-methyl-acetamide

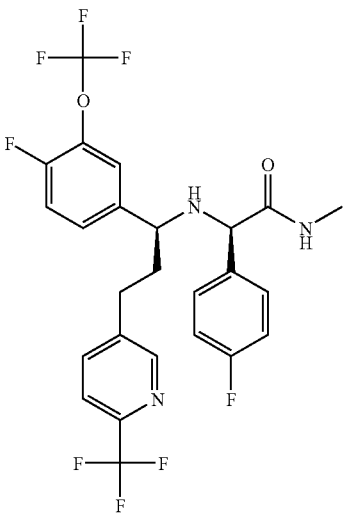

and

Example 62

(S,R)-2-(4-Fluoro-phenyl)-2-[(S,R)-1-(4-fluoro-3-trifluoromethoxy-phenyl)-3-(6-trifluoromethyl-pyridin-3-yl)-propylamino]-N-methyl-acetamide

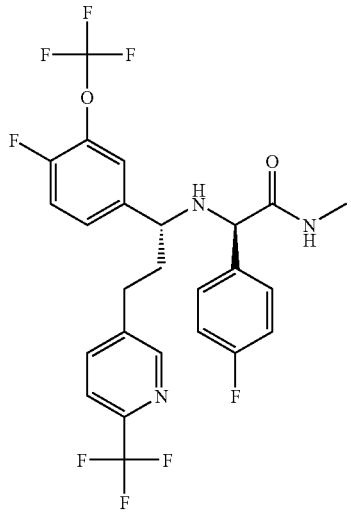

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(4-fluoro-3-trifluoromethoxy-phenyl)-3-(6-trifluoromethyl-pyridin-3-yl)-propan-1-one (prepared from 1-(4-fluoro-3-trifluoromethoxy-phenyl)-ethanone, 6-trifluoromethyl-pyridine-3-carbaldehyde with subsequent reduction in analogy to the procedure described in example 44 step 1 & 2) through reductive amination with 2-amino-2-(4-fluoro-phenyl)-N-methyl-acetamide. Example 61: MS (m/e): 548.4 (MH$^+$). Example 62: MS (m/e): 548.4 (MH$^+$).

Example 63

(S,R)-2-(4-Fluoro-phenyl)-N-methyl-2-[(R,S)-1-(4-trifluoromethoxy-phenyl)-3-(6-trifluoromethyl-pyridin-3-yl)-propylamino]-acetamide

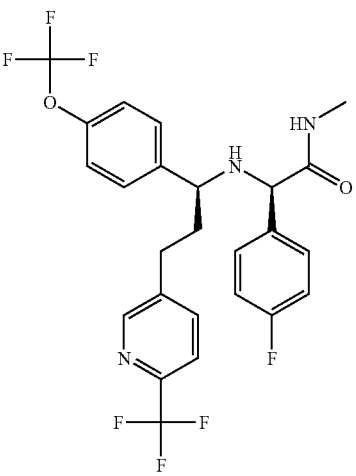

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(4-trifluoromethoxy-phenyl)-3-(6-trifluoromethyl-pyridin-3-yl)-propan-1-one (prepared from 1-(4-trifluoromethoxy-phenyl)-ethanone, 6-trifluoromethyl-pyridine-3-carbaldehyde with subsequent reduction in analogy to the procedure described in example 44 step 1 & 2) through reductive amination with 2-amino-2-(4-fluoro-phenyl)-N-methyl-acetamide. MS (m/e): 530.3 (MH$^+$).

Example 64

2-[1-(5-Chloro-2-methoxy-phenyl)-3-(6-trifluoromethyl-pyridin-3-yl)-propylamino]-2-(4-fluoro-phenyl)-N-methyl-acetamide

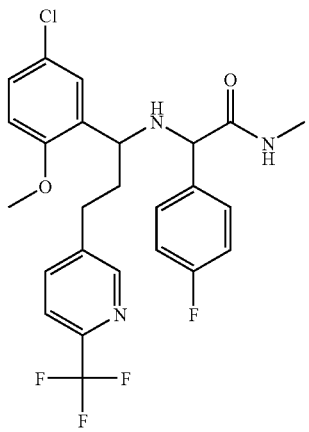

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(5-chloro-2-methoxy-phenyl)-3-(6-trifluoromethyl-pyridin-3-yl)-propan-1-one (prepared from 1-(5-chloro-2-methoxy-phenyl)-ethanone, 6-trifluoromethyl-pyridine-3-carbaldehyde with subsequent reduction in analogy to the procedure described in example 44 step 1 & 2) through reductive amination with 2-amino-2-(4-fluoro-phenyl)-N-methyl-acetamide. MS (m/e): 510.4 (MH$^+$).

Example 65

2-[3-(4-Chloro-phenyl)-1-(5-methoxy-pyridazin-3-yl)-propylamino]-N-methyl-2-phenyl-acetamide

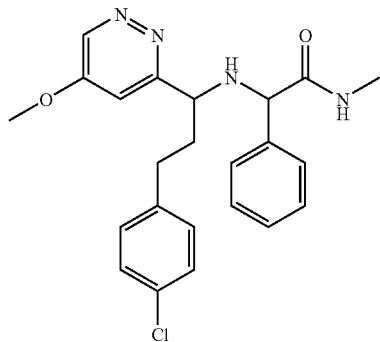

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 3-(4-chloro-phenyl)-1-(5-methoxy-pyridazin-3-yl)-propan-1-one (prepared from 5-methoxy-pyridazine-3-carboxylic acid ethyl ester (WO 2003097637) and 4-chlorophenethylmagnesium bromide in analogy to the procedure described in example 37/38 step 1 & 2) through reductive amination with 2-amino-N-methyl-2-phenyl-acetamide. MS (m/e): 425.3 (MH$^+$).

Example 66

2-[1-(4-Fluoro-3-methyl-phenyl)-3-pyrimidin-5-yl-propylamino]-N-methyl-2-phenyl-acetamide

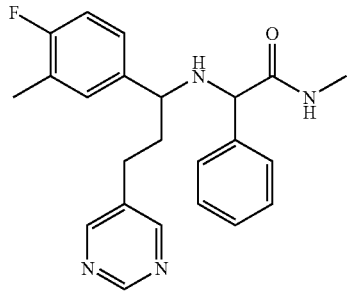

a) Step 1

(E)-1-(4-Fluoro-3-methyl-phenyl)-3-pyrimidin-5-yl-propenone

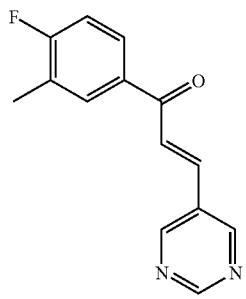

To a mixture of 19.2 g (155 mmol) dimethyl methylphosphonate in 150 mL THF at −70° C. was added 97 mL (155 mmol) 1.6M n-BuLi in hexane. The mixture was stirred for 45 min and a solution of 11.8 g (70 mmol) 4-fluoro-3-methyl-benzoic acid methyl ester in 15 mL THF was added. After 15 min at −70° C. the mixture was allowed to warm to 0° C. and neutralized with 4N HCl in dioxane. The mixture was diluted with 500 mL THF to obtain [2-(4-fluoro-3-methyl-phenyl)-2-oxo-ethyl]-phosphonic acid dimethyl ester. 6 mmol [2-(4-fluoro-3-methyl-phenyl)-2-oxo-ethyl]-phosphonic acid dimethyl ester in THF was stirred together with 0.5 g (4.6 mmol) pyrimidine-5-carboxaldehyde and 1.65 g Cs$_2$CO$_3$ for 16 h at room temperature. The mixture was diluted with NH$_4$Cl aq.

and ethyl acetate. The organic layer was separated, dried with MgSO₄ and evaporated to dryness. The residue was used crude in the consecutive step.

b) Step 2

1-(4-Fluoro-3-methyl-phenyl)-3-pyrimidin-5-yl-propan-1-one

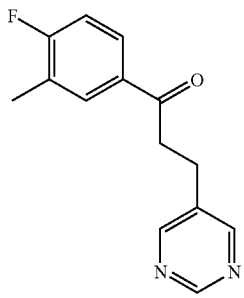

In analogy to the procedure described for the synthesis of 1-(3,4-dimethoxy-phenyl)-3-(4-trifluoromethyl-phenyl)-propan-1-ol (example 1, step 2) the title compound was prepared from (E)-1-(4-fluoro-3-methyl-phenyl)-3-pyrimidin-5-yl-propenone through reduction with H₂ over PtO₂. MS (m/e): 245.2 (MH⁺).

c) Step 3

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(4-fluoro-3-methyl-phenyl)-3-pyrimidin-5-yl-propan-1-one through reductive amination with 2-amino-N-methyl-2-phenyl-acetamide. MS (m/e): 393.3 (MH⁺).

Example 67

2-[1-(2-Fluoro-5-methyl-phenyl)-3-(6-trifluoromethyl-pyridin-3-yl)-propylamino]-2-(4-fluoro-phenyl)-N-methyl-acetamide

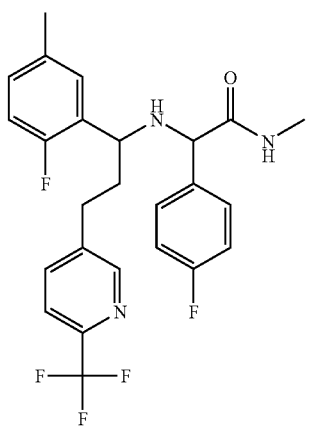

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(2-fluoro-5-methyl-phenyl)-3-(6-trifluoromethyl-pyridin-3-yl)-propan-1-one (prepared from 1-(2-fluoro-5-methyl-phenyl)-ethanone, 6-trifluoromethyl-pyridine-3-carbaldehyde with subsequent reduction in analogy to the procedure described in example 44 step 1 & 2) through reductive amination with 2-amino-2-(4-fluoro-phenyl)-N-methyl-acetamide. MS (m/e): 478.1 (MH⁺).

Example 68

2-[1-(3-Fluoro-4-methoxy-phenyl)-3-(6-trifluoromethyl-pyridin-3-yl)-propylamino]-2-(4-fluoro-phenyl)-N-methyl-acetamide

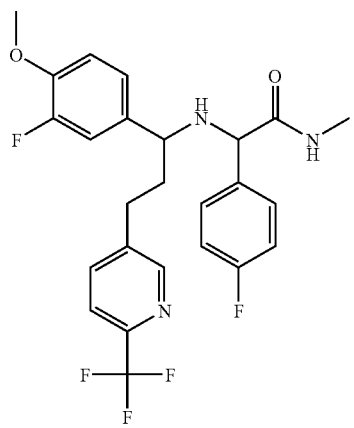

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(3-fluoro-4-methoxy-phenyl)-3-(6-trifluoromethyl-pyridin-3-yl)-propan-1-one (prepared from 1-(3-fluoro-4-methoxy-phenyl)-ethanone, 6-trifluoromethyl-pyridine-3-carbaldehyde with subsequent reduction in analogy to the procedure described in example 44 step 1 & 2) through reductive amination with 2-amino-2-(4-fluoro-phenyl)-N-methyl-acetamide. MS (m/e): 494.0 (MH⁺).

Example 69

2-[1-(2,4-Dimethyl-thiazol-5-yl)-3-(6-trifluoromethyl-pyridin-3-yl)-propylamino]-2-(4-fluoro-phenyl)-N-methyl-acetamide

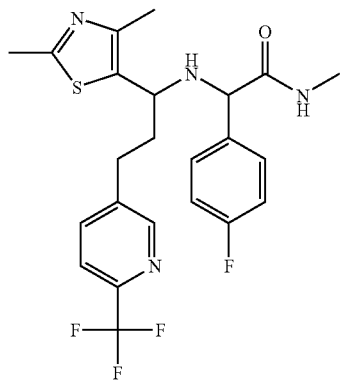

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(2,4-dimethyl-thiazol-5-yl)-3-(6-trifluoromethyl-pyridin-3-yl)-propan-1-one (prepared from 1-(2,4-dimethyl-thiazol-5-yl)-ethanone, 6-trifluoromethyl-pyridine-3-carbaldehyde with subsequent reduction in analogy to the procedure described in example 44 step 1 & 2) through reductive amination with 2-amino-2-(4-fluoro-phenyl)-N-methyl-acetamide. MS (m/e): 480.5 (MH⁺).

Example 70

2-(4-Fluoro-phenyl)-N-methyl-2-[1-(1-methyl-1H-pyrazol-3-yl)-3-(6-trifluoromethyl-pyridin-3-yl)-propylamino]-acetamide

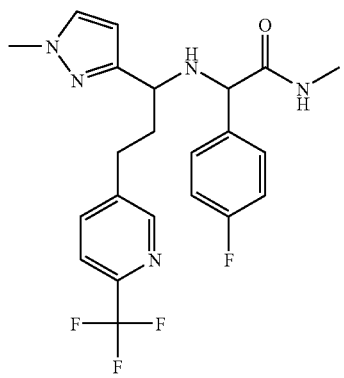

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(1-methyl-1H-pyrazol-3-yl)-3-(6-trifluoromethyl-pyridin-3-yl)-propan-1-one (prepared from 1-(1-methyl-1H-pyrazol-3-yl)-ethanone, 6-trifluoromethyl-pyridine-3-carbaldehyde with subsequent reduction in analogy to the procedure described in example 44 step 1 & 2) through reductive amination with 2-amino-2-(4-fluoro-phenyl)-N-methyl-acetamide. MS (m/e): 450.3 (MH⁺).

Example 71

2-[3-(5-Chloro-pyrazin-2-yl)-1-(4-fluoro-3-methyl-phenyl)-propylamino]-N-methyl-2-phenyl-acetamide

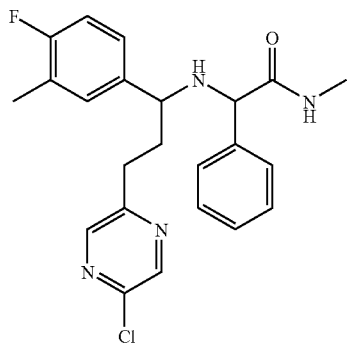

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 3-(5-chloro-pyrazin-2-yl)-1-(4-fluoro-3-methyl-phenyl)-propan-1-one (synthesised from [2-(4-fluoro-3-methyl-phenyl)-2-oxo-ethyl]-phosphonic acid dimethyl ester, 5-chloropyrazine-2-carbaldehyde (commercially available) and subsequent reduction with H₂ over PtO₂ (in analogy to the procedure described for the synthesis of example 66) through reductive amination with 2-amino-N-methyl-2-phenyl-acetamide. MS (m/e): 427.3 (MH⁺).

Example 72

2-[1-(5-Fluoro-2-methoxy-phenyl)-3-(6-trifluoromethyl-pyridin-3-yl)-propylamino]-2-(4-fluoro-phenyl)-N-methyl-acetamide

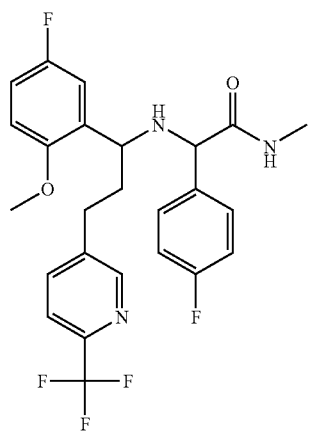

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-

1-(3,4-dimethoxy-phenyl)-3-(4-yl-phenyl)-propylamino]-N-methyl-2-phenyl-propionamide (diastereoisomer 2) (example 30) the title compound was prepared from 1-(5-fluoro-2-methoxy-phenyl)-3-(6-trifluoromethyl-pyridin-3-yl)-propan-1-one (prepared from 1-(5-fluoro-2-methoxy-phenyl)-ethanone, 6-Trifluoromethyl-pyridine-3-carbaldehyde with subsequent reduction in analogy to the procedure described in example 44 step 1 & 2) through reductive amination with 2-amino-2-(4-fluoro-phenyl)-N-methyl-acetamide. MS (m/e): 494.0 (MH+).

Example 73

2-[1-(4,5-Dimethyl-thiazol-2-yl)-3-(6-trifluoromethyl-pyridin-3-yl)-propylamino]-2-(4-fluoro-phenyl)-N-methyl-acetamide

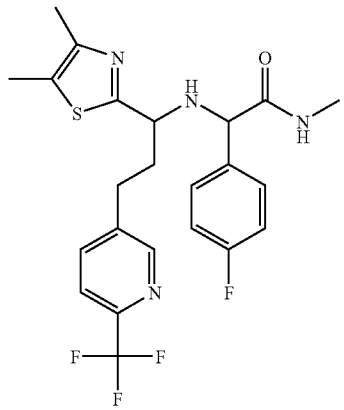

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(4,5-dimethyl-thiazol-2-yl)-3-(6-trifluoromethyl-pyridin-3-yl)-propan-1-one (prepared from 1-(4,5-Dimethyl-thiazol-2-yl)-ethanone, 6-trifluoromethyl-pyridine-3-carbaldehyde with subsequent reduction in analogy to the procedure described in example 44 step 1 & 2) through reductive amination with 2-amino-2-(4-fluoro-phenyl)-N-methyl-acetamide. MS (m/e): 481.1 (MH+).

Example 74

2-[1-(4-Fluoro-3-methyl-phenyl)-3-(1-methyl-1H-pyrazol-3-yl)-propylamino]-N-methyl-2-phenyl-acetamide

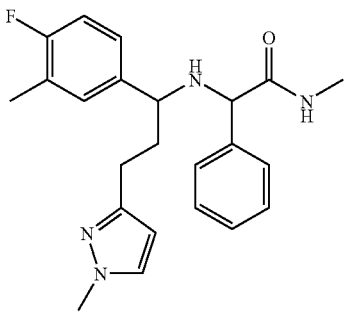

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(4-fluoro-3-methyl-phenyl)-3-(1-methyl-1H-pyrazol-3-yl)-propan-1-one (synthesised from [2-(4-fluoro-3-methyl-phenyl)-2-oxo-ethyl]-phosphonic acid dimethyl ester, 1-Methyl-1H-pyrazole-3-carbaldehyde (commercially available) and subsequent reduction with H2 over PtO2 (in analogy to the procedure described for the synthesis of example 66) through reductive amination with 2-amino-N-methyl-2-phenyl-acetamide. MS (m/e): 395.4 (MH+).

Example 75

2-[1-(4-Fluoro-3-methyl-phenyl)-3-(1-methyl-1H-pyrazol-4-yl)-propylamino]-N-methyl-2-phenyl-acetamide

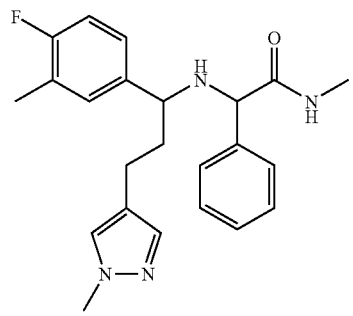

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(4-fluoro-3-methyl-phenyl)-3-(1-methyl-1H-pyrazol-4-yl)-propan-1-one (synthesised from [2-(4-fluoro-3-methyl-phenyl)-2-oxo-ethyl]-phosphonic acid dimethyl ester, 1-methyl-1H-pyrrole-3-carbaldehyde (commercially available) and subsequent reduction with H2 over PtO2 (in analogy to the procedure described for the synthesis of example 66) through reductive amination with 2-amino-N-methyl-2-phenyl-acetamide. MS (m/e): 395.4 (MH+).

Example 76

(S,R)-2-[(R,S)-1-Chroman-6-yl-3-(4-trifluoromethyl-phenyl)-propylamino]-N-methyl-2-phenyl-acetamide

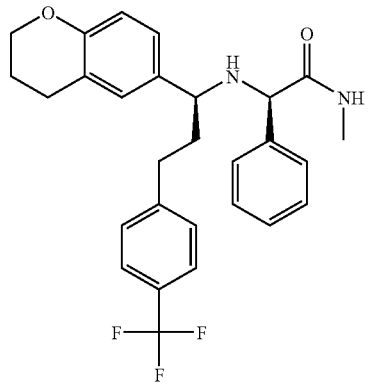

and

Example 77

(S,R)-2-[(S,R)-1-Chroman-6-yl-3-(4-trifluoromethyl-phenyl)-propylamino]-N-methyl-2-phenyl-acetamide

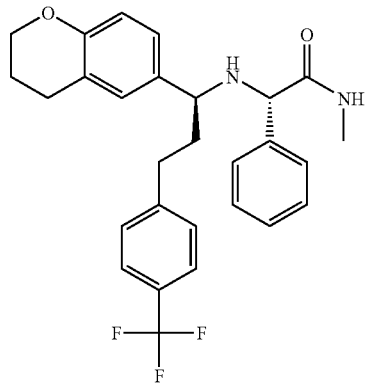

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-chroman-6-yl-3-(4-trifluoromethyl-phenyl)-propan-1-one (synthesised from chroman-6-carboxylic acid methyl ester, dimethyl methylphosphonate, 4-trifluoromethyl-benzaldehyde (commercially available) and subsequent reduction with H$_2$ over Pd/C (in analogy to the procedure described for the synthesis of example 66) through reductive amination with 2-amino-N-methyl-2-phenyl-acetamide. Example 76: MS (m/e): 483.1 (MH$^+$). Example 77: MS (m/e): 483.1 (MH$^+$).

Example 78

(S,R)—N-Methyl-2-[(R,S)-1-(4-methyl-3,4-dihydro-2H-benzo[1,4]oxazin-7-yl)-3-(4-trifluoromethyl-phenyl)-propylamino]-2-phenyl-acetamide

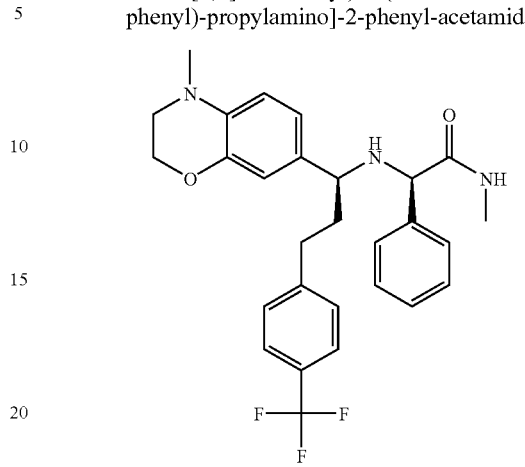

and

Example 79

(S,R)—N-Methyl-2-[(S,R)-1-(4-methyl-3,4-dihydro-2H-benzo[1,4]oxazin-7-yl)-3-(4-trifluoromethyl-phenyl)-propylamino]-2-phenyl-acetamide

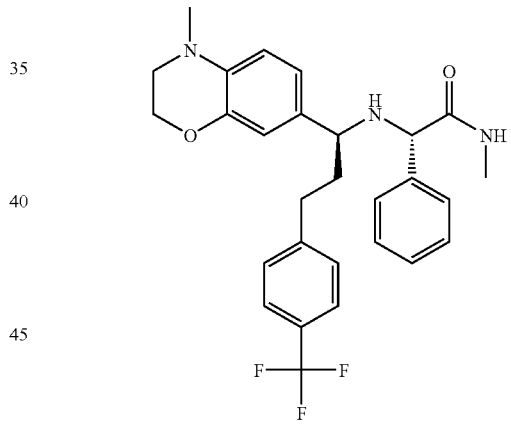

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(4-methyl-3,4-dihydro-2H-benzo[1,4]oxazin-7-yl)-3-(4-trifluoromethyl-phenyl)-propan-1-one (synthesised from 4-methyl-3,4-dihydro-2H-benzo[1,4]oxazine-7-carboxylic acid methyl ester, dimethyl methylphosphonate, 4-trifluoromethyl-benzaldehyde (commercially available) and subsequent reduction with H$_2$ over Pd/C (in analogy to the procedure described for the synthesis of example 66) through reductive amination with 2-amino-N-methyl-2-phenyl-acetamide. Example 78: MS (m/e): 498.5 (MH$^+$). Example 79: MS (m/e): 498.4 (MH$^+$).

Example 80

2-[1-(2,4-Dimethyl-thiazol-5-yl)-3-(4-trifluoromethyl-phenyl)-propylamino]-2-(4-fluoro-phenyl)-N-methyl-acetamide

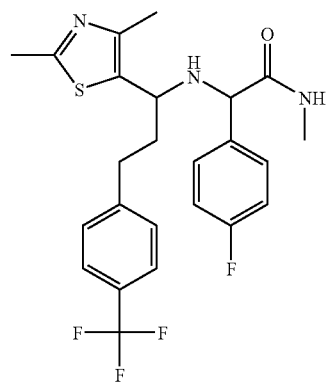

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(2,4-dimethyl-thiazol-5-yl)-3-(4-trifluoromethyl-phenyl)-propan-1-one (prepared from 1-(2,4-dimethyl-thiazol-5-yl)-ethanone and 4-trifluoromethyl-benzaldehyde with subsequent reduction in analogy to the procedure described in example 44 step 1 & 2) through reductive amination with 2-amino-2-(4-fluoro-phenyl)-N-methyl-acetamide. MS (m/e): 480.1 (MH+).

Example 81

(S,R)-2-[(R,S)-3-(5-Chloro-pyrazin-2-yl)-1-(4-fluoro-3-trifluoromethoxy-phenyl)-propylamino]-N-methyl-2-phenyl-acetamide

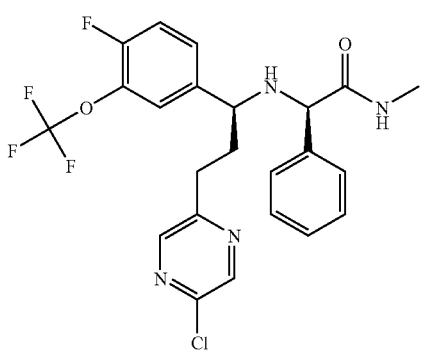

Example 82

(S,R)-2-[(S,R)-3-(5-Chloro-pyrazin-2-yl)-1-(4-fluoro-3-trifluoromethoxy-phenyl)-propylamino]-N-methyl-2-phenyl-acetamide

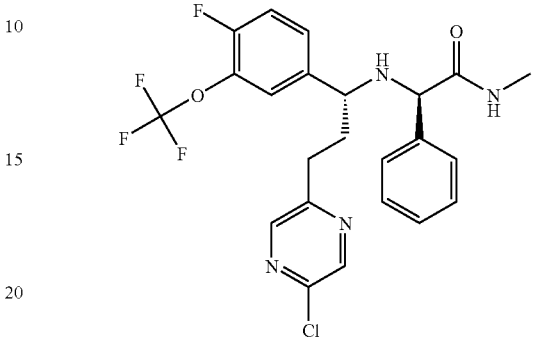

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 3-(5-chloro-pyrazin-2-yl)-1-(4-fluoro-3-trifluoromethoxy-phenyl)-propan-1-one (prepared from 1-(4-fluoro-3-trifluoromethoxy-phenyl)-ethanone and 5-chloro-pyrazine-2-carbaldehyde with subsequent reduction in analogy to the procedure described in example 44 step 1 & 2) through reductive amination with 2-amino-N-methyl-2-phenyl-acetamide. Example 81: MS (m/e): 497.3 (MH+). Example 82: MS (m/e): 497.3 (MH+).

Example 83

N-Methyl-2-phenyl-2-[1-(5,6,7,8-tetrahydro-naphthalen-2-yl)-3-(4-trifluoromethyl-phenyl)-propylamino]-acetamide

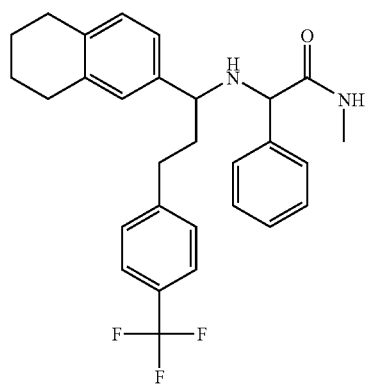

and and

Example 84

(S,R)—N-Methyl-2-phenyl-2-[(S,R)-1-(5,6,7,8-tetrahydro-naphthalen-2-yl)-3-(4-trifluoromethyl-phenyl)-propylamino]-acetamide

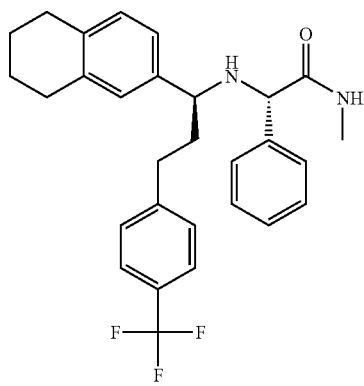

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(5,6,7,8-tetrahydro-naphthalen-2-yl)-3-(4-trifluoromethyl-phenyl)-propan-1-one (prepared from 1-(5,6,7,8-tetrahydro-naphthalen-2-yl)-ethanone and 4-trifluoromethyl-benzaldehyde with subsequent reduction in analogy to the procedure described in example 1 step 1 & example 44 step 2) through reductive amination with 2-amino-N-methyl-2-phenyl-acetamide. Example 83: MS (m/e): 481.1 (MH+). Example 84: MS (m/e): 481.1 (MH+).

Example 85

2-[1-(2-Fluoro-5-methyl-phenyl)-3-(4-trifluoromethyl-phenyl)-propylamino]-N-methyl-2-phenyl-acetamide

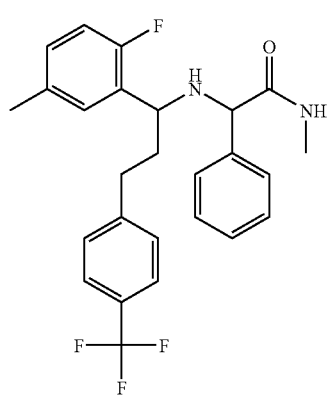

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(2-fluoro-5-methyl-phenyl)-3-(4-trifluoromethyl-phenyl)-propan-1-one (prepared from 1-(2-fluoro-5-methyl-phenyl)-ethanone and 4-Trifluoromethyl-benzaldehyde with subsequent reduction in analogy to the procedure described in example 1 step 1 & example 44 step 2) through reductive amination with 2-amino-N-methyl-2-phenyl-acetamide. MS (m/e): 459.4 (MH+).

Example 86

(S,R)-2-[(R,S)-1-(2-Fluoro-5-methyl-phenyl)-3-(4-trifluoromethyl-phenyl)-propylamino]-2-(4-fluoro-phenyl)-N-methyl-acetamide

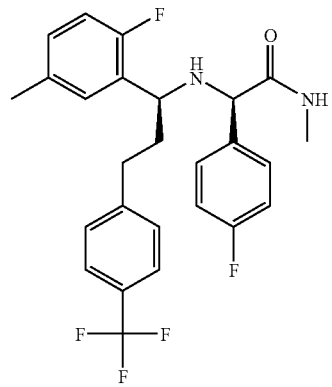

and

Example 87

(S,R)-2-[(S,R)-1-(2-Fluoro-5-methyl-phenyl)-3-(4-trifluoromethyl-phenyl)-propylamino]-2-(4-fluoro-phenyl)-N-methyl-acetamide

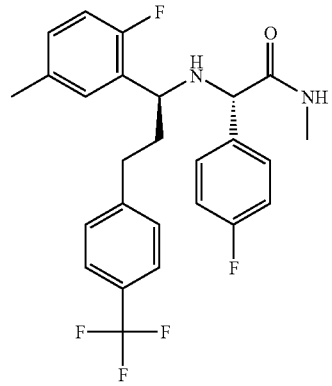

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-

1-(3,4-dimethoxy-phenyl)-3-(4-yl-phenyl)-propylamino]-N-methyl-2-phenyl-propionamide (diastereoisomer 2) (example 30) the title compound was prepared from 1-(2-fluoro-5-methyl-phenyl)-3-(4-trifluoromethyl-phenyl)-propan-1-one (prepared from 1-(2-fluoro-5-methyl-phenyl)-ethanone and 4-Trifluoromethyl-benzaldehyde with subsequent reduction in analogy to the procedure described in example 1 step 1 & example 44 step 2) through reductive amination with 2-amino-2-(4-fluoro-phenyl)-N-methyl-acetamide. Example 86: MS (m/e): 477.1 (MH+) and Example 87: MS (m/e): 477.1 (MH+).

Example 88

2-[1-(4-Fluoro-3-methyl-phenyl)-3-(5-methyl-pyrazin-2-yl)-propylamino]-N-methyl-2-phenyl-acetamide

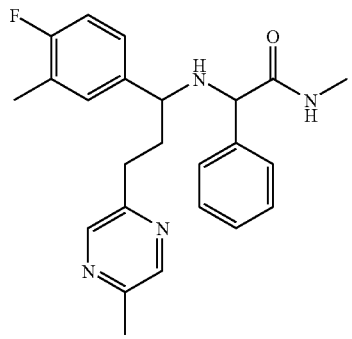

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-(4-fluoro-3-methyl-phenyl)-3-(5-methyl-pyrazin-2-yl)-propan-1-one (prepared from 1-(4-fluoro-3-methyl-phenyl)-ethanone and 5-methyl-pyrazine-2-carbaldehyde with subsequent reduction in analogy to the procedure described in example 44 step 1 & 2) through reductive amination with 2-amino-N-methyl-2-phenyl-acetamide. MS (m/e): 407.3 (MH+).

Example 89

N-Methyl-2-phenyl-2-[1-thiazol-2-yl-3-(4-trifluoromethyl-phenyl)-propylamino]-acetamide

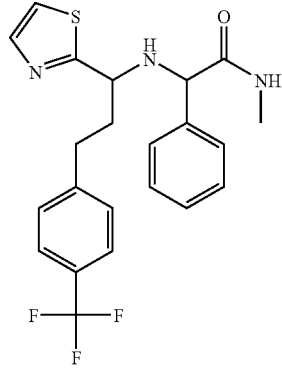

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propiona-mide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-thiazol-2-yl-3-(4-trifluoromethyl-phenyl)-propan-1-one (prepared from thiazole-2-carboxylic acid, N,O-dimethylhydroxylamine and 4-trifluoromethylphenethylmagnesium bromide in analogy to the procedure described in example 37 step 1 & 2) through reductive amination with 2-amino-N-methyl-2-phenyl-acetamide. MS (m/e): 434.3 (MH+).

Example 90

2-[1-Isoxazol-3-yl-3-(4-trifluoromethyl-phenyl)-propylamino]-N-methyl-2-phenyl-acetamide

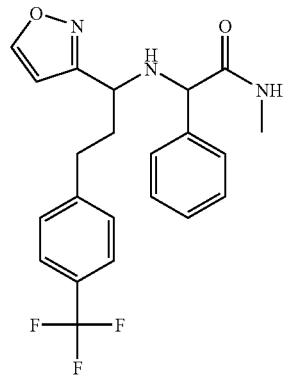

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propiona-mide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-Isoxazol-3-yl-3-(4-trifluoromethyl-phenyl)-propan-1-one (prepared from Isoxazole-3-carboxylic acid, N,O-dimethylhydroxylamine and 4-trifluoromethylphenethylmagnesium bromide in analogy to the procedure described in example 37 step 1 & 2) through reductive amination with 2-amino-N-methyl-2-phenyl-acetamide. MS (m/e): 418.4 (MH+).

Example 91

2-[1-Isoxazol-5-yl-3-(4-trifluoromethyl-phenyl)-propylamino]-N-methyl-2-phenyl-acetamide

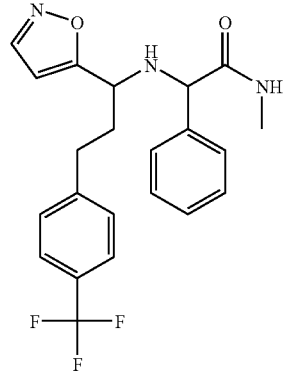

In analogy to the procedure described for the synthesis of (S,R)-2-[(R,S)-1-(3,4-dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-dimethoxy-phenyl)-3-(4-yl-phenyl)-propylamino]-N-methyl-2-phenyl-propionamide (diastereoisomer 2) (example 30) the title compound was prepared from 1-isoxazol-5-yl-3-(4-trifluoromethyl-phenyl)-propan-1-one (prepared from Isoxazole-5-carboxylic acid, N,O-dimethylhydroxylamine and 4-trifluoromethylphenethylmagnesium bromide in analogy to the procedure described in example 37 step 1 & 2) through reductive amination with 2-amino-N-methyl-2-phenyl-acetamide. MS (m/e): 418.3 (MH$^+$).

Example 92

2-[1-(3-Isopropyl-isoxazol-5-yl)-3-(4-trifluoromethyl-phenyl)-propylamino]-N-methyl-2-phenyl-acetamide

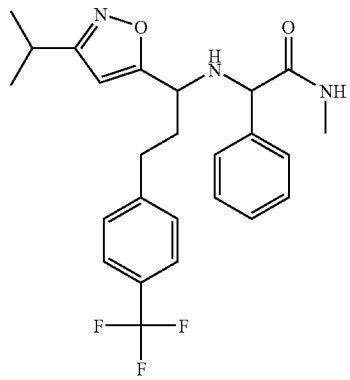

In analogy to the procedure described for the synthesis of (S,R)-2-[(R,S)-1-(3,4-Dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-Dimethoxy-phenyl)-3-(4-yl-phenyl)-propylamino]-N-methyl-2-phenyl-propionamide (diastereoisomer 2) (example 30) the title compound was prepared from 1-(3-Isopropyl-isoxazol-5-yl)-3-(4-trifluoromethyl-phenyl)-propan-1-one (prepared from 3-Isopropyl-isoxazole-5-carboxylic acid, N,O-dimethylhydroxylamine and 4-Trifluoromethylphenethylmagnesium bromide in analogy to the procedure described in example 37 step 1 & 2) through reductive amination with 2-Amino-N-methyl-2-phenyl-acetamide. MS (m/e): 460.4 (MH$^+$).

Example 93

2-[1-(2,4-Dimethyl-thiazol-5-yl)-3-(4-trifluoromethyl-phenyl)-propylamino]-N-methyl-2-phenyl-acetamide

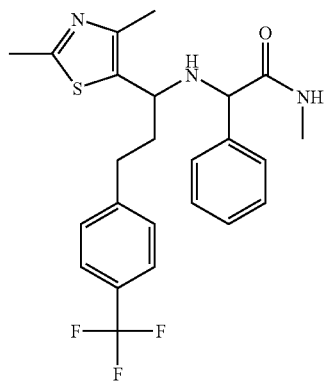

In analogy to the procedure described for the synthesis of (S,R)-2-[(R,S)-1-(3,4-Dimethoxy-phenyl)-3-(4-trifluoromethyl-phenyl)-propylamino]-N-methyl-2-phenyl-propionamide (diastereoisomer 1) (example 29) and (S,R)-2-[(S,R)-1-(3,4-Dimethoxy-phenyl)-3-(4-yl-phenyl)-propylamino]-N-methyl-2-phenyl-propionamide (diastereoisomer 2) (example 30) the title compound was prepared from 1-(2,4-Dimethyl-thiazol-5-yl)-3-(4-trifluoromethyl-phenyl)-propan-1-one (prepared from 1-(2,4-Dimethyl-thiazol-5-yl)-ethanone and 4-Trifluoromethyl-benzaldehyde with subsequent reduction in analogy to the procedure described in example 44 step 1 & 2) through reductive amination with 2-Amino-N-methyl-2-phenyl-acetamide. MS (m/e): 462.1 (MH$^+$).

Example 94

(R)-2-(4-Chloro-phenyl)-2-[(S)-1-(3,4-dimethoxy-phenyl)-3-(4-trifluoromethyl-phenyl)-propylamino]-N-methyl-acetamide

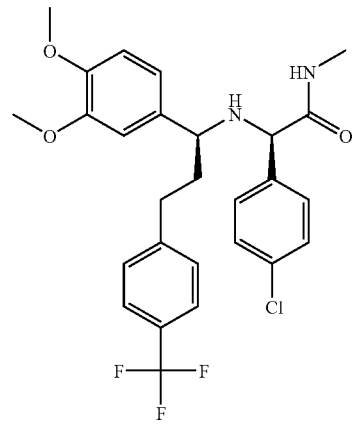

Cis-2-(4-Chloro-phenyl)-2-[1-(3,4-dimethoxy-phenyl)-3-(4-trifluoromethyl-phenyl)-propylamino]-N-methyl-acetamide (Example 32) was separated on chiral phase HPLC (chialpack AD column) to provide the title compound: (MS (m/e): 521.3 (MH$^+$).

Example 95

(R)-2-[(S)-1-(3,4-Dimethoxy-phenyl)-3-(4-trifluoromethyl-phenyl)-propylamino]-2-(4-fluoro-phenyl)-N-methyl-acetamide

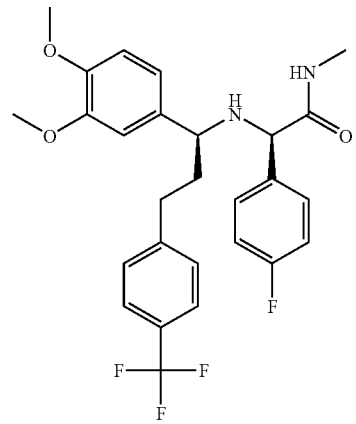

Cis-2-[1-(3,4-Dimethoxy-phenyl)-3-(4-trifluoromethyl-phenyl)-propylamino]-2-(4-fluoro-phenyl)-N-methyl-acetamide (Example 34) was separated on chiral phase HPLC (chialpack AD column) to provide the title compound: (MS (m/e): 527.3 (MH$^+$).

Example 96

(R)-2-[(S)-3-(4-Chloro-phenyl)-1-(2,3-dihydro-benzofuran-5-yl)-propylamino]-N-methyl-2-phenyl-acetamide

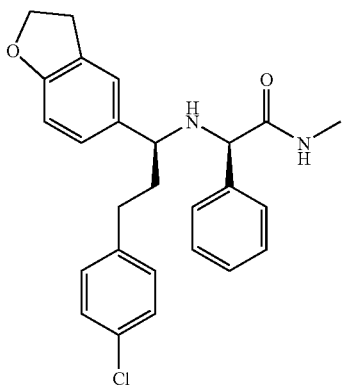

and

Example 97

(S)-2-[(R)-3-(4-Chloro-phenyl)-1-(2,3-dihydro-benzofuran-5-yl)-propylamino]-N-methyl-2-phenyl-acetamide

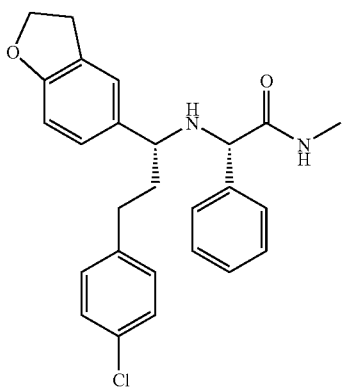

Cis-2-[3-(4-Chloro-phenyl)-1-(2,3-dihydro-benzofuran-5-yl)-propylamino]-N-methyl-2-phenyl-acetamide (Example 38) was separated on chiral phase HPLC (chialpack AD column) to provide the title compounds: Example 96: (MS (m/e): 435.3 (MH$^+$) and Example 97:(MS (m/e): 435.3 (MH$^+$).

Example 98

(R)-2-[(S)-1-(2-Chloro-3,4-dimethoxy-phenyl)-3-(4-chloro-phenyl)-propylamino]-N-methyl-2-phenyl-acetamide

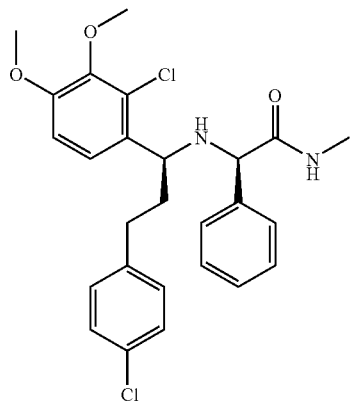

and

Example 99

(S)-2-[(R)-1-(2-Chloro-3,4-dimethoxy-phenyl)-3-(4-chloro-phenyl)-propylamino]-N-methyl-2-phenyl-acetamide

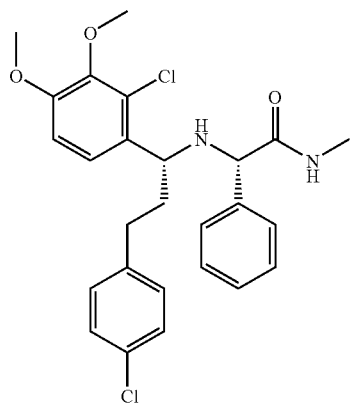

Cis-2-[1-(2-Chloro-3,4-dimethoxy-phenyl)-3-(4-chloro-phenyl)-propylamino]-N-methyl-2-phenyl-acetamide (example 40) was separated on chiral phase HPLC (chialpack AD column) to provide the title compounds: Example 98: (MS (m/e): 487.3 (MH$^+$) and Example 99:(MS (m/e): 487.3 (MH$^+$).

Example 100

(R)-2-[(S)-1-(4-Fluoro-2-methoxy-phenyl)-3-(6-trifluoromethyl-pyridin-3-yl)-propylamino]-2-(4-fluoro-phenyl)-N-methyl-acetamide

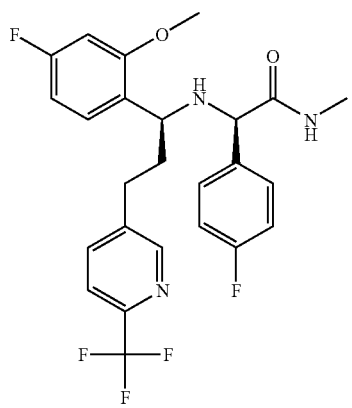

and

Example 101

(S)-2-[(R)-1-(4-Fluoro-2-methoxy-phenyl)-3-(6-trifluoromethyl-pyridin-3-yl)-propylamino]-2-(4-fluoro-phenyl)-N-methyl-acetamide

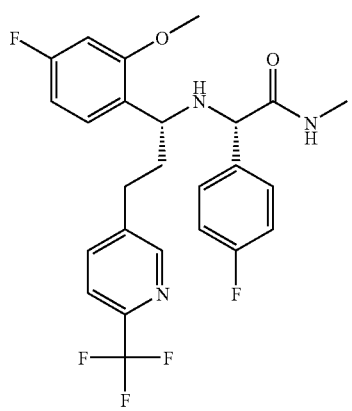

2-[1-(4-Fluoro-2-methoxy-phenyl)-3-(6-trifluoromethyl-pyridin-3-yl)-propylamino]-2-(4-fluoro-phenyl)-N-methyl-acetamide (example 46) was separated on chiral phase HPLC (chialpack AD column) to provide the title compounds: Example 100:(MS (m/e): 494.3 (MH$^+$) and Example 101:(MS (m/e): 494.3 (MH$^+$).

Example 102

(R)-2-(4-Fluoro-phenyl)-N-methyl-2-[(S)-1-(5,6,7,8-tetrahydro-naphthalen-2-yl)-3-(6-trifluoromethyl-pyridin-3-yl)-propylamino]-acetamide

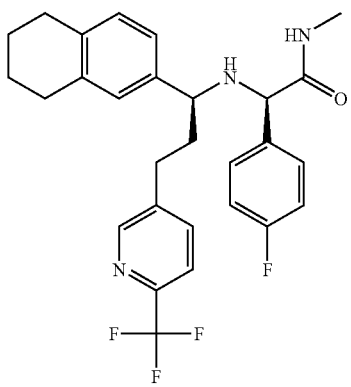

Cis-2-(4-Fluoro-phenyl)-N-methyl-2-[1-(5,6,7,8-tetrahydro-naphthalen-2-yl)-3-(6-trifluoromethyl-pyridin-3-yl)-propylamino]-acetamide (example 57) was separated on chiral phase HPLC (chialpack AD column) to provide the title compounds: Example 101:(MS (m/e): 494.3 (MH$^+$) and Example 102:(MS (m/e): 500.5 (MH$^+$).

Example 103

(S)-2-[(R)-1-(5-Chloro-2-methoxy-phenyl)-3-(6-trifluoromethyl-pyridin-3-yl)-propylamino]-2-(4-fluoro-phenyl)-N-methyl-acetamide

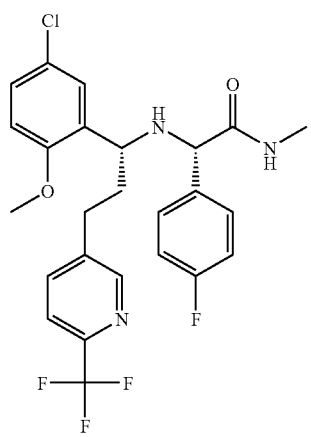

and

Example 104

(R)-2-[(S)-1-(5-Chloro-2-methoxy-phenyl)-3-(6-trifluoromethyl-pyridin-3-yl)-propylamino]-2-(4-fluoro-phenyl)-N-methyl-acetamide

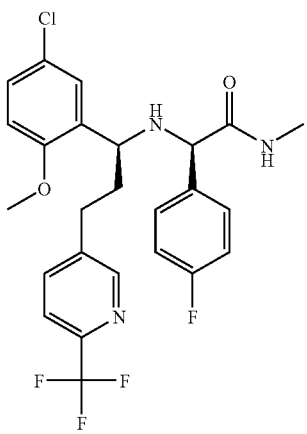

2-[1-(5-Chloro-2-methoxy-phenyl)-3-(6-trifluoromethyl-pyridin-3-yl)-propylamino]-2-(4-fluoro-phenyl)-N-methyl-acetamide (example 64) was separated on chiral phase HPLC (chialpack AD column) to provide the title compounds: Example 103:(MS (m/e): 510.1 (MH$^+$) and Example 104: (MS (m/e): 510.4 (MH$^+$).

Example 105

(S)-2-[(S)-1-(2-Fluoro-5-methyl-phenyl)-3-(6-trifluoromethyl-pyridin-3-yl)-propylamino]-2-(4-fluoro-phenyl)-N-methyl-acetamide

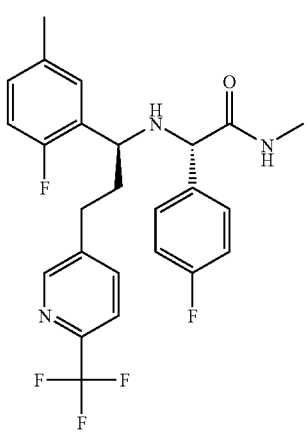

and

Example 106

(S)-2-[(R)-1-(2-Fluoro-5-methyl-phenyl)-3-(6-trifluoromethyl-pyridin-3-yl)-propylamino]-2-(4-fluoro-phenyl)-N-methyl-acetamide

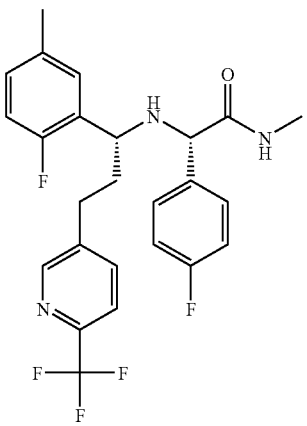

and

Example 107

(R)-2-[(S)-1-(2-Fluoro-5-methyl-phenyl)-3-(6-trifluoromethyl-pyridin-3-yl)-propylamino]-2-(4-fluoro-phenyl)-N-methyl-acetamide

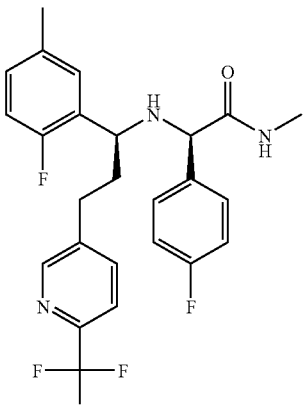

2-[1-(2-Fluoro-5-methyl-phenyl)-3-(6-trifluoromethyl-pyridin-3-yl)-propylamino]-2-(4-fluoro-phenyl)-N-methyl-acetamide (example 67) was separated on chiral phase HPLC (chialpack AD column) to provide the title compounds: Example 105:(MS (m/e): 478.0 (MH$^+$) and Example 106: (MS (m/e): 478.0 (MH$^+$) and Example 107:(MS (m/e): 478.0 (MH$^+$).

Example 108

(R)-2-[(S)-1-(2,4-Dimethyl-thiazol-5-yl)-3-(6-trifluoromethyl-pyridin-3-yl)-propylamino]-2-(4-fluoro-phenyl)-N-methyl-acetamide

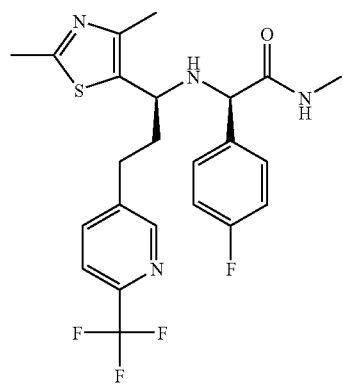

2-[1-(2,4-Dimethyl-thiazol-5-yl)-3-(6-trifluoromethyl-pyridin-3-yl)-propylamino]-2-(4-fluoro-phenyl)-N-methyl-acetamide (example 69) was separated on chiral phase HPLC (chialpack AD column) to provide the title compound: (MS (m/e): 481.0 (MH$^+$).

Example 109

(R)-2-[(R)-3-(5-Chloro-pyrazin-2-yl)-1-(4-fluoro-3-methyl-phenyl)-propylamino]-N-methyl-2-phenyl-acetamide

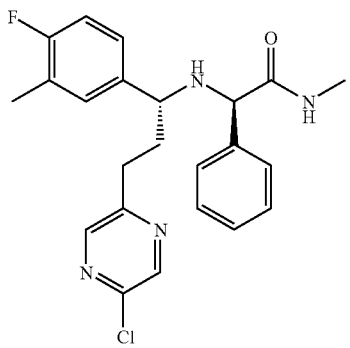

and

Example 110

(S)-2-[(R)-3-(5-Chloro-pyrazin-2-yl)-1-(4-fluoro-3-methyl-phenyl)-propylamino]-N-methyl-2-phenyl-acetamide

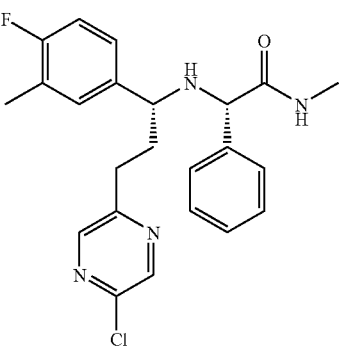

and

Example 111

(S)-2-[(S)-3-(5-Chloro-pyrazin-2-yl)-1-(4-fluoro-3-methyl-phenyl)-propylamino]-N-methyl-2-phenyl-acetamide

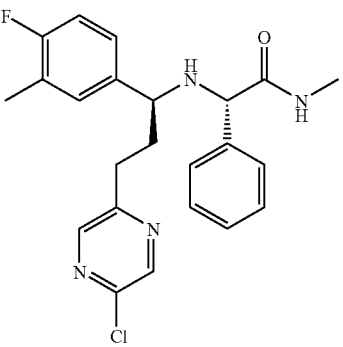

and

Example 112

(R)-2-[(S)-3-(5-Chloro-pyrazin-2-yl)-1-(4-fluoro-3-methyl-phenyl)-propylamino]-N-methyl-2-phenyl-acetamide

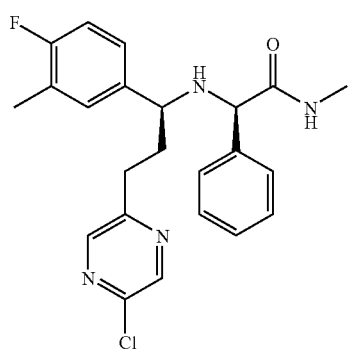

2-[3-(5-Chloro-pyrazin-2-yl)-1-(4-fluoro-3-methyl-phenyl)-propylamino]-N-methyl-2-phenyl-acetamide (example 71) was separated on chiral phase HPLC (chialpack AD column) to provide the title compounds: Example 109:(MS (m/e): 427.3 (MH$^+$) and Example 110:(MS (m/e): 427.3 (MH$^+$) and Example 111:(MS (m/e): 427.3 (MH$^+$) and Example 112:(MS (m/e): 427.3 (MH$^+$).

Example 113

(R)-2-[(S)-1-Chroman-6-yl-3-(4-trifluoromethyl-phenyl)-propylamino]-N-methyl-2-phenyl-acetamide

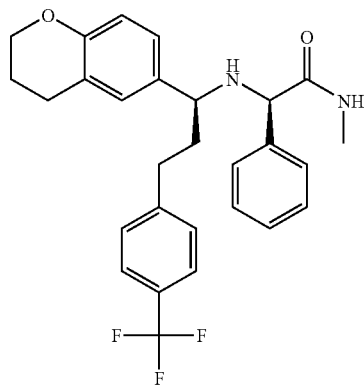

Cis-2-[1-Chroman-6-yl-3-(4-trifluoromethyl-phenyl)-propylamino]-N-methyl-2-phenyl-acetamide (example 76) was separated on chiral phase HPLC (chialpack AD column) to provide the title compound: (MS (m/e): 483.3 (MH$^+$).

Example 114

(S)—N-Methyl-2-[(R)-1-(4-methyl-3,4-dihydro-2H-benzo[1,4]oxazin-7-yl)-3-(4-trifluoromethyl-phenyl)-propylamino]-2-phenyl-acetamide

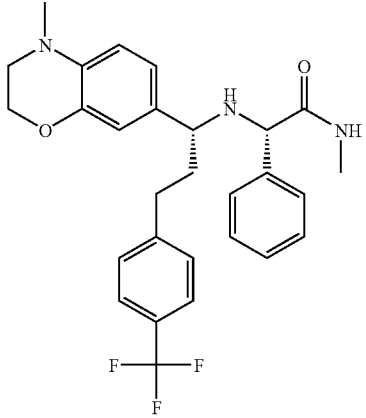

and

Example 115

(R)—N-Methyl-2-[(S)-1-(4-methyl-3,4-dihydro-2H-benzo[1,4]oxazin-7-yl)-3-(4-trifluoromethyl-phenyl)-propylamino]-2-phenyl-acetamide

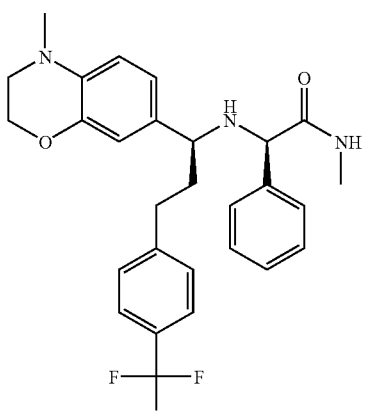

Cis-N-Methyl-2-[1-(4-methyl-3,4-dihydro-2H-benzo[1,4]oxazin-7-yl)-3-(4-trifluoromethyl-phenyl)-propylamino]-2-phenyl-acetamide (example 78) was separated on chiral phase HPLC (chialpack AD column) to provide the title compounds: Example 114 (MS (m/e): 497.9 (MH$^+$) and Example 115 (MS (m/e): 498.0 (MH$^+$).

Example 116

(R)-2-[(S)-1-(2,4-Dimethyl-thiazol-5-yl)-3-(4-trifluoromethyl-phenyl)-propylamino]-2-(4-fluoro-phenyl)-N-methyl-acetamide

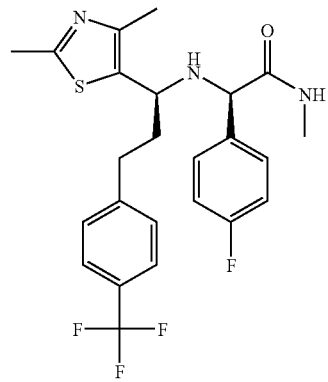

and

Example 117

(R)-2-[(R)-1-(2,4-Dimethyl-thiazol-5-yl)-3-(4-trifluoromethyl-phenyl)-propylamino]-2-(4-fluoro-phenyl)-N-methyl-acetamide

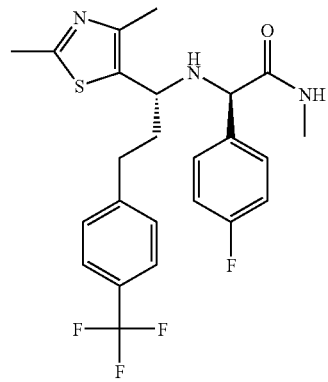

and

Example 118

(S)-2-[(R)-1-(2,4-Dimethyl-thiazol-5-yl)-3-(4-trifluoromethyl-phenyl)-propylamino]-2-(4-fluoro-phenyl)-N-methyl-acetamide

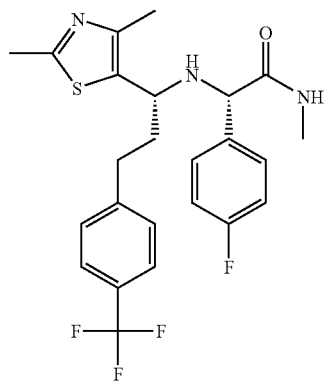

and

Example 119

(S)-2-[(S)-1-(2,4-Dimethyl-thiazol-5-yl)-3-(4-trifluoromethyl-phenyl)-propylamino]-2-(4-fluoro-phenyl)-N-methyl-acetamide

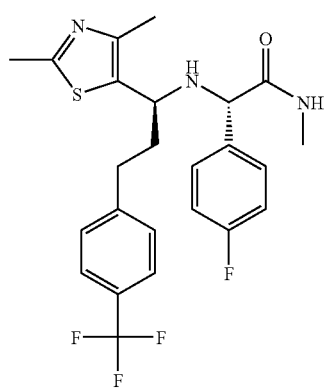

2-[1-(2,4-Dimethyl-thiazol-5-yl)-3-(4-trifluoromethyl-phenyl)-propylamino]-2-(4-fluoro-phenyl)-N-methyl-acetamide (example 80) was separated on chiral phase HPLC (chialpack AD column) to provide the title compounds: Example 116 (MS (m/e): 480.1 (MH$^+$) and Example 117 (MS (m/e): 480.1 (MH$^+$) and Example 118 (MS (m/e): 480.1 (MH$^+$) and Example 119 (MS (m/e): 480.1 (MH$^+$).

Example 120

(R)—N-Methyl-2-phenyl-2-[(R)-1-(5,6,7,8-tetrahydro-naphthalen-2-yl)-3-(4-trifluoromethyl-phenyl)-propylamino]-acetamide

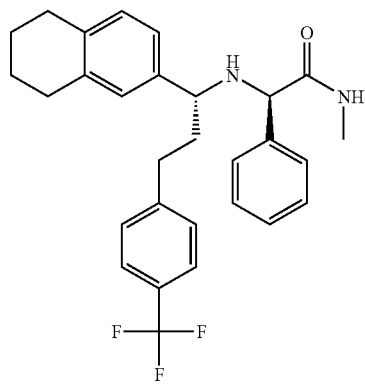

and

Example 121

(R)—N-Methyl-2-phenyl-2-[(S)-1-(5,6,7,8-tetrahydro-naphthalen-2-yl)-3-(4-trifluoromethyl-phenyl)-propylamino]-acetamide

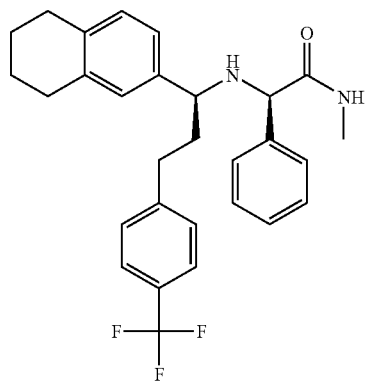

N-Methyl-2-phenyl-2-[1-(5,6,7,8-tetrahydro-naphthalen-2-yl)-3-(4-trifluoromethyl-phenyl)-propylamino]-acetamide (example 83) and Trans-N-Methyl-2-phenyl-2-[(S)-1-(5,6,7,8-tetrahydro-naphthalen-2-yl)-3-(4-trifluoromethyl-phenyl)-propylamino]-acetamide (example 84) were separated on chiral phase HPLC (chialpack AD column) to provide the title compounds: Example 120 (MS (m/e): 481.0 (MH$^+$) and Example 121 (MS (m/e): 481.0 (MH$^+$).

Example 122

(R)-2-[(R)-1-(2-Fluoro-5-methyl-phenyl)-3-(4-trifluoromethyl-phenyl)-propylamino]-N-methyl-2-phenyl-acetamide

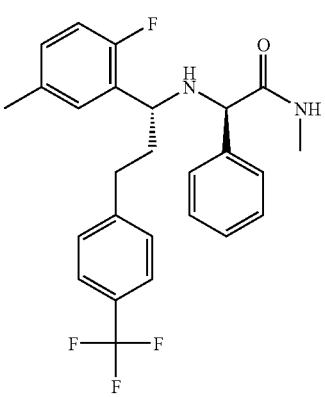

and

Example 123

(R)-2-[(S)-1-(2-Fluoro-5-methyl-phenyl)-3-(4-trifluoromethyl-phenyl)-propylamino]-N-methyl-2-phenyl-acetamide

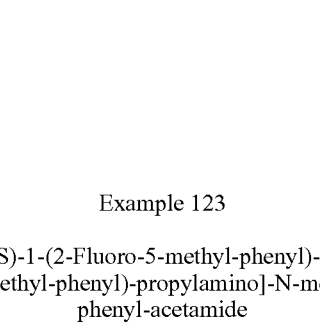

2-[1-(2-Fluoro-5-methyl-phenyl)-3-(4-trifluoromethyl-phenyl)-propylamino]-N-methyl-2-phenyl-acetamide (example 85) was separated on chiral phase HPLC (chialpack AD column) to provide the title compounds: Example 122 (MS (m/e): 459.3 (MH$^+$) and Example 123 (MS (m/e): 459.4 (MH$^+$).

Example 124

(R)-2-[(S)-1-(2-Fluoro-5-methyl-phenyl)-3-(4-trifluoromethyl-phenyl)-propylamino]-2-(4-fluoro-phenyl)-N-methyl-acetamide

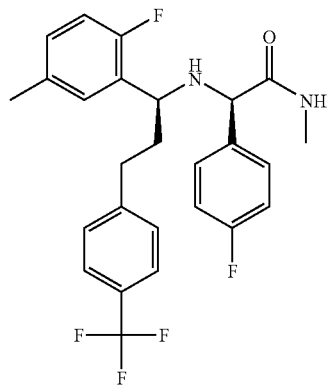

Cis-2-[(S)-1-(2-Fluoro-5-methyl-phenyl)-3-(4-trifluoromethyl-phenyl)-propylamino]-2-(4-fluoro-phenyl)-N-methyl-acetamide (example 86) was separated on chiral phase HPLC (chialpack AD column) to provide the title compound: (MS (m/e): 477.0 (MH$^+$).

Example 125

(R)-2-[(S)-1-(4-Fluoro-3-methyl-phenyl)-3-(5-methyl-pyrazin-2-yl)-propylamino]-N-methyl-2-phenyl-acetamide

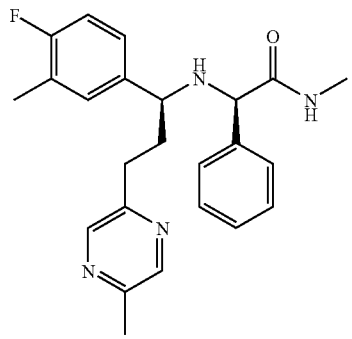

2-[1-(4-Fluoro-3-methyl-phenyl)-3-(5-methyl-pyrazin-2-yl)-propylamino]-N-methyl-2-phenyl-acetamide (example 88) was separated on chiral phase HPLC (chialpack AD column) to provide the title compound: (MS (m/e): 407.3 (MH$^+$).

Example 126

(S,R)-2-[(S,R)-1-(4-Chloro-phenyl)-3-(4-trifluoromethyl-phenyl)-propylamino]-N-methyl-2-phenyl-acetamide

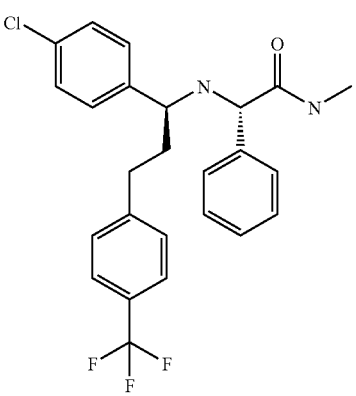

and

Example 127

(S,R)-2-[(R,S)-1-(4-Chloro-phenyl)-3-(4-trifluoromethyl-phenyl)-propylamino]-N-methyl-2-phenyl-acetamide

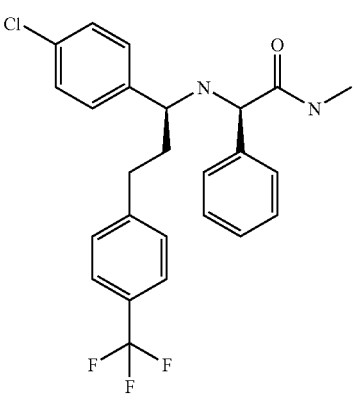

a) Step 1

2-Methyl-propane-2-sulfinic acid [1-(4-chloro-phenyl)-3-(4-trifluoromethyl-phenyl)-propyl]-amide

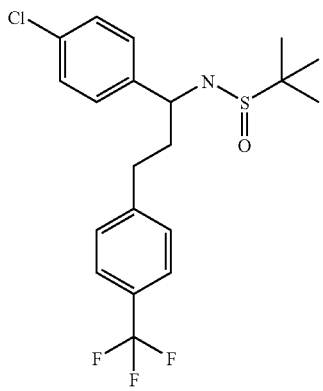

To a solution of 100 mg (0.8 mmol) 2-methyl-2-propanesulfinamide in THF (1.5 mL) were added 0.35 mL (1.6 mmol) Ti(OEt)$_4$ and 122 mg (0.85 mmol) 4-chlorobenzaldehyde. The mixture was stirred at room temperature for 3 hours. Brine (1.5 ml) was added. The mixture was diluted with ethyl acetate and Na$_2$SO$_4$ was added. The mixture was filtered through a plug of celite and the filtrate was concentrated in vacuo to provide 200 mg of white solid. The solid was dissolved in dichloromethane (2.0 mL) under argon. The solution was cooled to −50° C. 2.3 ml (1.6 mmol) of a 0.71M of 4-trifluoromethylphenethyl magnesium bromide solution in THF was added dropwise. The mixture was stirred at −50° C. for 30 minutes and then at room temperature for 1.5 hour. The mixture was cooled in an ice-bath and quenched with a 20% NH$_4$Cl solution (1 mL). Ethyl acetate and Na$_2$SO$_4$ were added. The mixture was filtered and the filtrate was concentrated in vacuo. The crude oil was purified with flash column chromatography on silica eluting with a gradient formed from ethyl acetate and heptane to provide 0.21 g (65%) of the title compound as yellow oil. MS (m/e): 418.2 (MH$^+$).

b) Step 2 rac-1-(4-Chloro-phenyl)-3-(4-trifluoromethyl-phenyl)-propylamine hydrochloride

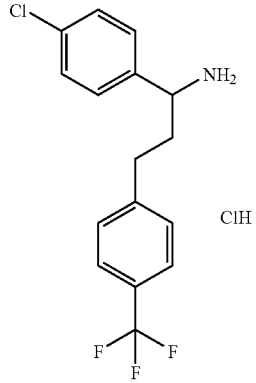

To a solution of 210 mg (0.5 mmol) 2-Methyl-propane-2-sulfinic acid [1-(4-chloro-phenyl)-3-(4-trifluoromethyl-phenyl)-propyl]-amide in methanol (0.5 mL) was added a 4M HCl solution in dioxane (0.5 mL1) at room temperature under argon. The mixture was stirred at room temperature for 30 minutes. The solvent was removed in vacuo. The solid was stirred in ether, filtered and dried to provide 138 mg (78%) of the title compound as white solid. MS (m/e): 313.9 (MH$^+$).

c) Step 3

To a suspension of 120 mg (0.34 mmol) 2-Methyl-propane-2-sulfinic acid [1-(4-chloro-phenyl)-3-(4-trifluoromethyl-phenyl)-propyl]-amide in acetonitrile (4 mL) was added 0.23 ml (1.37 mmol) N-ethyldiisopropylamine, 101 mg (0.446 mmol) rac-2-Bromo-N-methyl-2-phenyl-acetamide (CAS: 51685-62-2) and 52 mg (0.34 mmol) sodium iodide were added. The mixture was heated in a 65° C. oil bath for 23 hours. The solvent was removed in vacuo. The residue was taken in ethyl acetate. The mixture was washed once with water and once with a 2M Na$_2$CO$_3$ solution, dried over Na$_2$SO$_4$, filtered and concentrated in vacuo. The crude oil was purified with flash column chromatography on silica eluting with a gradient formed from ethyl acetate and heptane to provide 0.046 g (29%) of (S,R)-2-[(S,R)-1-(4-Chloro-phenyl)-3-(4-trifluoromethyl-phenyl)-propylamino]-N-methyl-2-phenyl-acetamide (1$^{st}$ eluting compound) as light brown oil. MS (m/e): 461.2 (MH$^+$) and 0.042 g (27%) of (S,R)-2-[(R,S)-1-(4-Chloro-phenyl)-3-(4-trifluoromethyl-phenyl)-propylamino]-N-methyl-2-phenyl-acetamide (2$^{nd}$ eluting compound) as light brown oil. MS (m/e): 461.2 (MH$^+$).

Example 128

(S,R)-2-[(S,R)-1-(4-Chloro-phenyl)-3-(4-methoxy-phenyl)-propylamino]-N-methyl-2-phenyl-acetamide

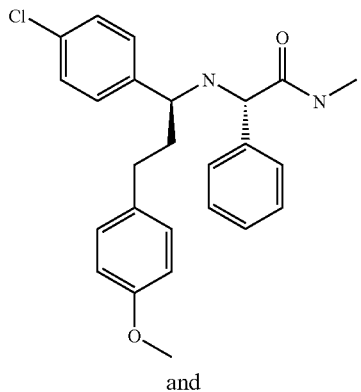

and

Example 129

(S,R)-2-[(R,S)-1-(4-Chloro-phenyl)-3-(4-methoxy-phenyl)-propylamino]-N-methyl-2-phenyl-acetamide

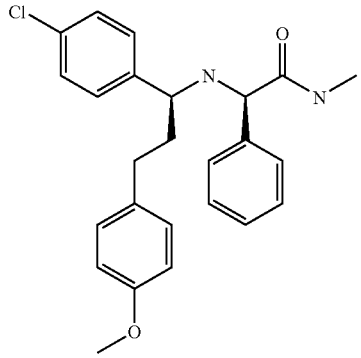

In analogy to the procedure described for the synthesis of examples 126 and 127 (step 3), the title compounds: (S,R)-2-[(S,R)-1-(4-Chloro-phenyl)-3-(4-methoxy-phenyl)-propylamino]-N-methyl-2-phenyl-acetamide (MS (m/e): 423.2 (MH⁺)) and (S,R)-2-[(R,S)-1-(4-Chloro-phenyl)-3-(4-methoxy-phenyl)-propylamino]-N-methyl-2-phenyl-acetamide (MS (m/e): 423.2 (MH⁺)) were prepared from rac-1-(4-Chloro-phenyl)-3-(4-methoxy-phenyl)-propylamine hydrochloride (accessed according to the procedure described for examples 126 and 127, step 2 from 2-Methyl-propane-2-sulfinic acid [1-(4-chloro-phenyl)-3-(4-methoxy-phenyl)-propyl]-amide).

Example 130

(S,R)-2-[(S,R)-3-(4-Methoxy-phenyl)-1-(6-trifluoromethyl-pyridin-3-yl)-propylamino]-N-methyl-2-phenyl-acetamide

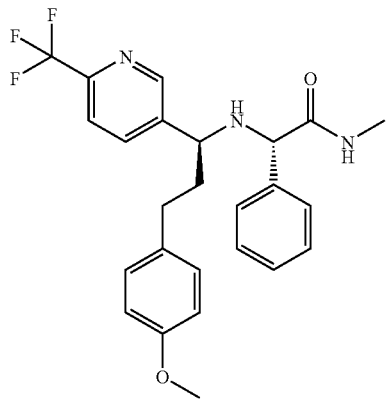

and

Example 131

(S,R)-2-[(R,S)-3-(4-Methoxy-phenyl)-1-(6-trifluoromethyl-pyridin-3-yl)-propylamino]-N-methyl-2-phenyl-acetamide

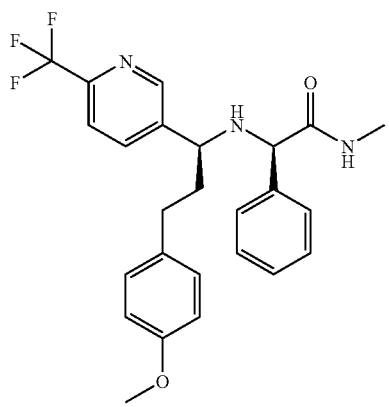

In analogy to the procedure described for the synthesis of examples 126 and 127 (step 3), the title compounds: (S,R)-2-[(S,R)-3-(4-Methoxy-phenyl)-1-(6-trifluoromethyl-pyridin-3-yl)-propylamino]-N-methyl-2-phenyl-acetamide (MS (m/e): 458.2 (MH⁺)) and (S,R)-2-[(R,S)-3-(4-Methoxy-phenyl)-1-(6-trifluoromethyl-pyridin-3-yl)-propylamino]-N-methyl-2-phenyl-acetamide (MS (m/e): 458.2 (MH⁺)) were prepared from rac-3-(4-Methoxy-phenyl)-1-(6-trifluoromethyl-pyridin-3-yl)-propylamine (accessed according to the procedure described for examples 126 and 127, step 2 from 2-Methyl-propane-2-sulfinic acid [3-(4-methoxy-phenyl)-1-(6-trifluoromethyl-pyridin-3-yl)-propyl]-amide).

Example 132

(S,R)—N-Methyl-2-phenyl-2-[(S,R)-1-phenyl-3-(4-trifluoromethyl-phenyl)-propylamino]-acetamide

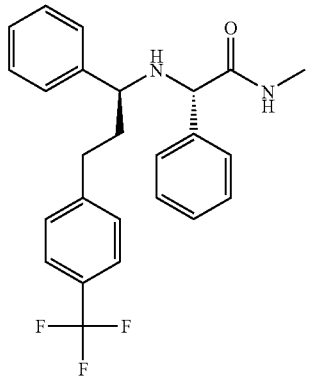

and

Example 133

(S,R)—N-Methyl-2-phenyl-2-[(R,S)-1-phenyl-3-(4-trifluoromethyl-phenyl)-propylamino]-acetamide

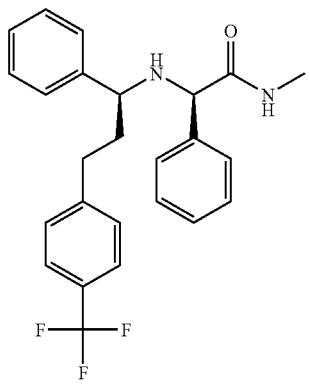

In analogy to the procedure described for the synthesis of examples 126 and 127 (step 3), the title compounds: (S,R)—N-Methyl-2-phenyl-2-[(S,R)-1-phenyl-3-(4-trifluoromethyl-phenyl)-propylamino]-acetamide (MS (m/e): 427.2 (MH⁺)) and (S,R)—N-Methyl-2-phenyl-2-[(R,S)-1-phenyl-3-(4-trifluoromethyl-phenyl)-propylamino]-acetamide (MS (m/e): 427.2 (MH⁺)) were prepared from rac-1-Phenyl-3-(4-trifluoromethyl-phenyl)-propylamine hydrochloride (accessed according to the procedure described for examples 126 and 127, step 2 from 2-Methyl-propane-2-sulfinic acid [1-phenyl-3-(4-trifluoromethyl-phenyl)-propyl]-amide).

Example 134

(S,R)-2-[(S,R)-3-(4-Methoxy-phenyl)-1-(2-methoxy-pyridin-3-yl)-propylamino]-N-methyl-2-phenyl-acetamide

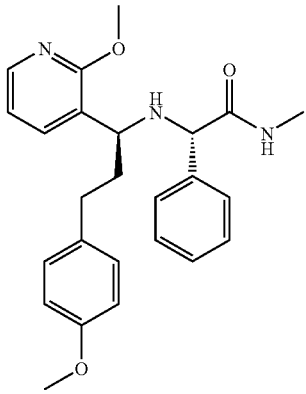

and

Example 135

(S,R)-2-[(R,S)-3-(4-Methoxy-phenyl)-1-(2-methoxy-pyridin-3-yl)-propylamino]-N-methyl-2-phenyl-acetamide

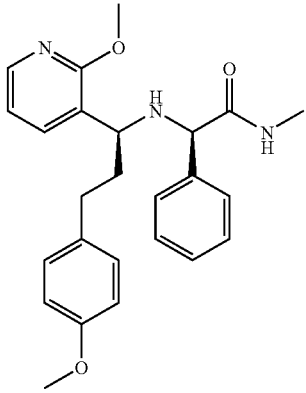

Example 136

(S,R)-2-[(S,R)-1-(4-Methoxy-phenyl)-3-(4-trifluoromethyl-phenyl)-propylamino]-N-methyl-2-phenyl-acetamide

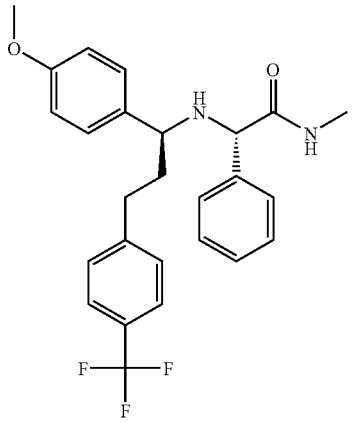

and

Example 137

(S,R)-2-[(R,S)-1-(4-Methoxy-phenyl)-3-(4-trifluoromethyl-phenyl)-propylamino]-N-methyl-2-phenyl-acetamide

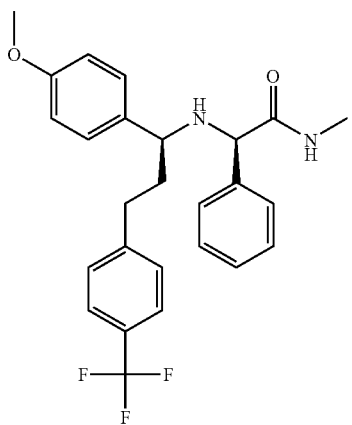

In analogy to the procedure described for the synthesis of examples 126 and 127 (step 3), the title compounds: (S,R)-2-[(S,R)-3-(4-Methoxy-phenyl)-1-(2-methoxy-pyridin-3-yl)-propylamino]-N-methyl-2-phenyl-acetamide (MS (m/e): 420.2 (MH$^+$)) and (S,R)-2-[(R,S)-3-(4-Methoxy-phenyl)-1-(2-methoxy-pyridin-3-yl)-propylamino]-N-methyl-2-phenyl-acetamide (MS (m/e): 420.2 (MH$^+$)) were prepared from 3-(4-Methoxy-phenyl)-1-(2-methoxy-pyridin-3-yl)-propylamine (accessed according to the procedure described for examples 126 and 127, step 2 from 2-Methyl-propane-2-sulfinic acid [3-(4-methoxyphenyl)-1-(2-methoxy-pyridin-3-yl)-propyl]-amide).

In analogy to the procedure described for the synthesis of examples 126 and 127 (step 3), the title compounds: (S,R)-2-[(S,R)-1-(4-Methoxy-phenyl)-3-(4-trifluoromethyl-phenyl)-propylamino]-N-methyl-2-phenyl-acetamide (MS (m/e): 457.3 (MH$^+$)) and (S,R)-2-[(R,S)-1-(4-Methoxy-phenyl)-3-(4-trifluoromethyl-phenyl)-propylamino]-N-methyl-2-phenyl-acetamide (MS (m/e): 457.3 (MH$^+$)) were prepared from rac-1-(4-Methoxy-phenyl)-3-(4-trifluoromethyl-phenyl)-propylamine hydrochloride (accessed according to the procedure described for examples 126 and 127, step 2 from 2-Methyl-propane-2-sulfinic acid [1-(4-methoxy-phenyl)-3-(4-trifluoromethyl-phenyl)-propyl]-amide).

Example 138

(R)-2-[(S)-1-(4-Chloro-phenyl)-3-(4-methoxy-phenyl)-propylamino]-N-methyl-2-phenyl-acetamide

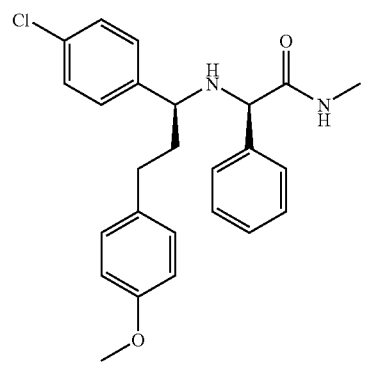

In analogy to the procedure described for the synthesis of examples 126 and 127 (step 3), the title compound: (R)-2-[(S)-1-(4-Chloro-phenyl)-3-(4-methoxy-phenyl)-propylamino]-N-methyl-2-phenyl-acetamide (MS (m/e): 423.3 (MH$^+$)) was prepared from (S)-1-(4-Chloro-phenyl)-3-(4-methoxy-phenyl)-propylamine; hydrochloride (accessed according to the procedure described for examples 126 and 127, step 2 from 2-Methyl-propane-2-sulfinic acid [(S)-1-(4-chloro-phenyl)-3-(4-methoxy-phenyl)-propyl]-amide).

Example 139

(S,R)-2-[(S,R-3-(4-Chloro-phenyl)-1-(3,4-dimethoxy-phenyl)-propylamino]-N-methyl-2-phenyl-acetamide

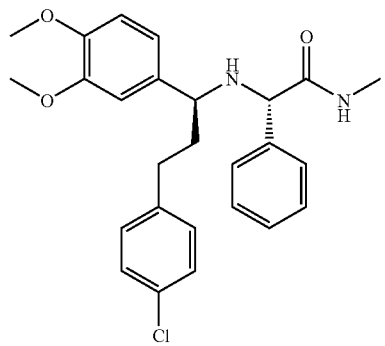

and

Example 140

(S,R)-2-[(R,S)-3-(4-Chloro-phenyl)-1-(3,4-dimethoxy-phenyl)-propylamino]-N-methyl-2-phenyl-acetamide

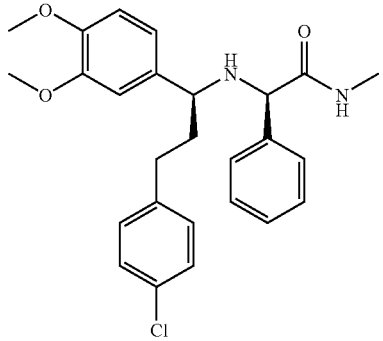

a) Step 1 rac-3-(4-Chloro-phenyl)-1-(3,4-dimethoxy-phenyl)-propylamine

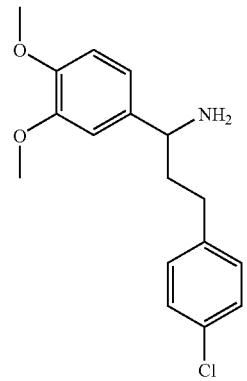

In analogy to the procedure described for the synthesis of examples 126 and 127 (step 2), the title compound: rac-3-(4-Chloro-phenyl)-1-(3,4-dimethoxy-phenyl)-propylamine was prepared from 2-Methyl-propane-2-sulfinic acid [3-(4-chloro-phenyl)-1-(3,4-dimethoxy-phenyl)-propyl]-amide.

a) Step 2

A mixture of 375 mg (1.23 mmol) rac-3-(4-Chloro-phenyl)-1-(3,4-dimethoxy-phenyl)-propylamine, 200 mg (1.23 mmol) N-Methyl-2-oxo-2-phenyl-acetamide (CAS: 83490-71-5), 200 mg (1.23 mmol) N-Methyl-2-oxo-2-phenyl-acetamide (CAS: 83490-71-5) and 11 mg (0.06 mol) 4-toluenesulfonic acid in toluene (4 mL) was refluxed with a Dean Stark apparatus for 22 hours. The solvent was removed in vacuo and mixture was dissolved in methanol (2.0 mL). 35 mg (4.9 mmol) NaBH$_4$ was added portionwise. The mixture was stirred at room temperature for 1 hour and then refluxed for 1 hour. The solution was cooled to room temperature. 35 mg (4.9 mmol) NaBH$_4$ was added again portionwise. The mixture was stirred for 30 minutes and quenched with a 20% NH$_4$Cl solution (5 mL). The mixture was extracted 3 times with ethyl acetate. The combined extracts were dried over Na$_2$SO$_4$, filtered and concentrated in vacuo. The crude oil was purified with flash column chromatography on silica eluting with a gradient formed from dichloromethane and methanol to provide 0.11 g (20%) of (S,R)-2-[(S,R-3-(4-Chloro-phenyl)-1-(3,4-dimethoxy-phenyl)-propylamino]-N-methyl-2-phenyl-acetamide (1$^{st}$ eluting compound) as colorless oil. MS (m/e): 453.4 (MH$^+$) and 0.083 g (15%) of (S,R)-2-[(R,S)-3-(4-Chloro-phenyl)-1-(3,4-dimethoxy-phenyl)-propylamino]-N-methyl-2-phenyl-acetamide (2$^{nd}$ eluting compound) as colorless oil. MS (m/e): 453.4 (MH$^+$).

Example 141

(S,R)-2-[(S,R)-1-(3,4-Dimethoxy-phenyl)-3-(4-trifluoromethyl-phenyl)-propylamino]-N-methyl-2-phenyl-acetamide

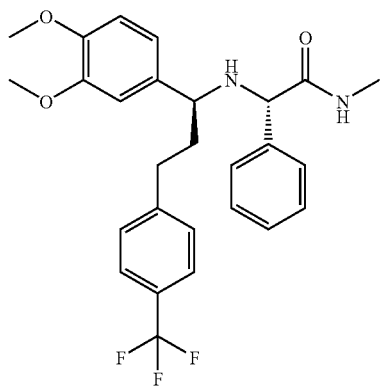

and

Example 142

(S,R)-2-[(R,S)-1-(3,4-Dimethoxy-phenyl)-3-(4-trifluoromethyl-phenyl)-propylamino]-N-methyl-2-phenyl-acetamide

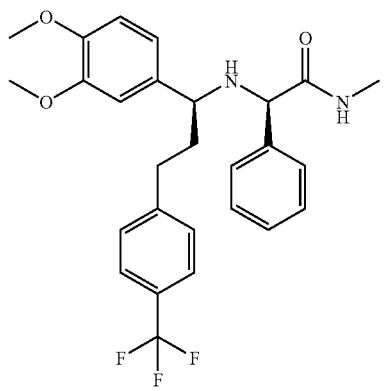

In analogy to the procedure described for the synthesis of examples 139 and 140 (step 2), the title compounds: (S,R)-2-[(S,R)-1-(3,4-Dimethoxy-phenyl)-3-(4-trifluoromethyl-phenyl)-propylamino]-N-methyl-2-phenyl-acetamide (MS (m/e): 487.3 (MH$^+$)) and (S,R)-2-[(R,S)-1-(3,4-Dimethoxy-phenyl)-3-(4-trifluoromethyl-phenyl)-propylamino]-N-methyl-2-phenyl-acetamide (MS (m/e): 487.3 (MH$^+$)) were prepared from rac-1-(3,4-Dimethoxy-phenyl)-3-(4-trifluoromethyl-phenyl)-propylamine (accessed according to the procedure described for examples 126 and 127, step 2 from 2-Methyl-propane-2-sulfinic acid [1-(3,4-dimethoxy-phenyl)-3-(4-trifluoromethyl-phenyl)-propyl]-amide).

Example 143

(S,R)-2-[(S,R)-1-(3,4-Dimethoxy-phenyl)-3-(4-fluoro-phenyl)-propylamino]-N-methyl-2-phenyl-acetamide

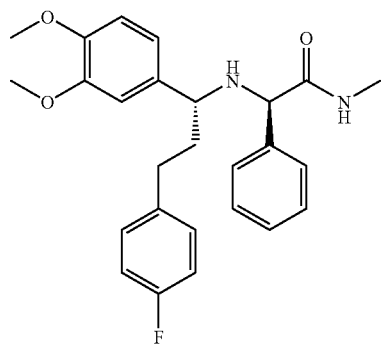

and

Example 144

(S,R)-2-[(R,S)-1-(3,4-Dimethoxy-phenyl)-3-(4-fluoro-phenyl)-propylamino]-N-methyl-2-phenyl-acetamide

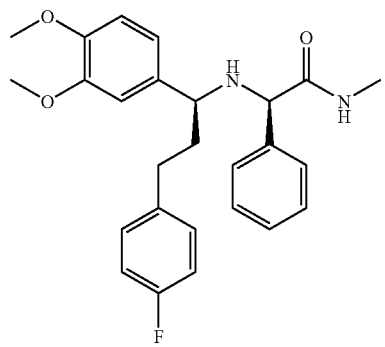

a) Step 1

(E)-1-(3,4-Dimethoxy-phenyl)-3-(4-fluoro-phenyl) propenone

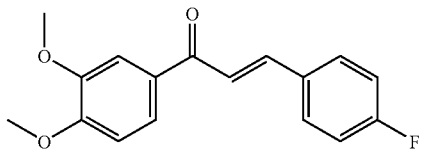

To a solution of 1.84 g (10 mmol) 3,4-dimethoxyacetophenone in 40 ml methanol under argon at RT, was added 1.08 ml (10 mmol) 4-fluorobenzaldehyde, followed by 0.65 g (10 mmol) potassium hydroxide. The mixture was stirred at room temperature for 2 days and then cooled to 0° C. The solid was filtered, washed with methanol and dried (HV, 40° C.) to provide the title compound 1.93 g (67%) as light yellow solid. MS (m/e): 287.1 (MH$^+$).

b) Step 2

1-(3,4-Dimethoxy-phenyl)-3-(4-fluoro-phenyl)-propan-1-one

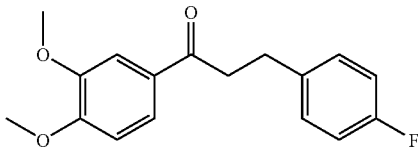

To a solution of 1 g (3.5 mmol) (E)-1-(3,4-Dimethoxy-phenyl)-3-(4-fluoro-phenyl)propenone in 12 mL ethyl acetate and 6 ml dichloromethane was added 16 mg $PtO_2$. The mixture was stirred at room temperature under hydrogen at atmospheric pressure for 1 hour. The catalyst was filtered and the filtrate was concentrated in vacuo. The crude oil was purified with flash column chromatography on silica eluting with a gradient formed from heptane and ethyl acetate to provide 0.82 g (81%) of title compound as white solid. MS (m/e): 289.0 ($MH^+$).

c) Step 3

A mixture of 0.2 g (0.69 mmol) 1-(3,4-Dimethoxy-phenyl)-3-(4-fluoro-phenyl)-propan-1-one, 0.14 g (0.69 mmol) rac-2-Amino-N-methyl-2-phenyl-acetamide (CAS: 93782-07-1) and 0.15 ml (0.69 mmol) titanium (IV) ethoxide in toluene (4 mL) was refluxed for 64 hours. The solvent was removed in vacuo. The reaction mixture was dissolved with 1,2-dichloroethane (2 mL). 0.02 ml acetic acid and 0.23 g (1.0 mmol) $NaBH(OAc)_3$ were added. After 3 hours stirring at room temperature the mixture was quenched with sat $NaHCO_3$ solution. Dichloromethane was added. The mixture was filtered through a plug of decalite. The aqueous layer was extracted twice with dichloromethane. The combined extracts were dried over $Na_2SO_4$, filtered and concentrated in vacuo. The crude oil was purified with flash column chromatography on silica gel eluting with a gradient formed from heptane and ethylacetate to provide 0.034 g (11%) of (S,R)-2-[(S,R)-1-(3,4-Dimethoxy-phenyl)-3-(4-fluoro-phenyl)-propylamino]-N-methyl-2-phenyl-acetamide ($1^{st}$ eluting compound) as colorless oil. MS (m/e): 437.5 ($MH^+$) and 0.74 g (22%) of (S,R)-2-[(R,S)-1-(3,4-Dimethoxy-phenyl)-3-(4-fluoro-phenyl)-propylamino]-N-methyl-2-phenyl-acetamide ($2^{nd}$ eluting compound) as colorless oil. MS (m/e): 437.5 ($MH^+$).

Example 145

(S,R)-2-[(S,R)-1-(3,4-Dimethoxy-phenyl)-3-(4-methoxy-phenyl)-propylamino]-N-methyl-2-phenyl-acetamide

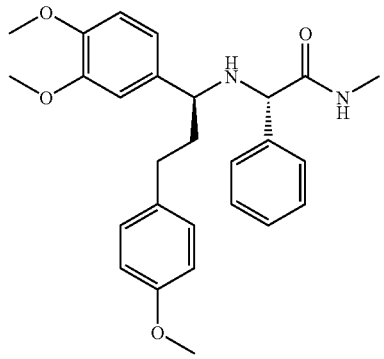

and

Example 146

(S,R)-2-[(R,S)-1-(3,4-Dimethoxy-phenyl)-3-(4-methoxy-phenyl)-propylamino]-N-methyl-2-phenyl-acetamide

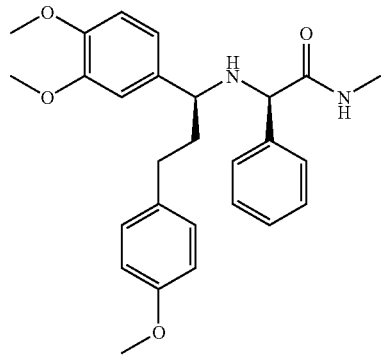

In analogy to the procedure described for the synthesis of examples 139 and 140 (step 2), the title compounds: (S,R)-2-[(S,R)-1-(3,4-Dimethoxy-phenyl)-3-(4-methoxy-phenyl)-propylamino]-N-methyl-2-phenyl-acetamide (MS (m/e): 449.7 ($MH^+$)) and (S,R)-2-[(R,S)-1-(3,4-Dimethoxy-phenyl)-3-(4-methoxy-phenyl)-propylamino]-N-methyl-2-phenyl-acetamide (MS (m/e): 449.7 ($MH^+$)) were prepared from rac-1-(3,4-Dimethoxy-phenyl)-3-(4-methoxy-phenyl)-propylamine (accessed according to the procedure described for examples 126 and 127, step 2 from 2-Methyl-propane-2-sulfinic acid [1-(3,4-dimethoxy-phenyl)-3-(4-methoxy-phenyl)-propyl]-amide).

Example 147

(S,R)-2-[(S,R)-3-(4-Methoxy-phenyl)-1-(4-trifluoromethyl-phenyl)-propylamino]-N-methyl-2-phenyl-acetamide

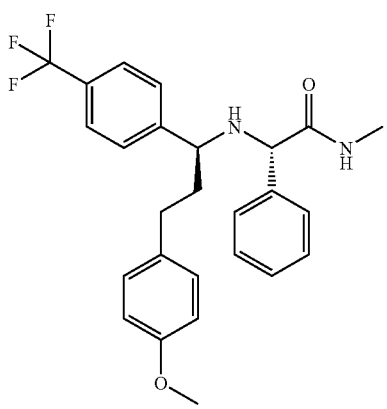

and

Example 148

(S,R)-2-[(R,S)-3-(4-Methoxy-phenyl)-1-(4-trifluoromethyl-phenyl)-propylamino]-N-methyl-2-phenyl-acetamide

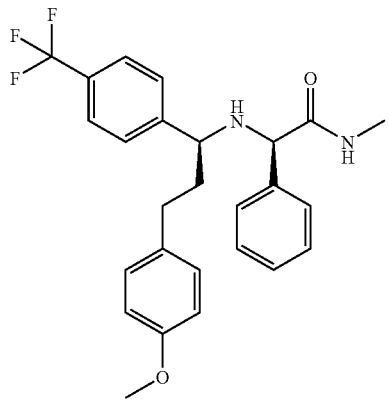

In analogy to the procedure described for the synthesis of examples 139 and 140 (step 2), the title compounds: (S,R)-2-[(S,R)-3-(4-Methoxy-phenyl)-1-(4-trifluoromethyl-phenyl)-propylamino]-N-methyl-2-phenyl-acetamide (MS (m/e): 457.5 (MH$^+$)) and (S,R)-2-[(R,S)-3-(4-Methoxy-phenyl)-1-(4-trifluoromethyl-phenyl)-propylamino]-N-methyl-2-phenyl-acetamide (MS (m/e): 457.5 (MH$^+$)) were prepared from rac-3-(4-Methoxy-phenyl)-1-(4-trifluoromethyl-phenyl)-propylamine (accessed according to the procedure described for examples 126 and 127, step 2 from 2-Methyl-propane-2-sulfinic acid [3-(4-methoxy-phenyl)-1-(4-trifluoromethyl-phenyl)-propyl]-amide).

Example 149

(S,R)-2-[(S,R)-1-(3-Methoxy-phenyl)-3-(4-trifluoromethyl-phenyl)-propylamino]-N-methyl-2-phenyl-acetamide

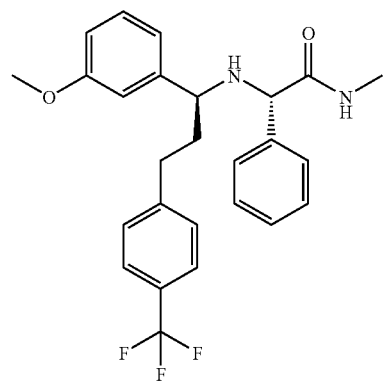

and

Example 150

(S,R)-2-[(R,S)-1-(3-Methoxy-phenyl)-3-(4-trifluoromethyl-phenyl)-propylamino]-N-methyl-2-phenyl-acetamide

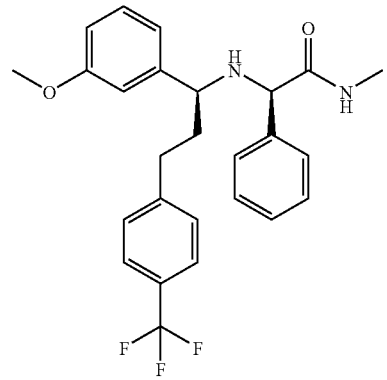

In analogy to the procedure described for the synthesis of examples 139 and 140 (step 2), the title compounds: (S,R)-2-[(S,R)-1-(3-Methoxy-phenyl)-3-(4-trifluoromethyl-phenyl)-propylamino]-N-methyl-2-phenyl-acetamide (MS (m/e): 457.5 (MH$^+$)) and (S,R)-2-[(R,S)-1-(3-Methoxy-phenyl)-3-(4-trifluoromethyl-phenyl)-propylamino]-N-methyl-2-phenyl-acetamide (MS (m/e): 457.5 (MH$^+$)) were prepared from rac-1-(3-Methoxy-phenyl)-3-(4-trifluoromethyl-phenyl)-propylamine (accessed according to the procedure described for examples 126 and 127, step 2 from 2-Methyl-propane-2-sulfinic acid [1-(3-methoxy-phenyl)-3-(4-trifluoromethyl-phenyl)-propyl]-amide.

Example 151

(S,R)-2-[(S,R)-1-(3-Chloro-phenyl)-3-(4-trifluoromethyl-phenyl)-propylamino]-N-methyl-2-phenyl-acetamide

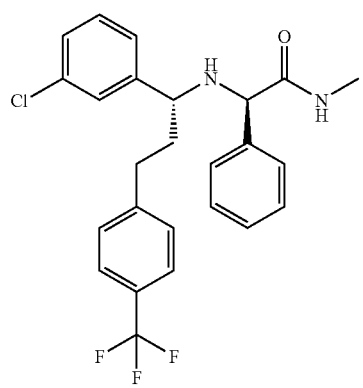

and

Example 152

(S,R)-2-[(R,S)-1-(3-Chloro-phenyl)-3-(4-trifluoromethyl-phenyl)-propylamino]-N-methyl-2-phenyl-acetamide

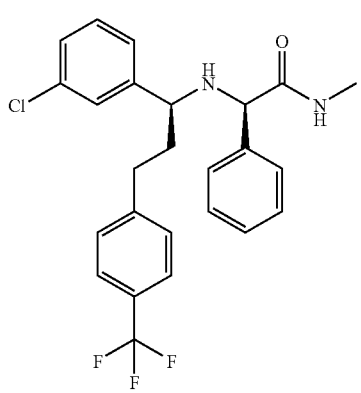

In analogy to the procedure described for the synthesis of examples 143 and 144 (step 3), the title compounds: (S,R)-2-[(S,R)-1-(3-Chloro-phenyl)-3-(4-trifluoromethyl-phenyl)-propylamino]-N-methyl-2-phenyl-acetamide (MS (m/e): 461.7 (MH$^+$)) and (S,R)-2-[(R,S)-1-(3-Chloro-phenyl)-3-(4-trifluoromethyl-phenyl)-propylamino]-N-methyl-2-phenyl-acetamide (MS (m/e): 461.7 (MH$^+$)) were prepared from rac-2-Amino-N-methyl-2-phenyl-acetamide (CAS: 93782-07-1) and 1-(3-Chloro-phenyl)-3-(4-trifluoromethyl-phenyl)-propan-1-one (accessed according to the procedure described for examples 143 and 144, step 2 from (E)-1-(3-Chloro-phenyl)-3-(4-trifluoromethyl-phenyl)-propenone).

Example 153

(S,R)—N-Methyl-2-phenyl-2-[(S,R)-1-(3-trifluoromethoxy-phenyl)-3-(4-trifluoromethyl-phenyl)-propylamino]-acetamide

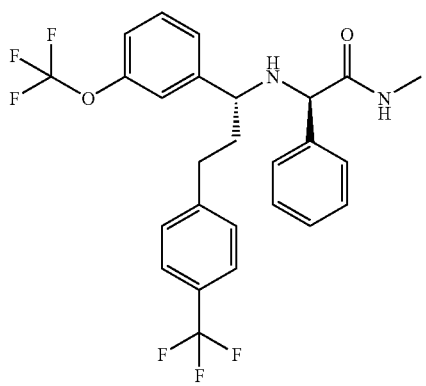

and

Example 154

(S,R)—N-Methyl-2-phenyl-2-[(R,S)-1-(3-trifluoromethoxy-phenyl)-3-(4-trifluoromethyl-phenyl)-propylamino]-acetamide

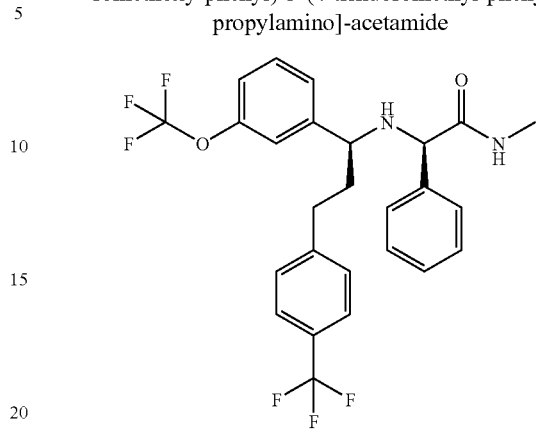

a) Step 1

1-(3-Trifluoromethoxy-phenyl)-3-(4-trifluoromethyl-phenyl)-propan-1-one

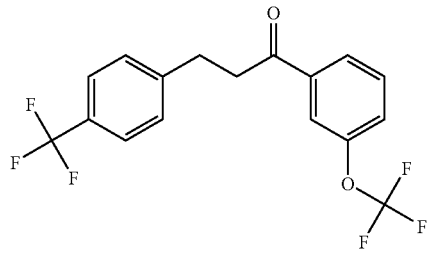

To a solution of 522 mg (2.5 mmol) 3-(trifluoromethoxy) phenylboronic acid in 10 ml toluene under argon at RT, was added successively 29.7 mg (0.04 mmol) Pd(PPh$_3$)$_2$Cl, 776.5 mg (3.2 mmol) K$_3$PO$_4$.H$_2$O and 500 mg (2.1 mmol) 3-(4-Trifluoromethyl-phenyl)-propionyl chloride (CAS: 539855-79-3). The reaction mixture was heated at 110° C. for 3 h, cooled to RT and ethyl acetate was added. The solution was washed successively with NaHCO$_3$ sat., water and brine. The organic phase was dried over Na$_2$SO$_4$ and evaporated. The crude oil was purified with flash column chromatography on silica eluting with a gradient formed from heptane and ethylacetate to provide 0.44 g (58%) of the title compound as colorless oil. MS (m/e): 363.0 (MH$^+$).

b) Step 2

In analogy to the procedure described for the synthesis of examples 143 and 144 (step 3), the title compounds (S,R)—N-Methyl-2-phenyl-2-[(S,R)-1-(3-trifluoromethoxy-phenyl)-3-(4-trifluoromethyl-phenyl)-propylamino]-acetamide (MS (m/e): 511.7 (MH$^+$)) and (S,R)—N-Methyl-2-phenyl-2-[(R,S)-1-(3-trifluoromethoxy-phenyl)-3-(4-trifluoromethyl-phenyl)-propylamino]-acetamide (MS (m/e): 511.7 (MH$^+$)) were prepared from rac-2-Amino-N-methyl-2-phenyl-acetamide (CAS: 93782-07-1) and 1-(3-Trifluoromethoxy-phenyl)-3-(4-trifluoromethyl-phenyl)-propan-1-one.

Example 155

(S,R)-2-[(S,R)-1-Benzo[1,3]dioxol-5-yl-3-(4-trifluoromethyl-phenyl)-propylamino]-N-methyl-2-phenyl-acetamide

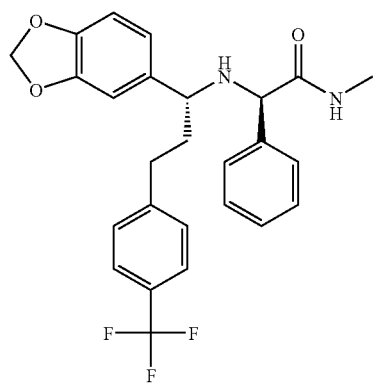

and

Example 156

(S,R)-2-[(R,S)-1-Benzo[1,3]dioxol-5-yl-3-(4-trifluoromethyl-phenyl)-propylamino]-N-methyl-2-phenyl-acetamide

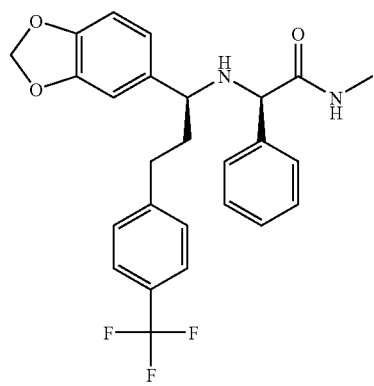

In analogy to the procedure described for the synthesis of examples 143 and 144 (step 3), the title compounds: (S,R)-2-[(S,R)-1-Benzo[1,3]dioxol-5-yl-3-(4-trifluoromethyl-phenyl)-propylamino]-N-methyl-2-phenyl-acetamide (MS (m/e): 471.1 (MH$^+$)) and (S,R)-2-[(R,S)-1-Benzo[1,3]dioxol-5-yl-3-(4-trifluoromethyl-phenyl)-propylamino]-N-methyl-2-phenyl-acetamide (MS (m/e): 471.1 (MH$^+$)) were prepared from rac-2-Amino-N-methyl-2-phenyl-acetamide (CAS: 93782-07-1) and 1-Benzo[1,3]dioxol-5-yl-3-(4-trifluoromethyl-phenyl)-propan-1-one (accessed according to the procedure described for examples 153 and 154, step 1 from 3,4-(Methylenedioxy)phenylboronic acid).

Example 157

(S,R)—N-Methyl-2-phenyl-2-[(S,R)-1-p-tolyl-3-(4-trifluoromethyl-phenyl)-propylamino]-acetamide

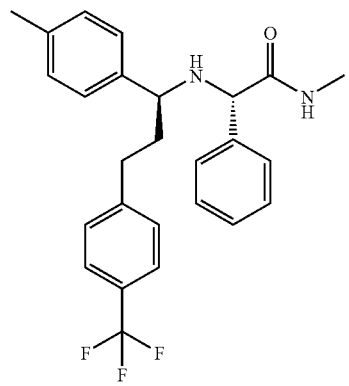

and

Example 158

(S,R)—N-Methyl-2-phenyl-2-[(R,S)-1-p-tolyl-3-(4-trifluoromethyl-phenyl)-propylamino]-acetamide

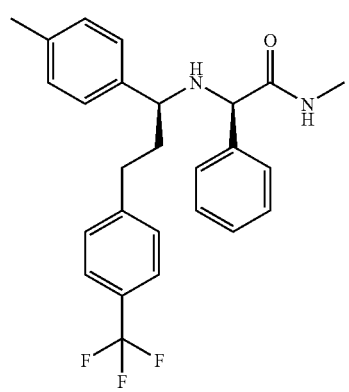

In analogy to the procedure described for the synthesis of examples 139 and 140 (step 2), the title compounds: (S,R)—N-Methyl-2-phenyl-2-[(S,R)-1-p-tolyl-3-(4-trifluoromethyl-phenyl)-propylamino]-acetamide (MS (m/e): 441.3 (MH$^+$)) and (S,R)—N-Methyl-2-phenyl-2-[(R,S)-1-p-tolyl-3-(4-trifluoromethyl-phenyl)-propylamino]-acetamide (MS (m/e): 441.3 (MH$^+$)) were prepared from rac-1-p-Tolyl-3-(4-trifluoromethyl-phenyl)-propylamine (accessed according to the procedure described for examples 126 and 127, step 2 from 2-Methyl-propane-2-sulfinic acid [1-p-tolyl-3-(4-trifluoromethyl-phenyl)-propyl]-amide)

Example 159

(S,R)-2-[(S,R)-1-(6-Methoxy-pyridin-3-yl)-3-(4-trifluoromethyl-phenyl)-propylamino]-N-methyl-2-phenyl-acetamide

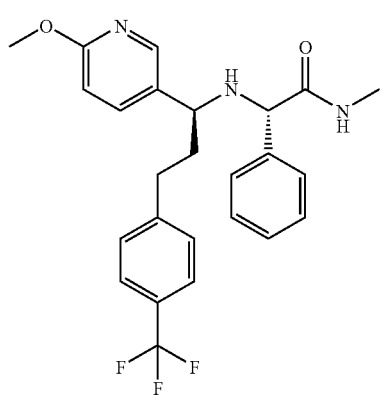

and

Example 160

(S,R)-2-[(R,S)-1-(6-Methoxy-pyridin-3-yl)-3-(4-trifluoromethyl-phenyl)-propylamino]-N-methyl-2-phenyl-acetamide

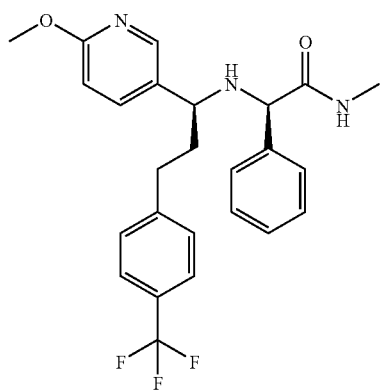

In analogy to the procedure described for the synthesis of examples 139 and 140 (step 2), the title compounds: (S,R)-2-[(S,R)-1-(6-Methoxy-pyridin-3-yl)-3-(4-trifluoromethyl-phenyl)-propylamino]-N-methyl-2-phenyl-acetamide (MS (m/e): 458.3 (MH$^+$)) and (S,R)-2-[(R,S)-1-(6-Methoxy-pyridin-3-yl)-3-(4-trifluoromethyl-phenyl)-propylamino]-N-methyl-2-phenyl-acetamide (MS (m/e): 458.3 (MH$^+$)) were prepared from rac-1-(6-Methoxy-pyridin-3-yl)-3-(4-trifluoromethyl-phenyl)-propylamine (accessed according to the procedure described for examples 126 and 127, step 2 from 2-Methyl-propane-2-sulfinic acid [1-(6-methoxy-pyridin-3-yl)-3-(4-trifluoromethyl-phenyl)-propyl]-amide).

Example 161

(S,R)-2-[(R,S)-1-(4-Fluoro-phenyl)-3-(4-methoxy-phenyl)-propylamino]-N-methyl-2-phenyl-acetamide

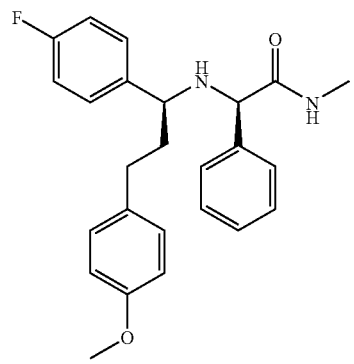

In analogy to the procedure described for the synthesis examples 139 and 140 (step 2), the title compound: (S,R)-2-[(R,S)-1-(4-Fluoro-phenyl)-3-(4-methoxy-phenyl)-propylamino]-N-methyl-2-phenyl-acetamide (MS (m/e): 407.5 (MH$^+$)) was prepared from rac-1-(4-Fluoro-phenyl)-3-(4-methoxy-phenyl)-propylamine (accessed according to the procedure described for examples 126 and 127, step 2 from 2-Methyl-propane-2-sulfinic acid [1-(4-fluoro-phenyl)-3-(4-methoxy-phenyl)-propyl]-amide).

Example 162

(S)-2-[(R)-3-(4-Chloro-phenyl)-1-(3,4-dimethoxy-phenyl)-propylamino]-N-methyl-2-phenyl-acetamide

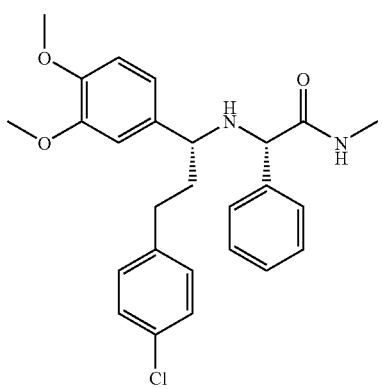

and

Example 163

(R)-2-[(S)-3-(4-Chloro-phenyl)-1-(3,4-dimethoxy-phenyl)-propylamino]-N-methyl-2-phenyl-acetamide

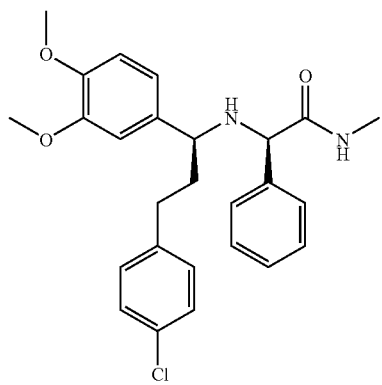

(S,R)-2-[(R,S)-3-(4-Chloro-phenyl)-1-(3,4-dimethoxy-phenyl)-propylamino]-N-methyl-2-phenyl-acetamide (Example 140) was separated on chiral phase HPLC (chialpack AD column) to provide the title compounds: (S)-2-[(R)-3-(4-Chloro-phenyl)-1-(3,4-dimethoxy-phenyl)-propylamino]-N-methyl-2-phenyl-acetamide (MS (m/e): 453.1 (MH$^+$)) and (R)-2-[(S)-3-(4-Chloro-phenyl)-1-(3,4-dimethoxy-phenyl)-propylamino]-N-methyl-2-phenyl-acetamide (MS (m/e): 453.1 (MH$^+$)) as colorless oil.

Example 164

(S,R)—N-Methyl-2-phenyl-2-[(S,R)-1-m-tolyl-3-(4-trifluoromethyl-phenyl)-propylamino]-acetamide

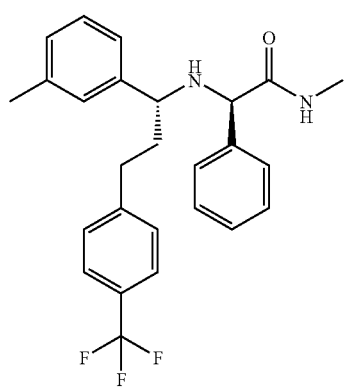

and

Example 165

(S,R)—N-Methyl-2-phenyl-2-[(R,S)-1-m-tolyl-3-(4-trifluoromethyl-phenyl)-propylamino]-acetamide

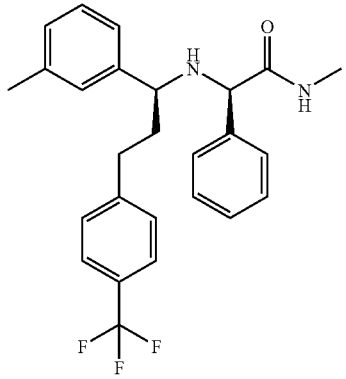

a) Step 1

N-Methoxy-N-methyl-3-(4-trifluoromethyl-phenyl)-propionamide

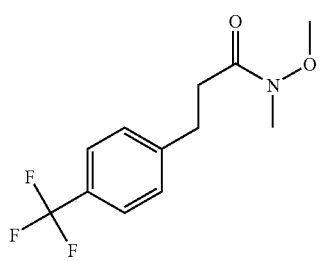

To a mixture of 3.034 g (13 mmol) 3-(4-Trifluoromethyl-phenyl)-propionyl chloride (CAS: 539855-79-3) and 1.4 g (14.1 mmol) N,O-Dimethylhydroxylamine hydrochloride in 55 mLl chloroform, under argon, was added dropwise 2.28 mL (28 mmol) pyridine at 0° C. The solution was allowed to warm to RT and was stirred for 2 hour. The mixture was washed with 1N HCl (50 mL). The organic layer was washed once with 1N NaOH. The organic phases was dried over Na$_2$SO$_4$, filtered and the solvent was removed in vacuo. The crude oil was purified with flash column chromatography on silica gel eluting with a gradient formed from heptane and ethylacetate to provide 2.1 g (63%) of title compound as colorless oil. MS (m/e): 262.0 (MH$^+$).

b) Step 2

1-m-Tolyl-3-(4-trifluoromethyl-phenyl)-propan-1-one

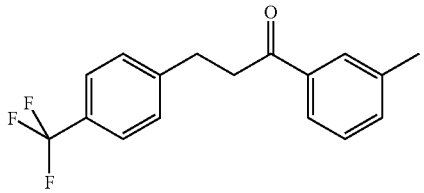

To a solution of 0.4 g (1.5 mmol) N-Methoxy-N-methyl-3-(4-trifluoromethyl-phenyl)-propionamide in 7 mL THF under argon at 0° C., was added dropwise 3.062 ml (3.1 mmol) m-Tolylmagnesiumbromid (1M in THF). The reaction mixture was stirred for 15 minutes at 0° C. and at RT for 50 minutes, cooled to 0° C. and acidified with 1N HCl to pH 1-2. Water and ethyl acetate were added and the water phase was extracted twice with ethyl acetate. The organic phases were dried over $Na_2SO_4$, filtered and the solvent was removed in vacuo. The crude oil was purified with flash column chromatography on silica gel eluting with a gradient formed from heptane and ethylacetate to provide 0.36 g (81%) of title compound as colorless oil. MS (m/e): 293.0 ($MH^+$).

c) Step 3

In analogy to the procedure described for the synthesis of examples 143 and 144 (step 3), the title compounds: (S,R)—N-Methyl-2-phenyl-2-[(S,R)-1-m-tolyl-3-(4-trifluoromethyl-phenyl)-propylamino]-acetamide (MS (m/e): 441.1 ($MH^+$)) and (S,R)—N-Methyl-2-phenyl-2-[(R,S)-1-m-tolyl-3-(4-trifluoromethyl-phenyl)-propylamino]-acetamide (MS (m/e): 441.1 ($MH^+$)) were prepared from rac-2-Amino-N-methyl-2-phenyl-acetamide (CAS: 93782-07-1) and 1-m-Tolyl-3-(4-trifluoromethyl-phenyl)-propan-1-one.

Example 166

(S,R)-2-[(S,R)-1-(3,4-Difluoro-phenyl)-3-(4-trifluoromethyl-phenyl)-propylamino]-N-methyl-2-phenyl-acetamide

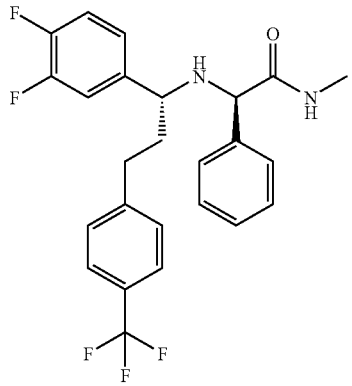

and

Example 167

(S,R)-2-[(R,S)-1-(3,4-Difluoro-phenyl)-3-(4-trifluoromethyl-phenyl)-propylamino]-N-methyl-2-phenyl-acetamide

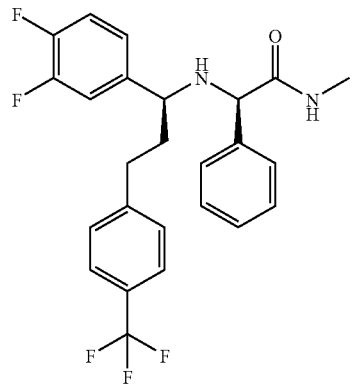

In analogy to the procedure described for the synthesis of examples 143 and 144 (step 3), the title compounds: (S,R)-2-[(S,R)-1-(3,4-Difluoro-phenyl)-3-(4-trifluoromethyl-phenyl)-propylamino]-N-methyl-2-phenyl-acetamide (MS (m/e): 463.0 ($MH^+$)) and (S,R)-2-[(R,S)-1-(3,4-Difluoro-phenyl)-3-(4-trifluoromethyl-phenyl)-propylamino]-N-methyl-2-phenyl-acetamide (MS (m/e): 463.0 ($MH^+$)) were prepared from rac-2-Amino-N-methyl-2-phenyl-acetamide (CAS: 93782-07-1) and 1-(3,4-Difluoro-phenyl)-3-(4-trifluoromethyl-phenyl)-propan-1-one (accessed according to the procedure described for examples 164 and 165, step 2 from N-Methoxy-N-methyl-3-(4-trifluoromethyl-phenyl)-propionamide and 3,4-difluorophenyl magnesium bromide).

Example 168

(S,R)-2-[(S,R)-1-(6-Chloro-pyridin-3-yl)-3-(4-trifluoromethyl-phenyl)-propylamino]-N-methyl-2-phenyl-acetamide

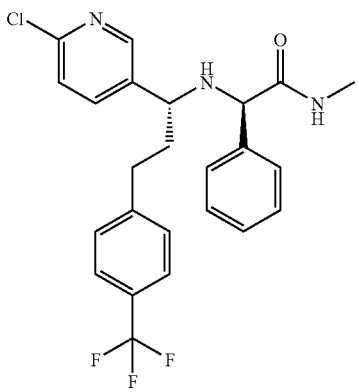

and

Example 169

(S,R)-2-[(R,S)-1-(6-Chloro-pyridin-3-yl)-3-(4-trifluoromethyl-phenyl)-propylamino]-N-methyl-2-phenyl-acetamide

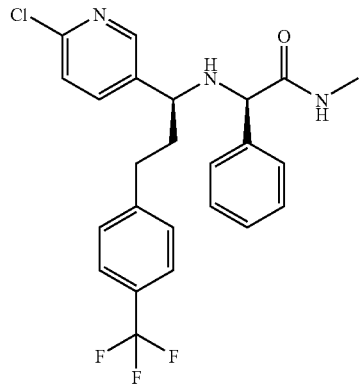

In analogy to the procedure described for the synthesis of examples 143 and 144 (step 3), the title compounds: (S,R)-2-[(S,R)-1-(6-Chloro-pyridin-3-yl)-3-(4-trifluoromethyl-phenyl)-propylamino]-N-methyl-2-phenyl-acetamide (MS (m/e): 462.0 (MH$^+$)) and (S,R)-2-[(R,S)-1-(6-Chloro-pyridin-3-yl)-3-(4-trifluoromethyl-phenyl)-propylamino]-N-methyl-2-phenyl-acetamide (MS (m/e): 462.0 (MH$^+$)) were prepared from rac-2-Amino-N-methyl-2-phenyl-acetamide (CAS: 93782-07-1) and 1-(6-Chloro-pyridin-3-yl)-3-(4-trifluoromethyl-phenyl)-propan-1-one (accessed according to the procedure described for examples 143 and 144, step 2 from (E)-1-(6-Chloro-pyridin-3-yl)-3-(4-trifluoromethyl-phenyl)-propenone).

Example 170

(S,R)-2-[(S,R)-1-(3,4-Dimethoxy-phenyl)-3-(6-trifluoromethyl-pyridin-3-yl)-propylamino]-N-methyl-2-phenyl-acetamide

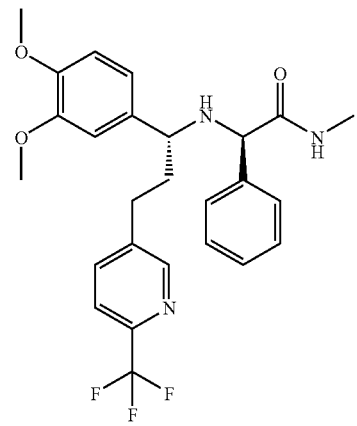

and

Example 171

(S,R)-2-[(R,S)-1-(3,4-Dimethoxy-phenyl)-3-(6-trifluoromethyl-pyridin-3-yl)-propylamino]-N-methyl-2-phenyl-acetamide

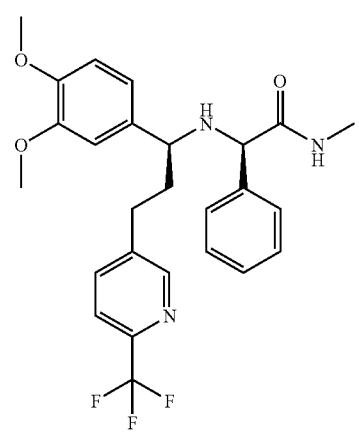

In analogy to the procedure described for the synthesis of examples 143 and 144 (step 3), the title compounds: (S,R)-2-[(S,R)-1-(3,4-Dimethoxy-phenyl)-3-(6-trifluoromethyl-pyridin-3-yl)-propylamino]-N-methyl-2-phenyl-acetamide (MS (m/e): 488.0 (MH$^+$)) and (S,R)-2-[(R,S)-1-(3,4-Dimethoxy-phenyl)-3-(6-trifluoromethyl-pyridin-3-yl)-propylamino]-N-methyl-2-phenyl-acetamide (MS (m/e): 488.0 (MH$^+$)) were prepared from rac-2-Amino-N-methyl-2-phenyl-acetamide (CAS: 93782-07-1) and 1-(3,4-Dimethoxy-phenyl)-3-(6-trifluoromethyl-pyridin-3-yl)-propan-1-one (accessed according to the procedure described for examples 143 and 144, step 2 from (E)-1-(3,4-Dimethoxy-phenyl)-3-(6-trifluoromethyl-pyridin-3-yl)-propenone).

Example 172

(S,R)—N-Methyl-2-phenyl-2-[(S,R)-1-o-tolyl-3-(4-trifluoromethyl-phenyl)-propylamino]-acetamide

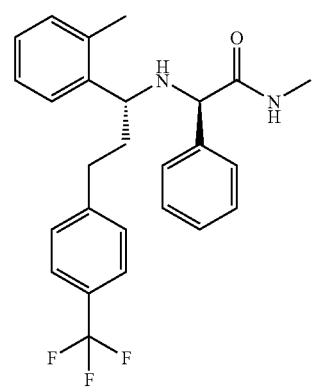

and

Example 173

(S,R)—N-Methyl-2-phenyl-2-[(R,S)-1-o-tolyl-3-(4-trifluoromethyl-phenyl)-propylamino]-acetamide

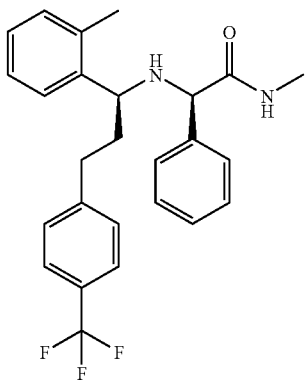

In analogy to the procedure described for the synthesis of examples 143 and 144 (step 3), the title compounds: (S,R)—N-Methyl-2-phenyl-2-[(S,R)-1-o-tolyl-3-(4-trifluoromethyl-phenyl)-propylamino]-acetamide (MS (m/e): 441.0 (MH$^+$)) and (S,R)—N-Methyl-2-phenyl-2-[(R,S)-1-O—tolyl-3-(4-trifluoromethyl-phenyl)-propylamino]-acetamide (MS (m/e): 441.0 (MH$^+$)) were prepared from rac-2-Amino-N-methyl-2-phenyl-acetamide (CAS: 93782-07-1) and 1-o-Tolyl-3-(4-trifluoromethyl-phenyl)-propan-1-one (accessed according to the procedure described for examples 164 and 165, step 2 from N-Methoxy-N-methyl-3-(4-trifluoromethyl-phenyl)-propionamide and o-tolyl magnesium bromide).

Example 174

(R)—N-Methyl-2-phenyl-2-[(S)-1-(3-trifluoromethoxy-phenyl)-3-(4-trifluoromethyl-phenyl)-propylamino]-acetamide hydrochloride

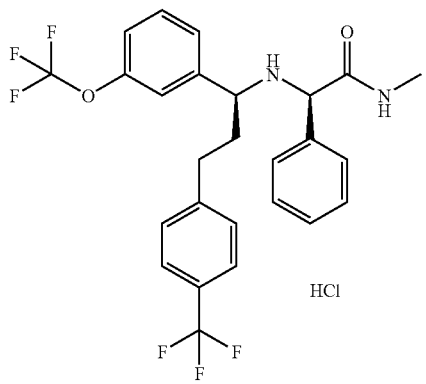

and

Example 175

(S)—N-Methyl-2-phenyl-2-[(R)-1-(3-trifluoromethoxy-phenyl)-3-(4-trifluoromethyl-phenyl)-propylamino]-acetamide hydrochloride

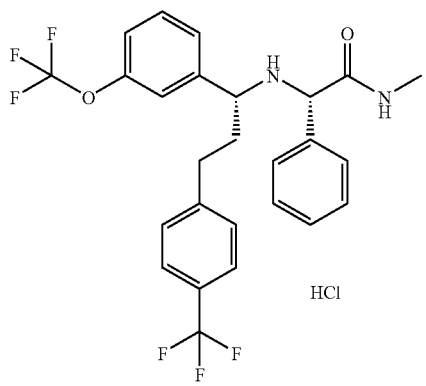

(S,R)—N-Methyl-2-phenyl-2-[(R,S)-1-(3-trifluoromethoxy-phenyl)-3-(4-trifluoromethyl-phenyl)-propylamino]-acetamide (Example 154) was separated on chiral phase HPLC (Chiralpak AD column) and each obtained enantiomer was treated with HCl methanol to provide after evaporation the title compounds: (R)—N-Methyl-2-phenyl-2-[(S)-1-(3-trifluoromethoxy-phenyl)-3-(4-trifluoromethyl-phenyl)-propylamino]-acetamide hydrochloride (MS (m/e): 511.0 (MH$^+$)) and (S)—N-Methyl-2-phenyl-2-[(R)-1-(3-trifluoromethoxy-phenyl)-3-(4-trifluoromethyl-phenyl)-propylamino]-acetamide hydrochloride (MS (m/e): 511.0 (MH$^+$)) as white solid.

Example 176

(S,R)-2-[(S,R)-1-(4-Chloro-3-methoxy-phenyl)-3-(4-trifluoromethyl-phenyl)-propylamino]-N-methyl-2-phenyl-acetamide

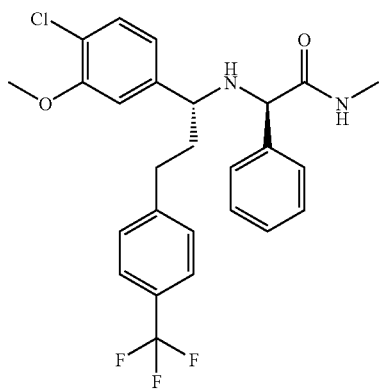

and

Example 177

(S,R)-2-[(R,S)-1-(4-Chloro-3-methoxy-phenyl)-3-(4-trifluoromethyl-phenyl)-propylamino]-N-methyl-2-phenyl-acetamide

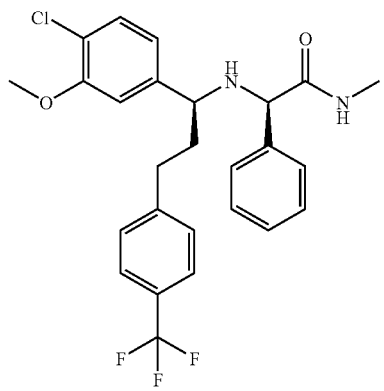

In analogy to the procedure described for the synthesis of examples 143 and 144 (step 3), the title compounds: (S,R)-2-[(S,R)-1-(4-Chloro-3-methoxy-phenyl)-3-(4-trifluoromethyl-phenyl)-propylamino]-N-methyl-2-phenyl-acetamide (MS (m/e): 491.4 (MH$^+$)) and (S,R)-2-[(R,S)-1-(4-Chloro-3-methoxy-phenyl)-3-(4-trifluoromethyl-phenyl)-propylamino]-N-methyl-2-phenyl-acetamide (MS (m/e): 491.3 (MH$^+$)) were prepared from rac-2-Amino-N-methyl-2-phenyl-acetamide (CAS: 93782-07-1) and 1-(4-Chloro-3-methoxy-phenyl)-3-(4-trifluoromethyl-phenyl)-propan-1-one (accessed according to the procedure described for examples 164 and 165, step 2 from N-Methoxy-N-methyl-3-(4-trifluoromethyl-phenyl)-propionamide and 4-chloro-3-methoxy-phenyl magnesium bromide).

Example 178

(S,R)-2-[(R,S)-1-(2-Methoxy-phenyl)-3-(4-trifluoromethyl-phenyl)-propylamino]-N-methyl-2-phenyl-acetamide

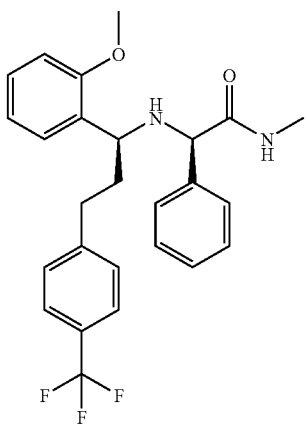

In analogy to the procedure described for the synthesis of examples 143 and 144 (step 3), the title compound: (S,R)-2-[(R,S)-1-(2-Methoxy-phenyl)-3-(4-trifluoromethyl-phenyl)-propylamino]-N-methyl-2-phenyl-acetamide (MS (m/e): 457.3 (MH$^+$)) was prepared from rac-2-Amino-N-methyl-2-phenyl-acetamide (CAS: 93782-07-1) and 1-(2-Methoxy-phenyl)-3-(4-trifluoromethyl-phenyl)-propan-1-one (accessed according to the procedure described for examples 164 and 165, step 2 from N-Methoxy-N-methyl-3-(4-trifluoromethyl-phenyl)-propionamide and 2-methoxy-phenyl magnesium bromide).

Example 179

(S,R)-2-[(R,S)-1-(2-Methoxy-pyridin-3-yl)-3-(4-trifluoromethyl-phenyl)-propylamino]-N-methyl-2-phenyl-acetamide

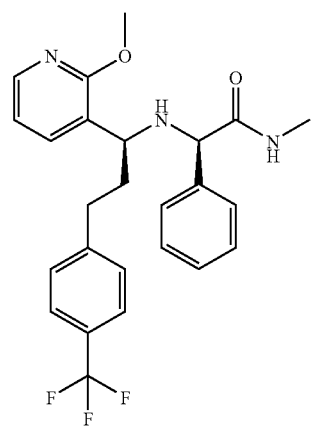

In analogy to the procedure described for the synthesis of examples 143 and 144 (step 3), the title compound: (S,R)-2-[(R,S)-1-(2-Methoxy-pyridin-3-yl)-3-(4-trifluoromethyl-phenyl)-propylamino]-N-methyl-2-phenyl-acetamide (MS (m/e): 458.4 (MH$^+$)) was prepared from rac-2-Amino-N-methyl-2-phenyl-acetamide (CAS: 93782-07-1) and 1-(2-Methoxy-pyridin-3-yl)-3-(4-trifluoromethyl-phenyl)-propan-1-one (accessed according to the procedure described for examples 164 and 165, step 2 from 2,N-Dimethoxy-N-methyl-nicotinamide and p-trifluoromethylphenylethyl magnesium bromide.

Example 180

(R)—N-Methyl-2-phenyl-2-[(R)-1-(3-trifluoromethoxy-phenyl)-3-(4-trifluoromethyl-phenyl)-propylamino]-acetamide

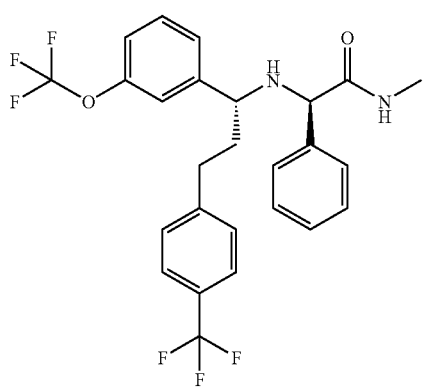

and

Example 181

(S)—N-Methyl-2-phenyl-2-[(S)-1-(3-trifluoromethoxy-phenyl)-3-(4-trifluoromethyl-phenyl)-propylamino]-acetamide

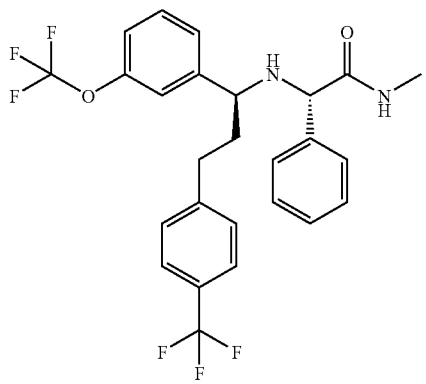

(S,R)—N-Methyl-2-phenyl-2-[(S,R)-1-(3-trifluoromethoxy-phenyl)-3-(4-trifluoromethyl-phenyl)-propylamino]-acetamide (Example 153) was separated on chiral phase HPLC (Chiralcel OD column) to provide the title compounds: (R)—N-Methyl-2-phenyl-2-[(R)-1-(3-trifluoromethoxy-phenyl)-3-(4-trifluoromethyl-phenyl)-propylamino]-acetamide(MS (m/e): 511.3 (MH$^+$)) and (S)—N-Methyl-2-phenyl-2-[(S)-1-(3-trifluoromethoxy-phenyl)-3-(4-trifluoromethyl-phenyl)-propylamino]-acetamide (MS (m/e): 511.3 (MH$^+$)) as colorless oil.

Example 182

(R)-2-[(R)-3-(4-Chloro-phenyl)-1-(3,4-dimethoxy-phenyl)-propylamino]-N-methyl-2-phenyl-acetamide

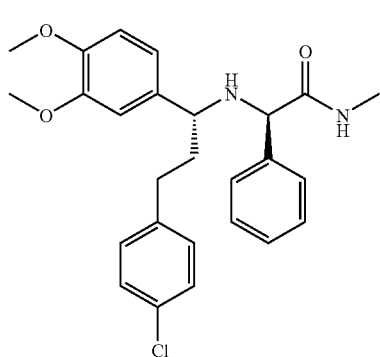

and

Example 183

(S)-2-[(S)-3-(4-Chloro-phenyl)-1-(3,4-dimethoxy-phenyl)-propylamino]-N-methyl-2-phenyl-acetamide

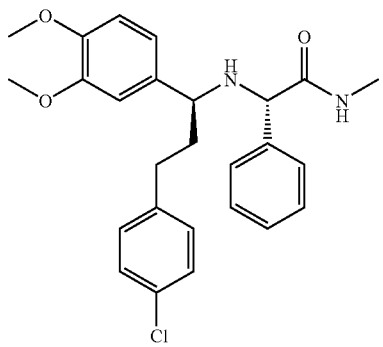

(R,S)-2-[(R,S)-3-(4-Chloro-phenyl)-1-(3,4-dimethoxy-phenyl)-propylamino]-N-methyl-2-phenyl-acetamide (Example 139) was separated on chiral phase HPLC (Chiralpak AD column) to provide the title compounds: (R)-2-[(R)-3-(4-Chloro-phenyl)-1-(3,4-dimethoxy-phenyl)-propylamino]-N-methyl-2-phenyl-acetamide (MS (m/e): 453.1 (MH$^+$)) and (S)-2-[(S)-3-(4-Chloro-phenyl)-1-(3,4-dimethoxy-phenyl)-propylamino]-N-methyl-2-phenyl-acetamide (MS (m/e): 453.2 (MH$^+$)) as colorless oil.

Example 184

(R)—N-Methyl-2-phenyl-2-[(S)-1-m-tolyl-3-(4-trifluoromethyl-phenyl)-propylamino]-acetamide hydrochloride

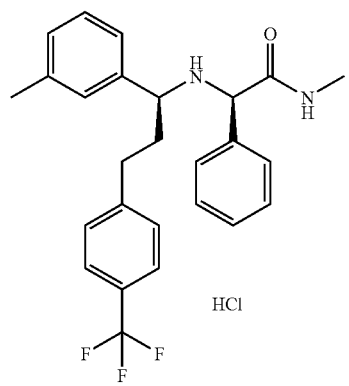

and

Example 185

(S)—N-Methyl-2-phenyl-2-[(R)-1-m-tolyl-3-(4-trifluoromethyl-phenyl)-propylamino]-acetamide hydrochloride

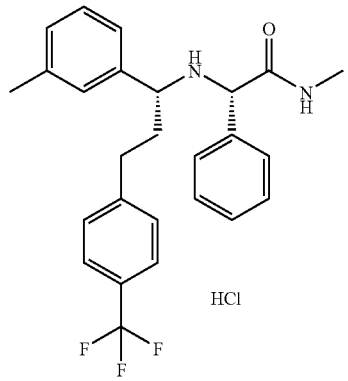

(S,R)—N-Methyl-2-phenyl-2-[(R,S)-1-m-tolyl-3-(4-trifluoromethyl-phenyl)-propylamino]-acetamide (Example 165) was separated on chiral phase HPLC (Chiralcel OD column) and each obtained enantiomer was treated with HCl methanol to provide after evaporation the title compounds: (R)—N-Methyl-2-phenyl-2-[(S)-1-m-tolyl-3-(4-trifluoromethyl-phenyl)-propylamino]-acetamide hydrochloride (MS (m/e): 441.2 (MH$^+$)) and (S)—N-Methyl-2-phenyl-2-[(R)-1-m-tolyl-3-(4-trifluoromethyl-phenyl)-propylamino]-acetamide hydrochloride (MS (m/e): 441.2 (MH$^+$)) as white solid.

Example 187

(S,R)-2-[(R,S)-1-(2-Fluoro-phenyl)-3-(4-trifluoromethyl-phenyl)-propylamino]-N-methyl-2-phenyl-acetamide

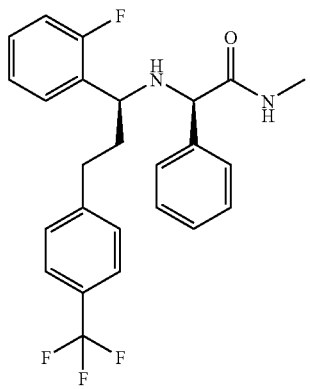

In analogy to the procedure described for the synthesis of examples 143 and 144 (step 3), the title compounds: (S,R)-2-[(S,R)-1-(2-Fluoro-phenyl)-3-(4-trifluoromethyl-phenyl)-propylamino]-N-methyl-2-phenyl-acetamide (MS (m/e): 445.1 (MH$^+$)) and (S,R)-2-[(R,S)-1-(2-Fluoro-phenyl)-3-(4-trifluoromethyl-phenyl)-propylamino]-N-methyl-2-phenyl-acetamide (MS (m/e): 445.1 (MH$^+$)) were prepared from rac-2-Amino-N-methyl-2-phenyl-acetamide (CAS: 93782-07-1) and 1-(2-Fluoro-phenyl)-3-(4-trifluoromethyl-phenyl)-propan-1-one (accessed according to the procedure described for example 153 and 154, step 1 from 2-fluorobenzeneboronic acid.

Example 186

(S,R)-2-[(S,R)-1-(2-Fluoro-phenyl)-3-(4-trifluoromethyl-phenyl)-propylamino]-N-methyl-2-phenyl-acetamide

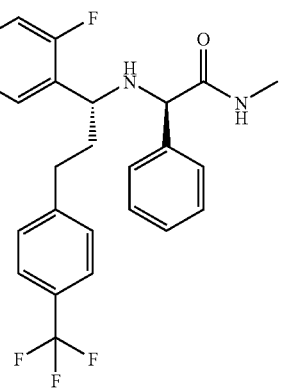

and

Example 188

(S,R)-2-[(S,R)-1-(3-Chloro-4-fluoro-phenyl)-3-(4-trifluoromethyl-phenyl)-propylamino]-N-methyl-2-phenyl-acetamide

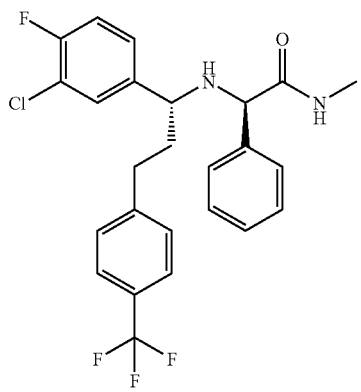

and

Example 189

(S,R)-2-[(R,S)-1-(3-Chloro-4-fluoro-phenyl)-3-(4-trifluoromethyl-phenyl)-propylamino]-N-methyl-2-phenyl-acetamide

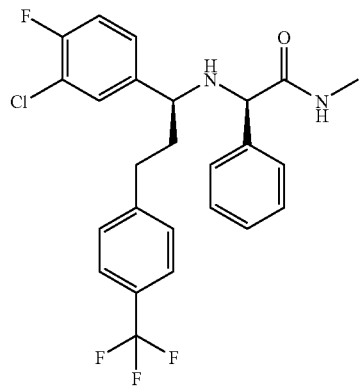

In analogy to the procedure described for the synthesis of examples 143 and 144 (step 3), the title compounds: (S,R)-2-[(S,R)-1-(3-Chloro-4-fluoro-phenyl)-3-(4-trifluoromethyl-phenyl)-propylamino]-N-methyl-2-phenyl-acetamide (MS (m/e): 479.0 (MH$^+$)) and (S,R)-2-[(R,S)-1-(3-Chloro-4-fluoro-phenyl)-3-(4-trifluoromethyl-phenyl)-propylamino]-N-methyl-2-phenyl-acetamide (MS (m/e): 479.0 (MH$^+$)) were prepared from rac-2-Amino-N-methyl-2-phenyl-acetamide (CAS: 93782-07-1) and 1-(3-Chloro-4-fluoro-phenyl)-3-(4-trifluoromethyl-phenyl)-propan-1-one (accessed according to the procedure described for examples 153 and 154, step 1 from 3-chloro-4 fluorobenzene boronic acid).

Example 190

(S,R)-2-[(S,R)-1-(4-Chloro-3-methyl-phenyl)-3-(4-trifluoromethyl-phenyl)-propylamino]-N-methyl-2-phenyl-acetamide

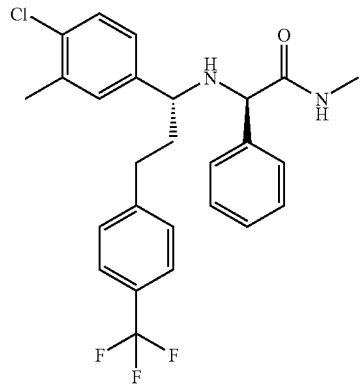

and

Example 191

(S,R)-2-[(R,S)-1-(4-Chloro-3-methyl-phenyl)-3-(4-trifluoromethyl-phenyl)-propylamino]-N-methyl-2-phenyl-acetamide

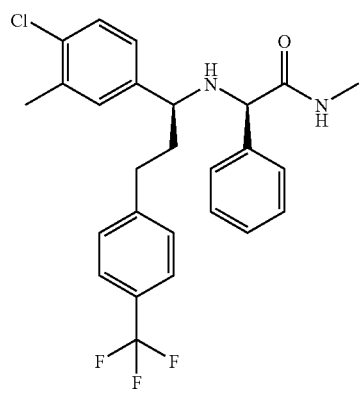

In analogy to the procedure described for the synthesis of examples 143 and 144 (step 3), the title compounds: (S,R)-2-[(S,R)-1-(4-Chloro-3-methyl-phenyl)-3-(4-trifluoromethyl-phenyl)-propylamino]-N-methyl-2-phenyl-acetamide (MS (m/e): 475.0 (MH$^+$)) and (S,R)-2-[(R,S)-1-(4-Chloro-3-methyl-phenyl)-3-(4-trifluoromethyl-phenyl)-propylamino]-N-methyl-2-phenyl-acetamide (MS (m/e): 474.9 (MH$^+$)) were prepared from rac-2-Amino-N-methyl-2-phenyl-acetamide (CAS: 93782-07-1) and 1-(4-Chloro-3-methyl-phenyl)-3-(4-trifluoromethyl-phenyl)-propan-1-one (accessed according to the procedure described for examples 153 and 154, step 1 from 4-chloro-m-toluene boronic acid).

Example 192

(S,R)-2-[(S,R)-1-(2-Methoxy-pyridin-4-yl)-3-(4-trifluoromethyl-phenyl)-propylamino]-N-methyl-2-phenyl-acetamide

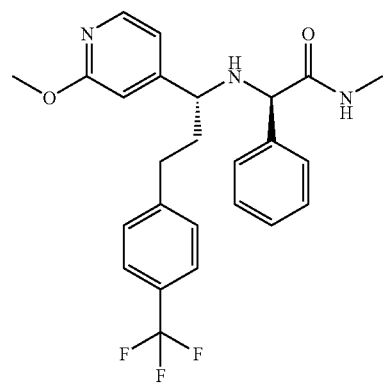

and

Example 193

(S,R)-2-[(R,S)-1-(2-Methoxy-pyridin-4-yl)-3-(4-trifluoromethyl-phenyl)-propylamino]-N-methyl-2-phenyl-acetamide

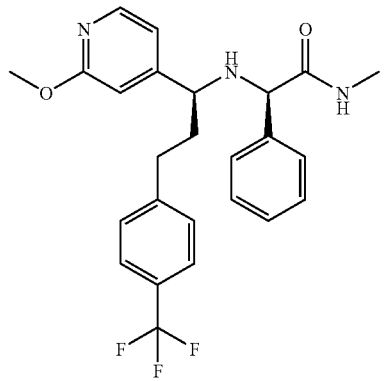

In analogy to the procedure described for the synthesis of examples 143 and 144 (step 3), the title compounds: (S,R)-2-[(S,R)-1-(2-Methoxy-pyridin-4-yl)-3-(4-trifluoromethyl-phenyl)-propylamino]-N-methyl-2-phenyl-acetamide (MS (m/e): 458.3 (MH$^+$)) and (S,R)-2-[(R,S)-1-(2-Methoxy-pyridin-4-yl)-3-(4-trifluoromethyl-phenyl)-propylamino]-N-methyl-2-phenyl-acetamide (MS (m/e): 458.3 (MH$^+$)) were prepared from rac-2-Amino-N-methyl-2-phenyl-acetamide (CAS: 93782-07-1) and 1-(2-Methoxy-pyridin-4-yl)-3-(4-trifluoromethyl-phenyl)-propan-1-one (accessed according to the procedure described for examples 164 and 165, step 2 from 2,N-Dimethoxy-N-methyl-isonicotinamide and p-trifluoromethylphenylethyl magnesium bromide).

Example 194

(R)-2-[(S)-1-(2-Methoxy-phenyl)-3-(4-trifluoromethyl-phenyl)-propylamino]-N-methyl-2-phenyl-acetamide

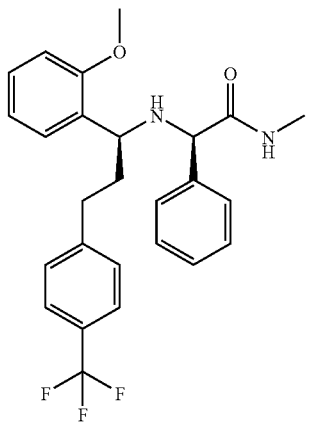

and

Example 195

(S)-2-[(R)-1-(2-Methoxy-phenyl)-3-(4-trifluoromethyl-phenyl)-propylamino]-N-methyl-2-phenyl-acetamide

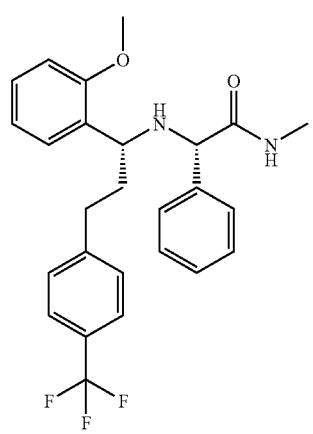

(S,R)-2-[(R,S)-1-(2-Methoxy-phenyl)-3-(4-trifluoromethyl-phenyl)-propylamino]-N-methyl-2-phenyl-acetamide (Example 178) was separated on chiral phase HPLC (Chiralpak AD column) to provide the title compounds: (R)-2-[(S)-1-(2-Methoxy-phenyl)-3-(4-trifluoromethyl-phenyl)-propylamino]-N-methyl-2-phenyl-acetamide (MS (m/e): 458.3 (MH$^+$)) and (S)-2-[(R)-1-(2-Methoxy-phenyl)-3-(4-trifluoromethyl-phenyl)-propylamino]-N-methyl-2-phenyl-acetamide (MS (m/e): 458.3 (MH$^+$)) as colorless oil.

Example 196

(S,R)-2-[(S,R)-1-(4-Fluoro-3-methyl-phenyl)-3-(4-trifluoromethyl-phenyl)-propylamino]-N-methyl-2-phenyl-acetamide

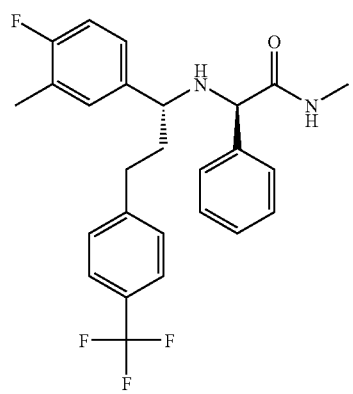

and

Example 197

(S,R)-2-[(R,S)-1-(4-Fluoro-3-methyl-phenyl)-3-(4-trifluoromethyl-phenyl)-propylamino]-N-methyl-2-phenyl-acetamide

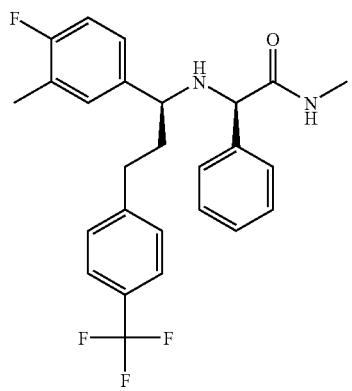

In analogy to the procedure described for the synthesis of examples 143 and 144 (step 3), the title compounds: (S,R)-2-[(S,R)-1-(4-Fluoro-3-methyl-phenyl)-3-(4-trifluoromethyl-phenyl)-propylamino]-N-methyl-2-phenyl-acetamide (MS (m/e): 459.3 (MH$^+$)) and (S,R)-2-[(R,S)-1-(4-Fluoro-3-methyl-phenyl)-3-(4-trifluoromethyl-phenyl)-propylamino]-N-methyl-2-phenyl-acetamide (MS (m/e): 459.3 (MH$^+$)) were prepared from rac-2-Amino-N-methyl-2-phenyl-acetamide (CAS: 93782-07-1) and 1-(4-Fluoro-3-methyl-phenyl)-3-(4-trifluoromethyl-phenyl)-propan-1-one (accessed according to the procedure described for examples 153 and 154, step 1 from 4-fluoro-m-toluene boronic acid).

Example 198

(S,R)-2-[(S,R)-1-(3,4-Dimethyl-phenyl)-3-(4-trifluoromethyl-phenyl)-propylamino]-N-methyl-2-phenyl-acetamide

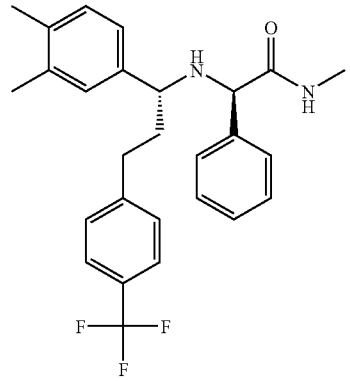

and

Example 199

(S,R)-2-[(R,S)-1-(3,4-Dimethyl-phenyl)-3-(4-trifluoromethyl-phenyl)-propylamino]-N-methyl-2-phenyl-acetamide

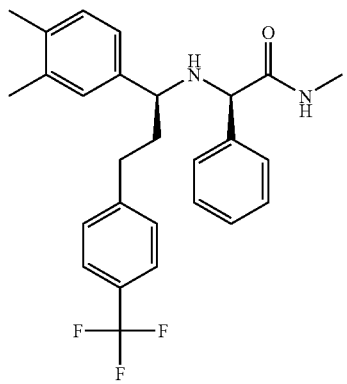

In analogy to the procedure described for the synthesis of examples 143 and 144 (step 3), the title compounds: (S,R)-2-[(S,R)-1-(3,4-Dimethyl-phenyl)-3-(4-trifluoromethyl-phenyl)-propylamino]-N-methyl-2-phenyl-acetamide (MS (m/e): 455.3 (MH$^+$)) and (S,R)-2-[(R,S)-1-(3,4-Dimethyl-phenyl)-3-(4-trifluoromethyl-phenyl)-propylamino]-N-methyl-2-phenyl-acetamide (MS (m/e): 455.1 (MH$^+$)) were prepared from rac-2-Amino-N-methyl-2-phenyl-acetamide (CAS: 93782-07-1) and 1-(3,4-Dimethyl-phenyl)-3-(4-trifluoromethyl-phenyl)-propan-1-one (accessed according to the procedure described for examples 164 and 165, step 2 from N-Methoxy-N-methyl-3-(4-trifluoromethyl-phenyl)-propionamide and 3,4-dimethylphenyl magnesium bromide).

Example 200

(R)-2-[(S)-1-(3,4-Dimethoxy-phenyl)-3-(6-trifluoromethyl-pyridin-3-yl)-propylamino]-N-methyl-2-phenyl-acetamide hydrochloride

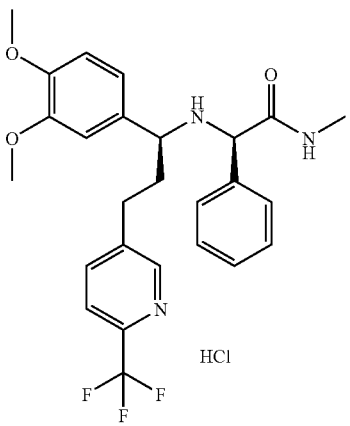

(S,R)-2-[(R,S)-1-(3,4-Dimethoxy-phenyl)-3-(6-trifluoromethyl-pyridin-3-yl)-propylamino]-N-methyl-2-phenyl-acetamide (Example 171) was separated on chiral phase HPLC (Chiralpak AD column) to provide after treatment with HCl in methanol the title compound: (R)-2-[(S)-1-(3,4-Dimethoxy-phenyl)-3-(6-trifluoromethyl-pyridin-3-yl)-propylamino]-N-methyl-2-phenyl-acetamide hydrochloride (MS (m/e): 488.0 (MH⁺)) as white solid.

Example 201

(S,R)-2-[(S,R)-1-(3-Chloro-4-methyl-phenyl)-3-(4-trifluoromethyl-phenyl)-propylamino]-N-methyl-2-phenyl-acetamide

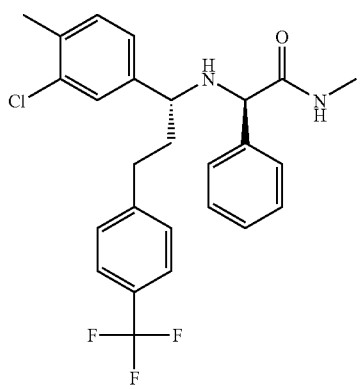

and

Example 202

(S,R)-2-[(R,S)-1-(3-Chloro-4-methyl-phenyl)-3-(4-trifluoromethyl-phenyl)-propylamino]-N-methyl-2-phenyl-acetamide

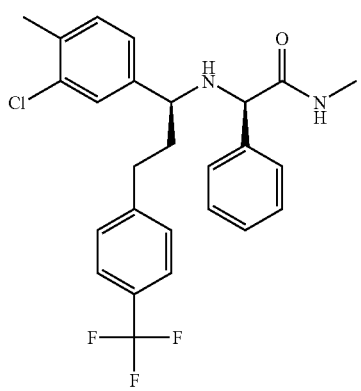

In analogy to the procedure described for the synthesis of examples 143 and 144 (step 3), the title compounds: (S,R)-2-[(S,R)-1-(3-Chloro-4-methyl-phenyl)-3-(4-trifluoromethyl-phenyl)-propylamino]-N-methyl-2-phenyl-acetamide (MS (m/e): 475.0 (MH⁺)) and (S,R)-2-[(R,S)-1-(3-Chloro-4-methyl-phenyl)-3-(4-trifluoromethyl-phenyl)-propylamino]-N-methyl-2-phenyl-acetamide (MS (m/e): 475.0 (MH⁺)) were prepared from rac-2-Amino-N-methyl-2-phenyl-acetamide (CAS: 93782-07-1) and 1-(3-Chloro-4-methyl-phenyl)-3-(4-trifluoromethyl-phenyl)-propan-1-one (accessed according to the procedure described for examples 164 and 165, step 2 from N-Methoxy-N-methyl-3-(4-trifluoromethyl-phenyl)-propionamide and 3-chloro-4-methylphenyl magnesium bromide).

Example 203

(S,R)—N-Methyl-2-phenyl-2-[(S,R)-3-(4-trifluoromethyl-phenyl)-1-(3-trifluoromethyl-phenyl)-propylamino]-acetamide

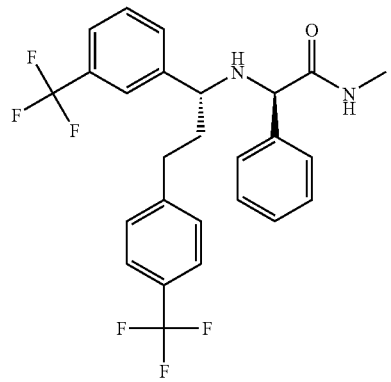

and

Example 204

(S,R)—N-Methyl-2-phenyl-2-[(R,S)-3-(4-trifluoromethyl-phenyl)-1-(3-trifluoromethyl-phenyl)-propylamino]-acetamide

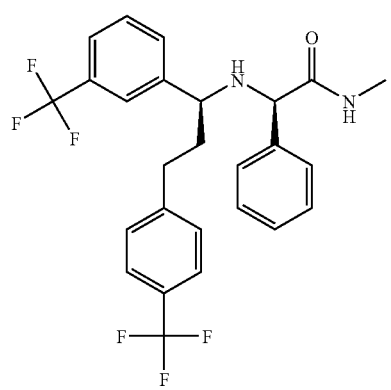

In analogy to the procedure described for the synthesis of examples 143 and 144 (step 3), the title compounds: (S,R)—N-Methyl-2-phenyl-2-[(S,R)-3-(4-trifluoromethyl-phenyl)-1-(3-trifluoromethyl-phenyl)-propylamino]-acetamide (MS (m/e): 495.1 (MH⁺)) and (S,R)—N-Methyl-2-phenyl-2-[(R,S)-3-(4-trifluoromethyl-phenyl)-1-(3-trifluoromethyl-phenyl)-propylamino]-acetamide (MS (m/e): 495.1 (MH⁺)) were prepared from rac-2-Amino-N-methyl-2-phenyl-acetamide (CAS: 93782-07-1) and 3-(4-Trifluoromethyl-phenyl)-1-(3-trifluoromethyl-phenyl)-propan-1-one (accessed according to the procedure described for examples 164 and 165, step 2 from N-Methoxy-N-methyl-3-(4-trifluoromethyl-phenyl)-propionamide and 3-trifluoromethylphenyl magnesium bromide).

Example 205

(S,R)-2-[(S,R)-1-(2-Chloro-phenyl)-3-(4-trifluoromethyl-phenyl)-propylamino]-N-methyl-2-phenyl-acetamide

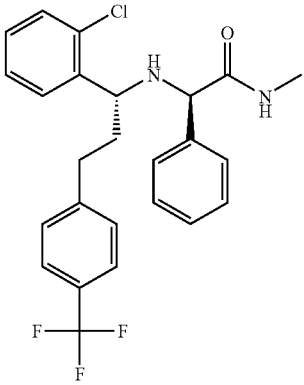

and

Example 206

(S,R)-2-[(R,S)-1-(2-Chloro-phenyl)-3-(4-trifluoromethyl-phenyl)-propylamino]-N-methyl-2-phenyl-acetamide

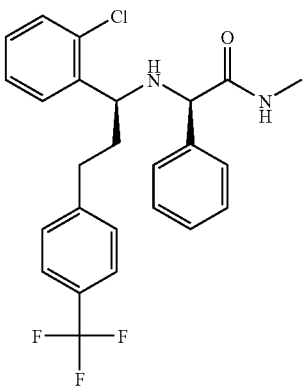

In analogy to the procedure described for the synthesis of examples 143 and 144 (step 3), the title compounds: (S,R)-2-[(S,R)-1-(2-Chloro-phenyl)-3-(4-trifluoromethyl-phenyl)-propylamino]-N-methyl-2-phenyl-acetamide (MS (m/e): 461.1 (MH$^+$)) and (S,R)-2-[(R,S)-1-(2-Chloro-phenyl)-3-(4-trifluoromethyl-phenyl)-propylamino]-N-methyl-2-phenyl-acetamide (MS (m/e): 461.0 (MH$^+$)) were prepared from rac-2-Amino-N-methyl-2-phenyl-acetamide (CAS: 93782-07-1) and 1-(2-Chloro-phenyl)-3-(4-trifluoromethyl-phenyl)-propan-1-one (accessed according to the procedure described for examples 164 and 165, step 2 from 2-Chloro-N-methoxy-N-methyl-benzamide and p-trifluoromethylphenyl ethyl magnesium bromide).

Example 207

(S,R)—N-Methyl-2-[(R,S)-1-(6-methyl-pyridin-2-yl)-3-(4-trifluoromethyl-phenyl)-propylamino]-2-phenyl-acetamide

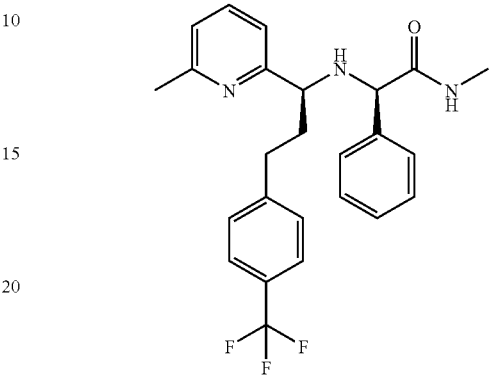

In analogy to the procedure described for the synthesis of examples 143 and 144 (step 3), the title compound: (S,R)—N-Methyl-2-[(R,S)-1-(6-methyl-pyridin-2-yl)-3-(4-trifluoromethyl-phenyl)-propylamino]-2-phenyl-acetamide (MS (m/e): 442.3 (MH$^+$)) was prepared from rac-2-Amino-N-methyl-2-phenyl-acetamide (CAS: 93782-07-1) and 1-(6-Methyl-pyridin-2-yl)-3-(4-trifluoromethyl-phenyl)-propan-1-one (accessed according to the procedure described for examples 164 and 165, step 2 from 6-Methyl-pyridine-2-carboxylic acid methoxy-methyl-amide and p-trifluoromethylphenyl ethyl magnesium bromide).

Example 208

(S,R)-2-[(S,R)-1-(3,4-Dimethoxy-phenyl)-3-p-tolyl-propylamino]-N-methyl-2-phenyl-acetamide

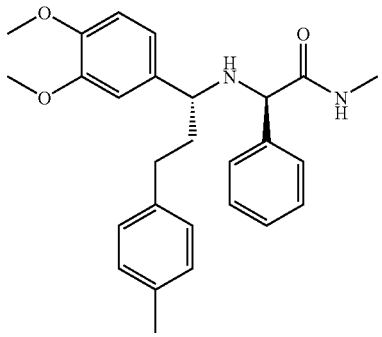

and

Example 209

(S,R)-2-[(R,S)-1-(3,4-Dimethoxy-phenyl)-3-p-tolyl-propylamino]-N-methyl-2-phenyl-acetamide

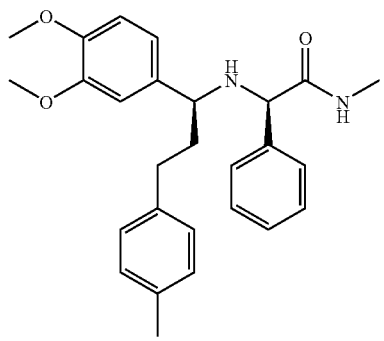

In analogy to the procedure described for the synthesis of examples 143 and 144 (step 3), the title compounds: (S,R)-2-[(S,R)-1-(3,4-Dimethoxy-phenyl)-3-p-tolyl-propylamino]-N-methyl-2-phenyl-acetamide (MS (m/e): 433.4 (MH$^+$)) and (S,R)-2-[(R,S)-1-(3,4-Dimethoxy-phenyl)-3-p-tolyl-propylamino]-N-methyl-2-phenyl-acetamide (MS (m/e): 433.4 (MH$^+$)) were prepared from rac-2-Amino-N-methyl-2-phenyl-acetamide (CAS: 93782-07-1) and 1-(3,4-Dimethoxy-phenyl)-3-p-tolyl-propan-1-one (accessed according to the procedure described for examples 143 and 144, step 2 from (E)-1-(3,4-Dimethoxy-phenyl)-3-p-tolyl-propenone).

Example 210

(S,R)-2-[(R,S)-1-(4-Methoxy-pyridin-2-yl)-3-(4-trifluoromethyl-phenyl)-propylamino]-N-methyl-2-phenyl-acetamide

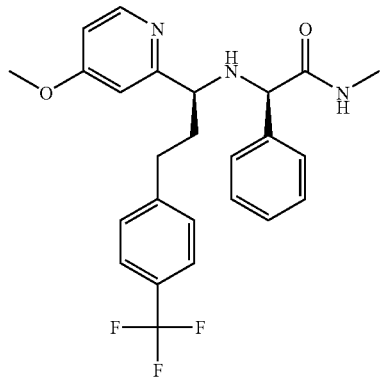

In analogy to the procedure described for the synthesis of examples 143 and 144 (step 3), the title compound: (S,R)-2-[(R,S)-1-(4-Methoxy-pyridin-2-yl)-3-(4-trifluoromethyl-phenyl)-propylamino]-N-methyl-2-phenyl-acetamide (MS (m/e): 458.3 (MH$^+$)) was prepared from rac-2-Amino-N-methyl-2-phenyl-acetamide (CAS: 93782-07-1) and 1-(4-Methoxy-pyridin-2-yl)-3-(4-trifluoromethyl-phenyl)-propan-1-one (accessed according to the procedure described for examples 164 and 165, step 2 from 4-Methoxy-pyridine-2-carboxylic acid methoxy-methyl-amide and p-trifluoromethylphenyl ethyl magnesium bromide).

Example 211

(S,R)-2-[(S,R)-1-(3-Chloro-phenyl)-3-(6-trifluoromethyl-pyridin-3-yl)-propylamino]-N-methyl-2-phenyl-acetamide

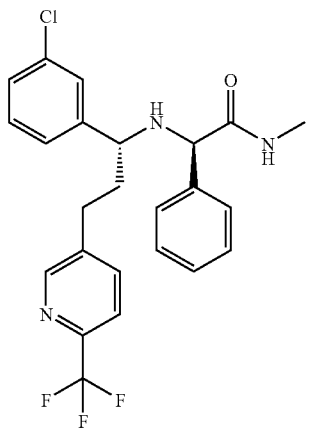

and

Example 212

(S,R)-2-[(R,S)-1-(3-Chloro-phenyl)-3-(6-trifluoromethyl-pyridin-3-yl)-propylamino]-N-methyl-2-phenyl-acetamide

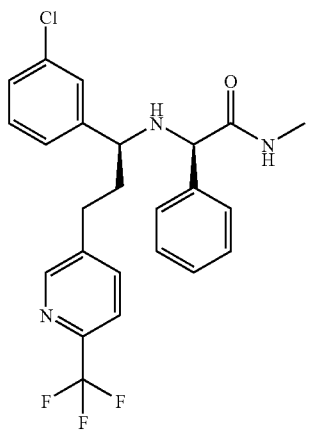

In analogy to the procedure described for the synthesis of examples 143 and 144 (step 3), the title compounds: (S,R)-2-[(S,R)-1-(3-Chloro-phenyl)-3-(6-trifluoromethyl-pyridin-3-yl)-propylamino]-N-methyl-2-phenyl-acetamide (MS (m/e): 462.0 (MH$^+$)) and (S,R)-2-[(R,S)-1-(3-Chloro-phenyl)-3-(6-trifluoromethyl-pyridin-3-yl)-propylamino]-N-methyl-2-phenyl-acetamide (MS (m/e): 462.0 (MH$^+$)) were prepared from rac-2-Amino-N-methyl-2-phenyl-acetamide (CAS: 93782-07-1) and 1-(3-Chloro-phenyl)-3-(6-trifluoromethyl-pyridin-3-yl)-propan-1-one (accessed according to the procedure described for examples 143 and 144, step 2 from (E)-1-(3-Chloro-phenyl)-3-(6-trifluoromethyl-pyridin-3-yl)-propenone).

Example 213

(R)—N-Methyl-2-[(S)-1-(6-methyl-pyridin-2-yl)-3-(4-trifluoromethyl-phenyl)-propylamino]-2-phenyl-acetamide

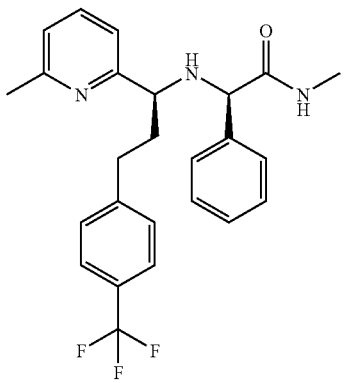

and

Example 214

(S)—N-Methyl-2-[(R)-1-(6-methyl-pyridin-2-yl)-3-(4-trifluoromethyl-phenyl)-propylamino]-2-phenyl-acetamide

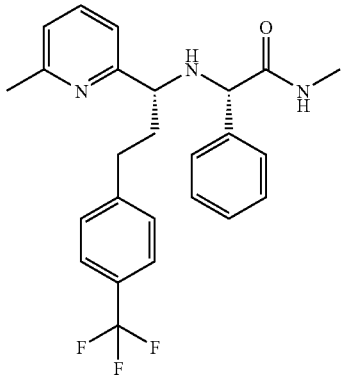

(S,R)—N-Methyl-2-[(R,S)-1-(6-methyl-pyridin-2-yl)-3-(4-trifluoromethyl-phenyl)-propylamino]-2-phenyl-acetamide (Example 207) was separated on chiral phase HPLC (ChiralpakAD column) to provide the title compounds: (R)—N-Methyl-2-[(S)-1-(6-methyl-pyridin-2-yl)-3-(4-trifluoromethyl-phenyl)-propylamino]-2-phenyl-acetamide (MS (m/e): 442.3 (MH$^+$)) and (S)—N-Methyl-2-[(R)-1-(6-methyl-pyridin-2-yl)-3-(4-trifluoromethyl-phenyl)-propylamino]-2-phenyl-acetamide (MS (m/e): 442.3 (MH$^+$)) as colorless oil.

Example 215

(S,R)-2-[(S,R)-1-(4-Chloro-3-methoxy-phenyl)-3-(6-trifluoromethyl-pyridin-3-yl)-propylamino]-N-methyl-2-phenyl-acetamide

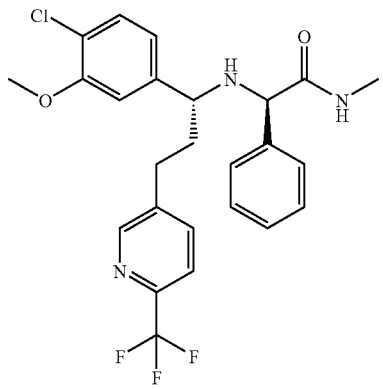

and

Example 216

(S,R)-2-[(R,S)-1-(4-Chloro-3-methoxy-phenyl)-3-(6-trifluoromethyl-pyridin-3-yl)-propylamino]-N-methyl-2-phenyl-acetamide

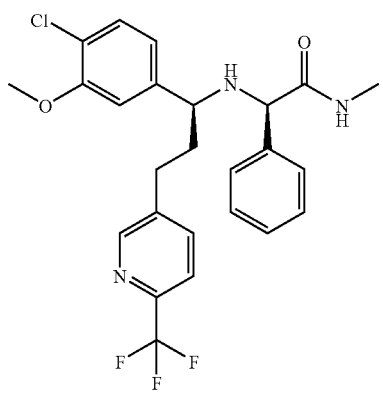

In analogy to the procedure described for the synthesis of examples 143 and 144 (step 3), the title compounds: (S,R)-2-[(S,R)-1-(4-Chloro-3-methoxy-phenyl)-3-(6-trifluoromethyl-pyridin-3-yl)-propylamino]-N-methyl-2-phenyl-acetamide (MS (m/e): 492.2 (MH$^+$)) and (S,R)-2-[(R,S)-1-(4-Chloro-3-methoxy-phenyl)-3-(6-trifluoromethyl-pyridin-3-yl)-propylamino]-N-methyl-2-phenyl-acetamide (MS (m/e): 492.1 (MH$^+$)) were prepared from rac-2-Amino-N-methyl-2-phenyl-acetamide (CAS: 93782-07-1) and 1-(4-Chloro-3-methoxy-phenyl)-3-(6-trifluoromethyl-pyridin-3-yl)-propan-1-one (accessed according to the procedure described for examples 164 and 165, step 2 from N-Methoxy-N-methyl-3-

Example 217

(R)-2-[(S)-1-(6-Methoxy-pyridin-2-yl)-3-(4-trifluoromethyl-phenyl)-propylamino]-N-methyl-2-phenyl-acetamide

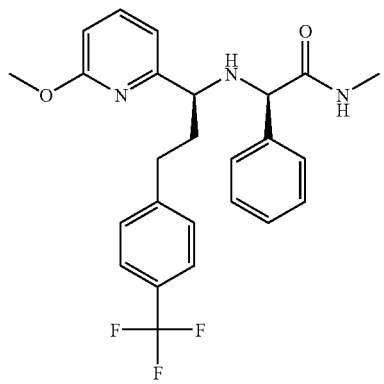

and

Example 218

(S)-2-[(S)-1-(6-Methoxy-pyridin-2-yl)-3-(4-trifluoromethyl-phenyl)-propylamino]-N-methyl-2-phenyl-acetamide

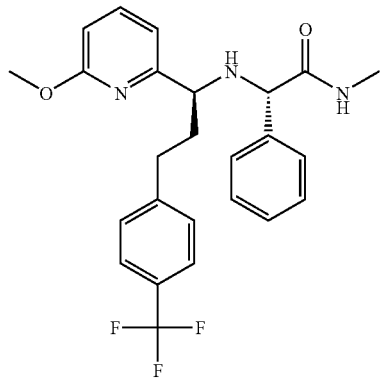

In analogy to the procedure described for the synthesis of examples 139 and 140 (step 2), the title compounds: (R)-2-[(S)-1-(6-Methoxy-pyridin-2-yl)-3-(4-trifluoromethyl-phenyl)-propylamino]-N-methyl-2-phenyl-acetamide (MS (m/e): 458.3 (MH⁺)) and (S)-2-[(S)-1-(6-Methoxy-pyridin-2-yl)-3-(4-trifluoromethyl-phenyl)-propylamino]-N-methyl-2-phenyl-acetamide (MS (m/e): 458.3 (MH⁺)) were prepared from rac-1-(6-Methoxy-pyridin-2-yl)-3-(4-trifluoromethyl-phenyl)-propylamine (accessed according to the procedure described for examples 126 and 127, step 2 from 2-Methyl-propane-2-sulfinic acid [1-(6-methoxy-pyridin-2-yl)-3-(4-trifluoromethyl-phenyl)-propyl]-amide) followed by chiral phase HPLC (chiralpak AD column).

Example 219

(S,R)-2-[(S,R)-1-(4-Chloro-3-methoxy-phenyl)-3-(6-trifluoromethyl-pyridin-3-yl)-propylamino]-2-(4-chloro-phenyl)-N-methyl-acetamide

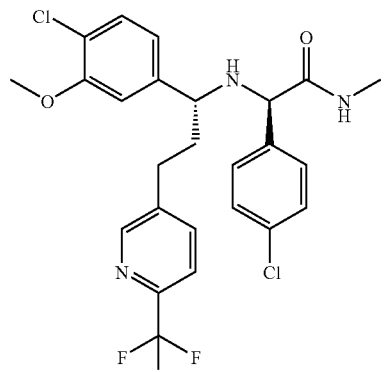

and

Example 220

(S,R)-2-[(R,S)-1-(4-Chloro-3-methoxy-phenyl)-3-(6-trifluoromethyl-pyridin-3-yl)-propylamino]-2-(4-chloro-phenyl)-N-methyl-acetamide

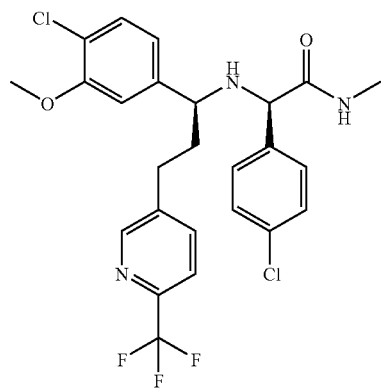

In analogy to the procedure described for the synthesis of examples 143 and 144 (step 3), the title compounds: (S,R)-2-[(S,R)-1-(4-Chloro-3-methoxy-phenyl)-3-(6-trifluoromethyl-pyridin-3-yl)-propylamino]-2-(4-chloro-phenyl)-N-methyl-acetamide (MS (m/e): 526.3 (MH⁺)) and (S,R)-2-[(R,S)-1-(4-Chloro-3-methoxy-phenyl)-3-(6-trifluoromethyl-pyridin-3-yl)-propylamino]-2-(4-chloro-phenyl)-N-methyl-acetamide (MS (m/e): 526.3 (MH⁺)) were prepared from rac-2-Amino-2-(4-chloro-phenyl)-N-methyl-acetamide and 1-(4-Chloro-3-methoxy-phenyl)-3-(6-trifluoromethyl-pyridin-3-yl)-propan-1-one (accessed according to the procedure described for examples 164 and 165, step 2 from N-Methoxy-N-methyl-3-(6-trifluoromethyl-pyridin-3-yl)-propionamide and 3-methoxy-4-chlororophenyl magnesium bromide).

Example 221

(R)-2-[(S)-1-(3-Methoxy-phenyl)-3-(4-trifluoromethyl-phenyl)-propylamino]-N-methyl-2-phenyl-acetamide hydrochloride

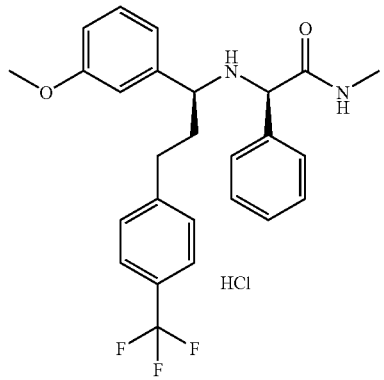

and

Example 222

(S)-2-[(R)-1-(3-Methoxy-phenyl)-3-(4-trifluoromethyl-phenyl)-propylamino]-N-methyl-2-phenyl-acetamide hydrochloride

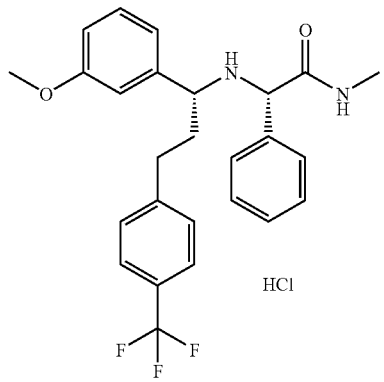

(S,R)-2-[(R,S)-1-(3-Methoxy-phenyl)-3-(4-trifluoromethyl-phenyl)-propylamino]-N-methyl-2-phenyl-acetamide (Example 150) was separated on chiral phase HPLC (Chiralcel OD column) and each obtained enantiomer was treated with HCl methanol to provide after evaporation the title compounds: (R)-2-[(S)-1-(3-Methoxy-phenyl)-3-(4-trifluoromethyl-phenyl)-propylamino]-N-methyl-2-phenyl-acetamide hydrochloride (MS (m/e): 457.3 (MH$^+$)) and (S)-2-[(R)-1-(3-Methoxy-phenyl)-3-(4-trifluoromethyl-phenyl)-propylamino]-N-methyl-2-phenyl-acetamide hydrochloride (MS (m/e): 457.3 (MH$^+$)) as white solid.

Example 223

(S,R)-2-[(S,R)-1-(4-Chloro-3-methoxy-phenyl)-3-(6-trifluoromethyl-pyridin-3-yl)-propylamino]-2-(4-fluoro-phenyl)-N-methyl-acetamide

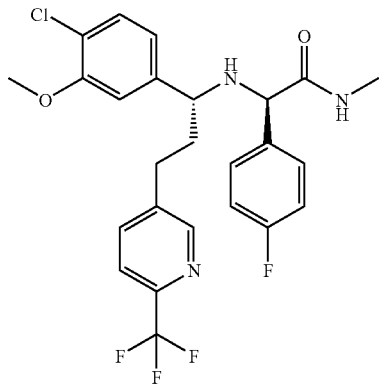

and

Example 224

(S,R)-2-[(R,S)-1-(4-Chloro-3-methoxy-phenyl)-3-(6-trifluoromethyl-pyridin-3-yl)-propylamino]-2-(4-fluoro-phenyl)-N-methyl-acetamide

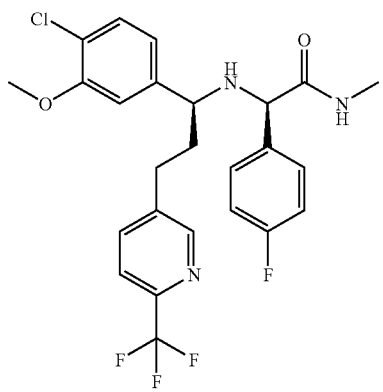

In analogy to the procedure described for the synthesis of examples 143 and 144 (step 3), the title compounds: (S,R)-2-[(S,R)-1-(4-Chloro-3-methoxy-phenyl)-3-(6-trifluoromethyl-pyridin-3-yl)-propylamino]-2-(4-fluoro-phenyl)-N-methyl-acetamide (MS (m/e): 510.0 (MH$^+$)) and (S,R)-2-[(R,S)-1-(4-Chloro-3-methoxy-phenyl)-3-(6-trifluoromethyl-pyridin-3-yl)-propylamino]-2-(4-fluoro-phenyl)-N-methyl-acetamide (MS (m/e): 510.0 (MH$^+$)) were prepared from rac-2-Amino-2-(4-fluoro-phenyl)-N-methyl-acetamide and 1-(4-Chloro-3-methoxy-phenyl)-3-(6-trifluoromethyl-pyridin-3-yl)-propan-1-one (accessed according to the procedure described for examples 164 and 165, step 2 from N-Methoxy-N-methyl-3-(6-trifluoromethyl-pyridin-3-yl)-propionamide and 3-methoxy-4-chlororophenyl magnesium bromide).

Example 225

(S,R)-2-[(R,S)-1-(3-Difluoromethoxy-phenyl)-3-(6-trifluoromethyl-pyridin-3-yl)-propylamino]-N-methyl-2-phenyl-acetamide

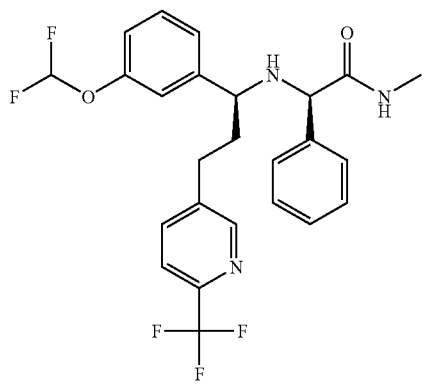

In analogy to the procedure described for the synthesis of examples 143 and 144 (step 3), the title compound: (S,R)-2-[(R,S)-1-(3-Difluoromethoxy-phenyl)-3-(6-trifluoromethyl-pyridin-3-yl)-propylamino]-N-methyl-2-phenyl-acetamide (MS (m/e): 494.0 (MH$^+$)) was prepared from rac-2-Amino-N-methyl-2-phenyl-acetamide (CAS: 93782-07-1) and 1-(3-Difluoromethoxy-phenyl)-3-(6-trifluoromethyl-pyridin-3-yl)-propan-1-one (accessed according to the procedure described for examples 143 and 144, step 2 from (E)-1-(3-Difluoromethoxy-phenyl)-3-(6-trifluoromethyl-pyridin-3-yl)-propenone).

Example 226

(S,R)—N-Methyl-2-phenyl-2-[(S,R)-1-(3-trifluoromethoxy-phenyl)-3-(6-trifluoromethyl-pyridin-3-yl)-propylamino]-acetamide

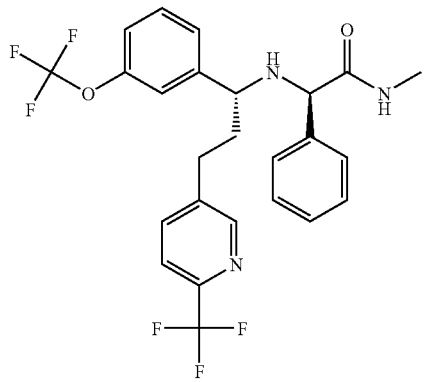

and

Example 227

(S,R)—N-Methyl-2-phenyl-2-[(R,S)-1-(3-trifluoromethoxy-phenyl)-3-(6-trifluoromethyl-pyridin-3-yl)-propylamino]-acetamide

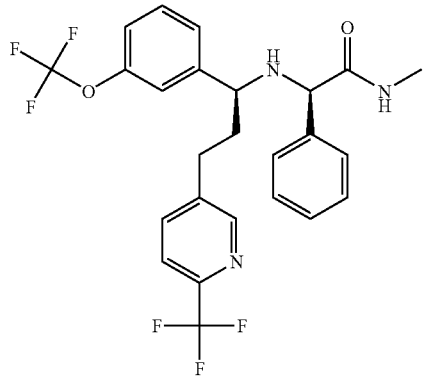

In analogy to the procedure described for the synthesis of examples 143 and 144 (step 3), the title compounds: (S,R)—N-Methyl-2-phenyl-2-[(S,R)-1-(3-trifluoromethoxy-phenyl)-3-(6-trifluoromethyl-pyridin-3-yl)-propylamino]-acetamide (MS (m/e): 512.0 (MH$^+$)) and (S,R)—N-Methyl-2-phenyl-2-[(R,S)-1-(3-trifluoromethoxy-phenyl)-3-(6-trifluoromethyl-pyridin-3-yl)-propylamino]-acetamide (MS (m/e): 512.0 (MH$^+$)) were prepared from rac-2-Amino-N-methyl-2-phenyl-acetamide (CAS: 93782-07-1) and 1-(3-Trifluoromethoxy-phenyl)-3-(6-trifluoromethyl-pyridin-3-yl)-propan-1-one (accessed according to the procedure described for examples 143 and 144, step 2 from (E)-1-(3-Trifluoromethoxy-phenyl)-3-(6-trifluoromethyl-pyridin-3-yl)-propenone).

Example 228

(S,R)-2-[(R,S)-1-(4-Fluoro-3-methyl-phenyl)-3-(6-trifluoromethyl-pyridin-3-yl)-propylamino]-N-methyl-2-phenyl-acetamide

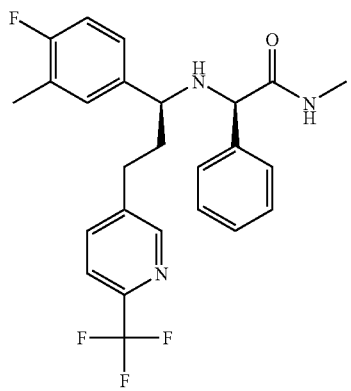

In analogy to the procedure described for the synthesis of examples 143 and 144 (step 3), the title compound: (S,R)-2-[(R,S)-1-(4-Fluoro-3-methyl-phenyl)-3-(6-trifluoromethylpyridin-3-yl)-propylamino]-N-methyl-2-phenyl-acetamide (MS (m/e): 460.1 (MH+)) was prepared from rac-2-Amino-N-methyl-2-phenyl-acetamide (CAS: 93782-07-1) and 1-(4-Fluoro-3-methyl-phenyl)-3-(6-trifluoromethyl-pyridin-3-yl)-propan-1-one (accessed according to the procedure described for examples 143 and 144, step 2 from (E)-1-(4-Fluoro-3-methyl-phenyl)-3-(6-trifluoromethyl-pyridin-3-yl)-propenone).

acetamide (MS (m/e): 510.0 (MH+)) were prepared from rac-2-Amino-2-(4-chloro-phenyl)-N-methyl-acetamide and 1-(4-Fluoro-3-methoxy-phenyl)-3-(6-trifluoromethyl-pyridin-3-yl)-propan-1-one (accessed according to the procedure described for example 143 and 144, step 2 from (E)-1-(4-Fluoro-3-methoxy-phenyl)-3-(6-trifluoromethyl-pyridin-3-yl)-propenone).

Example 229

(S,R)-2-(4-Chloro-phenyl)-2-[(S,R)-1-(4-fluoro-3-methoxy-phenyl)-3-(6-trifluoromethyl-pyridin-3-yl)-propylamino]-N-methyl-acetamide

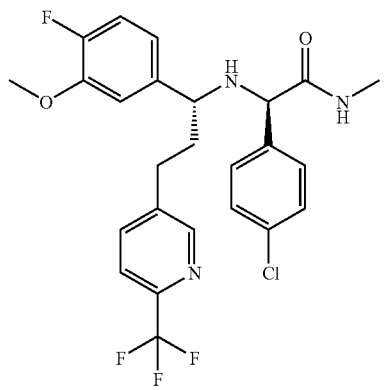

Example 231

(S,R)-2-[(S,R)-1-(4-Fluoro-3-methoxy-phenyl)-3-(6-trifluoromethyl-pyridin-3-yl)-propylamino]-N-methyl-2-phenyl-acetamide

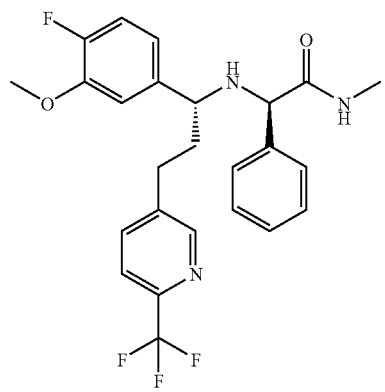

and

Example 230

(S,R)-2-(4-Chloro-phenyl)-2-[(R,S)-1-(4-fluoro-3-methoxy-phenyl)-3-(6-trifluoromethyl-pyridin-3-yl)-propylamino]-N-methyl-acetamide

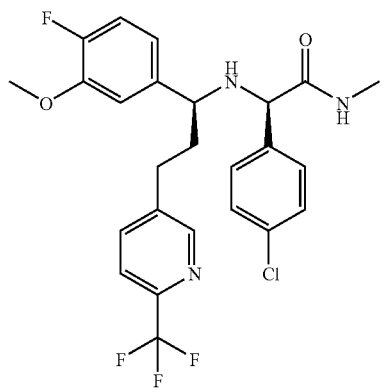

and

Example 232

(S,R)-2-[(R,S)-1-(4-Fluoro-3-methoxy-phenyl)-3-(6-trifluoromethyl-pyridin-3-yl)-propylamino]-N-methyl-2-phenyl-acetamide

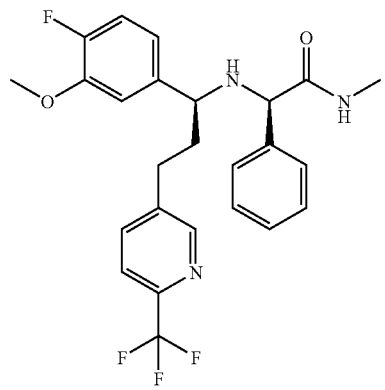

In analogy to the procedure described for the synthesis of examples 143 and 144 (step 3), the title compounds: (S,R)-2-(4-Chloro-phenyl)-2-[(S,R)-1-(4-fluoro-3-methoxy-phenyl)-3-(6-trifluoromethyl-pyridin-3-yl)-propylamino]-N-methyl-acetamide (MS (m/e): 510.1 (MH+)) and (S,R)-2-(4-Chloro-phenyl)-2-[(R,S)-1-(4-fluoro-3-methoxy-phenyl)-3-(6-trifluoromethyl-pyridin-3-yl)-propylamino]-N-methyl- In analogy to the procedure described for the synthesis of examples 143 and 144 (step 3), the title compounds: (S,R)-2-[(S,R)-1-(4-Fluoro-3-methoxy-phenyl)-3-(6-trifluoromethyl-pyridin-3-yl)-propylamino]-N-methyl-2-phenyl-acetamide (MS (m/e): 476.0 (MH+)) and (S,R)-2-[(R,S)-1-(4-Fluoro-3-methoxy-phenyl)-3-(6-trifluoromethyl-pyridin-3-yl)-propylamino]-N-methyl-2-phenyl-acetamide (MS (m/e): 476.0 (MH+)) were prepared from rac-2-Amino-N-methyl- 2-phenyl-acetamide (CAS: 93782-07-1) and 1-(4-Fluoro-3-methoxy-phenyl)-3-(6-trifluoromethyl-pyridin-3-yl)-propan-1-one (accessed according to the procedure described for examples 143 and 144, step 2 from (E)-1-(4-Fluoro-3-methoxy-phenyl)-3-(6-trifluoromethyl-pyridin-3-yl)-propenone).

Example 233

(S,R)-2-(4-Chloro-phenyl)-2-[(S,R)-1-(4-difluoromethoxy-3-methoxy-phenyl)-3-(6-trifluoromethyl-pyridin-3-yl)-propylamino]-N-methyl-acetamide

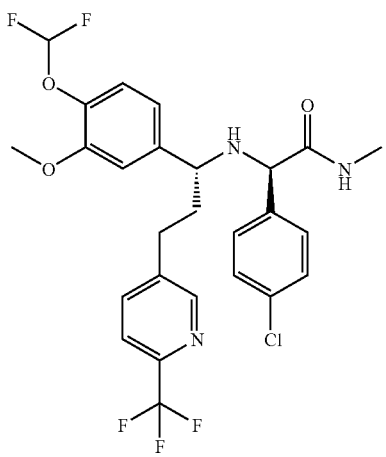

and

Example 234

(S,R)-2-(4-Chloro-phenyl)-2-[(R,S)-1-(4-difluoromethoxy-3-methoxy-phenyl)-3-(6-trifluoromethyl-pyridin-3-yl)-propylamino]-N-methyl-acetamide

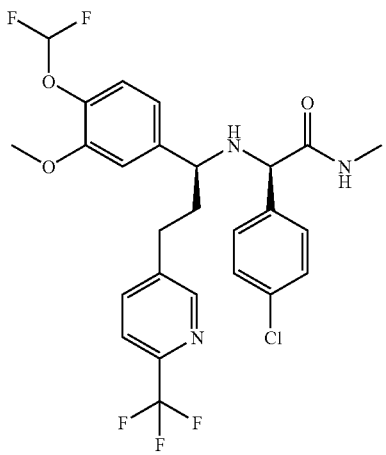

a) Step 1

(E)-1-(4-Difluoromethoxy-3-methoxy-phenyl)-3-(6-trifluoromethyl-pyridin-3-yl)-propenone

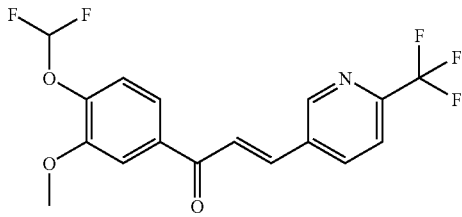

To a solution of 0.82 mL (7.5 mmol) dimethyl methylphosphonate in THF (15 mL) was added 4.6 ml (7.5 mmol) n-BuLi (1.6M in hexane) by keeping the temperature below −65° C. Stirring was continued for 30 minutes. A solution of 0.9 g (3.7 mmol) 4-Difluoromethoxy-3-methoxy-benzoic acid methyl ester (CAS: 77387-12-7) in THF (3.0 ml) was added by keeping the temperature below −70° C. The mixture was stirred for an additional 15 minutes at −70° C. and then allowed to warm to 0° C. The mixture was neutralized with HCl/dioxane 4N (1.9 mLl) and allowed to warm to RT. 1.2 g (3.7 mmol) $Cs_2CO_3$ and a solution of 0.6 g (3.4 mmol) 6-(trifluoromethyl)pyridine-3-carboxaldehyde in THF (3.0 mL) were added. The mixture was stirred at room temperature overnight and then diluted with a 20% $NH_4Cl$ solution (20 mL) and ethyl acetate. The organic layer was separated and the aqueous layer was extracted once with ethyl acetate. The combined extracts were dried over $Na_2SO_4$, filtered and concentrated in vacuo. The crude oil was purified with flash column chromatography on silica eluting with a gradient formed from heptane and ethylacetate to provide 1.05 g (83%) of the title compound as a yellow solid. MS (m/e): 374.2 (MH$^+$).

b) Step 2

1-(4-Difluoromethoxy-3-methoxy-phenyl)-3-(6-trifluoromethyl-pyridin-3-yl)-propan-1-one

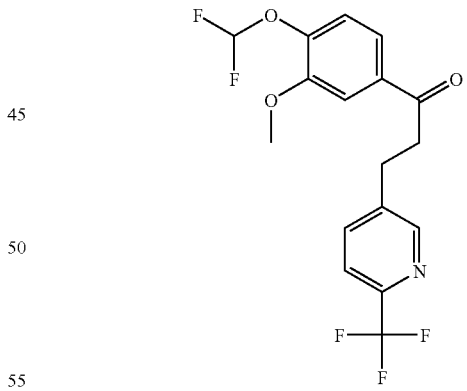

In analogy to the procedure described for the synthesis of examples 143 and 144 (step 2), the title compound: 1-(4-Difluoromethoxy-3-methoxy-phenyl)-3-(6-trifluoromethyl-pyridin-3-yl)-propan-1-one (MS (m/e): 376.3 (MH$^+$)) was prepared from (E)-1-(4-Difluoromethoxy-3-methoxy-phenyl)-3-(6-trifluoromethyl-pyridin-3-yl)-propenone.

c) Step 3

In analogy to the procedure described for the synthesis of examples 143 and 144 (step 3), the title compounds: (S,R)-2-(4-Chloro-phenyl)-2-[(S,R)-1-(4-difluoromethoxy-3- methoxy-phenyl)-3-(6-trifluoromethyl-pyridin-3-yl)-propylamino]-N-methyl-acetamide (MS (m/e): 557.7 (MH$^+$)) and (S,R)-2-(4-Chloro-phenyl)-2-[(R,S)-1-(4-difluoromethoxy-3-methoxy-phenyl)-3-(6-trifluoromethyl-pyridin-3-yl)-propylamino]-N-methyl-acetamide (MS (m/e): 557.5 (MH$^+$)) were prepared from rac-2-Amino-2-(4-chloro-phenyl)-N-methyl-acetamide and 1-(4-Difluoromethoxy-3-methoxy-phenyl)-3-(6-trifluoromethyl-pyridin-3-yl)-propan-1-one).

Example 235

(S,R)-2-[(S,R)-1-(4-Difluoromethoxy-3-methoxy-phenyl)-3-(6-trifluoromethyl-pyridin-3-yl)-propylamino]-2-(4-fluoro-phenyl)-N-methyl-acetamide

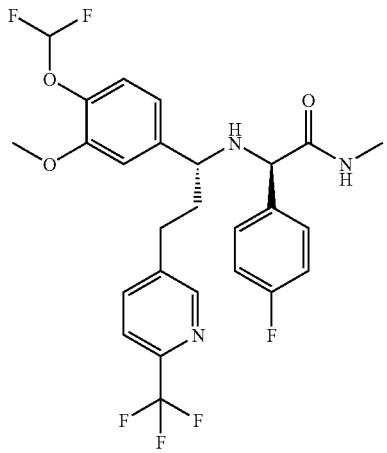

and

Example 236

(S,R)-2-[(R,S)-1-(4-Difluoromethoxy-3-methoxy-phenyl)-3-(6-trifluoromethyl-pyridin-3-yl)-propylamino]-2-(4-fluoro-phenyl)-N-methyl-acetamide

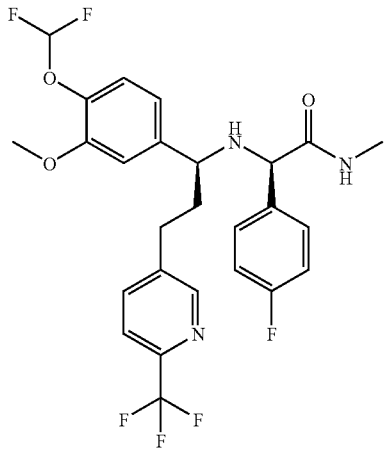

In analogy to the procedure described for the synthesis of examples 143 and 144 (step 3), the title compounds: (S,R)-2-[(S,R)-1-(4-Difluoromethoxy-3-methoxy-phenyl)-3-(6-trifluoromethyl-pyridin-3-yl)-propylamino]-2-(4-fluoro-phenyl)-N-methyl-acetamide (MS (m/e): 541.8 (MH$^+$)) and (S,R)-2-[(R,S)-1-(4-Difluoromethoxy-3-methoxy-phenyl)-3-(6-trifluoromethyl-pyridin-3-yl)-propylamino]-2-(4-fluoro-phenyl)-N-methyl-acetamide (MS (m/e): 541.8 (MH$^+$)) were prepared from rac-2-Amino-2-(4-fluoro-phenyl)-N-methyl-acetamide and 1-(4-Difluoromethoxy-3-methoxy-phenyl)-3-(6-trifluoromethyl-pyridin-3-yl)-propan-1-one (accessed according to the procedure described for examples 233 and 234, step 2 from (E)-1-(4-Difluoromethoxy-3-methoxy-phenyl)-3-(6-trifluoromethyl-pyridin-3-yl)-propenone).

Example 237

(S,R)-2-[(S,R)-1-(3-Chloro-4-methyl-phenyl)-3-(6-trifluoromethyl-pyridin-3-yl)-propylamino]-N-methyl-2-phenyl-acetamide

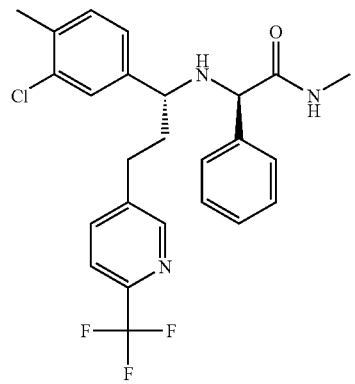

and

Example 238

(S,R)-2-[(R,S)-1-(3-Chloro-4-methyl-phenyl)-3-(6-trifluoromethyl-pyridin-3-yl)-propylamino]-N-methyl-2-phenyl-acetamide

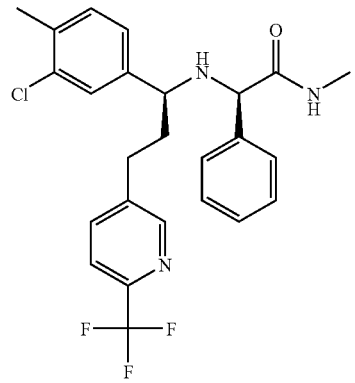

In analogy to the procedure described for the synthesis of examples 143 and 144 (step 3), the title compounds: (S,R)-2-[(S,R)-1-(3-Chloro-4-methyl-phenyl)-3-(6-trifluoromethyl-pyridin-3-yl)-propylamino]-N-methyl-2-phenyl-acetamide (MS (m/e): 476.0 (MH$^+$)) and (S,R)-2-[(R,S)-1-(3-Chloro-4-methyl-phenyl)-3-(6-trifluoromethyl-pyridin-3-yl)-propylamino]-N-methyl-2-phenyl-acetamide (MS (m/e): 476.1 (MH$^+$)) were prepared from rac-2-Amino-N-methyl- 2-phenyl-acetamide (CAS: 93782-07-1) and 1-(3-Chloro-4-methyl-phenyl)-3-(6-trifluoromethyl-pyridin-3-yl)-propan-1-one (accessed according to the procedure described for examples 164 and 165, step 2 from N-Methoxy-N-methyl-3-(6-trifluoromethyl-pyridin-3-yl)-propionamide and 4-methyl-3-chlorophenyl magnesium bromide).

Example 239

(S,R)-2-[(S,R)-1-(4-Fluoro-3-methoxy-phenyl)-3-(6-trifluoromethyl-pyridin-3-yl)-propylamino]-2-(4-fluoro-phenyl)-N-methyl-acetamide

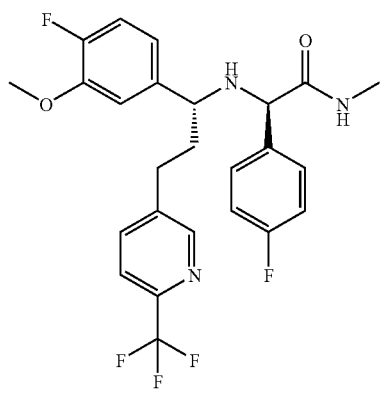

and

Example 240

(S,R)-2-[(R,S)-1-(4-Fluoro-3-methoxy-phenyl)-3-(6-trifluoromethyl-pyridin-3-yl)-propylamino]-2-(4-fluoro-phenyl)-N-methyl-acetamide

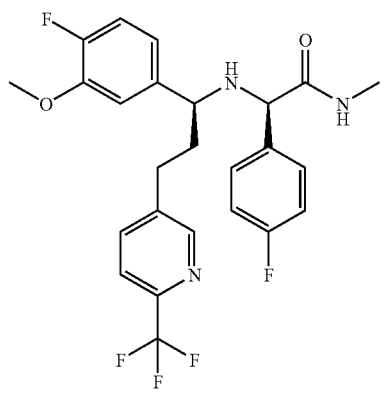

In analogy to the procedure described for the synthesis of examples 143 and 144 (step 3), the title compounds: (S,R)-2-[(S,R)-1-(4-Fluoro-3-methoxy-phenyl)-3-(6-trifluoromethyl-pyridin-3-yl)-propylamino]-2-(4-fluoro-phenyl)-N-methyl-acetamide (MS (m/e): 494.0 (MH$^+$)) and (S,R)-2-[(R,S)-1-(4-Fluoro-3-methoxy-phenyl)-3-(6-trifluoromethyl-pyridin-3-yl)-propylamino]-2-(4-fluoro-phenyl)-N-methyl-acetamide (MS (m/e): 494.0 (MH$^+$)) were prepared from rac-2-Amino-2-(4-fluoro-phenyl)-N-methyl-acetamide and 1-(4-Fluoro-3-methoxy-phenyl)-3-(6-trifluoromethyl-pyridin-3-yl)-propan-1-one (accessed according to the procedure described for examples 143 and 144, step 2 from (E)-1-(4-Fluoro-3-methoxy-phenyl)-3-(6-trifluoromethyl-pyridin-3-yl)-propenone).

Example 241

(S,R)-2-[(S,R)-1-(4-Fluoro-3-methyl-phenyl)-3-(5-fluoro-pyridin-2-yl)-propylamino]-N-methyl-2-phenyl-acetamide

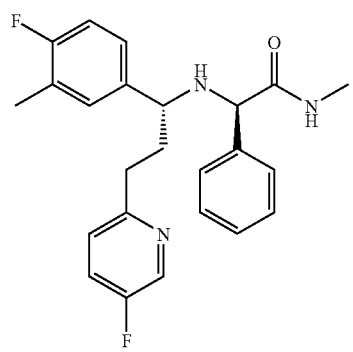

and

Example 242

(S,R)-2-[(R,S)-1-(4-Fluoro-3-methyl-phenyl)-3-(5-fluoro-pyridin-2-yl)-propylamino]-N-methyl-2-phenyl-acetamide

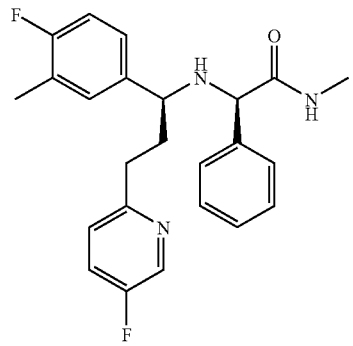

In analogy to the procedure described for the synthesis of examples 143 and 144 (step 3), the title compounds: (S,R)-2-[(S,R)-1-(4-Fluoro-3-methyl-phenyl)-3-(5-fluoro-pyridin-2-yl)-propylamino]-N-methyl-2-phenyl-acetamide (MS (m/e): 410.1 (MH$^+$)) and (S,R)-2-[(R,S)-1-(4-Fluoro-3-methyl-phenyl)-3-(5-fluoro-pyridin-2-yl)-propylamino]-N-methyl-2-phenyl-acetamide (MS (m/e): 410.1 (MH$^+$)) were prepared from rac-2-Amino-N-methyl-2-phenyl-acetamide (CAS: 93782-07-1) and 1-(4-Fluoro-3-methyl-phenyl)-3-(5-fluoro-pyridin-2-yl)-propan-1-one (accessed according to the procedure described for examples 233 and 234, step 2 from (E)-1-(4-Fluoro-3-methyl-phenyl)-3-(5-fluoro-pyridin-2-yl)-propenone).

Example 243

(S,R)-2-[(S,R)-1-(4-Chloro-3-methyl-phenyl)-3-(6-trifluoromethyl-pyridin-3-yl)-propylamino]-N-methyl-2-phenyl-acetamide

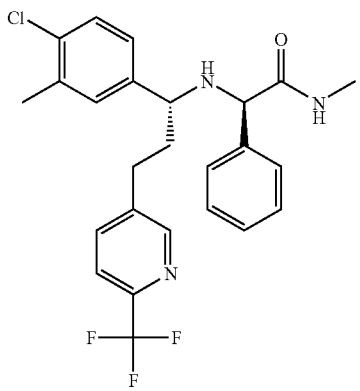

and

Example 244

(S,R)-2-[(R,S)-1-(4-Chloro-3-methyl-phenyl)-3-(6-trifluoromethyl-pyridin-3-yl)-propylamino]-N-methyl-2-phenyl-acetamide

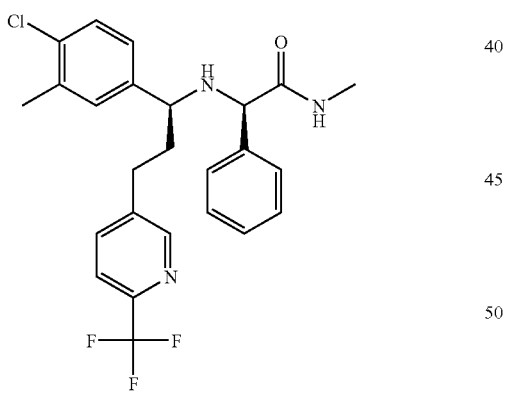

In analogy to the procedure described for the synthesis of examples 143 and 144 (step 3), the title compounds: (S,R)-2-[(S,R)-1-(4-Chloro-3-methyl-phenyl)-3-(6-trifluoromethyl-pyridin-3-yl)-propylamino]-N-methyl-2-phenyl-acetamide (MS (m/e): 476.2 (MH⁺)) and (S,R)-2-[(R,S)-1-(4-Chloro-3-methyl-phenyl)-3-(6-trifluoromethyl-pyridin-3-yl)-propylamino]-N-methyl-2-phenyl-acetamide (MS (m/e): 476.2 (MH⁺)) were prepared from rac-2-Amino-N-methyl-2-phenyl-acetamide (CAS: 93782-07-1) and 1-(4-Chloro-3-methyl-phenyl)-3-(6-trifluoromethyl-pyridin-3-yl)-propan-1-one (accessed according to the procedure described for examples 143 and 144, step 2 from (E)-1-(4-Chloro-3-methyl-phenyl)-3-(6-trifluoromethyl-pyridin-3-yl)-propenone).

Example 245

(S,R)-2-[(R,S)-1-(4-Fluoro-3-methyl-phenyl)-3-(4-methanesulfonyl-phenyl)-propylamino]-N-methyl-2-phenyl-acetamide

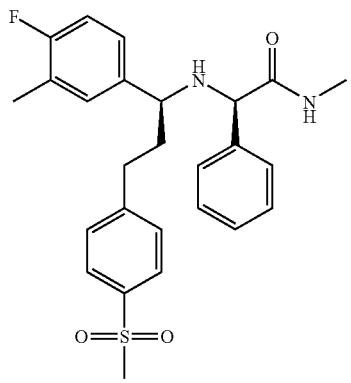

In analogy to the procedure described for the synthesis of examples 143 and 144 (step 3), the title compound: (S,R)-2-[(R,S)-1-(4-Fluoro-3-methyl-phenyl)-3-(4-methanesulfonyl-phenyl)-propylamino]-N-methyl-2-phenyl-acetamide (MS (m/e): 469.0 (MH⁺)) was prepared from rac-2-Amino-N-methyl-2-phenyl-acetamide (CAS: 93782-07-1) and 1-(4-Fluoro-3-methyl-phenyl)-3-(4-methanesulfonyl-phenyl)-propan-1-one (accessed according to the procedure described for examples 233 and 234, step 2 from (E)-1-(4-Fluoro-3-methyl-phenyl)-3-(4-methanesulfonyl-phenyl)-propenone).

Example 246

(S,R)-2-[(S,R)-1-(4-Fluoro-3-methyl-phenyl)-3-(2-fluoro-phenyl)-propylamino]-N-methyl-2-phenyl-acetamide

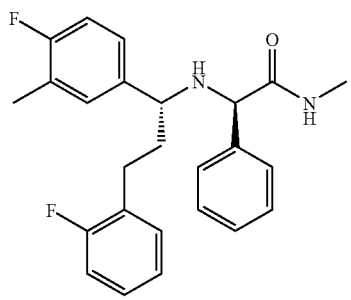

and

Example 247

(S,R)-2-[(R,S)-1-(4-Fluoro-3-methyl-phenyl)-3-(2-fluoro-phenyl)-propylamino]-N-methyl-2-phenyl-acetamide

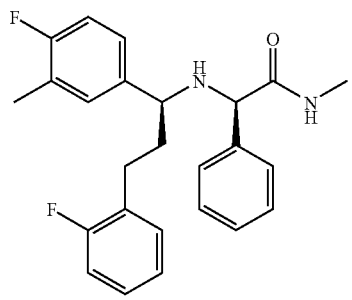

In analogy to the procedure described for the synthesis of examples 143 and 144 (step 3), the title compounds: (S,R)-2-[(S,R)-1-(4-Fluoro-3-methyl-phenyl)-3-(2-fluoro-phenyl)-propylamino]-N-methyl-2-phenyl-acetamide (MS (m/e): 409.0 (MH$^+$)) and (S,R)-2-[(R,S)-1-(4-Fluoro-3-methyl-phenyl)-3-(2-fluoro-phenyl)-propylamino]-N-methyl-2-phenyl-acetamide (MS (m/e): 409.0 (MH$^+$)) were prepared from rac-2-Amino-N-methyl-2-phenyl-acetamide (CAS: 93782-07-1) and 1-(4-Fluoro-3-methyl-phenyl)-3-(2-fluoro-phenyl)-propan-1-one (accessed according to the procedure described for examples 233 and 234, step 2 from (E)-1-(4-Fluoro-3-methyl-phenyl)-3-(2-fluoro-phenyl)-propenone).

Example 248

(S,R)-2-(4-Chloro-phenyl)-2-[(S,R)-1-(3-difluoromethoxy-phenyl)-3-(6-trifluoromethyl-pyridin-3-yl)-propylamino]-N-methyl-acetamide

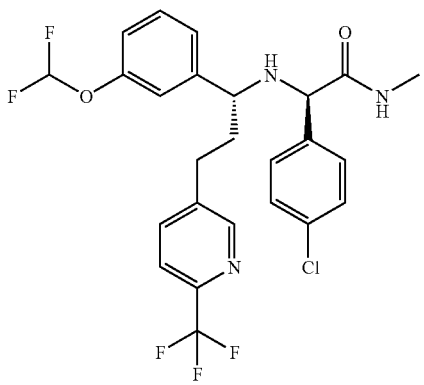

and

Example 249

(S,R)-2-(4-Chloro-phenyl)-2-[(R,S)-1-(3-difluoromethoxy-phenyl)-3-(6-trifluoromethyl-pyridin-3-yl)-propylamino]-N-methyl-acetamide

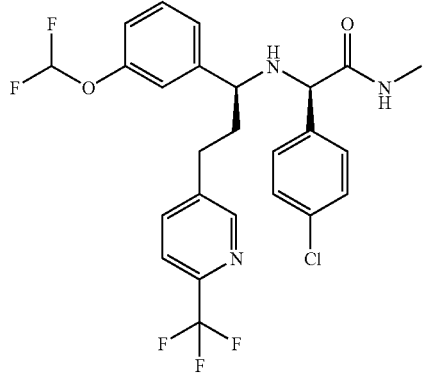

In analogy to the procedure described for the synthesis of examples 143 and 144 (step 3), the title compounds: (S,R)-2-(4-Chloro-phenyl)-2-[(S,R)-1-(3-difluoromethoxy-phenyl)-3-(6-trifluoromethyl-pyridin-3-yl)-propylamino]-N-methyl-acetamide (MS (m/e): 528.0 (MH$^+$)) and (S,R)-2-(4-Chloro-phenyl)-2-[(R,S)-1-(3-difluoromethoxy-phenyl)-3-(6-trifluoromethyl-pyridin-3-yl)-propylamino]-N-methyl-acetamide (MS (m/e): 528.0 (MH$^+$)) were prepared from rac-2-Amino-2-(4-chloro-phenyl)-N-methyl-acetamide and 1-(3-Difluoromethoxy-phenyl)-3-(6-trifluoromethyl-pyridin-3-yl)-propan-1-one (accessed according to the procedure described for examples 143 and 144, step 2 from (E)-1-(3-Difluoromethoxy-phenyl)-3-(6-trifluoromethyl-pyridin-3-yl)-propenone).

Example 250

(S,R)-2-[(S,R)-1-(3,4-Dimethyl-phenyl)-3-(6-trifluoromethyl-pyridin-3-yl)-propylamino]-N-methyl-2-phenyl-acetamide

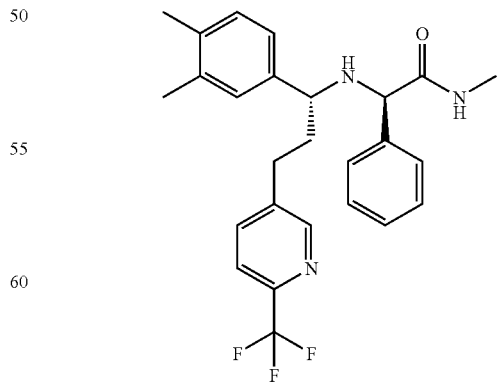

and

Example 251

(S,R)-2-[(R,S)-1-(3,4-Dimethyl-phenyl)-3-(6-trifluoromethyl-pyridin-3-yl)-propylamino]-N-methyl-2-phenyl-acetamide

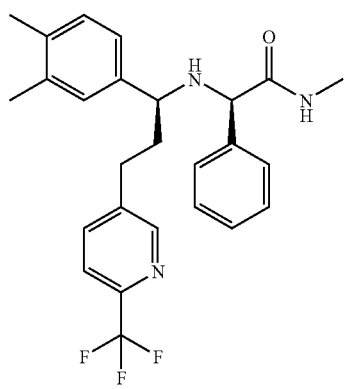

In analogy to the procedure described for the synthesis of examples 143 and 144 (step 3), the title compounds: (S,R)-2-[(S,R)-1-(3,4-Dimethyl-phenyl)-3-(6-trifluoromethyl-pyridin-3-yl)-propylamino]-N-methyl-2-phenyl-acetamide (MS (m/e): 456.4 (MH$^+$)) and (S,R)-2-[(R,S)-1-(3,4-Dimethyl-phenyl)-3-(6-trifluoromethyl-pyridin-3-yl)-propylamino]-N-methyl-2-phenyl-acetamide (MS (m/e): 456.4 (MH$^+$)) were prepared from rac-2-Amino-N-methyl-2-phenyl-acetamide (CAS: 93782-07-1) and 1-(3,4-Dimethyl-phenyl)-3-(6-trifluoromethyl-pyridin-3-yl)-propan-1-one (accessed according to the procedure described for examples 143 and 144, step 2 from (E)-1-(3,4-Dimethyl-phenyl)-3-(6-trifluoromethyl-pyridin-3-yl)-propenone).

Example 252

(S,R)-2-[(S,R)-1-(3-Methoxy-4-methyl-phenyl)-3-(6-trifluoromethyl-pyridin-3-yl)-propylamino]-N-methyl-2-phenyl-acetamide

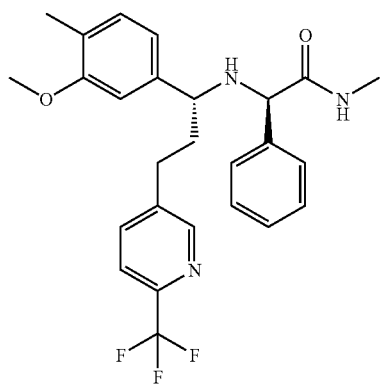

and

Example 253

(S,R)-2-[(R,S)-1-(3-Methoxy-4-methyl-phenyl)-3-(6-trifluoromethyl-pyridin-3-yl)-propylamino]-N-methyl-2-phenyl-acetamide

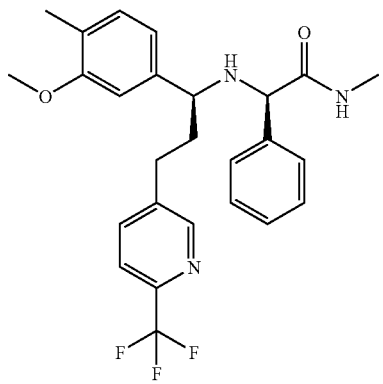

In analogy to the procedure described for the synthesis of examples 143 and 144 (step 3), the title compounds: (S,R)-2-[(S,R)-1-(3-Methoxy-4-methyl-phenyl)-3-(6-trifluoromethyl-pyridin-3-yl)-propylamino]-N-methyl-2-phenyl-acetamide (MS (m/e): 472.3 (MH$^+$)) and (S,R)-2-[(R,S)-1-(3-Methoxy-4-methyl-phenyl)-3-(6-trifluoromethyl-pyridin-3-yl)-propylamino]-N-methyl-2-phenyl-acetamide (MS (m/e): 472.3 (MH$^+$)) were prepared from rac-2-Amino-N-methyl-2-phenyl-acetamide (CAS: 93782-07-1) and 1-(3-Methoxy-4-methyl-phenyl)-3-(6-trifluoromethyl-pyridin-3-yl)-propan-1-one (accessed according to the procedure described for examples 233 and 234, step 2 from (E)-1-(3-Methoxy-4-methyl-phenyl)-3-(6-trifluoromethyl-pyridin-3-yl)-propenone).

Example 254

(S,R)—N-Methyl-2-[(R,S)-1-(6-methyl-pyridin-2-yl)-3-(6-trifluoromethyl-pyridin-3-yl)-propylamino]-2-phenyl-acetamide

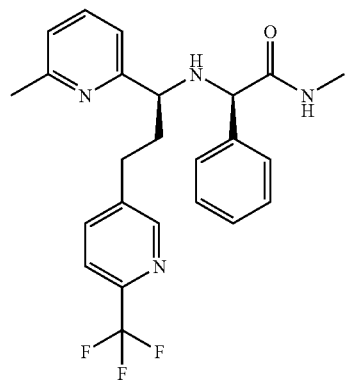

In analogy to the procedure described for the synthesis examples 143 and 144 (step 3), the title compound: (S,R)—N-Methyl-2-[(R,S)-1-(6-methyl-pyridin-2-yl)-3-(6-trifluoromethyl-pyridin-3-yl)-propylamino]-2-phenyl-acetamide (MS (m/e): 443.3 (MH+)) was prepared from rac-2-Amino-N-methyl-2-phenyl-acetamide (CAS: 93782-07-1) and 1-(6-Methyl-pyridin-2-yl)-3-(6-trifluoromethyl-pyridin-3-yl)-propan-1-one (accessed according to the procedure described for examples 143 and 144, step 2 from (E)-1-(6-Methyl-pyridin-2-yl)-3-(6-trifluoromethyl-pyridin-3-yl)-propenone).

Example 255

(S,R)-2-[(S,R)-1-(4-Fluoro-3-methyl-phenyl)-3-(5-trifluoromethyl-pyridin-2-yl)-propylamino]-N-methyl-2-phenyl-acetamide

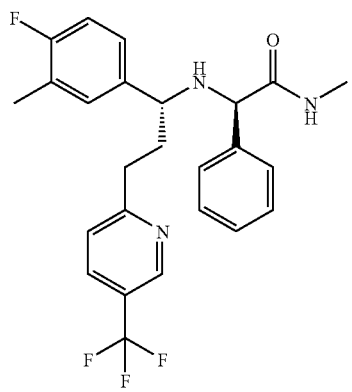

and

Example 256

(S,R)-2-[(R,S)-1-(4-Fluoro-3-methyl-phenyl)-3-(5-trifluoromethyl-pyridin-2-yl)-propylamino]-N-methyl-2-phenyl-acetamide

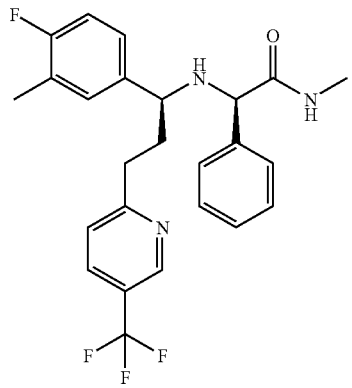

In analogy to the procedure described for the synthesis of examples 143 and 144 (step 3), the title compounds: (S,R)-2-[(S,R)-1-(4-Fluoro-3-methyl-phenyl)-3-(5-trifluoromethyl-pyridin-2-yl)-propylamino]-N-methyl-2-phenyl-acetamide (MS (m/e): 460.3 (MH+)) and (S,R)-2-[(R,S)-1-(4-Fluoro-3-methyl-phenyl)-3-(5-trifluoromethyl-pyridin-2-yl)-propylamino]-N-methyl-2-phenyl-acetamide (MS (m/e): 460.0 (MH+)) were prepared from rac-2-Amino-N-methyl-2-phenyl-acetamide (CAS: 93782-07-1) and 1-(4-Fluoro-3-methyl-phenyl)-3-(5-trifluoromethyl-pyridin-2-yl)-propan-1-one (accessed according to the procedure described for examples 233 and 234, step 2 from (E)-1-(4-Fluoro-3-methyl-phenyl)-3-(5-trifluoromethyl-pyridin-2-yl)-propenone).

Example 257

(S,R)-2-[(R,S)-1-(6-Chloro-pyridin-2-yl)-3-(6-trifluoromethyl-pyridin-3-yl)-propylamino]-N-methyl-2-phenyl-acetamide

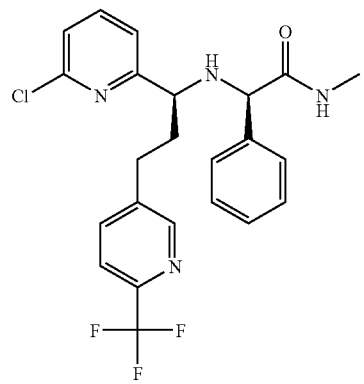

In analogy to the procedure described for the synthesis of examples 143 and 144 (step 3), the title compound: (S,R)-2-[(R,S)-1-(6-Chloro-pyridin-2-yl)-3-(6-trifluoromethyl-pyridin-3-yl)-propylamino]-N-methyl-2-phenyl-acetamide (MS (m/e): 463.2 (MH+)) was prepared from rac-2-Amino-N-methyl-2-phenyl-acetamide (CAS: 93782-07-1) and 1-(6-Chloro-pyridin-2-yl)-3-(6-trifluoromethyl-pyridin-3-yl)-propan-1-one (accessed according to the procedure described for examples 233 and 234, step 2 from (E)-1-(6-Chloro-pyridin-2-yl)-3-(6-trifluoromethyl-pyridin-3-yl)-propenone).

Example 258

2-[1-(4-Fluoro-3-methyl-phenyl)-3-(6-methyl-pyridin-3-yl)-propylamino]-N-methyl-2-phenyl-acetamide

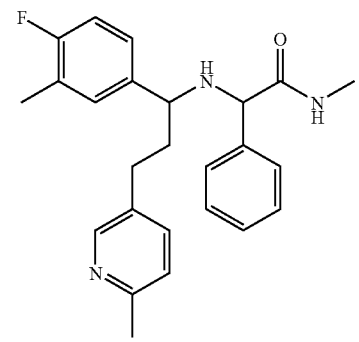

In analogy to the procedure described for the synthesis of examples 143 and 144 (step 3), the title compound: 2-[1-(4-Fluoro-3-methyl-phenyl)-3-(6-methyl-pyridin-3-yl)-propylamino]-N-methyl-2-phenyl-acetamide (as a mixture of four diastereoisomers) (MS (m/e): 406.5 (MH⁺)) was prepared from rac-2-Amino-N-methyl-2-phenyl-acetamide (CAS: 93782-07-1) and 1-(4-Fluoro-3-methyl-phenyl)-3-(6-methyl-pyridin-3-yl)-propan-1-one (accessed according to the procedure described for examples 233 and 234, step 2 from (E)-1-(4-Fluoro-3-methyl-phenyl)-3-(6-methyl-pyridin-3-yl)-propenone).

Example 259

(S)-2-[(S)-1-(4-Fluoro-3-methyl-phenyl)-3-(6-methyl-pyridin-3-yl)-propylamino]-N-methyl-2-phenyl-acetamide

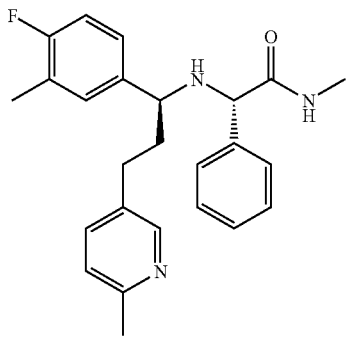

and

Example 260

(R)-2-[(R)-1-(4-Fluoro-3-methyl-phenyl)-3-(6-methyl-pyridin-3-yl)-propylamino]-N-methyl-2-phenyl-acetamide

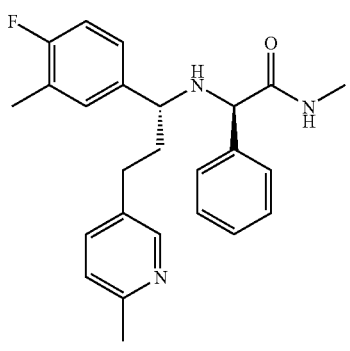

and

Example 261

(S)-2-[(R)-1-(4-Fluoro-3-methyl-phenyl)-3-(6-methyl-pyridin-3-yl)-propylamino]-N-methyl-2-phenyl-acetamide

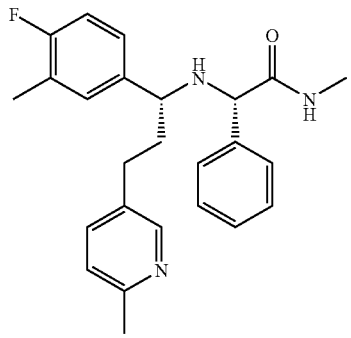

and

Example 262

(R)-2-[(S)-1-(4-Fluoro-3-methyl-phenyl)-3-(6-methyl-pyridin-3-yl)-propylamino]-N-methyl-2-phenyl-acetamide

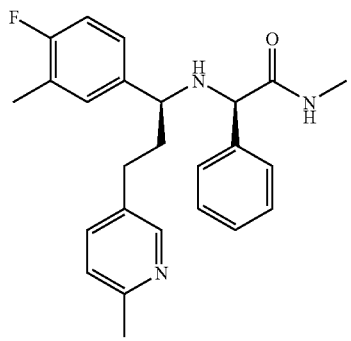

2-[1-(4-Fluoro-3-methyl-phenyl)-3-(6-methyl-pyridin-3-yl)-propylamino]-N-methyl-2-phenyl-acetamide (Example 258) was separated on chiral phase HPLC (Chiralpak AD column) to provide the title compounds: (S)-2-[(S)-1-(4-Fluoro-3-methyl-phenyl)-3-(6-methyl-pyridin-3-yl)-propylamino]-N-methyl-2-phenyl-acetamide (MS (m/e): 406.5 (MH⁺)) and (R)-2-[(R)-1-(4-Fluoro-3-methyl-phenyl)-3-(6-methyl-pyridin-3-yl)-propylamino]-N-methyl-2-phenyl-acetamide (MS (m/e): 406.5 (MH⁺)) and (S)-2-[(R)-1-(4-Fluoro-3-methyl-phenyl)-3-(6-methyl-pyridin-3-yl)-propylamino]-N-methyl-2-phenyl-acetamide (MS (m/e): 406.5 (MH⁺)) and (R)-2-[(S)-1-(4-Fluoro-3-methyl-phenyl)-3-(6-methyl-pyridin-3-yl)-propylamino]-N-methyl-2-phenyl-acetamide (MS (m/e): 406.5 (MH⁺)) as colorless oils.

Example 263

2-[1-(3,4-Bis-difluoromethoxy-phenyl)-3-(6-trifluoromethyl-pyridin-3-yl)-propylamino]-N-methyl-2-phenyl-acetamide

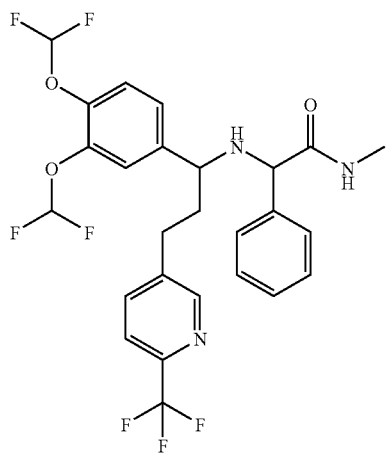

In analogy to the procedure described for the synthesis of examples 143 and 144 (step 3), the title compound: 2-[1-(3,4-Bis-difluoromethoxy-phenyl)-3-(6-trifluoromethyl-pyridin-3-yl)-propylamino]-N-methyl-2-phenyl-acetamide (as a mixture of four diastereoisomers) (MS (m/e): 559.7 (MH$^+$)) was prepared from rac-2-Amino-N-methyl-2-phenyl-acetamide (CAS: 93782-07-1) and 1-(3,4-Bis-difluoromethoxy-phenyl)-3-(6-trifluoromethyl-pyridin-3-yl)-propan-1-one (accessed according to the procedure described for examples 233 and 234, step 2 from (E)-1-(3,4-Bis-difluoromethoxy-phenyl)-3-(6-trifluoromethyl-pyridin-3-yl)-propenone).

Example 264

2-[1-(4-Fluoro-3-methyl-phenyl)-3-pyrazin-2-yl-propylamino]-N-methyl-2-phenyl-acetamide

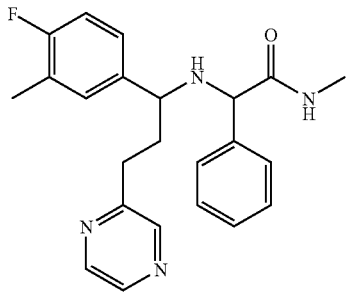

In analogy to the procedure described for the synthesis of examples 143 and 144 (step 3), the title compound: 2-[1-(4-Fluoro-3-methyl-phenyl)-3-pyrazin-2-yl-propylamino]-N-methyl-2-phenyl-acetamide (as a mixture of four diastereoisomers) (MS (m/e): 393.3 (MH$^+$)) was prepared from rac-2-Amino-N-methyl-2-phenyl-acetamide (CAS: 93782-07-1) and 1-(4-Fluoro-3-methyl-phenyl)-3-pyrazin-2-yl-propan-1-one (accessed according to the procedure described for examples 233 and 234, step 2 from (E)-1-(4-Fluoro-3-methyl-phenyl)-3-pyrazin-2-yl-propenone).

Example 265

(S,R)-2-[(S,R)-3-(6-Chloro-pyridin-3-yl)-1-(4-fluoro-3-methyl-phenyl)-propylamino]-N-methyl-2-phenyl-acetamide

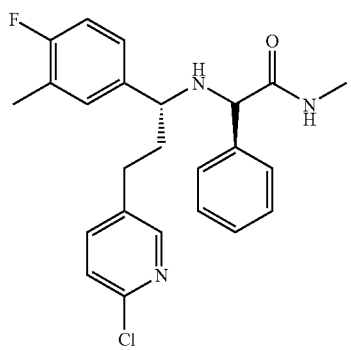

and

Example 266

(S,R)-2-[(R,S)-3-(6-Chloro-pyridin-3-yl)-1-(4-fluoro-3-methyl-phenyl)-propylamino]-N-methyl-2-phenyl-acetamide

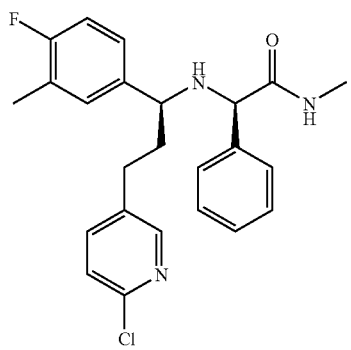

In analogy to the procedure described for the synthesis of examples 143 and 144 (step 3), the title compounds: (S,R)-2-[(S,R)-3-(6-Chloro-pyridin-3-yl)-1-(4-fluoro-3-methyl-phenyl)-propylamino]-N-methyl-2-phenyl-acetamide (MS (m/e): 426.4 (MH$^+$)) and (S,R)-2-[(R,S)-3-(6-Chloro-pyridin-3-yl)-1-(4-fluoro-3-methyl-phenyl)-propylamino]-N-methyl-2-phenyl-acetamide (MS (m/e): 426.4 (MH$^+$)) were prepared from rac-2-Amino-N-methyl-2-phenyl-acetamide (CAS: 93782-07-1) and 3-(6-Chloro-pyridin-3-yl)-1-(4-fluoro-3-methyl-phenyl)-propan-1-one (accessed according to the procedure described for examples 233 and 234, step 2 from (E)-3-(6-Chloro-pyridin-3-yl)-1-(4-fluoro-3-methyl-phenyl)-propenone).

Example 267

(S,R)-2-[(S,R)-3-(4-Cyano-phenyl)-1-(4-fluoro-3-methyl-phenyl)-propylamino]-N-methyl-2-phenyl-acetamide

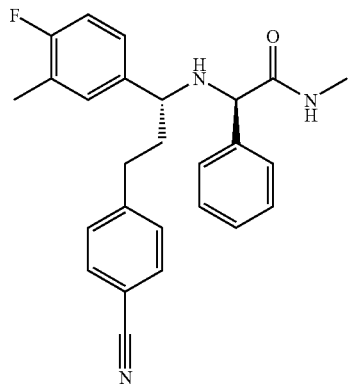

and

Example 268

(S,R)-2-[(R,S)-3-(4-Cyano-phenyl)-1-(4-fluoro-3-methyl-phenyl)-propylamino]-N-methyl-2-phenyl-acetamide

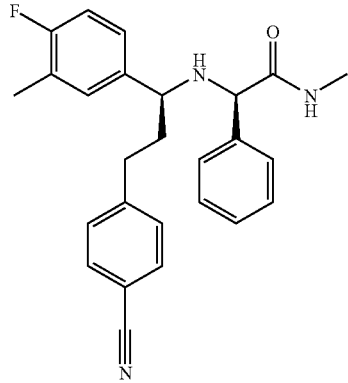

In analogy to the procedure described for the synthesis of examples 143 and 144 (step 3), the title compounds: (S,R)-2-[(S,R)-3-(4-Cyano-phenyl)-1-(4-fluoro-3-methyl-phenyl)-propylamino]-N-methyl-2-phenyl-acetamide (MS (m/e): 416.4 (MH$^+$)) and (S,R)-2-[(R,S)-3-(4-Cyano-phenyl)-1-(4-fluoro-3-methyl-phenyl)-propylamino]-N-methyl-2-phenyl-acetamide (MS (m/e): 416.5 (MH$^+$)) were prepared from rac-2-Amino-N-methyl-2-phenyl-acetamide (CAS: 93782-07-1) and 4-[3-(4-Fluoro-3-methyl-phenyl)-3-oxo-propyl]-benzonitrile (accessed according to the procedure described for examples 233 and 234, step 2 from 4-[(E)-3-(4-Fluoro-3-methyl-phenyl)-3-oxo-propenyl]-benzonitrile).

Example 269

(S,R)-2-[(S,R)-1-(4-Fluoro-3-methyl-phenyl)-3-(4-trifluoromethyl-phenyl)-propylamino]-2-phenyl-acetamide

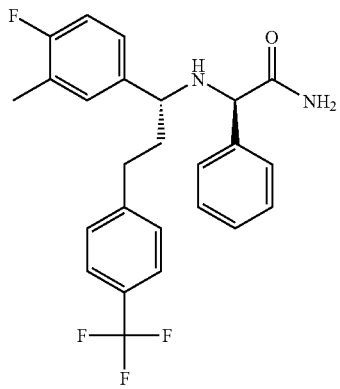

and

Example 270

(S,R)-2-[(R,S)-1-(4-Fluoro-3-methyl-phenyl)-3-(4-trifluoromethyl-phenyl)-propylamino]-2-phenyl-acetamide

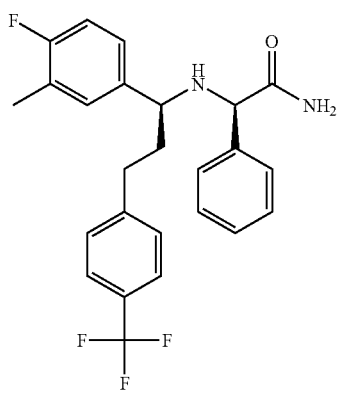

In analogy to the procedure described for the synthesis of examples 143 and 144 (step 3), the title compounds: (S,R)-2-[(S,R)-1-(4-Fluoro-3-methyl-phenyl)-3-(4-trifluoromethyl-phenyl)-propylamino]-2-phenyl-acetamide (MS (m/e): 445.5 (MH$^+$)) and (S,R)-2-[(R,S)-1-(4-Fluoro-3-methyl-phenyl)-3-(4-trifluoromethyl-phenyl)-propylamino]-2-phenyl-acetamide (MS (m/e): 445.3 (MH$^+$)) were prepared from rac-2-Amino-2-phenyl-acetamide (CAS: 700-63-0) and 1-(4-Fluoro-3-methyl-phenyl)-3-(4-trifluoromethyl-phenyl)-propan-1-one (accessed according to the procedure described for examples 233 and 234, step 2 from (E)-1-(4-Fluoro-3-methyl-phenyl)-3-(4-trifluoromethyl-phenyl)-propenone).

Example 271

(S,R)-2-[(S,R)-1-(2,3-Dihydro-benzo[1,4]dioxin-6-yl)-3-(4-trifluoromethyl-phenyl)-propylamino]-N-methyl-2-phenyl-acetamide

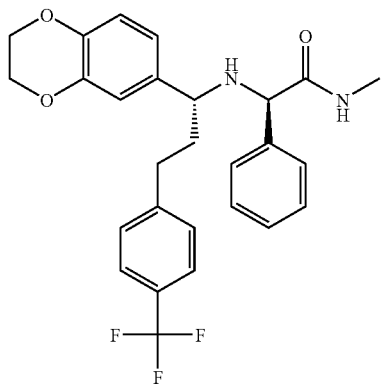

and

Example 272

(S,R)-2-[(R,S)-1-(2,3-Dihydro-benzo[1,4]dioxin-6-yl)-3-(4-trifluoromethyl-phenyl)-propylamino]-N-methyl-2-phenyl-acetamide

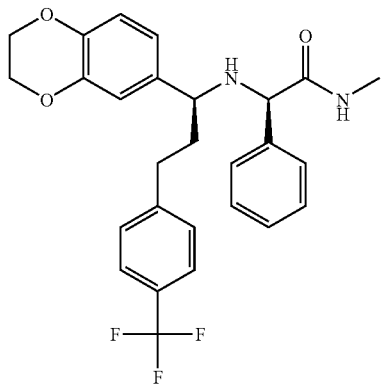

In analogy to the procedure described for the synthesis of examples 143 and 144 (step 3), the title compounds: (S,R)-2-[(S,R)-1-(2,3-Dihydro-benzo[1,4]dioxin-6-yl)-3-(4-trifluoromethyl-phenyl)-propylamino]-N-methyl-2-phenyl-acetamide (MS (m/e): 485.0 (MH$^+$)) and (S,R)-2-[(R,S)-1-(2,3-Dihydro-benzo[1,4]dioxin-6-yl)-3-(4-trifluoromethyl-phenyl)-propylamino]-N-methyl-2-phenyl-acetamide (MS (m/e): 485.1 (MH$^+$)) were prepared from rac-2-Amino-N-methyl-2-phenyl-acetamide (CAS: 93782-07-1) and 1-(2,3-Dihydro-benzo[1,4]dioxin-6-yl)-3-(4-trifluoromethyl-phenyl)-propan-1-one (accessed according to the procedure described for examples 233 and 234, step 2 from (E)-1-(2,3-Dihydro-benzo[1,4]dioxin-6-yl)-3-(4-trifluoromethyl-phenyl)-propenone).

Example 273

(S,R)-2-[(S,R)-1-(4-Isopropoxy-3-methoxy-phenyl)-3-(4-trifluoromethyl-phenyl)-propylamino]-N-methyl-2-phenyl-acetamide

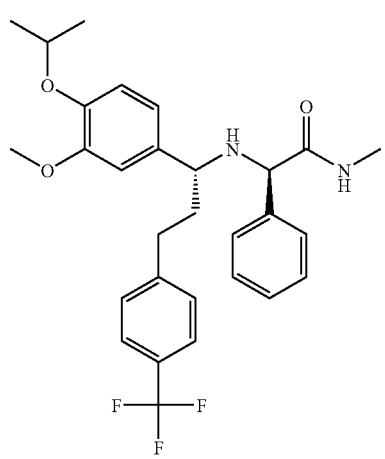

and

Example 274

(S,R)-2-[(R,S)-1-(4-Isopropoxy-3-methoxy-phenyl)-3-(4-trifluoromethyl-phenyl)-propylamino]-N-methyl-2-phenyl-acetamide

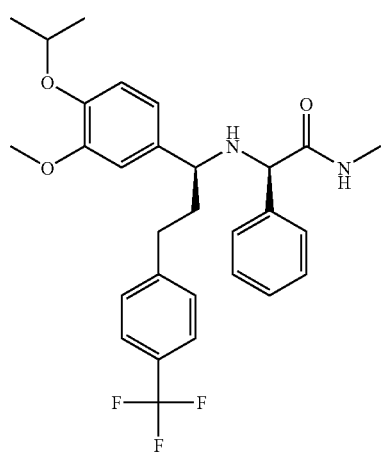

In analogy to the procedure described for the synthesis of examples 143 and 144 (step 3), the title compounds: (S,R)-2-[(S,R)-1-(4-Isopropoxy-3-methoxy-phenyl)-3-(4-trifluoromethyl-phenyl)-propylamino]-N-methyl-2-phenyl-acetamide (MS (m/e): 515.0 (MH$^+$)) and (S,R)-2-[(R,S)-1-(4-Isopropoxy-3-methoxy-phenyl)-3-(4-trifluoromethyl-phenyl)-propylamino]-N-methyl-2-phenyl-acetamide (MS (m/e): 515.0 (MH$^+$)) were prepared from rac-2-Amino-N- methyl-2-phenyl-acetamide (CAS: 93782-07-1) and 1-(4-Isopropoxy-3-methoxy-phenyl)-3-(4-trifluoromethyl-phenyl)-propan-1-one (accessed according to the procedure described for example 233 and 234, step 2 from (E)-1-(4-Isopropoxy-3-methoxy-phenyl)-3-(4-trifluoromethyl-phenyl)-propenone).

Example 275

2-[1-(2,2-Difluoro-benzo[1,3]dioxol-5-yl)-3-(4-trifluoromethyl-phenyl)-propylamino]-N-methyl-2-phenyl-acetamide

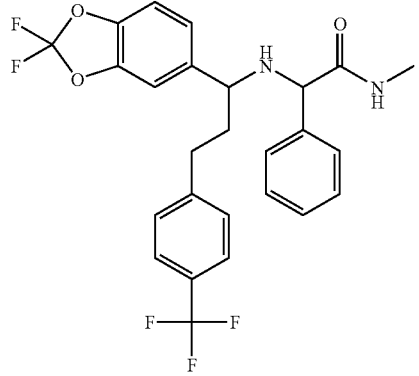

In analogy to the procedure described for the synthesis of examples 143 and 144 (step 3), the title compound: 2-[1-(2,2-Difluoro-benzo[1,3]dioxol-5-yl)-3-(4-trifluoromethyl-phenyl)-propylamino]-N-methyl-2-phenyl-acetamide (as a mixture of four diastereoisomers) (MS (m/e): 507.4 (MH$^+$)) was prepared from rac-2-Amino-N-methyl-2-phenyl-acetamide (CAS: 93782-07-1) and 1-(2,2-Difluoro-benzo[1,3]dioxol-5-yl)-3-(4-trifluoromethyl-phenyl)-propan-1-one (accessed according to the procedure described for examples 233 and 234, step 2 from (E)-1-(2,2-Difluoro-benzo[1,3]dioxol-5-yl)-3-(4-trifluoromethyl-phenyl)-propenone).

Example 276

(S,R)-2-[(R,S)-1-Benzothiazol-6-yl-3-(4-trifluoromethyl-phenyl)-propylamino]-N-methyl-2-phenyl-acetamide

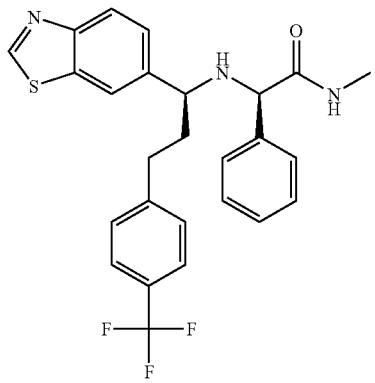

In analogy to the procedure described for the synthesis of examples 143 and 144 (step 3), the title compound: (S,R)-2-[(R,S)-1-Benzothiazol-6-yl-3-(4-trifluoromethyl-phenyl)-propylamino]-N-methyl-2-phenyl-acetamide (MS (m/e): 484.3 (MH$^+$)) was prepared from rac-2-Amino-N-methyl-2-phenyl-acetamide (CAS: 93782-07-1) and 1-Benzothiazol-6-yl-3-(4-trifluoromethyl-phenyl)-propan-1-one (accessed according to the procedure described for examples 164 and 165, step 2 from 2-Methyl-benzothiazole-6-carboxylic acid methoxy-methyl-amide and p-trifluoromethylphenyl ethyl magnesium bromide).

Example 277

2-(4-Chloro-phenyl)-2-[3-(4-cyano-phenyl)-1-(4-fluoro-3-methyl-phenyl)-propylamino]-N-methyl-acetamide

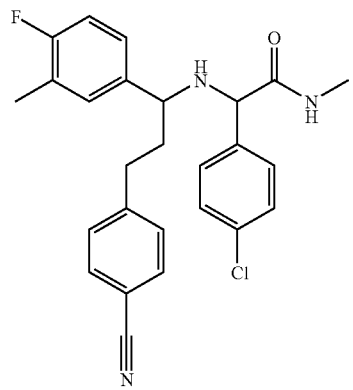

In analogy to the procedure described for the synthesis of examples 143 and 144 (step 3), the title compound: 2-(4-Chloro-phenyl)-2-[3-(4-cyano-phenyl)-1-(4-fluoro-3-methyl-phenyl)-propylamino]-N-methyl-acetamide (as a mixture of four stereoisomers) (MS (m/e): 450.3 (MH$^+$)) was prepared from rac-2-Amino-2-(4-chloro-phenyl)-N-methyl-acetamide and 4-[3-(4-Fluoro-3-methyl-phenyl)-3-oxo-propyl]-benzonitrile (accessed according to the procedure described for examples 233 and 234, step 2 from 4-[(E)-3-(4-Fluoro-3-methyl-phenyl)-3-oxo-propenyl]-benzonitrile).

Example 278

(S,R)-2-[(S,R)-1-(3,4-Diethoxy-phenyl)-3-(4-trifluoromethyl-phenyl)-propylamino]-N-methyl-2-phenyl-acetamide

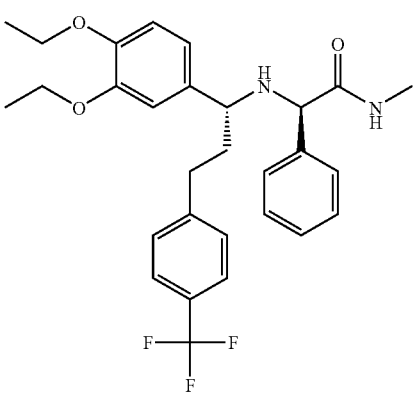

and

Example 279

(S,R)-2-[(R,S)-1-(3,4-Diethoxy-phenyl)-3-(4-trifluoromethyl-phenyl)-propylamino]-N-methyl-2-phenyl-acetamide

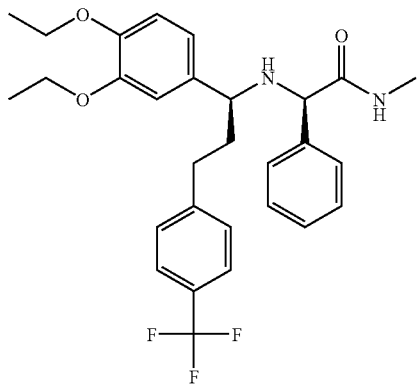

In analogy to the procedure described for the synthesis of examples 143 and 144 (step 3), the title compounds: (S,R)-2-[(S,R)-1-(3,4-Diethoxy-phenyl)-3-(4-trifluoromethyl-phenyl)-propylamino]-N-methyl-2-phenyl-acetamide (MS (m/e): 515.0 (MH$^+$)) and (S,R)-2-[(R,S)-1-(3,4-Diethoxy-phenyl)-3-(4-trifluoromethyl-phenyl)-propylamino]-N-methyl-2-phenyl-acetamide (MS (m/e): 515.0 (MH$^+$)) were prepared from rac-2-Amino-N-methyl-2-phenyl-acetamide (CAS: 93782-07-1) and 1-(3,4-Diethoxy-phenyl)-3-(4-trifluoromethyl-phenyl)-propan-1-one (accessed according to the procedure described for examples 233 and 234, step 2 from (E)-1-(3,4-Diethoxy-phenyl)-3-(4-trifluoromethyl-phenyl)-propenone).

Example 280

(S,R)-2-[(S,R)-1-(3-Isopropoxy-4-methoxy-phenyl)-3-(4-trifluoromethyl-phenyl)-propylamino]-N-methyl-2-phenyl-acetamide

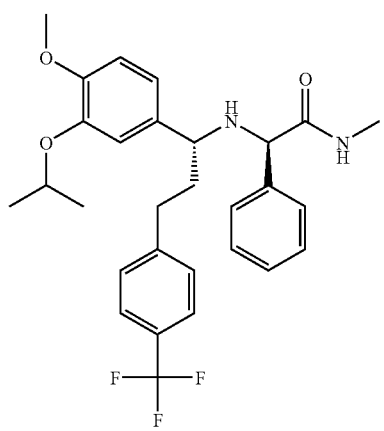

and

Example 281

(S,R)-2-[(R,S)-1-(3-Isopropoxy-4-methoxy-phenyl)-3-(4-trifluoromethyl-phenyl)-propylamino]-N-methyl-2-phenyl-acetamide

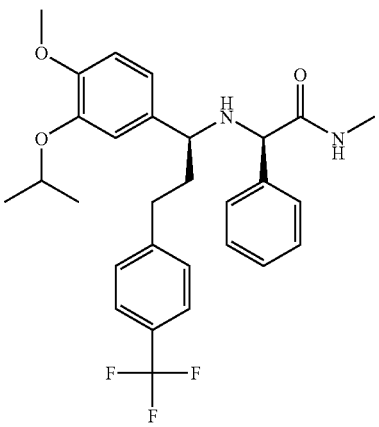

In analogy to the procedure described for the synthesis of examples 143 and 144 (step 3), the title compounds: (S,R)-2-[(S,R)-1-(3-Isopropoxy-4-methoxy-phenyl)-3-(4-trifluoromethyl-phenyl)-propylamino]-N-methyl-2-phenyl-acetamide (MS (m/e): 515.1 (MH$^+$)) and (S,R)-2-[(R,S)-1-(3-Isopropoxy-4-methoxy-phenyl)-3-(4-trifluoromethyl-phenyl)-propylamino]-N-methyl-2-phenyl-acetamide (MS (m/e): 515.1 (MH$^+$)) were prepared from rac-2-Amino-N-methyl-2-phenyl-acetamide (CAS: 93782-07-1) and 1-(3-Isopropoxy-4-methoxy-phenyl)-3-(4-trifluoromethyl-phenyl)-propan-1-one (accessed according to the procedure described for examples 233 and 234, step 2 from (E)-1-(3-Isopropoxy-4-methoxy-phenyl)-3-(4-trifluoromethyl-phenyl)-propenone).

Example 282

2-[1-(4-Fluoro-3-methyl-phenyl)-3-(6-methyl-pyridazin-3-yl)-propylamino]-N-methyl-2-phenyl-acetamide

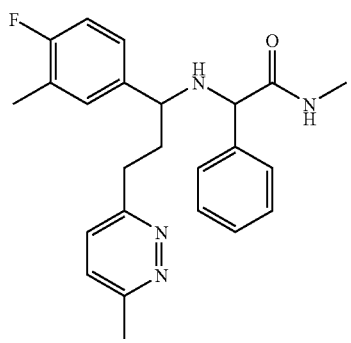

In analogy to the procedure described for the synthesis of examples 143 and 144 (step 3), the title compound: 2-[1-(4-Fluoro-3-methyl-phenyl)-3-(6-methyl-pyridazin-3-yl)-propylamino]-N-methyl-2-phenyl-acetamide (as a mixture of four stereoisomers) (MS (m/e): 407.3 (MH+)) was prepared from rac-2-Amino-N-methyl-2-phenyl-acetamide (CAS: 93782-07-1) and 1-(4-Fluoro-3-methyl-phenyl)-3-(6-methyl-pyridazin-3-yl)-propan-1-one (accessed according to the procedure described for examples 233 and 234, step 2 from (E)-1-(4-Fluoro-3-methyl-phenyl)-3-(6-methyl-pyridazin-3-yl)-propenone).

Example 283

(S,R)—N-Methyl-2-[(S,R)-1-(2-methyl-benzothiazol-6-yl)-3-(4-trifluoromethyl-phenyl)-propylamino]-2-phenyl-acetamide

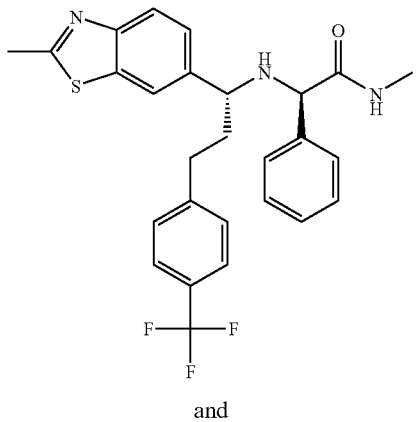

and

Example 284

(S,R)—N-Methyl-2-[(R,S)-1-(2-methyl-benzothiazol-6-yl)-3-(4-trifluoromethyl-phenyl)-propylamino]-2-phenyl-acetamide

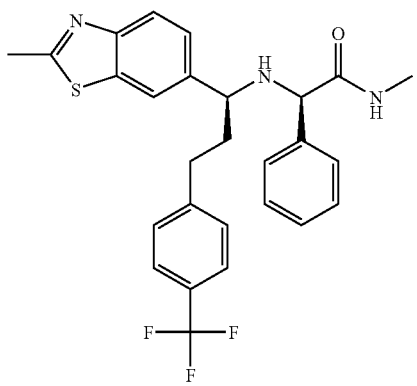

In analogy to the procedure described for the synthesis of examples 143 and 144 (step 3), the title compounds: (S,R)—N-Methyl-2-[(S,R)-1-(2-methyl-benzothiazol-6-yl)-3-(4-trifluoromethyl-phenyl)-propylamino]-2-phenyl-acetamide (MS (m/e): 498.4 (MH+)) and (S,R)—N-Methyl-2-[(R,S)-1-(2-methyl-benzothiazol-6-yl)-3-(4-trifluoromethyl-phenyl)-propylamino]-2-phenyl-acetamide (MS (m/e): 498.4 (MH+)) were prepared from rac-2-Amino-N-methyl-2-phenyl-acetamide (CAS: 93782-07-1) and 1-(2-Methyl-benzothiazol-6-yl)-3-(4-trifluoromethyl-phenyl)-propan-1-one (accessed according to the procedure described for examples 164 and 165, step 2 from 2-Methyl-benzothiazole-6-carboxylic acid methoxy-methyl-amide and p-trifluoromethylphenyl ethyl magnesium bromide.

Example 285

(S,R)-2-[(S,R)-1-(3,4-Diisopropoxy-phenyl)-3-(4-trifluoromethyl-phenyl)-propylamino]-N-methyl-2-phenyl-acetamide

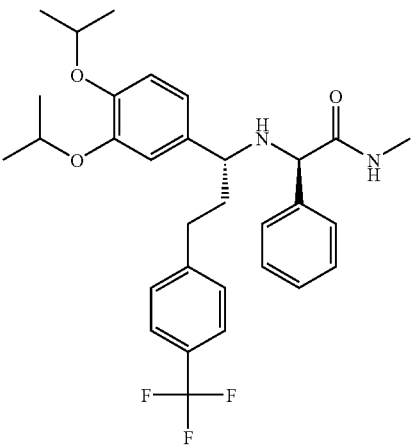

In analogy to the procedure described for the synthesis of examples 143 and 144 (step 3), the title compound: (S,R)-2-[(S,R)-1-(3,4-Diisopropoxy-phenyl)-3-(4-trifluoromethyl-phenyl)-propylamino]-N-methyl-2-phenyl-acetamide (MS (m/e): 543.5 (MH+)) was prepared from rac-2-Amino-N-methyl-2-phenyl-acetamide (CAS: 93782-07-1) and 1-(3,4-Diisopropoxy-phenyl)-3-(4-trifluoromethyl-phenyl)-propan-1-one (accessed according to the procedure described for examples 233 and 234, step 2 from (E)-1-(3,4-Diisopropoxy-phenyl)-3-(4-trifluoromethyl-phenyl)-propenone).

Example 286

(S,R)-2-[(R,S)-1-(6-Chloro-pyridin-2-yl)-3-(4-trifluoromethyl-phenyl)-propylamino]-N-methyl-2-phenyl-acetamide

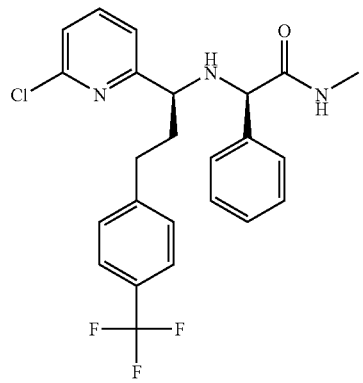

In analogy to the procedure described for the synthesis of examples 143 and 144 (step 3), the title compound: (S,R)-2-[(R,S)-1-(6-Chloro-pyridin-2-yl)-3-(4-trifluoromethyl-phenyl)-propylamino]-N-methyl-2-phenyl-acetamide (MS (m/e): 462.2 (MH+)) was prepared from rac-2-Amino-N-me- 1thyl-2-phenyl-acetamide (CAS: 93782-07-1) and 1-(6-Chloro-pyridin-2-yl)-3-(4-trifluoromethyl-phenyl)-propan-1-one (accessed according to the procedure described for examples 233 and 234, step 2 from (E)-1-(6-Chloro-pyridin-2-yl)-3-(4-trifluoromethyl-phenyl)-propenone).

Example 287

(S,R)-2-[(R,S)-1-(6-Chloro-pyridin-2-yl)-3-(4-trifluoromethyl-phenyl)-propylamino]-2-phenyl-acetamide

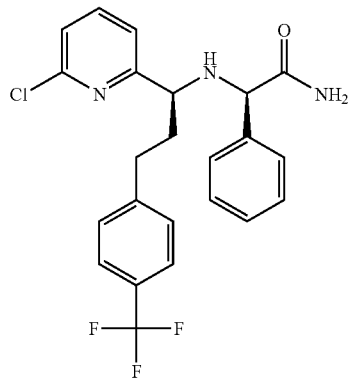

In analogy to the procedure described for the synthesis of examples 143 and 144 (step 3), the title compound: (S,R)-2-[(R,S)-1-(6-Chloro-pyridin-2-yl)-3-(4-trifluoromethyl-phenyl)-propylamino]-2-phenyl-acetamide (MS (m/e): 448.2 (MH$^+$)) was prepared from rac-2-Amino-2-phenyl-acetamide (CAS: 700-63-0) and 1-(6-Chloro-pyridin-2-yl)-3-(4-trifluoromethyl-phenyl)-propan-1-one (accessed according to the procedure described for examples 233 and 234, step 2 from (E)-1-(6-Chloro-pyridin-2-yl)-3-(4-trifluoromethyl-phenyl)-propenone).

Example 288

(S,R)—N-Methyl-2-[(S,R)-1-(2-methyl-benzooxazol-6-yl)-3-(4-trifluoromethyl-phenyl)-propylamino]-2-phenyl-acetamide

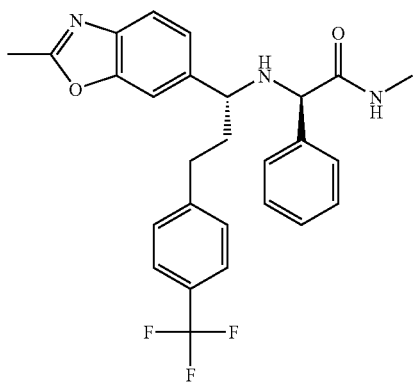

and

Example 289

(S,R)—N-Methyl-2-[(R,S)-1-(2-methyl-benzooxazol-6-yl)-3-(4-trifluoromethyl-phenyl)-propylamino]-2-phenyl-acetamide

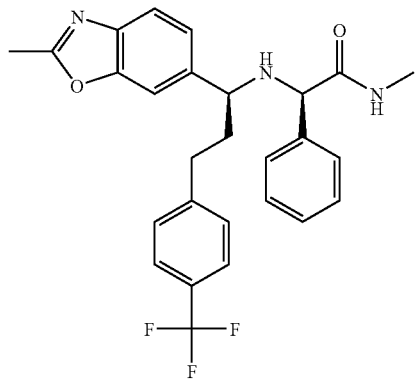

In analogy to the procedure described for the synthesis of examples 143 and 144 (step 3), the title compounds: (S,R)—N-Methyl-2-[(S,R)-1-(2-methyl-benzooxazol-6-yl)-3-(4-trifluoromethyl-phenyl)-propylamino]-2-phenyl-acetamide (MS (m/e): 482.2 (MH$^+$)) and (S,R)—N-Methyl-2-[(R,S)-1-(2-methyl-benzooxazol-6-yl)-3-(4-trifluoromethyl-phenyl)-propylamino]-2-phenyl-acetamide (MS (m/e): 482.2 (MH$^+$)) were prepared from rac-2-Amino-N-methyl-2-phenyl-acetamide (CAS: 93782-07-1) and 1-(2-Methyl-benzooxazol-6-yl)-3-(4-trifluoromethyl-phenyl)-propan-1-one (accessed according to the procedure described for examples 164 and 165, step 2 2-Methyl-benzooxazole-6-carboxylic acid methoxy-methyl-amide and p-trifluoromethylphenyl ethyl magnesium bromide.

Example 290

(S,R)-2-[(S,R)-1-(3,4-Bis-difluoromethoxy-phenyl)-3-(4-trifluoromethyl-phenyl)-propylamino]-N-methyl-2-phenyl-acetamide

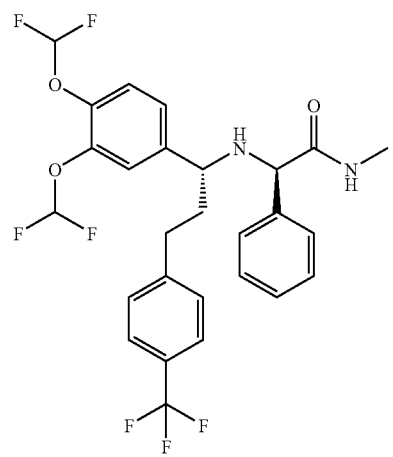

and

Example 291

(S,R)-2-[(R,S)-1-(3,4-Bis-difluoromethoxy-phenyl)-3-(4-trifluoromethyl-phenyl)-propylamino]-N-methyl-2-phenyl-acetamide

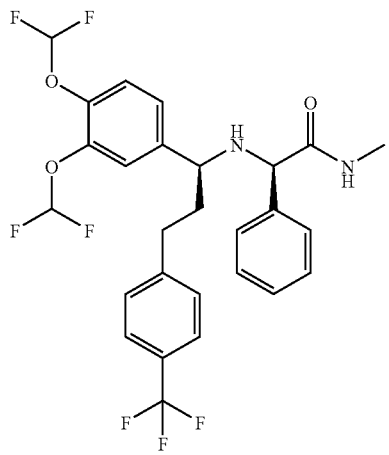

In analogy to the procedure described for the synthesis of examples 143 and 144 (step 3), the title compounds: (S,R)-2-[(S,R)-1-(3,4-Bis-difluoromethoxy-phenyl)-3-(4-trifluoromethyl-phenyl)-propylamino]-N-methyl-2-phenyl-acetamide (MS (m/e): 559.3 (MH$^+$)) and (S,R)-2-[(R,S)-1-(3,4-Bis-difluoromethoxy-phenyl)-3-(4-trifluoromethyl-phenyl)-propylamino]-N-methyl-2-phenyl-acetamide (MS (m/e): 559.3 (MH$^+$)) were prepared from rac-2-Amino-N-methyl-2-phenyl-acetamide (CAS: 93782-07-1) and 1-(3,4-Bis-difluoromethoxy-phenyl)-3-(4-trifluoromethyl-phenyl)-propan-1-one (accessed according to the procedure described for examples 233 and 234, step 2 from (E)-1-(3,4-Bis-difluoromethoxy-phenyl)-3-(4-trifluoromethyl-phenyl)-propenone).

Example 292

(S,R)-2-[(S,R)-1-(3,4-Bis-difluoromethoxy-phenyl)-3-(4-trifluoromethyl-phenyl)-propylamino]-2-phenyl-acetamide

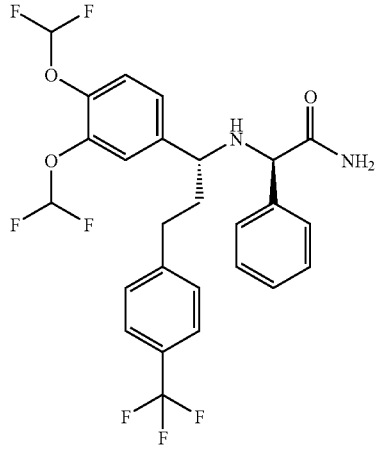

and

Example 293

(S,R)-2-[(R,S)-1-(3,4-Bis-difluoromethoxy-phenyl)-3-(4-trifluoromethyl-phenyl)-propylamino]-2-phenyl-acetamide

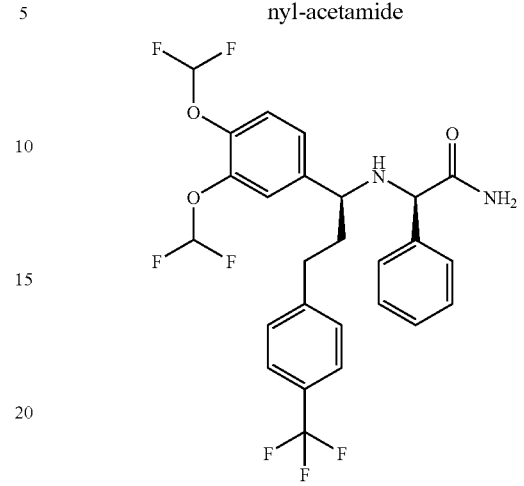

In analogy to the procedure described for the synthesis of examples 143 and 144 (step 3), the title compounds: (S,R)-2-[(S,R)-1-(3,4-Bis-difluoromethoxy-phenyl)-3-(4-trifluoromethyl-phenyl)-propylamino]-2-phenyl-acetamide (MS (m/e): 545.2 (MH$^+$)) and (S,R)-2-[(R,S)-1-(3,4-Bis-difluoromethoxy-phenyl)-3-(4-trifluoromethyl-phenyl)-propylamino]-2-phenyl-acetamide (MS (m/e): 545.2 (MH$^+$)) were prepared from rac-2-Amino-2-phenyl-acetamide (CAS: 700-63-0) and 1-(3,4-Bis-difluoromethoxy-phenyl)-3-(4-trifluoromethyl-phenyl)-propan-1-one (accessed according to the procedure described for examples 233 and 234, step 2 from (E)-1-(3,4-Bis-difluoromethoxy-phenyl)-3-(4-trifluoromethyl-phenyl)-propenone).

Example 294

(S,R)-2-(4-Chloro-phenyl)-2-[(R,S)-1-(6-chloro-pyridin-2-yl)-3-(4-trifluoromethyl-phenyl)-propylamino]-N-methyl-acetamide

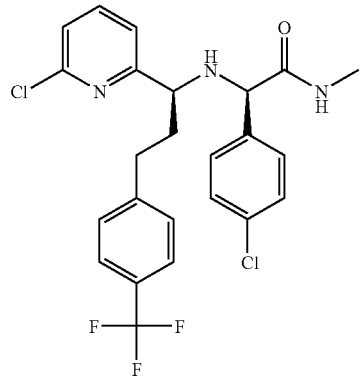

In analogy to the procedure described for the synthesis of examples 143 and 144 (step 3), the title compound (S,R)-2-(4-Chloro-phenyl)-2-[(R,S)-1-(6-chloro-pyridin-2-yl)-3-(4-trifluoromethyl-phenyl)-propylamino]-N-methyl-acetamide (MS (m/e): 496.1 (MH$^+$)) was prepared from rac-2-Amino-2-(4-chloro-phenyl)-N-methyl-acetamide and 1-(6-Chloro-pyridin-2-yl)-3-(4-trifluoromethyl-phenyl)-propan-1-one (accessed according to the procedure described for example 233 and 234, step 2 from (E)-1-(6-Chloro-pyridin-2-yl)-3-(4-trifluoromethyl-phenyl)-propenone).

Example 295

(S,R)-2-[(R,S)-1-(6-Chloro-pyridin-2-yl)-3-(4-trifluoromethyl-phenyl)-propylamino]-N-methyl-2-p-tolyl-acetamide

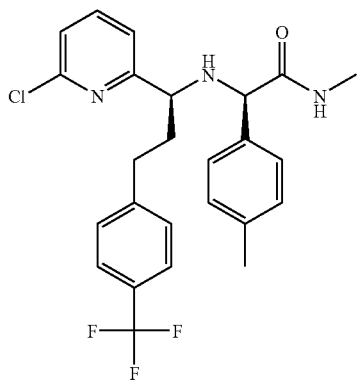

In analogy to the procedure described for the synthesis of examples 143 and 144 (step 3), the title compound (S,R)-2-[(R,S)-1-(6-Chloro-pyridin-2-yl)-3-(4-trifluoromethyl-phenyl)-propylamino]-N-methyl-2-p-tolyl-acetamide (MS (m/e): 476.0 (MH$^+$)) was prepared from rac-2-Amino-N-methyl-2-p-tolyl-acetamide and 1-(6-Chloro-pyridin-2-yl)-3-(4-trifluoromethyl-phenyl)-propan-1-one (accessed according to the procedure described for examples 233 and 234, step 2 from (E)-1-(6-Chloro-pyridin-2-yl)-3-(4-trifluoromethyl-phenyl)-propenone).

Example 296

(S,R)-2-[(R,S)-1-(3,4-Bis-difluoromethoxy-phenyl)-3-(6-chloro-pyridin-3-yl)-propylamino]-N-methyl-2-phenyl-acetamide

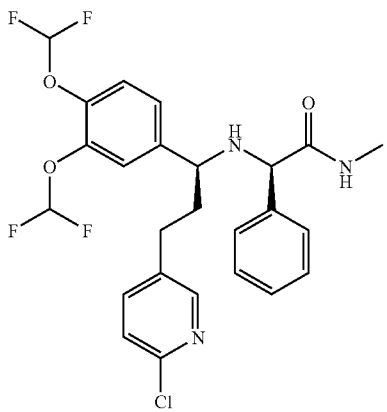

In analogy to the procedure described for the synthesis of examples 143 and 144 (step 3), the title compound: (S,R)-2-[(R,S)-1-(3,4-Bis-difluoromethoxy-phenyl)-3-(6-chloro-pyridin-3-yl)-propylamino]-N-methyl-2-phenyl-acetamide (MS (m/e): 526.0 (MH$^+$)) was prepared from rac-2-Amino-N-methyl-2-phenyl-acetamide (CAS: 93782-07-1) and 1-(3,4-Bis-difluoromethoxy-phenyl)-3-(6-chloro-pyridin-3-yl)-propan-1-one (accessed according to the procedure described for examples 233 and 234, step 2 (E)-1-(3,4-Bis-difluoromethoxy-phenyl)-3-(6-chloro-pyridin-3-yl)-propenone).

Example 297

(S,R)-2-[(R,S)-1-(3,4-Bis-difluoromethoxy-phenyl)-3-(5-chloro-pyrazin-2-yl)-propylamino]-N-methyl-2-phenyl-acetamide

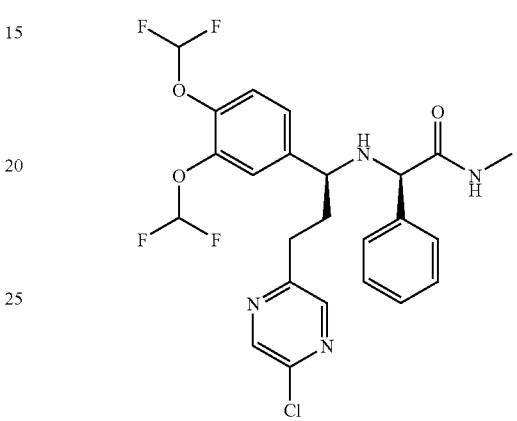

In analogy to the procedure described for the synthesis of examples 143 and 144 (step 3), the title compound: (S,R)-2-[(R,S)-1-(3,4-Bis-difluoromethoxy-phenyl)-3-(5-chloro-pyrazin-2-yl)-propylamino]-N-methyl-2-phenyl-acetamide (MS (m/e): 527.0 (MH$^+$)) was prepared from rac-2-Amino-N-methyl-2-phenyl-acetamide (CAS: 93782-07-1) and 1-(3,4-Bis-difluoromethoxy-phenyl)-3-(5-chloro-pyrazin-2-yl)-propan-1-one (accessed according to the procedure described for examples 233 and 234, step 2 (E)-1-(3,4-Bis-difluoromethoxy-phenyl)-3-(5-chloro-pyrazin-2-yl)-propenone).

Example 298

(S,R)-2-[(R,S)-3-(4-Chloro-phenyl)-1-(6-chloro-pyridin-2-yl)-propylamino]-2-(4-fluoro-phenyl)-N-methyl-acetamide

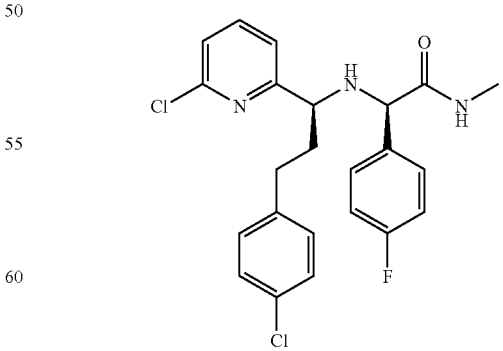

In analogy to the procedure described for the synthesis of examples 143 and 144 (step 3), the title compound: (S,R)-2-[(R,S)-3-(4-Chloro-phenyl)-1-(6-chloro-pyridin-2-yl)-propylamino]-2-(4-fluoro-phenyl)-N-methyl-acetamide (MS (m/e): 446.0 (MH$^+$)) was prepared from rac-2-Amino-2-(4-fluoro-phenyl)-N-methyl-acetamide and 3-(4-Chloro-phenyl)-1-(6-chloro-pyridin-2-yl)-propan-1-one (accessed according to the procedure described for examples 233 and 234, step 2 (E)-3-(4-Chloro-phenyl)-1-(6-chloro-pyridin-2-yl)-propenone).

Example 299

(S,R)-2-(4-Fluoro-phenyl)-2-[(S,R)-1-[3-(3-hydroxy-oxetan-3-yl)-phenyl]-3-(4-trifluoromethyl-phenyl)-propylamino]-N-methyl-acetamide

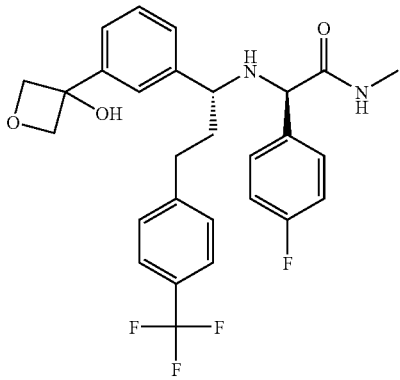

and

Example 300

(S,R)-2-(4-Fluoro-phenyl)-2-[(R,S)-1-[3-(3-hydroxy-oxetan-3-yl)-phenyl]-3-(4-trifluoromethyl-phenyl)-propylamino]-N-methyl-acetamide

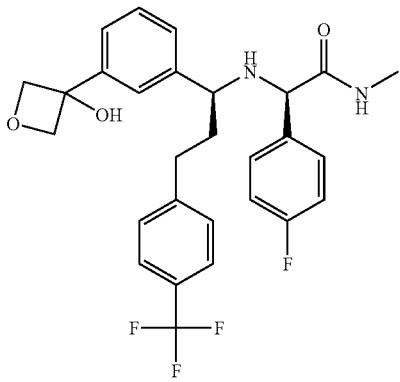

and 1-[3-(3-Hydroxy-oxetan-3-yl)-phenyl]-3-(4-trifluoromethyl-phenyl)-propan-1-one (accessed according to the procedure described for examples 233 and 234, step 2 from (E)-1-[3-(3-Hydroxy-oxetan-3-yl)-phenyl]-3-(4-trifluoromethyl-phenyl)-propenone).

Example 301

(S,R)—N-Methyl-2-[(S,R)-1-(5-methyl-isoxazol-3-yl)-3-(4-trifluoromethyl-phenyl)-propylamino]-2-phenyl-acetamide

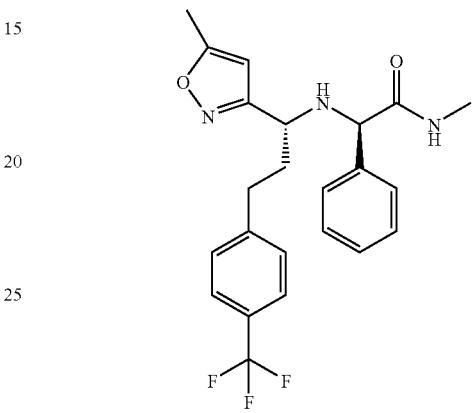

and

Example 302

(S,R)—N-Methyl-2-[(R,S)-1-(5-methyl-isoxazol-3-yl)-3-(4-trifluoromethyl-phenyl)-propylamino]-2-phenyl-acetamide

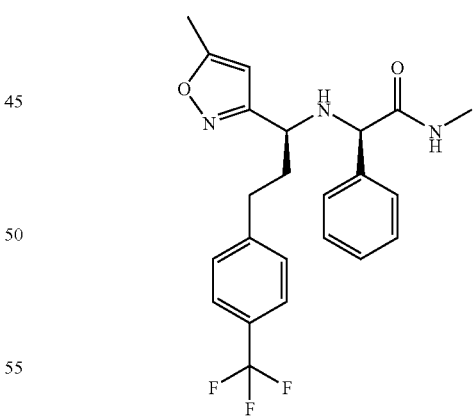

In analogy to the procedure described for the synthesis of examples 143 and 144 (step 3), the title compounds: (S,R)-2-(4-Fluoro-phenyl)-2-[(S,R)-1-[3-(3-hydroxy-oxetan-3-yl)-phenyl]-3-(4-trifluoromethyl-phenyl)-propylamino]-N-methyl-acetamide (MS (m/e): 516.9 (MH$^+$)) and (S,R)-2-(4-Fluoro-phenyl)-2-[(R,S)-1-[3-(3-hydroxy-oxetan-3-yl)-phenyl]-3-(4-trifluoromethyl-phenyl)-propylamino]-N-methyl-acetamide (MS (m/e): 516.8 (MH$^+$)) were prepared from -2-Amino-2-(4-fluoro-phenyl)-N-methyl-acetamide In analogy to the procedure described for the synthesis of examples 143 and 144 (step 3), the title compounds: (S,R)—N-Methyl-2-[(S,R)-1-(5-methyl-isoxazol-3-yl)-3-(4-trifluoromethyl-phenyl)-propylamino]-2-phenyl-acetamide (MS (m/e): 432.2 (MH$^+$)) and (S,R)—N-Methyl-2-[(R,S)-1-(5-methyl-isoxazol-3-yl)-3-(4-trifluoromethyl-phenyl)-propylamino]-2-phenyl-acetamide (MS (m/e): 432.2 (MH$^+$)) were prepared from rac-2-Amino-N-methyl-2-phenyl-acetamide (CAS: 93782-07-1) and 1-(5-Methyl-isoxazol-3-yl)-3-(4-trifluoromethyl-phenyl)-propan-1-one (accessed according to the procedure described for examples 164 and 165, step 2 from 5-Methyl-isoxazole-3-carboxylic acid methoxy-methyl-amide and p-trifluoromethylphenyl ethyl magnesium bromide.

Example 303

(S,R)—N-Methyl-2-[(S,R)-1-(3-methyl-isoxazol-5-yl)-3-(4-trifluoromethyl-phenyl)-propylamino]-2-phenyl-acetamide

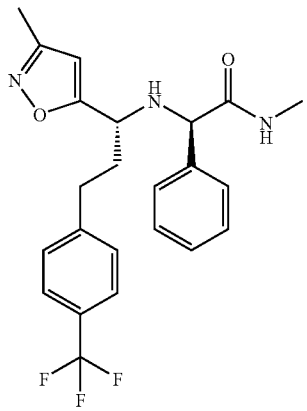

and

Example 304

(S,R)—N-Methyl-2-[(R,S)-1-(3-methyl-isoxazol-5-yl)-3-(4-trifluoromethyl-phenyl)-propylamino]-2-phenyl-acetamide

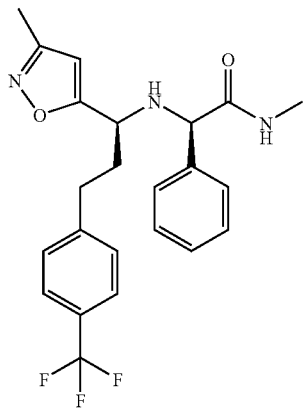

In analogy to the procedure described for the synthesis of examples 143 and 144 (step 3), the title compounds: (S,R)—N-Methyl-2-[(S,R)-1-(3-methyl-isoxazol-5-yl)-3-(4-trifluoromethyl-phenyl)-propylamino]-2-phenyl-acetamide (MS (m/e): 432.2 (MH$^+$)) and (S,R)—N-Methyl-2-[(R,S)-1-(3-methyl-isoxazol-5-yl)-3-(4-trifluoromethyl-phenyl)-propylamino]-2-phenyl-acetamide (MS (m/e): 432.2 (MH$^+$)) were prepared from rac-2-Amino-N-methyl-2-phenyl-acetamide (CAS: 93782-07-1) and 1-(3-Methyl-isoxazol-5-yl)-3-(4-trifluoromethyl-phenyl)-propan-1-one (accessed according to the procedure described for examples 164 and 165, step 2 from 3-Methyl-isoxazole-5-carboxylic acid methoxy-methyl-amide and p-trifluoromethylphenyl ethyl magnesium bromide.

Example 305

(S,R)-2-[(S,R)-1-(3,4-Bis-difluoromethoxy-phenyl)-3-(5-chloro-pyridin-2-yl)-propylamino]-N-methyl-2-phenyl-acetamide

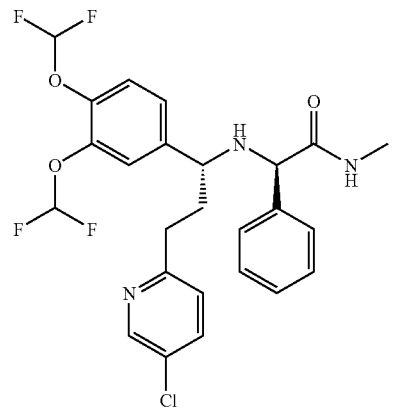

and

Example 306

(S,R)-2-[(R,S)-1-(3,4-Bis-difluoromethoxy-phenyl)-3-(5-chloro-pyridin-2-yl)-propylamino]-N-methyl-2-phenyl-acetamide

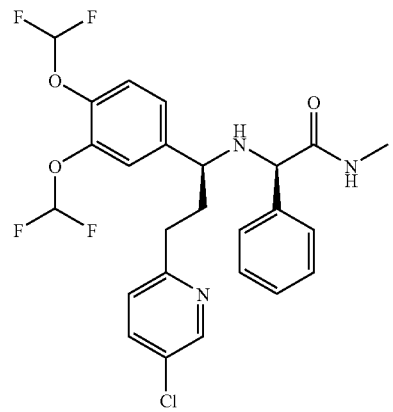

In analogy to the procedure described for the synthesis of examples 143 and 144 (step 3), the title compounds: (S,R)-2-[(S,R)-1-(3,4-Bis-difluoromethoxy-phenyl)-3-(5-chloro-pyridin-2-yl)-propylamino]-N-methyl-2-phenyl-acetamide (MS (m/e): 526.0 (MH$^+$)) and (S,R)-2-[(R,S)-1-(3,4-Bis-difluoromethoxy-phenyl)-3-(5-chloro-pyridin-2-yl)-propylamino]-N-methyl-2-phenyl-acetamide (MS (m/e): 526.0 (MH$^+$)) were prepared from rac-2-Amino-N-methyl-2-phenyl-acetamide (CAS: 93782-07-1) and 1-(3,4-Bis-difluoromethoxy-phenyl)-3-(5-chloro-pyridin-2-yl)-propan-1-one (accessed according to the procedure described for examples 233 and 234, step 2 from (E)-1-(3,4-Bis-difluoromethoxy-phenyl)-3-(5-chloro-pyridin-2-yl)-propenone).

Example 307

2-[1-(3,4-Bis-difluoromethoxy-phenyl)-3-(5-chloro-pyridin-2-yl)-propylamino]-2-phenyl-acetamide

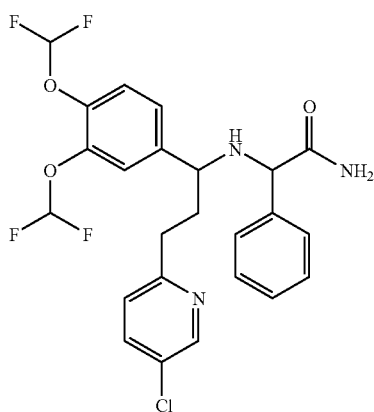

In analogy to the procedure described for the synthesis of examples 143 and 144 (step 3), the title compound: 2-[1-(3,4-Bis-difluoromethoxy-phenyl)-3-(5-chloro-pyridin-2-yl)-propylamino]-2-phenyl-acetamide (as a mixture of 4 stereoisomers) (MS (m/e): 512.3 (MH$^+$)) was prepared from rac-2-Amino-2-phenyl-acetamide (CAS: 700-63-0) and 1-(3,4-Bis-difluoromethoxy-phenyl)-3-(5-chloro-pyridin-2-yl)-propan-1-one (accessed according to the procedure described for examples 233 and 234, step 2 from (E)-1-(3,4-Bis-difluoromethoxy-phenyl)-3-(5-chloro-pyridin-2-yl)-propenone).

Example 308

2-[1-(3,4-Bis-difluoromethoxy-phenyl)-3-(5-methyl-pyrazin-2-yl)-propylamino]-N-methyl-2-phenyl-acetamide

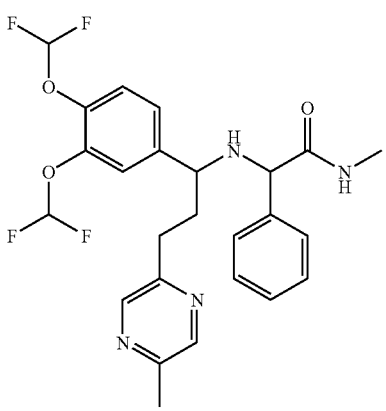

In analogy to the procedure described for the synthesis of examples 143 and 144 (step 3), the title compound: 2-[1-(3, 4-Bis-difluoromethoxy-phenyl)-3-(5-methyl-pyrazin-2-yl)-propylamino]-N-methyl-2-phenyl-acetamide (as a mixture of four stereoisomers) (MS (m/e): 507.2 (MH$^+$)) was prepared from rac-2-Amino-N-methyl-2-phenyl-acetamide (CAS: 93782-07-1) and 1-(3,4-Bis-difluoromethoxy-phenyl)-3-(5-methyl-pyrazin-2-yl)-propan-1-one (accessed according to the procedure described for examples 233 and 234, step 2 from (E)-1-(3,4-Bis-difluoromethoxy-phenyl)-3-(5-methyl-pyrazin-2-yl)-propenone).

Example 309

(S)-2-[(R)-1-(3,4-Bis-difluoromethoxy-phenyl)-3-(4-trifluoromethyl-phenyl)-propylamino]-2-phenyl-acetamide hydrochloride

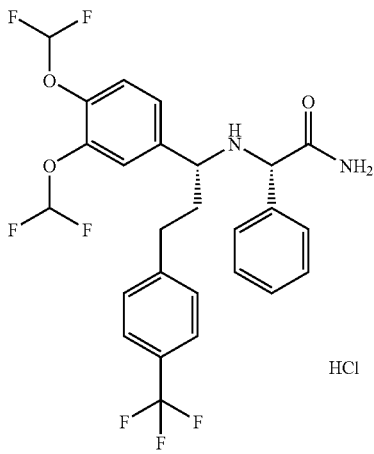

and

Example 310

(R)-2-[(S)-1-(3,4-Bis-difluoromethoxy-phenyl)-3-(4-trifluoromethyl-phenyl)-propylamino]-2-phenyl-acetamide hydrochloride

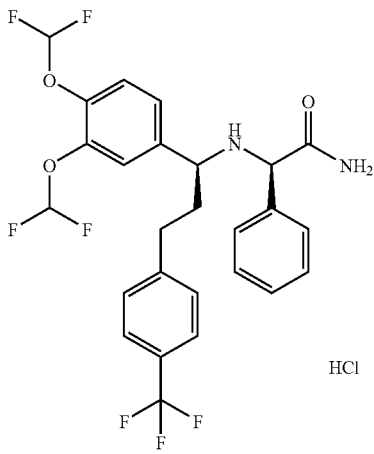

(S,R)-2-[(R,S)-1-(3,4-Bis-difluoromethoxy-phenyl)-3-(4-trifluoromethyl-phenyl)-propylamino]-2-phenyl-acetamide (Example 293) was separated on chiral phase HPLC (Chiralpack AD column) and each obtained enantiomer was treated with HCl methanol to provide after evaporation the title compounds: (S)-2-[(R)-1-(3,4-Bis-difluoromethoxy-phenyl)-3-(4-trifluoromethyl-phenyl)-propylamino]-2-phenyl-acetamide hydrochloride (MS (m/e): 545.3 (MH$^+$)) and (R)-2-[(S)-1-(3,4-Bis-difluoromethoxy-phenyl)-3-(4-trifluoromethylphenyl)-propylamino]-2-phenyl-acetamide hydrochloride (MS (m/e): 545.3 (MH$^+$)) as white solid.

Example 311

2-[1-(3,4-Bis-difluoromethoxy-phenyl)-3-(5-trifluoromethyl-pyridin-2-yl)-propylamino]-2-phenyl-acetamide

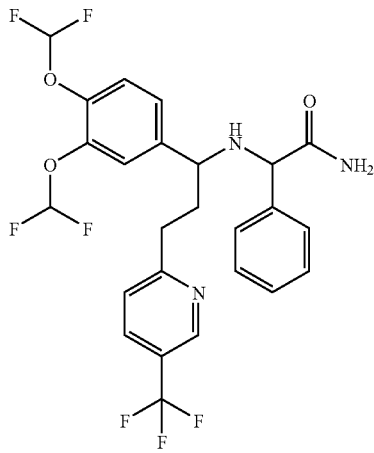

In analogy to the procedure described for the synthesis of examples 143 and 144 (step 3), the title compound: 2-[1-(3,4-Bis-difluoromethoxy-phenyl)-3-(5-trifluoromethyl-pyridin-2-yl)-propylamino]-2-phenyl-acetamide (as a mixture of 4 stereoisomers) (MS (m/e): 546.1 (MH$^+$)) was prepared from rac-2-Amino-2-phenyl-acetamide (CAS: 700-63-0) and 1-(3,4-Bis-difluoromethoxy-phenyl)-3-(5-trifluoromethyl-pyridin-2-yl)-propan-1-one (accessed according to the procedure described for examples 233 and 234, step 2 from (E)-1-(3,4-Bis-difluoromethoxy-phenyl)-3-(5-trifluoromethyl-pyridin-2-yl)-propenone).

Example 312

2-[1-(3,4-Bis-difluoromethoxy-phenyl)-3-(5-trifluoromethyl-pyridin-2-yl)-propylamino]-N-methyl-2-phenyl-acetamide

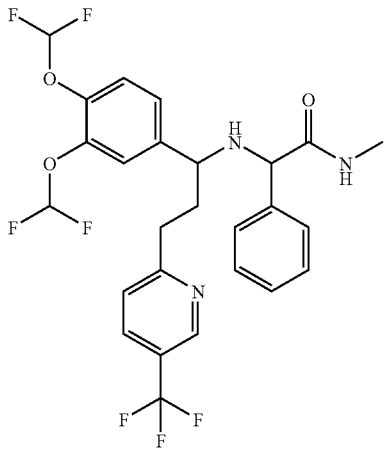

In analogy to the procedure described for the synthesis of examples 143 and 144 (step 3), the title compound: 2-[1-(3,4-Bis-difluoromethoxy-phenyl)-3-(5-trifluoromethyl-pyridin-2-yl)-propylamino]-N-methyl-2-phenyl-acetamide (as a mixture of 4 stereoisomers) (MS (m/e): 560.2 (MH$^+$)) was prepared from rac-2-Amino-N-methyl-2-phenyl-acetamide (CAS: 93782-07-1) and 1-(3,4-Bis-difluoromethoxy-phenyl)-3-(5-trifluoromethyl-pyridin-2-yl)-propan-1-one (accessed according to the procedure described for examples 233 and 234, step 2 from (E)-1-(3,4-Bis-difluoromethoxy-phenyl)-3-(5-trifluoromethyl-pyridin-2-yl)-propenone).

Example 313

(R)-2-[(R)-1-(3,4-Dimethoxy-phenyl)-3-phenyl-propylamino]-N-methyl-2-phenyl-acetamide

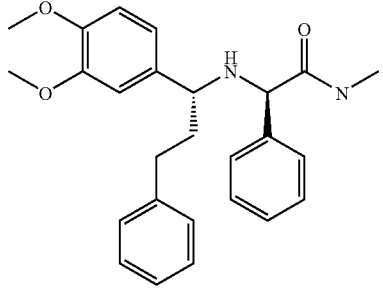

and

Example 314

(R)-2-[(S)-1-(3,4-Dimethoxy-phenyl)-3-phenyl-propylamino]-N-methyl-2-phenyl-acetamide

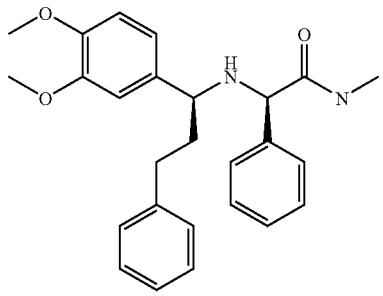

To a solution of 2-phenylethylmagnesium chloride (1 M in THF, 3.0 mL, 3.00 mmol) in THF (5 mL) was added dropwise a solution of 3,4-dimethoxybenzonitrile (326 mg, 2.00 mmol) in THF (5 mL). After 23 h of reflux, dry methanol (2.5 mL) and a solution of (R)-2-amino-N-methyl-2-phenyl acetamide (accessable via: J. Org. Chem. 2005, 70, 10792-10802, 672 mg, 4.00 mmol) in dry methanol (2.5 mL) were added successively at 0° C. After stirring at ambient temperature for 1 h the reaction mixture was cooled to 0° C. and sodium borohydride (158 mg, 4.00 mmol) was added in small portions. After stirring for 5.5 h at ambient temperature, aqueous ammonium chloride (sat.) was added and extracted with tert-butylmethylether. The organic layers were combined, dried over sodium sulfate and concentrated. Purification by chromatography (SiO$_2$, heptane:ethyl acetate:methanol=3:1:0 to 0:9:1) afforded the title compounds (R)-2-[(R)-1-(3,4-dimethoxy-phenyl)-3-phenyl-propylamino]-N-methyl-2-phenyl-acetamide (1$^{st}$ eluting compound, 175 mg, 21%) as a light yellow oil (MS: m/e=419.3 [M+H]$^+$ and (R)-2-[(S)-1-(3,4-dimethoxy-phenyl)-3-phenyl-propylamino]-N-methyl-2- phenyl-acetamide (2<sup>nd</sup> eluting compound, 175 mg, 21%) as a light yellow oil (MS: m/e=419.3 [M+H]+.

Example 315

(R,S)-2-[(R,S)-1-(3,4-Dimethoxy-phenyl)-3-(2-hydroxy-phenyl)-propylamino]-N-methyl-2-phenyl-acetamide

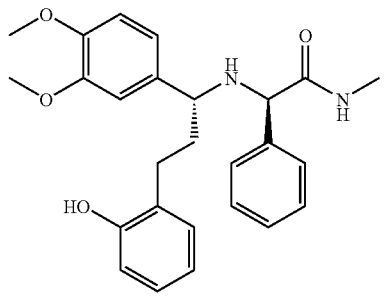

and

Example 316

(R,S)-2-[(S,R)-1-(3,4-Dimethoxy-phenyl)-3-(2-hydroxy-phenyl)-propylamino]-N-methyl-2-phenyl-acetamide

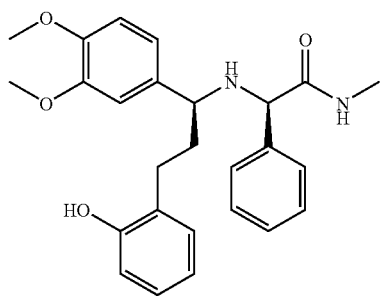

a) Step 1

1-(3,4-Dimethoxy-phenyl)-prop-2-en-1-ol

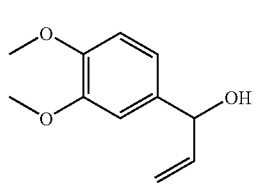

To a solution of 3,4-dimethoxybenzaldehyde (5.30 g, 31.9 mmol) in THF (50 mL) was added dropwise under a nitrogen atmosphere at 0° C. over a period of 30 min vinylmagnesium bromide (1 M in THF, 32 mL, 32 mmol) and stirred for 2 h at 0° C. followed by 1 h at ambient temperature. Further vinylmagnesium bromide (1 M in THF, 32 mL, 32 mmol) was added at 0° C. and the solution was stirred for 1 h at this temperature. The reaction mixture was added onto a mixture of ice (50 g) and aqueous ammonium chloride (saturated, 50 mL). The mixture was extracted with tert-butylmethylether and the organic layers were washed with water (50 mL) and brine (50 mL). Drying over sodium sulfate und purification by chromatography (SiO$_2$, heptane:ethyl acetate=100:0 to 50:50) afforded the title compound (5.18 g, 84%) as a light yellow oil.

b) Step 2

1-(3,4-Dimethoxy-phenyl)-3-(2-hydroxy-phenyl)-propan-1-one

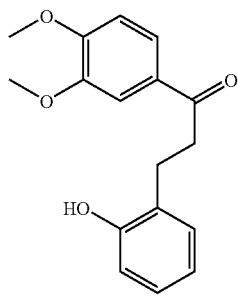

To a solution of 1-(3,4-dimethoxy-phenyl)-prop-2-en-1-ol (236 mg, 1.22 mmol) in THF (2 mL) was added under a nitrogen atmosphere 2-iodophenol (267 mg, 1.22 mmol), cesium carbonate (158 mg, 0.47 mmol) and palladium(II) acetate (8 mg, 0.04 mmol). The reaction mixture was stirred for 4 h at 80° C. After cooling to ambient temperature it was diluted with ethyl acetate (10 mL) and washed with water (10 mL) and brine (10 mL). The aqueous layers were extracted with ethyl acetate (10 mL) and the combined organic layers dried over sodium sulfate. Purification by chromatography (SiO$_2$, heptane:ethyl acetate=90:10 to 60:40) afforded the title compound (155 mg, 45%) as a colourless oil. MS m/e: 285.0 [M−H]

c) Step 3

In analogy to the procedure described for the synthesis example 143 and 144 (step 3), the title compounds: (R,S)-2-[(R,S)-1-(3,4-Dimethoxy-phenyl)-3-(2-hydroxy-phenyl)-propylamino]-N-methyl-2-phenyl-acetamide (MS (m/e): 433.2 [M−H]− and (R,S)-2-[(S,R)-1-(3,4-Dimethoxy-phenyl)-3-(2-hydroxy-phenyl)-propylamino]-N-methyl-2-phenyl-acetamide (MS (m/e): 433.1 [M−H]− were prepared from rac 2-amino-N-methyl-2-phenyl-acetamide (CAS: 93782-07-1) and 1-(3,4-Dimethoxy-phenyl)-3-(2-hydroxy-phenyl)-propan-1-one.

Example 317

2-[1-(3,4-Dimethoxy-phenyl)-3-(4-trifluoromethyl-phenyl)-propylamino]-2-pyridin-3-yl-acetamide

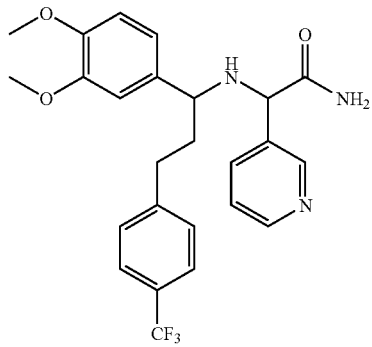

To a solution of rac 1-(3,4-dimethoxy-phenyl)-3-(4-trifluoromethyl-phenyl)-propylamine (accessed according to the procedure described for example 126 and 127, step 2 from 2-methyl-propane-2-sulfinic acid [1-(3,4-dimethoxy-phenyl)-3-(4-trifluoromethyl-phenyl)-propyl]-amide, 213 mg, 0.63 mmol) in THF (2 mL) was added 3-pyridinecarboxaldehyde (71 µl, 0.75 mmol), trimethylsilyl cyanide (118 µl, 0.94 mmol) and a catalytic amount of zinc iodide. The solution was stirred for 3 h at ambient temperature before it was diluted with DMSO (0.5 mL) and potassium carbonate (35 mg, 0.25 mmol) and hydrogen peroxide (35% in water, 82 µl, 0.94 mmol) were added. After stirring for 18 h at ambient temperature further hydrogen peroxide (35% in water, 41 µl, 0.47 mmol) was added and stirring continued for 3 h. It was diluted with methanol (0.5 mL) and palladium on charcoal 10% (5 mg) and acetic acid (50 µl) were added. Under an hydrogen atmosphere of hydrogen the reaction mixture was stirred for 3 h at ambient temperature. Sodium borohydride (50 mg) was added and the stirring was continued for 1 h. Purification by chromatography (SiO$_2$, heptane:(ethyl acetate:triethylamine=95:5)=50:50 to 0:100) afforded the title compound as a racemic mixture (1:1) of diastereomers (127 mg, 43%) as a white solid. MS m/e: 472.5 [M−H]$^−$

Example 318

(R,S)-2-(4-Chloro-phenyl)-2-[(R,S)-3-(4-chloro-phenyl)-1-(3,4-dimethoxy-phenyl)-propylamino]-N-methyl-acetamide

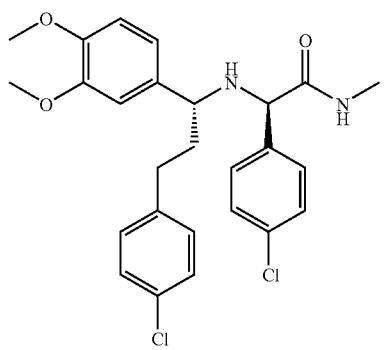

and

Example 319

(R,S)-2-(4-Chloro-phenyl)-2-[(S,R)-3-(4-chloro-phenyl)-1-(3,4-dimethoxy-phenyl)-propylamino]-N-methyl-acetamide

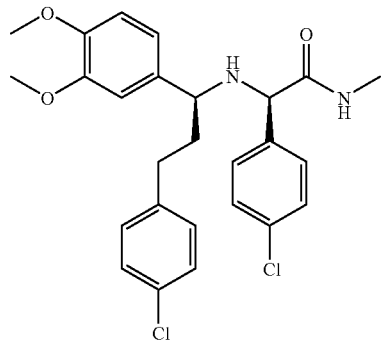

In analogy to the procedure described for the synthesis example 313 and 314, the title compounds (R,S)-2-(4-chloro-phenyl)-2-[(R,S)-3-(4-chloro-phenyl)-1-(3,4-dimethoxy-phenyl)-propylamino]-N-methyl-acetamide (MS (m/e): 487.3/489.2 [M+H]$^+$) and (R,S)-2-(4-chloro-phenyl)-2-[(S,R)-3-(4-chloro-phenyl)-1-(3,4-dimethoxy-phenyl)-propylamino]-N-methyl-acetamide (MS (m/e): 487.3/489.2 [M+H]$^+$) were prepared from rac 2-amino-N-methyl-2-(4-chloro-phenyl)-acetamide (accessable corresponding to: J. Org. Chem. 2005, 70, 10792-10802) and 4-chlorophenethyl-magnesium bromide.

Example 320

(R,S)-2-[(R,S)-1-(3,4-Dimethoxy-phenyl)-3-(3-trifluoromethyl-phenyl)-propylamino]-N-methyl-2-phenyl-acetamide

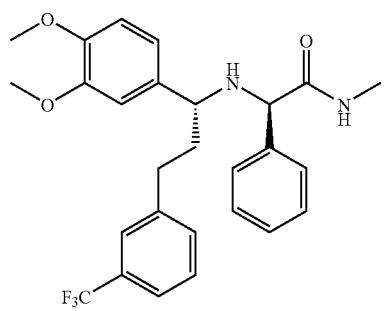

and

Example 321

(R,S)-2-[(S,R)-1-(3,4-Dimethoxy-phenyl)-3-(3-trifluoromethyl-phenyl)-propylamino]-N-methyl-2-phenyl-acetamide

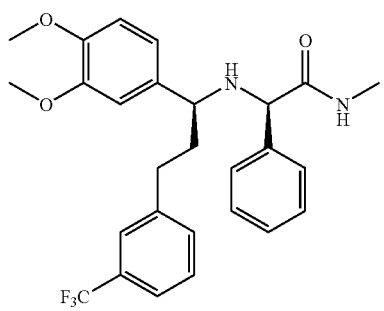

In analogy to the procedure described for the synthesis example 143 and 144 (step 3), the title compounds: (R,S)-2-[(R,S)-1-(3,4-dimethoxy-phenyl)-3-(3-trifluoromethyl-phenyl)-propylamino]-N-methyl-2-phenyl-acetamide (MS (m/e): 485.5 [M–H]$^-$ and (R,S)-2-[(S,R)-1-(3,4-dimethoxy-phenyl)-3-(3-trifluoromethyl-phenyl)-propylamino]-N-methyl-2-phenyl-acetamide (MS (m/e): 485.5 [M–H]$^-$ were prepared from rac 2-amino-N-methyl-2-phenyl-acetamide (CAS: 93782-07-1) and 1-(3,4-Dimethoxy-phenyl)-3-(3-trifluoromethyl-phenyl)-propan-1-one (accessed according to the procedure described for example 315 and 316, step 2 from 3-iodobenzotrifluoride).

Example 322

2-[1-Cyano-1-(3,4-dimethoxy-phenyl)-3-(4-trifluoromethyl-phenyl)-propylamino]-N-methyl-2-phenyl-acetamide

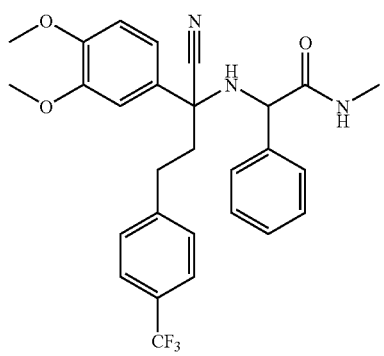

1-(4-Fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone, 203 mg, 0.60 mmol) and zinc iodide (2 mg, 0.01 mmol) were dissolved in THF (5 mL) and trimethylsilyl cyanide (94 uL, 0.75 mmol) was added. After 15 min stirring at ambient temperature rac 2-amino-N-methyl-2-phenyl-acetamide (CAS: 93782-07-1, 82 mg, 0.50 mmol) was added. After stirring for 18 h at ambient temperature sodium bisulfite (0.5 mL) was added and the reaction mixture was extracted with ethyl acetate. Drying over sodium sulfate an purification by chromatography (SiO$_2$, heptane:ethyl acetate=60:40 to 20:80) afforded the title compound as a racemic mixture (1:1) of diastereomers (11 mg, 3%) as a light brown oil. MS m/e: 485.4 [M–CN$^-$]$^+$

Example 323

(R,S)-2-(3,4-Difluoro-phenyl)-2-[(R,S)-1-(4-fluoro-3-methyl-phenyl)-3-(6-trifluoromethyl-pyridin-3-yl)-propylamino]-N-methyl-acetamide

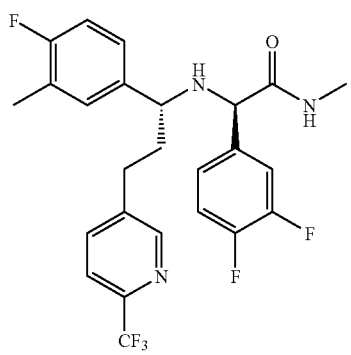

and

Example 324

(R,S)-2-(3,4-Difluoro-phenyl)-2-[(S,R)-1-(4-fluoro-3-methyl-phenyl)-3-(6-trifluoromethyl-pyridin-3-yl)-propylamino]-N-methyl-acetamide

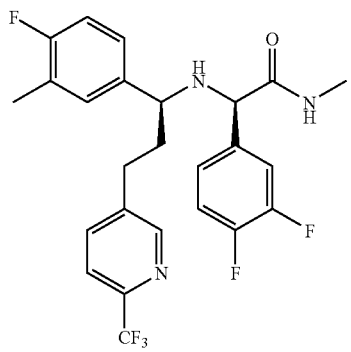

a) Step 1 rac 3,4-Difluorophenylglycine methyl ester

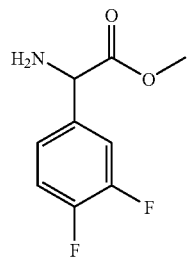

Through a suspension of 3,4-difluorophenylglycine (2.00 g, 10.7 mmol) in methanol (100 mL) was passed gaseous hydrochloric acid for 40 min while cooling with an ice-bath to keep ambient temperature. The resulting solution was stirred for 1 h at 5° C. and for 30 min at ambient temperature. Nitrogene was passed through the reaction mixture for 120 min. Concentration afforded the title compound (2.52 g, 99%) as a white solid. MS m/e: 202.2 [M−HCl+H]$^+$).

b) Step 2 rac
2-Amino-N-methyl-2-(3,4-difluorophenyl)-acetamide

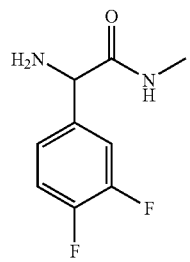

To a suspension of rac 3,4-difluorophenylglycine methyl ester (2.52 g, 10.6 mmol) in water (5 mL) was added methylamine solution (41% in water, 2.5 mL, 72.2 mmol) at 0° C. The mixture was stirred for 5 h at ambient temperature and was then separated between brine and EtOAc/THF 1:1. The organic layers were washed with brine, combined and dried over sodium sulfate. off and evaporated. Concentration afforded the title compound (1.62 g, 76%) as a light yellow oil. MS m/e: 202.2 [M−HCl+H]$^+$).

c) Step 3

In analogy to the procedure described for the synthesis example 143 and 144 (step 3), the title compounds: (R,S)-2-(3,4-difluoro-phenyl)-2-[(R,S)-1-(4-fluoro-3-methyl-phenyl)-3-(6-trifluoromethyl-pyridin-3-yl)-propylamino]-N-methyl-acetamide (MS (m/e): 496.4 [M+H]$^+$) and (R,S)-2-(3,4-difluoro-phenyl)-2-[(S,R)-1-(4-fluoro-3-methyl-phenyl)-3-(6-trifluoromethyl-pyridin-3-yl)-propylamino]-N-methyl-acetamide (MS (m/e): 496.4 [M+H]$^+$) were prepared from rac 2-amino-N-methyl-2-(3,4-difluorophenyl)-acetamide and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 325

(R,S)-2-(3,5-Difluoro-phenyl)-2-[(S,R)-1-(4-fluoro-3-methyl-phenyl)-3-(6-trifluoromethyl-pyridin-3-yl)-propylamino]-N-methyl-acetamide

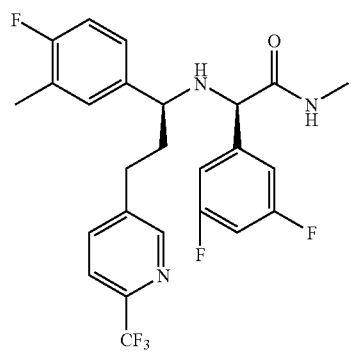

In analogy to the procedure described for the synthesis example 323 and 324 (step 3), the title compound: (R,S)-2-(3,5-difluoro-phenyl)-2-[(S,R)-1-(4-fluoro-3-methyl-phenyl)-3-(6-trifluoromethyl-pyridin-3-yl)-propylamino]-N-methyl-acetamide (MS (m/e): 496.3 [M+H]$^+$) was prepared from rac 2-amino-N-methyl-2-(3,5-difluorophenyl)-acetamide (accessed according to the procedure described for example 323 and 324, step 1 and step 2 starting from 3,5-difluorophenylglycine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 326

(R,S)-2-[(S,R)-1-(4-Fluoro-3-methyl-phenyl)-3-(6-trifluoromethyl-pyridin-3-yl)-propylamino]-N-methyl-2-pyridin-3-yl-acetamide

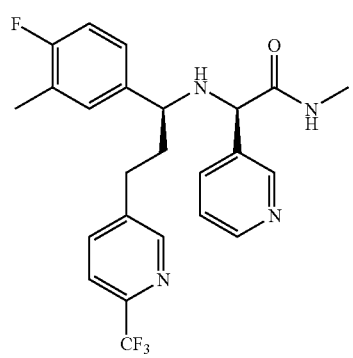

In analogy to the procedure described for the synthesis example 143 and 144 (step 3), the title compound: (R,S)-2-[(S,R)-1-(4-Fluoro-3-methyl-phenyl)-3-(6-trifluoromethyl-pyridin-3-yl)-propylamino]-N-methyl-2-pyridin-3-yl-acetamide (MS (m/e): 461.3 [M+H]⁺) was prepared from rac 2-amino-N-methyl-2-pyridin-3-yl-acetamide (accessed according to the procedure described for example 323 and 324, step 1 and step 2 starting from 2-amino-2-pyridin-3-yl-acetic acid) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 327

(R,S)-2-[(R,S)-1-(4-Fluoro-3-methyl-phenyl)-3-(6-trifluoromethyl-pyridin-3-yl)-propylamino]-2-phenyl-acetamide

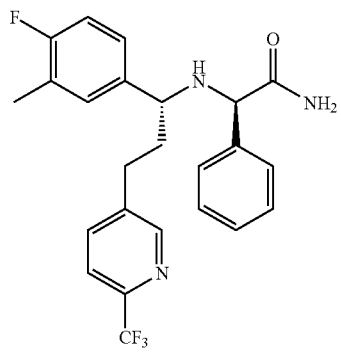

and

Example 328

(R,S)-2-[(S,R)-1-(4-Fluoro-3-methyl-phenyl)-3-(6-trifluoromethyl-pyridin-3-yl)-propylamino]-2-phenyl-acetamide

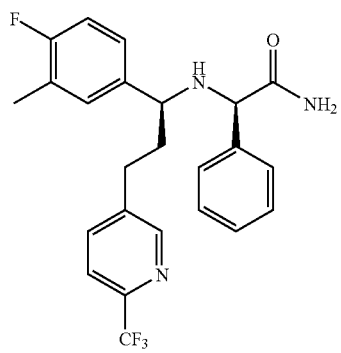

In analogy to the procedure described for the synthesis example 143 and 144 (step 3), the title compounds: (R,S)-2-[(R,S)-1-(4-fluoro-3-methyl-phenyl)-3-(6-trifluoromethyl-pyridin-3-yl)-propylamino]-2-phenyl-acetamide (MS (m/e): 446.2 [M+H]⁺) and (R,S)-2-[(S,R)-1-(4-fluoro-3-methyl-phenyl)-3-(6-trifluoromethyl-pyridin-3-yl)-propylamino]-2-phenyl-acetamide (MS (m/e): 446.2 [M+H]⁺) were prepared from rac 2-amino-2-phenyl-acetamide (commercially available) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 329

(R,S)-2-(3-Chloro-phenyl)-2-[(R,S)-1-(4-fluoro-3-methyl-phenyl)-3-(6-trifluoromethyl-pyridin-3-yl)-propylamino]-N-methyl-acetamide

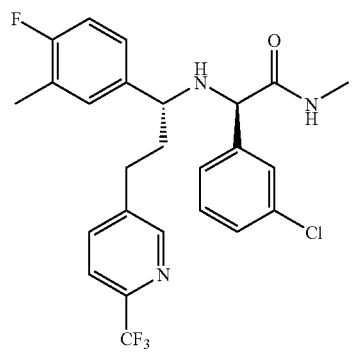

and

Example 330

(R,S)-2-(3-Chloro-phenyl)-2-[(S,R)-1-(4-fluoro-3-methyl-phenyl)-3-(6-trifluoromethyl-pyridin-3-yl)-propylamino]-N-methyl-acetamide

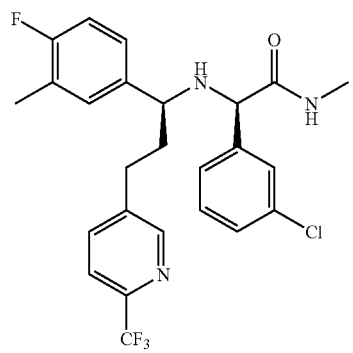

In analogy to the procedure described for the synthesis example 143 and 144 (step 3), the title compounds: (R,S)-2-(3-chloro-phenyl)-2-[(R,S)-1-(4-fluoro-3-methyl-phenyl)-3-(6-trifluoromethyl-pyridin-3-yl)-propylamino]-N-methyl-acetamide (MS (m/e): 494.2/494.3 [M+H]⁺) and (R,S)-2-(3-chloro-phenyl)-2-[(S,R)-1-(4-fluoro-3-methyl-phenyl)-3-(6-trifluoromethyl-pyridin-3-yl)-propylamino]-N-methyl-acetamide (MS (m/e): 494.3/494.3 [M+H]⁺) were prepared from rac 2-amino-N-methyl-2-(3-chlorophenyl)-acetamide (accessed according to the procedure described for example 323 and 324, step 1 and step 2 starting from 3-chlorophenylglycine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 331

(R,S)-2-[(R,S)-1-(4-Fluoro-3-methyl-phenyl)-3-(6-trifluoromethyl-pyridin-3-yl)-propylamino]-2-(3-fluoro-phenyl)-N-methyl-acetamide

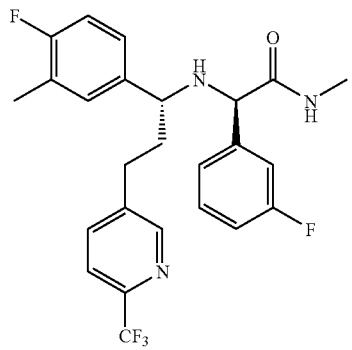

and

Example 332

(R,S)-2-[(S,R)-1-(4-Fluoro-3-methyl-phenyl)-3-(6-trifluoromethyl-pyridin-3-yl)-propylamino]-2-(3-fluoro-phenyl)-N-methyl-acetamide

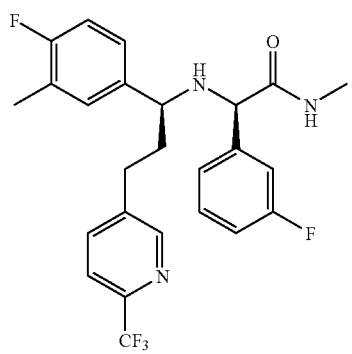

In analogy to the procedure described for the synthesis example 143 and 144 (step 3), the title compounds: (R,S)-2-[(R,S)-1-(4-Fluoro-3-methyl-phenyl)-3-(6-trifluoromethyl-pyridin-3-yl)-propylamino]-2-(3-fluoro-phenyl)-N-methyl-acetamide (MS (m/e): 478.2 [M+H]$^+$) and (R,S)-2-[(S,R)-1-(4-Fluoro-3-methyl-phenyl)-3-(6-trifluoromethyl-pyridin-3-yl)-propylamino]-2-(3-fluoro-phenyl)-N-methyl-acetamide (MS (m/e): 478.2 [M+H]$^+$) were prepared from rac 2-amino-N-methyl-2-(3-fluorophenyl)-acetamide (accessed according to the procedure described for example 323 and 324, step 1 and step 2 starting from 3-fluorophenylglycine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 333

(R,S)-2-[(R,S)-1-(4-Fluoro-3-methyl-phenyl)-3-(6-trifluoromethyl-pyridin-3-yl)-propylamino]-N-methyl-2-p-tolyl-acetamide

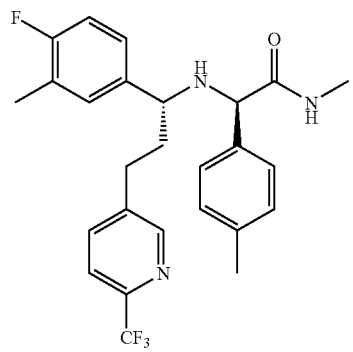

and

Example 334

(R,S)-2-[(S,R)-1-(4-Fluoro-3-methyl-phenyl)-3-(6-trifluoromethyl-pyridin-3-yl)-propylamino]-N-methyl-2-p-tolyl-acetamide

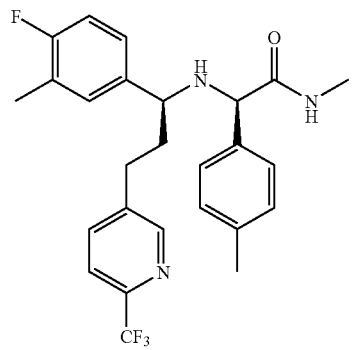

In analogy to the procedure described for the synthesis example 143 and 144 (step 3), the title compounds: (R,S)-2-[(R,S)-1-(4-Fluoro-3-methyl-phenyl)-3-(6-trifluoromethyl-pyridin-3-yl)-propylamino]-N-methyl-2-p-tolyl-acetamide (MS (m/e): 474.3 [M+H]$^+$) and (R,S)-2-[(S,R)-1-(4-Fluoro-3-methyl-phenyl)-3-(6-trifluoromethyl-pyridin-3-yl)-propylamino]-N-methyl-2-p-tolyl-acetamide (MS (m/e): 474.3 [M+H]$^+$) were prepared from rac 2-amino-N-methyl-2-p-toly-acetamide (accessed according to the procedure described for example 323 and 324, step 1 and step 2 starting from 4-methylphenylglycine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 335

(R,S)-2-(2,3-Difluoro-phenyl)-2-[(R,S)-1-(4-fluoro-3-methyl-phenyl)-3-(6-trifluoromethyl-pyridin-3-yl)-propylamino]-N-methyl-acetamide

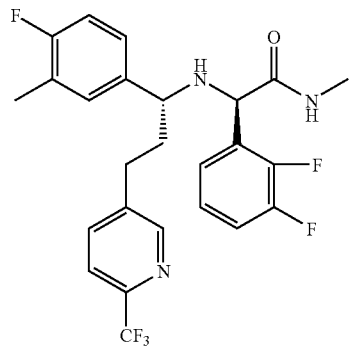

and

Example 336

(R,S)-2-(2,3-Difluoro-phenyl)-2-[(S,R)-1-(4-fluoro-3-methyl-phenyl)-3-(6-trifluoromethyl-pyridin-3-yl)-propylamino]-N-methyl-acetamide

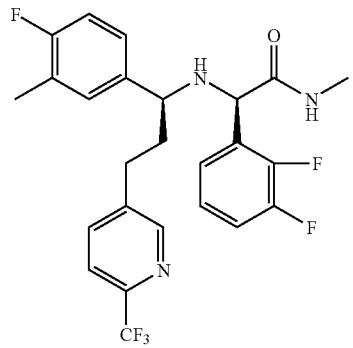

In analogy to the procedure described for the synthesis example 143 and 144 (step 3), the title compounds: (R,S)-2-(2,3-difluoro-phenyl)-2-[(R,S)-1-(4-fluoro-3-methyl-phenyl)-3-(6-trifluoromethyl-pyridin-3-yl)-propylamino]-N-methyl-acetamide (MS (m/e): 496.3 [M+H]$^+$) and (R,S)-2-(2,3-difluoro-phenyl)-2-[(S,R)-1-(4-fluoro-3-methyl-phenyl)-3-(6-trifluoromethyl-pyridin-3-yl)-propylamino]-N-methyl-acetamide (MS (m/e): 496.4 [M+H]$^+$) were prepared from rac 2-amino-N-methyl-2-(2,3-difluoro-phenyl)-acetamide (accessed according to the procedure described for example 323 and 324, step 1 and step 2 starting from 2,3-difluorophenylglycine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 337

(R,S)-2-(2,4-Difluoro-phenyl)-2-[(R,S)-1-(4-fluoro-3-methyl-phenyl)-3-(6-trifluoromethyl-pyridin-3-yl)-propylamino]-N-methyl-acetamide

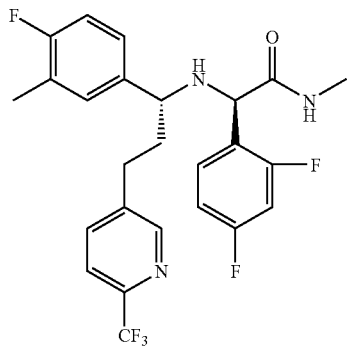

and

Example 338

(R,S)-2-(2,4-Difluoro-phenyl)-2-[(S,R)-1-(4-fluoro-3-methyl-phenyl)-3-(6-trifluoromethyl-pyridin-3-yl)-propylamino]-N-methyl-acetamide

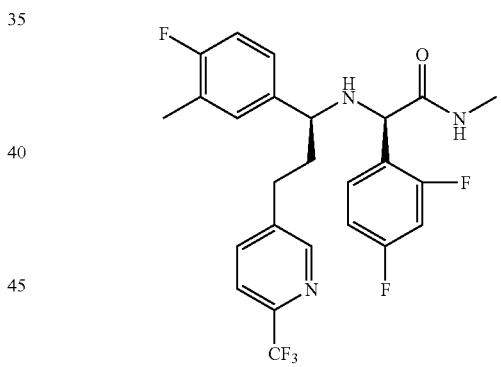

In analogy to the procedure described for the synthesis example 143 and 144 (step 3), the title compounds: (R,S)-2-(2,4-difluoro-phenyl)-2-[(R,S)-1-(4-fluoro-3-methyl-phenyl)-3-(6-trifluoromethyl-pyridin-3-yl)-propylamino]-N-methyl-acetamide (MS (m/e): 496.3 [M+H]$^+$) and (R,S)-2-(2,4-difluoro-phenyl)-2-[(S,R)-1-(4-fluoro-3-methyl-phenyl)-3-(6-trifluoromethyl-pyridin-3-yl)-propylamino]-N-methyl-acetamide (MS (m/e): 496.3 [M+H]$^+$) were prepared from rac 2-amino-N-methyl-2-(2,4-difluoro-phenyl)-acetamide (accessed according to the procedure described for example 323 and 324, step 1 and step 2 starting from 2,4-difluorophenylglycine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 339

(R,S)—N-Ethyl-2-[(R,S)-1-(4-fluoro-3-methyl-phenyl)-3-(6-trifluoromethyl-pyridin-3-yl)-propylamino]-2-phenyl-acetamide

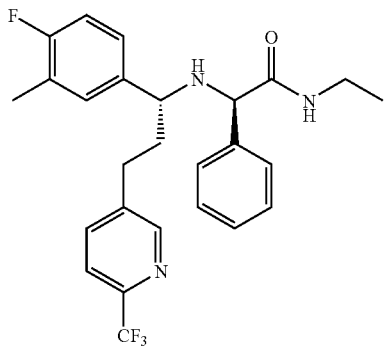

and

Example 340

(R,S)—N-Ethyl-2-[(S,R)-1-(4-fluoro-3-methyl-phenyl)-3-(6-trifluoromethyl-pyridin-3-yl)-propylamino]-2-phenyl-acetamide

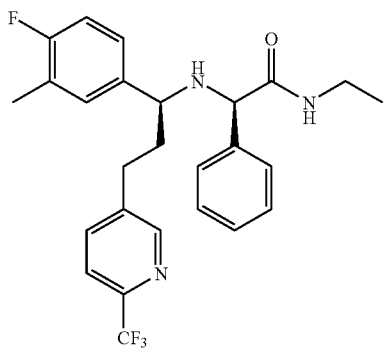

In analogy to the procedure described for the synthesis example 143 and 144 (step 3), the title compounds: (R,S)—N-Ethyl-2-[(R,S)-1-(4-fluoro-3-methyl-phenyl)-3-(6-trifluoromethyl-pyridin-3-yl)-propylamino]-2-phenyl-acetamide (MS (m/e): 474.1 [M+H]$^+$) and (R,S)—N-Ethyl-2-[(S,R)-1-(4-fluoro-3-methyl-phenyl)-3-(6-trifluoromethyl-pyridin-3-yl)-propylamino]-2-phenyl-acetamide (MS (m/e): 474.1 [M+H]$^+$) were prepared from rac 2-amino-N-ethyl-2-phenyl-acetamide (accessed according to the procedure described for example 323 and 324, step 2 starting from rac phenylglycine methyl ester and ethylamine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 341

(R,S)-2-(2,5-Difluoro-phenyl)-2-[(R,S)-1-(4-fluoro-3-methyl-phenyl)-3-(6-trifluoromethyl-pyridin-3-yl)-propylamino]-N-methyl-acetamide

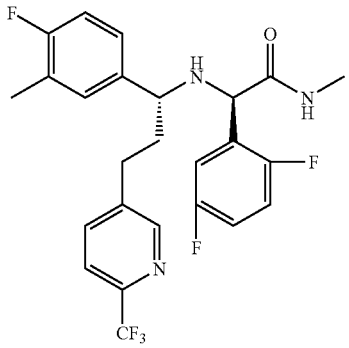

and

Example 342

(R,S)-2-(2,5-Difluoro-phenyl)-2-[(S,R)-1-(4-fluoro-3-methyl-phenyl)-3-(6-trifluoromethyl-pyridin-3-yl)-propylamino]-N-methyl-acetamide

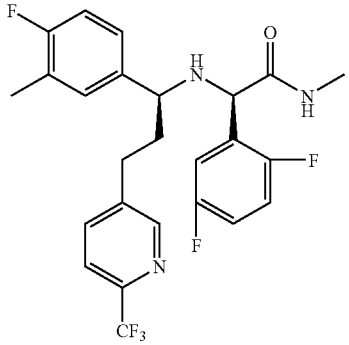

In analogy to the procedure described for the synthesis example 143 and 144 (step 3), the title compounds: (R,S)-2-(2,5-difluoro-phenyl)-2-[(R,S)-1-(4-fluoro-3-methyl-phenyl)-3-(6-trifluoromethyl-pyridin-3-yl)-propylamino]-N-methyl-acetamide (MS (m/e): 496.3 [M+H]$^+$) and (R,S)-2-(2,5-difluoro-phenyl)-2-[(S,R)-1-(4-fluoro-3-methyl-phenyl)-3-(6-trifluoromethyl-pyridin-3-yl)-propylamino]-N-methyl-acetamide (MS (m/e): 496.3 [M+H]$^+$) were prepared from rac 2-amino-N-methyl-2-(2,5-difluoro-phenyl)-acetamide (accessed according to the procedure described for example 323 and 324, step 1 and step 2 starting from 2,5-difluorophenylglycine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 343

(R,S)-2-[(R,S)-1-(4-Fluoro-3-methyl-phenyl)-3-(6-trifluoromethyl-pyridin-3-yl)-propylamino]-N-methyl-2-(4-trifluoromethyl-phenyl)-acetamide

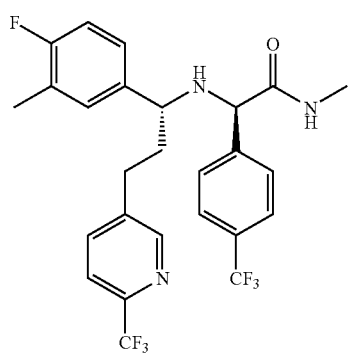

and

Example 344

(R,S)-2-[(S,R)-1-(4-Fluoro-3-methyl-phenyl)-3-(6-trifluoromethyl-pyridin-3-yl)-propylamino]-N-methyl-2-(4-trifluoromethyl-phenyl)-acetamide

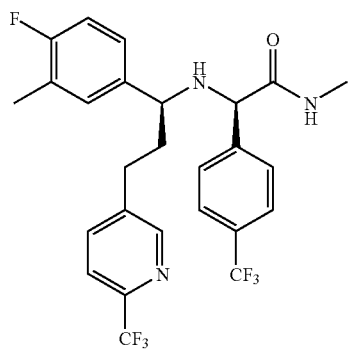

In analogy to the procedure described for the synthesis example 143 and 144 (step 3), the title compounds: (R,S)-2-[(R,S)-1-(4-fluoro-3-methyl-phenyl)-3-(6-trifluoromethyl-pyridin-3-yl)-propylamino]-N-methyl-2-(4-trifluoromethyl-phenyl)-acetamide (MS (m/e): 528.3 [M+H]$^+$) and (R,S)-2-[(S,R)-1-(4-fluoro-3-methyl-phenyl)-3-(6-trifluoromethyl-pyridin-3-yl)-propylamino]-N-methyl-2-(4-trifluoromethyl-phenyl)-acetamide (MS (m/e): 528.3 [M+H]$^+$) were prepared from rac 2-amino-N-methyl-2-(4-trifluoromethyl-phenyl)-acetamide (accessed according to the procedure described for example 323 and 324, step 1 and step 2 starting from 4-trifluoromethylphenylglycine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 345

(R,S)—N-Cyclopropylmethyl-2-[(S,R)-1-(4-fluoro-3-methyl-phenyl)-3-(6-trifluoromethyl-pyridin-3-yl)-propylamino]-2-phenyl-acetamide

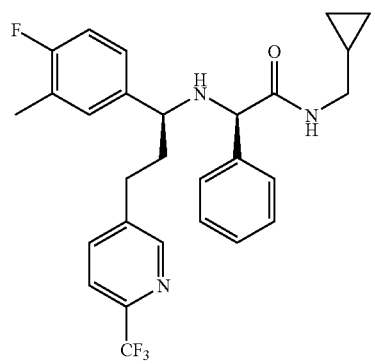

In analogy to the procedure described for the synthesis example 143 and 144 (step 3), the title compound: (R,S)—N-cyclopropylmethyl-2-[(S,R)-1-(4-fluoro-3-methyl-phenyl)-3-(6-trifluoromethyl-pyridin-3-yl)-propylamino]-2-phenyl-acetamide (MS (m/e): 500.3 [M+H]$^+$) was prepared from rac 2-amino-N-cyclopropylmethyl-2-phenyl-acetamide (accessed according to the procedure described for example 323 and 324, step 2 starting from rac phenylglycine methyl ester and cyclopropylmethylamine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 346

(R,S)-2-[(S,R)-1-(4-Fluoro-3-methyl-phenyl)-3-(6-trifluoromethyl-pyridin-3-yl)-propylamino]-N-methyl-2-(6-methyl-pyridin-3-yl)-acetamide

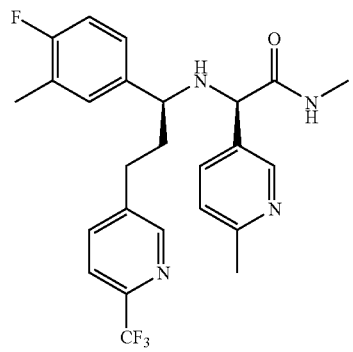

In analogy to the procedure described for the synthesis example 143 and 144 (step 3), the title compound: (R,S)-2-[(S,R)-1-(4-fluoro-3-methyl-phenyl)-3-(6-trifluoromethyl-pyridin-3-yl)-propylamino]-N-methyl-2-(6-methyl-pyridin-3-yl)-acetamide (MS (m/e): 475.1 [M+H]$^+$) was prepared from rac 2-amino-N-methyl-2-(6-methyl-pyridin-3-yl)-acetamide (accessed according to the procedure described for example 350, step 1 starting from 5-bromo-2-methylpyridine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 347

(R,S)-2-[(R,S)-1-(4-Fluoro-3-methyl-phenyl)-3-(6-trifluoromethyl-pyridin-3-yl)-propylamino]-N-(2-methoxy-ethyl)-2-phenyl-acetamide

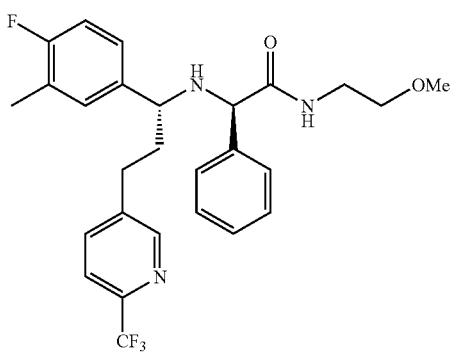

and

Example 348

(R,S)-2-[(S,R)-1-(4-Fluoro-3-methyl-phenyl)-3-(6-trifluoromethyl-pyridin-3-yl)-propylamino]-N-(2-methoxy-ethyl)-2-phenyl-acetamide

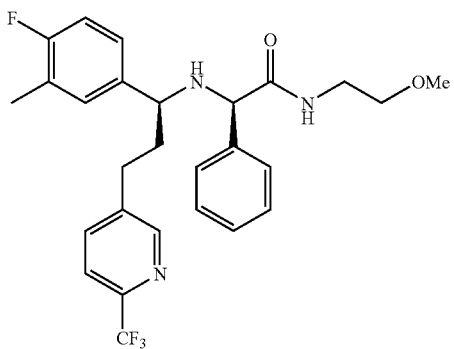

In analogy to the procedure described for the synthesis example 143 and 144 (step 3), the title compounds: (R,S)-2-[(R,S)-1-(4-fluoro-3-methyl-phenyl)-3-(6-trifluoromethyl-pyridin-3-yl)-propylamino]-N-(2-methoxy-ethyl)-2-phenyl-acetamide (MS (m/e): 504.2 [M+H]$^+$) and (R,S)-2-[(S,R)-1-(4-fluoro-3-methyl-phenyl)-3-(6-trifluoromethyl-pyridin-3-yl)-propylamino]-N-(2-methoxy-ethyl)-2-phenyl-acetamide (MS (m/e): 504.2 [M+H]$^+$) were prepared from rac 2-amino-N-(2-methoxy-ethyl)-2-phenyl-acetamide (accessed according to the procedure described for example 323 and 324, step 2 starting from rac phenylglycine methyl ester and 2-methoxy-ethylamine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 349

(S,R)-2-[(S,R)-1-(4-Fluoro-3-methyl-phenyl)-3-(6-trifluoromethyl-pyridin-3-yl)-propylamino]-N-methyl-2-thiophen-2-yl-acetamide

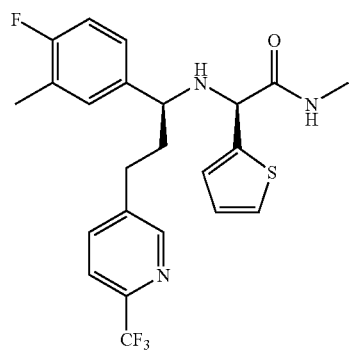

In analogy to the procedure described for the synthesis example 143 and 144 (step 3), the title compound: (S,R)-2-[(S,R)-1-(4-Fluoro-3-methyl-phenyl)-3-(6-trifluoromethyl-pyridin-3-yl)-propylamino]-N-methyl-2-thiophen-2-yl-acetamide (MS (m/e): 466.3 [M+H]$^+$) was prepared from rac 2-amino-N-methyl-2-thiophen-2-yl-acetamide (accessed according to the procedure described for example 323 and 324, step 2 starting from rac 2-amino-2-thiophen-2-yl-acetic acid methyl ester and methylamine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 350

(R,S)-2-[(S,R)-1-(4-Fluoro-3-methyl-phenyl)-3-(6-trifluoromethyl-pyridin-3-yl)-propylamino]-2-(4-methoxy-phenyl)-N-methyl-acetamide

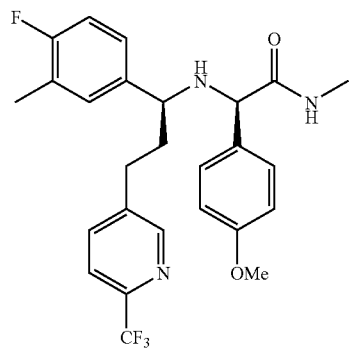

a) Step 1 rac
2-Amino-N-methyl-2-(4-methoxy-phenyl)-acetamide

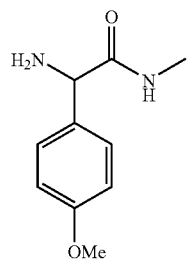

To a mixture of 4-bromoanisole (1.00 mL, 8.0 mmol), N-(diphenylmethylene)glycine ethyl ester (2.14 g, 8.0 mmol) and potassium phosphate tribasic (5.11 g, 24.1 mmol) in toluene (15 mL) under an argon atmosphere were added tri-tert-butylphosphine (79 µl, 0.32 mmol) and tris(dibenzylideneacetone)palladium(0) (147 mg, 0.16 mmol). The reaction mixture was stirred for 24 h at 100° C. It was filtered over Hyflo® and washed with toluene. The filtrate was concentrated and diluted with methanol (5 mL). At 5° C. aqueous methylamine (41% in water, 4.74 mL, 56.1 mmol) was added dropwise and stirring was continues for 22 h at ambient temperature. The resulting suspension was concentrated and the residue was taken in THF (5 mL), before aqueous HCl (1M, 40 mL, 40 mmol) was added. After stirring for 4 h at ambient temperature it was extracted with tert-butylmethylether, the organic layers were washed with aqueous HCl (1M). The aqueous. layers were washed with ethyl acetate and concentrated in vacuo. The residue was separated between THF and aqueous NaOH (1M). The organic layer was dried over sodium sulfate and concentrated affording the title compound (943 mg, 61%) as a light brown oil. MS m/e: 150.2 [M-Me-NHMe+H]$^+$).

b) Step 2

In analogy to the procedure described for the synthesis example 143 and 144 (step 3), the title compound: (R,S)-2-[(S,R)-1-(4-fluoro-3-methyl-phenyl)-3-(6-trifluoromethyl-pyridin-3-yl)-propylamino]-2-(4-methoxy-phenyl)-N-methyl-acetamide (MS (m/e): 490.3 [M+H]$^+$) was prepared from rac 2-amino-N-methyl-2-(4-methoxy-phenyl)-acetamide and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 351

(R,S)-2-(4-Cyano-phenyl)-2-[(S,S)-1-(4-fluoro-3-methyl-phenyl)-3-(6-trifluoromethyl-pyridin-3-yl)-propylamino]-N-methyl-acetamide

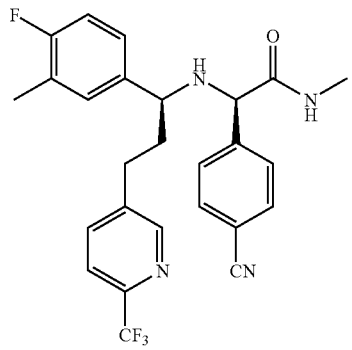

In analogy to the procedure described for the synthesis example 143 and 144 (step 3), the title compound: (R,S)-2-(4-cyano-phenyl)-2-[(S,S)-1-(4-fluoro-3-methyl-phenyl)-3-(6-trifluoromethyl-pyridin-3-yl)-propylamino]-N-methyl-acetamide (MS (m/e): 485.4 [M+H]$^+$) was prepared from rac 2-amino-N-methyl-2-(4-cyano-phenyl)-acetamide (accessed according to the procedure described for example 350, step 1 starting from 4-bromo-benzonitrile) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 352

(R,S)-2-[(S,R)-1-(4-Fluoro-3-methyl-phenyl)-3-(6-trifluoromethyl-pyridin-3-yl)-propylamino]-2-phenyl-N-(2,2,2-trifluoro-ethyl)-acetamide

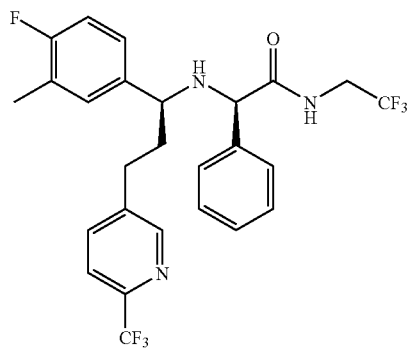

In analogy to the procedure described for the synthesis example 143 and 144 (step 3), the title compounds: (R,S)-2-[(S,R)-1-(4-fluoro-3-methyl-phenyl)-3-(6-trifluoromethyl-pyridin-3-yl)-propylamino]-2-phenyl-N-(2,2,2-trifluoro-ethyl)-acetamide (MS (m/e): 527.8 [M+H]$^+$) were prepared from rac 2-amino-N-(2-methoxy-ethyl)-2-phenyl-acetamide (accessed according to the procedure described for example 323 and 324, step 2 starting from rac phenylglycine methyl ester and 2,2,2-trifluoro-ethylamine) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 353

(R)-2-[(S)-1-(4-Fluoro-3-methyl-phenyl)-3-(6-trifluoromethyl-pyridin-3-yl)-propylamino]-2-phenyl-acetamide

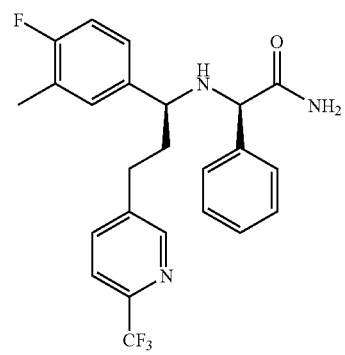

and

Example 354

(S)-2-[(R)-1-(4-Fluoro-3-methyl-phenyl)-3-(6-trifluoromethyl-pyridin-3-yl)-propylamino]-2-phenyl-acetamide

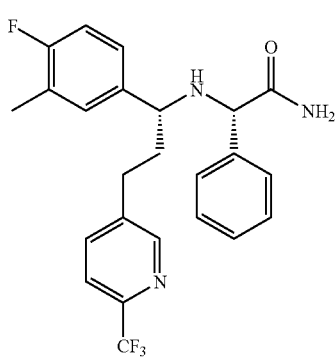

and

Example 355

(S)-2-[(S)-1-(4-Fluoro-3-methyl-phenyl)-3-(6-trifluoromethyl-pyridin-3-yl)-propylamino]-2-phenyl-acetamide

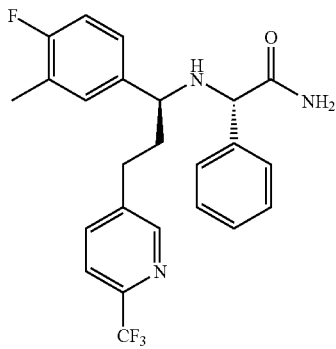

2-[1-(4-Fluoro-3-methyl-phenyl)-3-(6-trifluoromethyl-pyridin-3-yl)-propylamino]-2-phenyl-acetamide (examples 327 and 328) was separated on chiral phase HPLC (Chiralpak AD column) to provide the title compounds: (R)-2-[(S)-1-(4-Fluoro-3-methyl-phenyl)-3-(6-trifluoromethyl-pyridin-3-yl)-propylamino]-2-phenyl-acetamide (MS (m/e): 446.2 [M+H]$^+$) and (S)-2-[(R)-1-(4-Fluoro-3-methyl-phenyl)-3-(6-trifluoromethyl-pyridin-3-yl)-propylamino]-2-phenyl-acetamide (MS (m/e): 446.2 [M+H]$^+$) and (S)-2-[(S)-1-(4-Fluoro-3-methyl-phenyl)-3-(6-trifluoromethyl-pyridin-3-yl)-propylamino]-2-phenyl-acetamide (MS (m/e): 446.2 [M+H]$^+$) as off-white semisolids.

Example 356

(R,S)-2-[(S,R)-1-(4-Fluoro-3-methyl-phenyl)-3-(6-trifluoromethyl-pyridin-3-yl)-propylamino]-N-(2-hydroxy-ethyl)-2-phenyl-acetamide

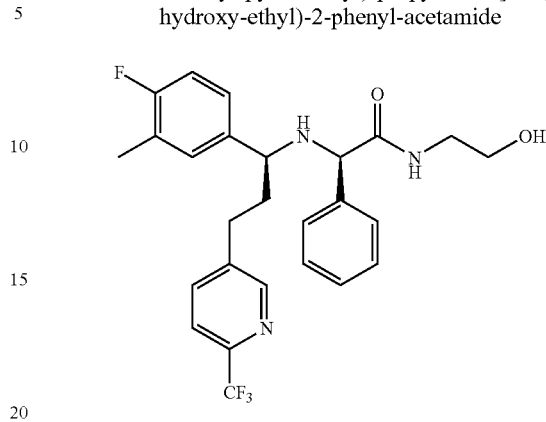

a) Step 1

(R,S)-[(S,R)-3-(6-Chloro-pyridin-3-yl)-1-(4-fluoro-3-methyl-phenyl)-propylamino]-phenyl-acetic acid ethyl ester

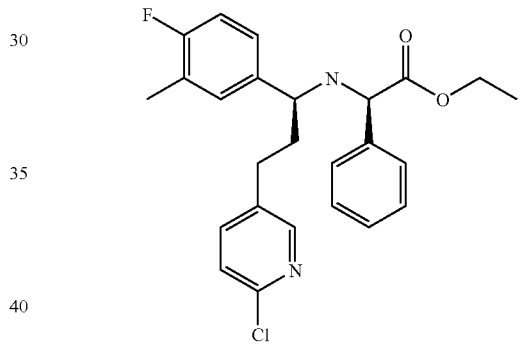

In analogy to the procedure described for the synthesis example 143 and 144 (step 3), the title compound: (R,S)-[(S,R)-3-(6-chloro-pyridin-3-yl)-1-(4-fluoro-3-methyl-phenyl)-propylamino]-phenyl-acetic acid ethyl ester (MS (m/e): 475.1 [M+H]$^+$) was prepared from rac phenylglycine tert-butyl ester (commercially available) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

b) Step 2

A mixture of (R,S)-[(S,R)-3-(6-chloro-pyridin-3-yl)-1-(4-fluoro-3-methyl-phenyl)-propylamino]-phenyl-acetic acid ethyl ester (113 mg, 0.238 mmol) and ethanolamine (571 μl, 9.53 mmol) was stirred for 18 h at ambient temperature. The reaction mixture was diluted with ethyl acetate and washed with a aqueous sodium carbonate (saturated) and brine. The aqueous layers were extracted with ethyl acetate and the combined organic layers were dried over sodium sulfate. Purification by chromatography (SiO$_2$, heptane:ethyl acetate=50:50 to 20:80) afforded the title compound (90 mg, 77%) as a light brown oil. MS m/e: 490.0 [M+H]$^+$

Example 357

(R,S)-2-[(S,R)-1-(4-Fluoro-3-methyl-phenyl)-3-(6-trifluoromethyl-pyridin-3-yl)-propylamino]-N-isobutyl-2-phenyl-acetamide

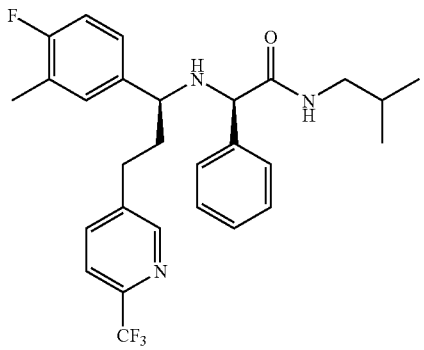

In analogy to the procedure described for the synthesis example 356 (step 2), the title compound: (R,S)-2-[(S,R)-1-(4-fluoro-3-methyl-phenyl)-3-(6-trifluoromethyl-pyridin-3-yl)-propylamino]-N-isobutyl-2-phenyl-acetamide (MS (m/e): 502.0 [M+H]$^+$) was prepared from (R,S)-[(S,R)-3-(6-chloro-pyridin-3-yl)-1-(4-fluoro-3-methyl-phenyl)-propylamino]-phenyl-acetic acid ethyl ester and isobutylamine.

Example 358

(R,S)-2-(4-Ethyl-phenyl)-2-[(R,S)-1-(4-fluoro-3-methyl-phenyl)-3-(6-trifluoromethyl-pyridin-3-yl)-propylamino]-N-methyl-acetamide

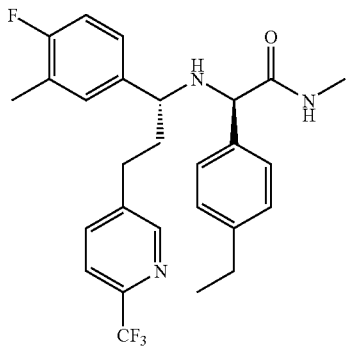

and

Example 359

(R,S)-2-(4-Ethyl-phenyl)-2-[(S,R)-1-(4-fluoro-3-methyl-phenyl)-3-(6-trifluoromethyl-pyridin-3-yl)-propylamino]-N-methyl-acetamide

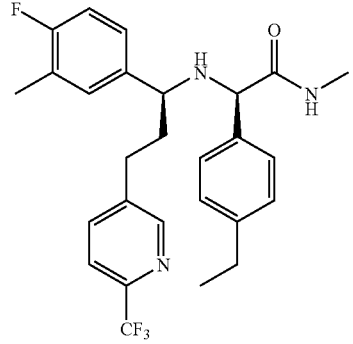

In analogy to the procedure described for the synthesis example 143 and 144 (step 3), the title compounds: (R,S)-2-(4-ethyl-phenyl)-2-[(R,S)-1-(4-fluoro-3-methyl-phenyl)-3-(6-trifluoromethyl-pyridin-3-yl)-propylamino]-N-methyl-acetamide (MS (m/e): 488.4 [M+H]$^+$) and (R,S)-2-(4-ethyl-phenyl)-2-[(S,R)-1-(4-fluoro-3-methyl-phenyl)-3-(6-trifluoromethyl-pyridin-3-yl)-propylamino]-N-methyl-acetamide (MS (m/e): 488.4 [M+H]$^+$) were prepared from rac 2-amino-N-methyl-2-(4-ethyl-phenyl)-acetamide (accessed according to the procedure described for example 350, step 1 starting from 1-ethyl-4-bromo-benzene) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 360

(R,S)-2-(4-Dimethylamino-phenyl)-2-[(S,R)-1-(4-fluoro-3-methyl-phenyl)-3-(6-trifluoromethyl-pyridin-3-yl)-propylamino]-N-methyl-acetamide

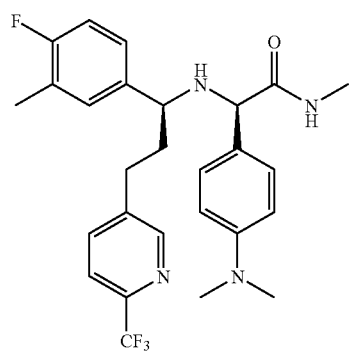

In analogy to the procedure described for the synthesis example 143 and 144 (step 3), the title compound: (R,S)-2-(4-dimethylamino-phenyl)-2-[(S,R)-1-(4-fluoro-3-methyl-phenyl)-3-(6-trifluoromethyl-pyridin-3-yl)-propylamino]-N-methyl-acetamide (MS (m/e): 501.5 [M+H]$^+$) was prepared from rac 2-amino-N-methyl-2-(4-dimethylamino-phenyl)-acetamide (accessed according to the procedure described for example 350, step 1 starting from 4-bromo-N,N-dimethylaniline) and 1-(4-fluoro-3-methyl-phenyl)-3-(6-trifluoromethyl-pyridin-3-yl)-propan-1-one (accessed according to the procedure described for example 143 and 144, step 2 from (E)-1-(4-fluoro-3-methyl-phenyl)-3-(6-trifluoromethyl-pyridin-3-yl)-propenone).

Example 361

(S)-2-[(S)-1-(4-Fluoro-3-methyl-phenyl)-3-(6-trifluoromethyl-pyridin-3-yl)-propylamino]-N-methyl-2-(6-methyl-pyridin-3-yl)-acetamide

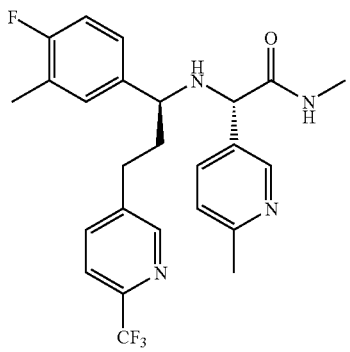

and

Example 362

(R)-2-[(S)-1-(4-Fluoro-3-methyl-phenyl)-3-(6-trifluoromethyl-pyridin-3-yl)-propylamino]-N-methyl-2-(6-methyl-pyridin-3-yl)-acetamide

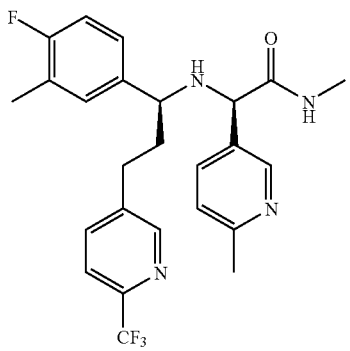

and

Example 363

(S)-2-[(R)-1-(4-Fluoro-3-methyl-phenyl)-3-(6-trifluoromethyl-pyridin-3-yl)-propylamino]-N-methyl-2-(6-methyl-pyridin-3-yl)-acetamide

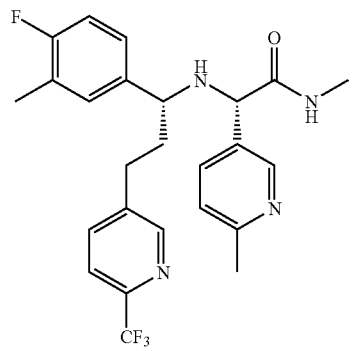

2-[1-(4-Fluoro-3-methyl-phenyl)-3-(6-trifluoromethyl-pyridin-3-yl)-propylamino]-N-methyl-2-(6-methyl-pyridin-3-yl)-acetamide (example 346) was separated on chiral phase HPLC (Chiralpak AD column) to provide the title compounds: (S)-2-[(S)-1-(4-fluoro-3-methyl-phenyl)-3-(6-trifluoromethyl-pyridin-3-yl)-propylamino]-N-methyl-2-(6-methyl-pyridin-3-yl)-acetamide (MS (m/e): 475.3 [M+H]$^+$) and (R)-2-[(S)-1-(4-fluoro-3-methyl-phenyl)-3-(6-trifluoromethyl-pyridin-3-yl)-propylamino]-N-methyl-2-(6-methyl-pyridin-3-yl)-acetamide (MS (m/e): 475.3 [M+H]$^+$) and (S)-2-[(R)-1-(4-fluoro-3-methyl-phenyl)-3-(6-trifluoromethyl-pyridin-3-yl)-propylamino]-N-methyl-2-(6-methyl-pyridin-3-yl)-acetamide (MS (m/e): 475.3 [M+H]$^+$) as light-brown foams.

Example 364

(R,S)-2-[(S,R)-1-(4-Fluoro-3-methyl-phenyl)-3-p-tolyl-propylamino]-N-methyl-2-p-tolyl-acetamide

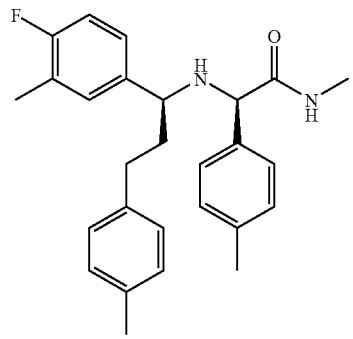

In analogy to the procedure described for the synthesis example 143 and 144 (step 3), the title compound: (R,S)-2-[(S,R)-1-(4-fluoro-3-methyl-phenyl)-3-p-tolyl-propylamino]-N-methyl-2-p-tolyl-acetamide (MS (m/e): 419.3 [M+H]$^+$) was prepared from rac 2-amino-N-methyl-2-p-tolyl-acetamide (accessed according to the procedure described for example 323 and 324, step 1 and step 2 starting from 4-methylphenylglycine) and 1-(4-fluoro-3-methyl-phenyl)-3-p-tolyl-propan-1-one (accessed according to the procedure described for example 234, step 1 and step 2 starting from ethyl 4-fluoro-3-methyl-benzoate and p-tolylaldehyde.

Example 365

(R,S)-2-[(S,R)-1-(4-Fluoro-3-methyl-phenyl)-3-p-tolyl-propylamino]-N-methyl-2-phenyl-acetamide

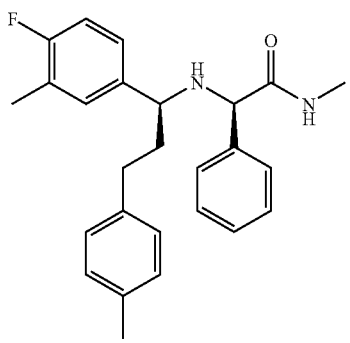

In analogy to the procedure described for the synthesis example 143 and 144 (step 3), the title compound: (R,S)-2-[(S,R)-1-(4-fluoro-3-methyl-phenyl)-3-p-tolyl-propylamino]-N-methyl-2-phenyl-acetamide (MS (m/e): 405.4 [M+H]$^+$) was prepared from rac 2-amino-N-methyl-2-phenyl-acetamide (CAS: 93782-07-1) and 1-(4-fluoro-3-methyl-phenyl)-3-p-tolyl-propan-1-one (accessed according to the procedure described for example 234, step 1 and step 2 starting from ethyl 4-fluoro-3-methyl-benzoate and p-tolylaldehyde.

Example 366

(R,S)-2-[(S,R)-1-(4-Fluoro-3-methyl-phenyl)-3-p-tolyl-propylamino]-2-phenyl-acetamide

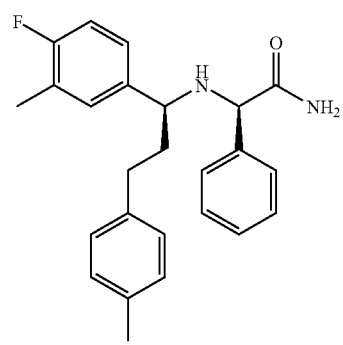

In analogy to the procedure described for the synthesis example 143 and 144 (step 3), the title compound: (R,S)-2-[(S,R)-1-(4-fluoro-3-methyl-phenyl)-3-p-tolyl-propylamino]-N-methyl-2-phenyl-acetamide (MS (m/e): 391.5 [M+H]$^+$) was prepared from rac 2-amino-2-phenyl-acetamide (commercially available) and 1-(4-fluoro-3-methyl-phenyl)-3-p-tolyl-propan-1-one (accessed according to the procedure described for example 234, step 1 and step 2 starting from ethyl 4-fluoro-3-methyl-benzoate and p-tolylaldehyde.

Example 367

(R,S)-2-[(R,S)-1-(4-Fluoro-3-trifluoromethoxy-phenyl)-3-(4-trifluoromethyl-phenyl)-propylamino]-N-methyl-2-phenyl-acetamide

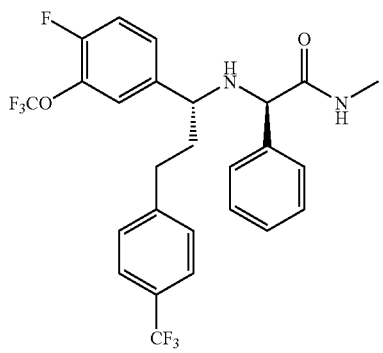

and

Example 368

(R,S)-2-[(S,R)-1-(4-Fluoro-3-trifluoromethoxy-phenyl)-3-(4-trifluoromethyl-phenyl)-propylamino]-N-methyl-2-phenyl-acetamide

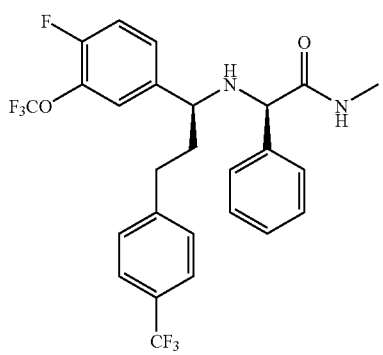

In analogy to the procedure described for the synthesis example 143 and 144 (step 3), the title compounds: (R,S)-2-[(R,S)-1-(4-fluoro-3-trifluoromethoxy-phenyl)-3-(4-trifluoromethyl-phenyl)-propylamino]-N-methyl-2-phenyl-acetamide (MS (m/e): 528.8 [M+H]$^+$) and (R,S)-2-[(S,R)-1-(4-fluoro-3-trifluoromethoxy-phenyl)-3-(4-trifluoromethyl-phenyl)-propylamino]-N-methyl-2-phenyl-acetamide (MS (m/e): 528.8 [M+H]$^+$) were prepared from rac 2-amino-N-methyl-2-phenyl-acetamide (CAS: 93782-07-1) and 1-(4-fluoro-3-trifluoromethoxy-phenyl)-3-(4-trifluoromethyl-phenyl)-propan-1-one (accessed according to the procedure described for example 234, step 1 and step 2 starting from methyl 4-fluoro-3-trifluoromethoxy-benzoate and 4-trifluoromethylbenzaldehyde.

Example 369

(R,S)-2-[(R,S)-1-(4-Fluoro-3-trifluoromethoxy-phenyl)-3-(4-trifluoromethyl-phenyl)-propylamino]-N-methyl-2-p-tolyl-acetamide

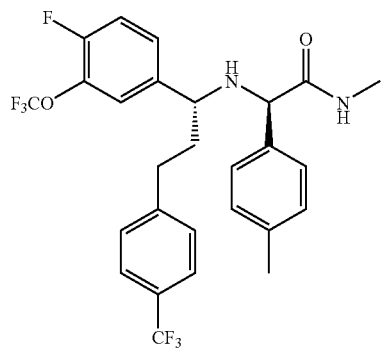

and

Example 370

(R,S)-2-[(S,R)-1-(4-Fluoro-3-trifluoromethoxy-phenyl)-3-(4-trifluoromethyl-phenyl)-propylamino]-N-methyl-2-p-tolyl-acetamide

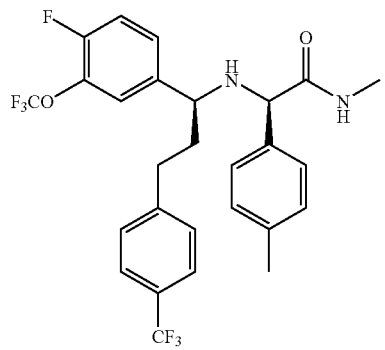

In analogy to the procedure described for the synthesis example 143 and 144 (step 3), the title compounds: (R,S)-2-[(R,S)-1-(4-fluoro-3-trifluoromethoxy-phenyl)-3-(4-trifluoromethyl-phenyl)-propylamino]-N-methyl-2-p-tolyl-acetamide (MS (m/e): 542.7 [M+H]$^+$) and (R,S)-2-[(S,R)-1-(4-fluoro-3-trifluoromethoxy-phenyl)-3-(4-trifluoromethyl-phenyl)-propylamino]-N-methyl-2-p-tolyl-acetamide (MS (m/e): 542.7 [M+H]$^+$) were prepared from rac 2-amino-N-methyl-2-p-tolyl-acetamide (accessed according to the procedure described for example 323 and 324, step 1 and step 2 starting from 4-methylphenylglycine) and 1-(4-fluoro-3-trifluoromethoxy-phenyl)-3-(4-trifluoromethyl-phenyl)-propan-1-one (accessed according to the procedure described for example 234, step 1 and step 2 starting from methyl 4-fluoro-3-trifluoromethoxy-benzoate and 4-trifluoromethylbenzaldehyde.

Example 371

(R,S)-2-[(S,R)-3-(4-Chloro-phenyl)-1-(4-fluoro-3-methyl-phenyl)-propylamino]-N-methyl-2-p-tolyl-acetamide

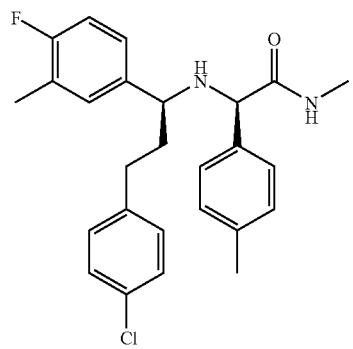

In analogy to the procedure described for the synthesis example 143 and 144 (step 3), the title compound: (R,S)-2-[(S,R)-3-(4-chloro-phenyl)-1-(4-fluoro-3-methyl-phenyl)-propylamino]-N-methyl-2-p-tolyl-acetamide (MS (m/e): 439.3 [M+H]$^+$) was prepared from rac 2-amino-N-methyl-2-p-tolyl-acetamide (accessed according to the procedure described for example 323 and 324, step 1 and step 2 starting from 4-methylphenylglycine) and 3-(4-chloro-phenyl)-1-(4-fluoro-3-methyl-phenyl)-propan-1-one (accessed according to the procedure described for example 234, step 1 and step 2 starting from ethyl 4-fluoro-3-methyl-benzoate and 4-chlorobenzaldehyde.

Example 372

(R,S)-2-[(R,S)-3-(4-Chloro-phenyl)-1-(4-fluoro-3-methyl-phenyl)-propylamino]-N-methyl-2-phenyl-acetamide

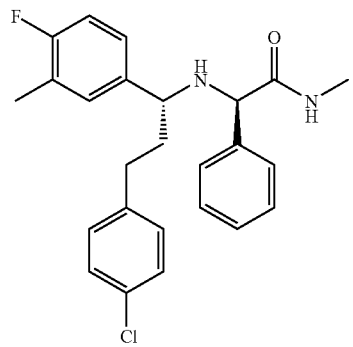

and

Example 373

(R,S)-2-[(S,R)-3-(4-Chloro-phenyl)-1-(4-fluoro-3-methyl-phenyl)-propylamino]-N-methyl-2-phenyl-acetamide

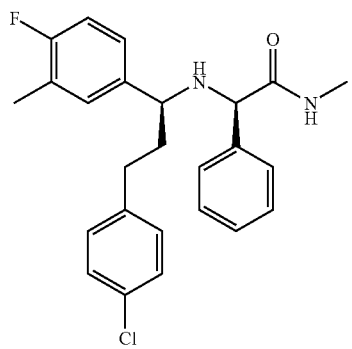

In analogy to the procedure described for the synthesis example 143 and 144 (step 3), the title compounds: (R,S)-2-[(R,S)-3-(4-chloro-phenyl)-1-(4-fluoro-3-methyl-phenyl)-propylamino]-N-methyl-2-phenyl-acetamide (MS (m/e): 425.1 [M+H]$^+$) and (R,S)-2-[(S,R)-3-(4-Chloro-phenyl)-1-(4-fluoro-3-methyl-phenyl)-propylamino]-N-methyl-2-phenyl-acetamide (MS (m/e): 425.1 [M+H]$^+$) were prepared from rac 2-amino-N-methyl-2-phenyl-acetamide (CAS: 93782-07-1) and 3-(4-chloro-phenyl)-1-(4-fluoro-3-methyl-phenyl)-propan-1-one (accessed according to the procedure described for example 234, step 1 and step 2 starting from ethyl 4-fluoro-3-methyl-benzoate and 4-chlorobenzaldehyde.

Example 374

(R,S)-2-[(R,S)-3-(4-Chloro-phenyl)-1-(4-fluoro-3-methyl-phenyl)-propylamino]-2-phenyl-acetamide

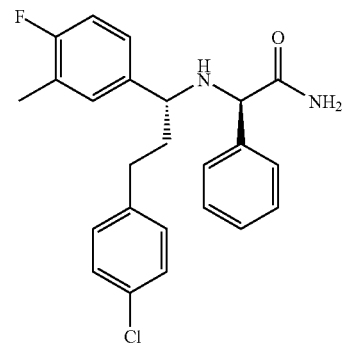

and

Example 375

(R,S)-2-[(S,R)-3-(4-Chloro-phenyl)-1-(4-fluoro-3-methyl-phenyl)-propylamino]-2-phenyl-acetamide

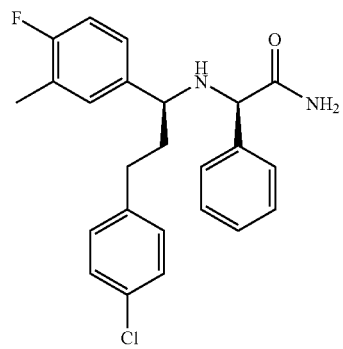

In analogy to the procedure described for the synthesis example 143 and 144 (step 3), the title compounds: (R,S)-2-[(R,S)-3-(4-chloro-phenyl)-1-(4-fluoro-3-methyl-phenyl)-propylamino]-2-phenyl-acetamide (MS (m/e): 411.2 [M+H]$^+$) and (R,S)-2-[(S,R)-3-(4-Chloro-phenyl)-1-(4-fluoro-3-methyl-phenyl)-propylamino]-2-phenyl-acetamide (MS (m/e): 411.2 [M+H]$^+$) were prepared from rac 2-amino-2-phenyl-acetamide (commercially available) and 3-(4-chloro-phenyl)-1-(4-fluoro-3-methyl-phenyl)-propan-1-one (accessed according to the procedure described for example 234, step 1 and step 2 starting from ethyl 4-fluoro-3-methyl-benzoate and 4-chlorobenzaldehyde.

Example 376

(R,S)-2-[(R,S)-1-(4-Fluoro-3-trifluoromethoxy-phenyl)-3-(4-trifluoromethyl-phenyl)-propylamino]-2-phenyl-acetamide

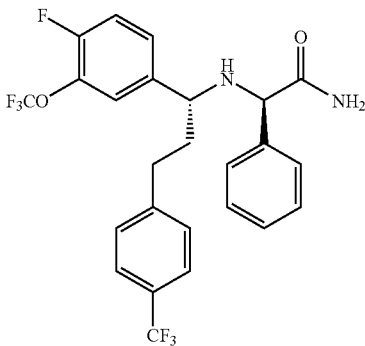

and

Example 377

(R,S)-2-[(S,R)-1-(4-Fluoro-3-trifluoromethoxy-phenyl)-3-(4-trifluoromethyl-phenyl)-propylamino]-2-phenyl-acetamide

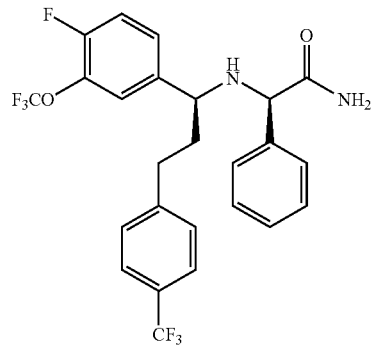

In analogy to the procedure described for the synthesis example 143 and 144 (step 3), the title compounds: (R,S)-2-[(R,S)-1-(4-fluoro-3-trifluoromethoxy-phenyl)-3-(4-trifluoromethyl-phenyl)-propylamino]-2-phenyl-acetamide (MS (m/e): 515.0 [M+H]$^+$) and (R,S)-2-[(S,R)-1-(4-fluoro-3-trifluoromethoxy-phenyl)-3-(4-trifluoromethyl-phenyl)-propylamino]-2-phenyl-acetamide (MS (m/e): 515.0 [M+H]$^+$) were prepared from rac 2-amino-2-phenyl-acetamide (commercially available) and 1-(4-fluoro-3-trifluoromethoxy-phenyl)-3-(4-trifluoromethyl-phenyl)-propan-1-one (accessed according to the procedure described for example 234, step 1 and step 2 starting from methyl 4-fluoro-3-trifluoromethoxy-benzoate and 4-trifluoromethylbenzaldehyde.

Example 378

(R,S)-2-[(R,S)-1-(3-Difluoromethoxy-phenyl)-3-(4-trifluoromethyl-phenyl)-propylamino]-N-methyl-2-p-tolyl-acetamide

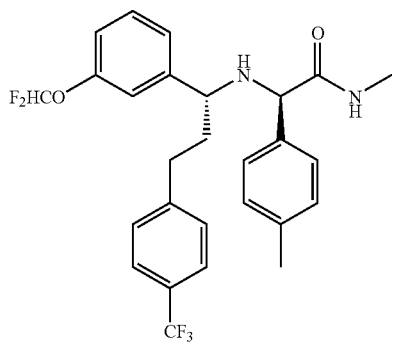

and

Example 379

(R,S)-2-[(S,R)-1-(3-Difluoromethoxy-phenyl)-3-(4-trifluoromethyl-phenyl)-propylamino]-N-methyl-2-p-tolyl-acetamide

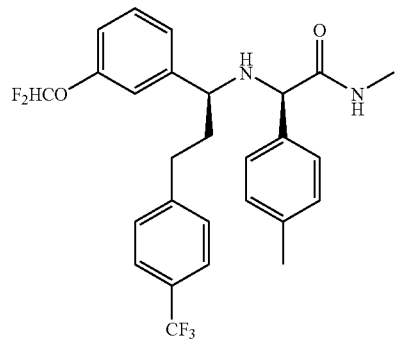

In analogy to the procedure described for the synthesis example 143 and 144 (step 3), the title compounds: (R,S)-2-[(R,S)-1-(3-difluoromethoxy-phenyl)-3-(4-trifluoromethyl-phenyl)-propylamino]-N-methyl-2-p-tolyl-acetamide (MS (m/e): 507.0 [M+H]$^+$) and (R,S)-2-[(S,R)-1-(3-difluoromethoxy-phenyl)-3-(4-trifluoromethyl-phenyl)-propylamino]-N-methyl-2-p-tolyl-acetamide (MS (m/e): 507.0 [M+H]$^+$) were prepared from rac 2-amino-N-methyl-2-p-tolyl-acetamide (accessed according to the procedure described for example 323 and 324, step 1 and step 2 starting from 4-methylphenylglycine) and 1-(3-difluoromethoxy-phenyl)-3-(4-trifluoromethyl-phenyl)-propan-1-one (accessed according to the procedure described for example 234, step 1 and step 2 starting from methyl 3-difluoromethoxy-benzoate and 4-trifluoromethylbenzaldehyde.

Example 380

(R,S)-2-[(R,S)-1-(3-Difluoromethoxy-phenyl)-3-(4-trifluoromethyl-phenyl)-propylamino]-N-methyl-2-phenyl-acetamide

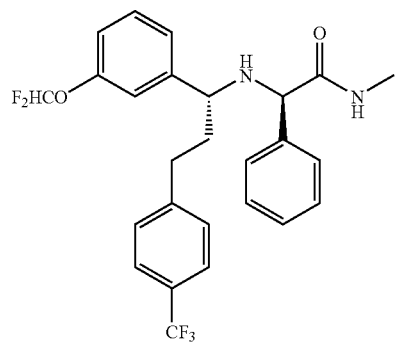

and

Example 381

(R,S)-2-[(S,R)-1-(3-Difluoromethoxy-phenyl)-3-(4-trifluoromethyl-phenyl)-propylamino]-N-methyl-2-phenyl-acetamide

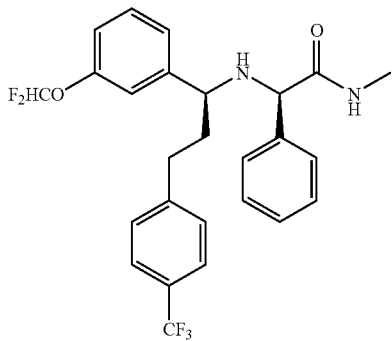

In analogy to the procedure described for the synthesis example 143 and 144 (step 3), the title compounds: (R,S)-2-[(R,S)-1-(3-difluoromethoxy-phenyl)-3-(4-trifluoromethyl-phenyl)-propylamino]-N-methyl-2-phenyl-acetamide (MS (m/e): 493.3 [M+H]$^+$) and (R,S)-2-[(S,R)-1-(3-difluoromethoxy-phenyl)-3-(4-trifluoromethyl-phenyl)-propylamino]-N-methyl-2-phenyl-acetamide (MS (m/e): 493.3 [M+H]$^+$) were prepared from rac 2-amino-N-methyl-2-phenyl-acetamide (CAS: 93782-07-1) and 1-(3-difluoromethoxy-phenyl)-3-(4-trifluoromethyl-phenyl)-propan-1-one (accessed according to the procedure described for example 234, step 1 and step 2 starting from methyl 3-difluoromethoxy-benzoate and 4-trifluoromethylbenzaldehyde.

Example 382

(R,S)-2-[(S,R)-1-(4-Fluoro-3-methyl-phenyl)-3-p-tolyl-propylamino]-2-p-tolyl-acetamide

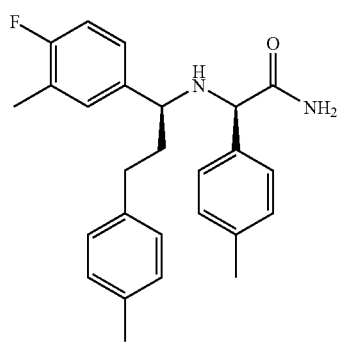

a) Step 1 rac 2-amino-2-p-tolyl-acetamide

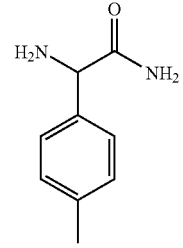

A mixture of p-tolylaldehyde (15.0 g, 125 mmol), ammonia (7 M in methanol, 142 mL, 1.00 mol) and tetraisopropyl orthotitanate (42.6 g, 150 mmol) was stirred at ambient temperature for 2 h. After addition of trimethylsilyl cyanide (12.8 g, 125 mmol) stirring was continued for 56 h. The resulting mixture was poured onto ice/water (1.5 L) and extracted with ethyl acetate. The organic layers were washed with brine, dried over sodium sulfate and concentrated. The residue was dissolved in formic acid (100 mL) and formic acid saturated with HCl (100 mL) was added while cooling with an ice bath. The reaction mixture was stirred for 18 h and concentrated, suspended in acetone and filtered, affording the title compound as hydrochloride salt (14.5 g, 61%) as an orange solid. MS (m/e): 165.4 [M+H]$^+$ b) Step 2

In analogy to the procedure described for the synthesis example 143 and 144 (step 3), the title compound: (R,S)-2-[(S,R)-1-(4-fluoro-3-methyl-phenyl)-3-p-tolyl-propylamino]-N-methyl-2-p-tolyl-acetamide (MS (m/e): 405.4 [M+H]$^+$) was prepared from rac 2-amino-2-p-tolyl-acetamide and 1-(4-fluoro-3-methyl-phenyl)-3-p-tolyl-propan-1-one (accessed according to the procedure described for example 234, step 1 and step 2 starting from ethyl 4-fluoro-3-methyl-benzoate and p-tolylaldehyde.

Example 383

(R,S)-2-[(R,S)-1-(3-Difluoromethoxy-phenyl)-3-(4-trifluoromethyl-phenyl)-propylamino]-2-p-tolyl-acetamide

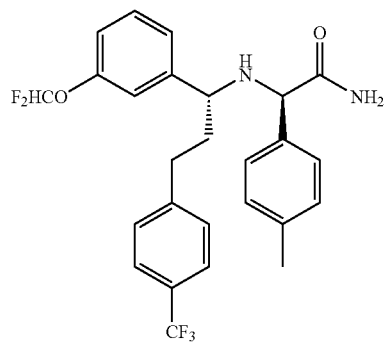

and

Example 384

(R,S)-2-[(S,R)-1-(3-Difluoromethoxy-phenyl)-3-(4-trifluoromethyl-phenyl)-propylamino]-2-p-tolyl-acetamide

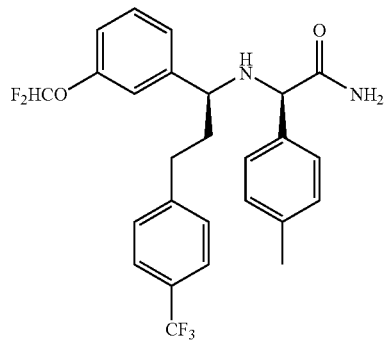

In analogy to the procedure described for the synthesis example 143 and 144 (step 3), the title compounds: (R,S)-2-[(R,S)-1-(3-difluoromethoxy-phenyl)-3-(4-trifluoromethyl-phenyl)-propylamino]-2-p-tolyl-acetamide (MS (m/e): 493.0 [M+H]$^+$) and (R,S)-2-[(S,R)-1-(3-difluoromethoxy-phenyl)-3-(4-trifluoromethyl-phenyl)-propylamino]-2-p-tolyl-acetamide (MS (m/e): 493.0 [M+H]$^+$) were prepared rac 2-amino-2-p-tolyl-acetamide (example 382, step 1) and 1-(3-difluoromethoxy-phenyl)-3-(4-trifluoromethyl-phenyl)-propan-1-one (accessed according to the procedure described for example 234, step 1 and step 2 starting from methyl 3-difluoromethoxy-benzoate and 4-trifluoromethylbenzaldehyde.

Example 386

(R,S)-2-[(S,R)-1-(4-Fluoro-3-trifluoromethoxy-phenyl)-3-(4-trifluoromethyl-phenyl)-propylamino]-2-p-tolyl-acetamide

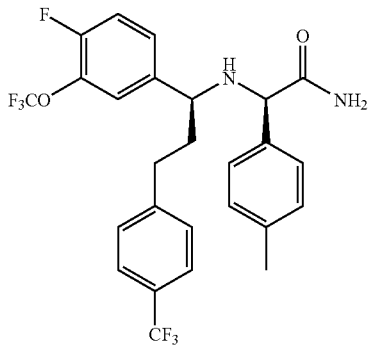

In analogy to the procedure described for the synthesis example 143 and 144 (step 3), the title compounds: (R,S)-2-[(R,S)-1-(4-fluoro-3-trifluoromethoxy-phenyl)-3-(4-trifluoromethyl-phenyl)-propylamino]-2-p-tolyl-acetamide (MS (m/e): 528.8 [M+H]$^+$) and (R,S)-2-[(S,R)-1-(4-fluoro-3-trifluoromethoxy-phenyl)-3-(4-trifluoromethyl-phenyl)-propylamino]-2-p-tolyl-acetamide (MS (m/e): 528.8 [M+H]$^+$) were prepared from rac 2-amino-2-p-tolyl-acetamide (example 382, step 1) and 1-(4-fluoro-3-trifluoromethoxy-phenyl)-3-(4-trifluoromethyl-phenyl)-propan-1-one (accessed according to the procedure described for example 234, step 1 and step 2 starting from methyl 4-fluoro-3-trifluoromethoxy-benzoate and 4-trifluoromethylbenzaldehyde.

Example 385

(R,S)-2-[(R,S)-1-(4-Fluoro-3-trifluoromethoxy-phenyl)-3-(4-trifluoromethyl-phenyl)-propylamino]-2-p-tolyl-acetamide

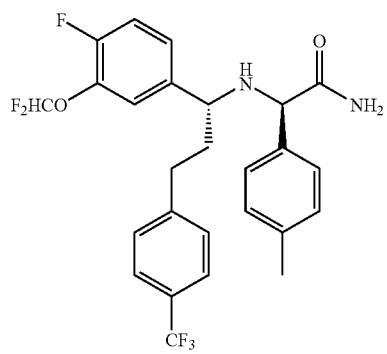

and

Example 387

(R)-2-[(S)-1-(3-Difluoromethoxy-phenyl)-3-(4-trifluoromethyl-phenyl)-propylamino]-N-methyl-2-phenyl-acetamide

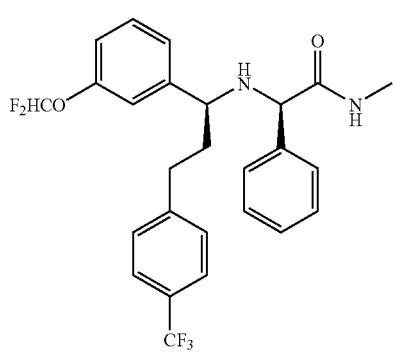

and

Example 388

(S)-2-[(R)-1-(3-Difluoromethoxy-phenyl)-3-(4-trifluoromethyl-phenyl)-propylamino]-N-methyl-2-phenyl-acetamide

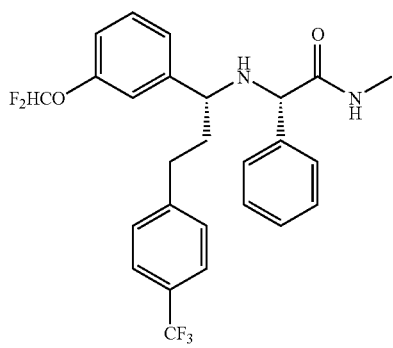

2-[1-(3-Difluoromethoxy-phenyl)-3-(4-trifluoromethylphenyl)-propylamino]-N-methyl-2-phenyl-acetamide (example 381) was separated on chiral phase HPLC (Chiralpak AD column) to provide the title compounds: (R)-2-[(S)-1-(3-Difluoromethoxy-phenyl)-3-(4-trifluoromethyl-phenyl)-propylamino]-N-methyl-2-phenyl-acetamide (MS (m/e): 493.0 [M+H]$^+$) and (S)-2-[(R)-1-(3-Difluoromethoxy-phenyl)-3-(4-trifluoromethyl-phenyl)-propylamino]-N-methyl-2-phenyl-acetamide (MS (m/e): 493.0 [M+H]$^+$) as light-brown oils.

Example 389

(R)-2-[(S)-1-(3-Difluoromethoxy-phenyl)-3-(4-trifluoromethyl-phenyl)-propylamino]-N-methyl-2-p-tolyl-acetamide

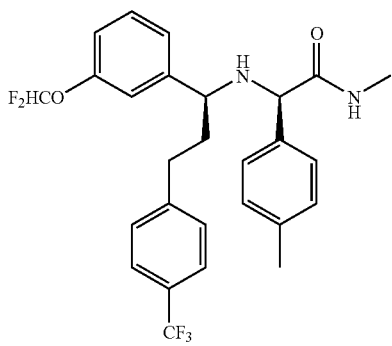

(R,S)-2-[(S,R)-1-(3-Difluoromethoxy-phenyl)-3-(4-trifluoromethyl-phenyl)-propylamino]-N-methyl-2-p-tolyl-acetamide (example 379) was separated on chiral phase HPLC (ChiralpakAD column) to provide the title compound: (R)-2-[(S)-1-(3-Difluoromethoxy-phenyl)-3-(4-trifluoromethyl-phenyl)-propylamino]-N-methyl-2-phenyl-acetamide (MS (m/e): 506.9 [M+H]$^+$) as a light-brown oil.

Example 392

(R)-2-[(S)-3-(4-Chloro-phenyl)-1-(4-fluoro-3-methyl-phenyl)-propylamino]-N-methyl-2-phenyl-acetamide

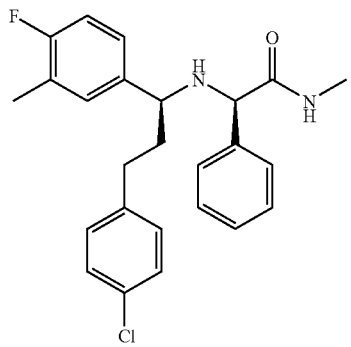

and

Example 393

(S)-2-[(R)-3-(4-Chloro-phenyl)-1-(4-fluoro-3-methyl-phenyl)-propylamino]-N-methyl-2-phenyl-acetamide

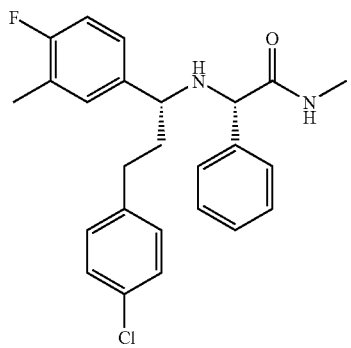

(R,S)-2-[(S,R)-3-(4-Chloro-phenyl)-1-(4-fluoro-3-methyl-phenyl)-propylamino]-N-methyl-2-phenyl-acetamide (example 373) was separated on chiral phase HPLC (Chiralpak AD column) to provide the title compounds: (R)-2-[(S)-3-(4-chloro-phenyl)-1-(4-fluoro-3-methyl-phenyl)-propylamino]-N-methyl-2-phenyl-acetamide (MS (m/e): 425.1 [M+H]$^+$) and (S)-2-[(R)-3-(4-chloro-phenyl)-1-(4-fluoro-3-methyl-phenyl)-propylamino]-N-methyl-2-phenyl-acetamide (MS (m/e): 425.1 [M+H]$^+$) as light-brown oils.

Example 394

(S)-2-[(R)-3-(4-Chloro-phenyl)-1-(4-fluoro-3-methyl-phenyl)-propylamino]-2-phenyl-acetamide

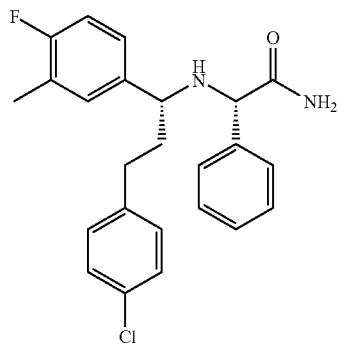

and

Example 395

(R)-2-[(S)-3-(4-Chloro-phenyl)-1-(4-fluoro-3-methyl-phenyl)-propylamino]-2-phenyl-acetamide

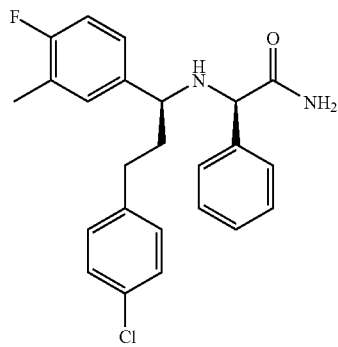

(R,S)-2-[(S,R)-3-(4-Chloro-phenyl)-1-(4-fluoro-3-methyl-phenyl)-propylamino]-2-phenyl-acetamide (example 375) was separated on chiral phase HPLC (Chiralpak AD column) to provide the title compounds: (S)-2-[(R)-3-(4-chloro-phenyl)-1-(4-fluoro-3-methyl-phenyl)-propylamino]-2-phenyl-acetamide (MS (m/e): 411.2 [M+H]$^+$) and (R)-2-[(S)-3-(4-chloro-phenyl)-1-(4-fluoro-3-methyl-phenyl)-propylamino]-2-phenyl-acetamide (MS (m/e): 411.2 [M+H]$^+$) as light-brown oils.

Example 396

(S)-2-[(R)-1-(4-Fluoro-3-methyl-phenyl)-3-p-tolyl-propylamino]-N-methyl-2-phenyl-acetamide

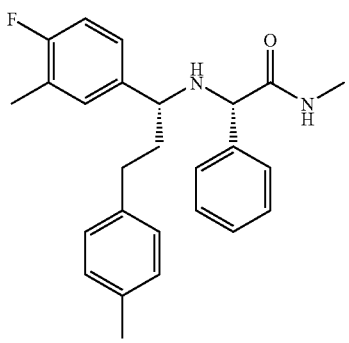

and

Example 397

(R)-2-[(S)-1-(4-Fluoro-3-methyl-phenyl)-3-p-tolyl-propylamino]-N-methyl-2-phenyl-acetamide

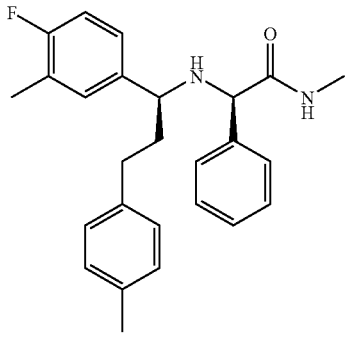

(R,S)-2-[(S,R)-1-(4-Fluoro-3-methyl-phenyl)-3-p-tolyl-propylamino]-N-methyl-2-phenyl-acetamide (example 365) was separated on chiral phase HPLC (Chiralpak AD column) to provide the title compounds: (S)-2-[(R)-1-(4-Fluoro-3-methyl-phenyl)-3-p-tolyl-propylamino]-N-methyl-2-phenyl-acetamide (MS (m/e): 405.3 [M+H]$^+$) and (R)-2-[(S)-1-(4-Fluoro-3-methyl-phenyl)-3-p-tolyl-propylamino]-N-methyl-2-phenyl-acetamide (MS (m/e): 405.3 [M+H]$^+$) as light-brown oils.

The invention claimed is:
1. A compound of formula I

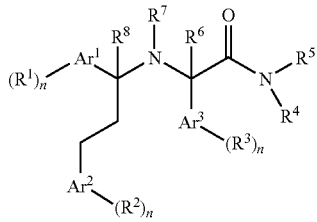

wherein
Ar¹, Ar² and Ar³ are each independently unsubstituted or substituted aryl or heteroaryl;
R¹, R² and R³ are each independently hydroxy, halogen, lower alkyl, lower alkyl substituted by hydroxy lower alkyl substituted by halogen, $(CH_2)_p$-cycloalkyl lower alkoxy, lower alkoxy substituted by halogen, cyano, 3-hydroxy-oxetan-3-yl, $SO_2$-lower alkyl or di-lower alkyl amino;
R⁴ and R⁵ are each independently hydrogen, lower alkyl, lower alkyl substituted by halogen, lower alkyl substituted by hydroxy, $—(CH_2)_o$—O-lower alkyl, $—(CH_2)_o$—N-(lower alkyl)$_2$, $(CH_2)_p$-cycloalkyl, $(CH_2)_p$-aryl, which aryl ring may be substituted by halogen, or
R⁴ and R⁵ together with the N-atom to which they are attached form a heterocyclic ring, optionally containing further ring-heteroatoms selected from N, O and S;
R⁶ is hydrogen or lower alkyl;
R⁷ is hydrogen or lower alkyl;
R⁸ is hydrogen or cyano;
n is 0, 1, 2 or 3;
o is 1, 2 or 3; and
p is 0, 1 or 2;
or a pharmaceutically suitable acid addition salt, an optically pure enantiomer, racemate or a diastereomeric mixture thereof.

2. A compound of claim 1 having formula I-1

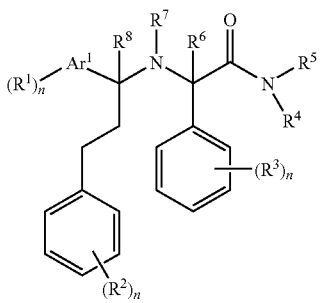

wherein
Ar¹ is heteroaryl;
R¹, R² and R³ are each independently hydroxy, halogen, lower alkyl, lower alkyl substituted by halogen, lower alkoxy, lower alkoxy substituted by halogen, cyano, 3-hydroxy-oxetan-3-yl, $SO_2$-lower alkyl or di-lower alkyl amino;
R⁴ and R⁵ are each independently hydrogen, lower alkyl, lower alkyl substituted by halogen, lower alkyl substituted by hydroxy, $—(CH_2)_o$—O-lower alkyl, $—(CH_2)_o$—N-(lower alkyl)$_2$, $(CH_2)_p$-cycloalkyl, $(CH_2)_p$-aryl, which aryl ring is optionally substituted by halogen, or
R⁴ and R⁵ together with the N-atom to which they are attached form a heterocyclic ring, optionally containing further ring-heteroatoms selected from N, O and S;
R⁶ is hydrogen or lower alkyl;
R⁷ is hydrogen or lower alkyl;
R⁸ is hydrogen or cyano;
n is 0, 1, 2 or 3;
o is 1, 2 or 3; and
p is 0, 1 or 2;
or a pharmaceutically suitable acid addition salts, an optically pure enantiomer, racemate or a diastereomeric mixture thereof.

3. A compound of claim 2, wherein one of R¹ or R² is hydrogen and the other is lower alkyl.

4. A compound of claim 1, selected from the group consisting of
(S,R)-2-[(R,S)-3-(4-chloro-phenyl)-1-(2,3-dihydro-benzofuran-5-yl)-propylamino]-N-methyl-2-phenyl-acetamide,
(S,R)—N-methyl-2-[(R,S)-1-(4-methyl-3,4-dihydro-2H-benzo[1,4]oxazin-7-yl)-3-(4-trifluoromethyl-phenyl)-propylamino]-2-phenyl-acetamide,
2-[1-(2,4-dimethyl-thiazol-5-yl)-3-(4-trifluoromethyl-phenyl)-propylamino]-2-(4-fluoro-phenyl)-N-methyl-acetamide,
2-[1-(3-isopropyl-isoxazol-5-yl)-3-(4-trifluoromethyl-phenyl)-propylamino]-N-methyl-2-phenyl-acetamide,
2-[1-(2,4-dimethyl-thiazol-5-yl)-3-(4-trifluoromethyl-phenyl)-propylamino]-N-methyl-2-phenyl-acetamide,
(R)-2-[(S)-3-(4-chloro-phenyl)-1-(2,3-dihydro-benzofuran-5-yl)-propylamino]-N-methyl-2-phenyl-acetamide,
(R)-2-[(S)-1-chroman-6-yl-3-(4-trifluoromethyl-phenyl)-propylamino]-N-methyl-2-phenyl-acetamide,
(R)—N-methyl-2-[(S)-1-(4-methyl-3,4-dihydro-2H-benzo[1,4]oxazin-7-yl)-3-(4-trifluoromethyl-phenyl)-propylamino]-2-phenyl-acetamide,
(R)-2-[(S)-1-(2,4-dimethyl-thiazol-5-yl)-3-(4-trifluoromethyl-phenyl)-propylamino]-2-(4-fluoro-phenyl)-N-methyl-acetamide,
(S,R)-2-[(R,S)-3-(4-methoxy-phenyl)-1-(2-methoxy-pyridin-3-yl)-propylamino]-N-methyl-2-phenyl-acetamide,
(S,R)-2-[(R,S)-1-(2-methoxy-pyridin-3-yl)-3-(4-trifluoromethyl-phenyl)-propylamino]-N-methyl-2-phenyl-acetamide,
(S,R)—N-methyl-2-[(R,S)-1-(6-methyl-pyridin-2-yl)-3-(4-trifluoromethyl-phenyl)-propylamino]-2-phenyl-acetamide,
(S,R)-2-[(R,S)-1-(4-methoxy-pyridin-2-yl)-3-(4-trifluoromethyl-phenyl)-propylamino]-N-methyl-2-phenyl-acetamide,
(S,R)—N-methyl-2-[(S,R)-1-(5-methyl-isoxazol-3-yl)-3-(4-trifluoromethyl-phenyl)-propylamino]-2-phenyl-acetamide, and
(S,R)—N-methyl-2-[(R,S)-1-(5-methyl-isoxazol-3-yl)-3-(4-trifluoromethyl-phenyl)-propylamino]-2-phenyl-acetamide.

5. A compound of claim 1 having formula I-2

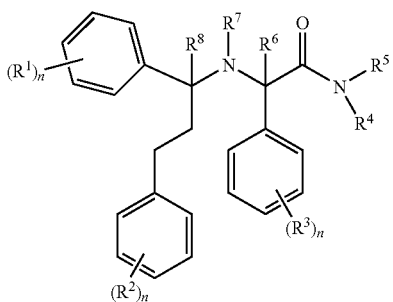

I-2 wherein

R$^1$, R$^2$ and R$^3$ are each independently hydroxy, halogen, lower alkyl, lower alkyl substituted by halogen, (CH$_2$)$_p$-cycloalkyl lower alkoxy, lower alkoxy substituted by halogen, cyano, 3-hydroxy-oxetan-3-yl, SO$_2$-lower alkyl or di-lower alkyl amino;

R$^4$ and R$^5$ are each independently hydrogen, lower alkyl, lower alkyl substituted by halogen, lower alkyl substituted by hydroxy, —(CH$_2$)$_o$—O-lower alkyl, —(CH$_2$)$_o$—N-(lower alkyl)$_2$, (CH$_2$)$_p$-cycloalkyl, (CH$_2$)$_p$-aryl, which aryl ring is optionally substituted by halogen, or R$^4$ and R$^5$ together with the N-atom to which they are attached form a heterocyclic ring, optionally containing further ring-heteroatoms selected from N, O and S;

R$^6$ is hydrogen or lower alkyl;

R$^7$ is hydrogen or lower alkyl;

R$^8$ is hydrogen or cyano;

n is 0, 1, 2 or 3;

o is 1, 2 or 3; and p is 0, 1 or 2;

or a pharmaceutically suitable acid addition salt, an optically pure enantiomer, racemate or a diastereomeric mixture thereof.

6. A compound of claim 5, wherein one of R$^1$ or R$^2$ is hydrogen and the other is lower alkyl.

7. A compound of claim 1, selected from the group consisting of (R)-2-[(S or R)-1-(3,4-dimethoxy-phenyl)-3-(4-trifluoromethyl-phenyl)-propylamino]-N-methyl-2-phenyl-acetamide, (R)-2-[(S or R)-1-(3,4-dimethoxy-phenyl)-3-(4-trifluoromethyl-phenyl)-propylamino]-N-methyl-2-phenyl-acetamide, (R)-2-[(R or S)-1-(3,4-dimethoxy-phenyl)-3-(4-trifluoromethyl-phenyl)-propylamino]-N-ethyl-2-phenyl-acetamide, (S,R)-2-[(R,S)-1-(3,4-dimethoxy-phenyl)-3-(4-trifluoromethyl-phenyl)-propylamino]-N-methyl-2-phenyl-propionamide (diastereoisomer 1), (S,R)-2-(4-chloro-phenyl)-2-[(S,R)-1-(3,4-dimethoxy-phenyl)-3-(4-trifluoromethyl-phenyl)-propylamino]-N-methyl-acetamide, (S,R)-2-[(R,S)-1-(3,4-dimethoxy-phenyl)-3-(4-trifluoromethyl-phenyl)-propylamino]-2-(4-fluoro-phenyl)-N-methyl-acetamide, (S,R)-2-[(R,S)-1-(2-chloro-3,4-dimethoxy-phenyl)-3-(4-chloro-phenyl)-propylamino]-N-methyl-2-phenyl-acetamide, (S,R)-2-[(S,R)-1-(2-chloro-3,4-dimethoxy-phenyl)-3-(4-chloro-phenyl)-propylamino]-N-methyl-2-phenyl-acetamide, (R)-2-(4-chloro-phenyl)-2-[(S)-1-(3,4-dimethoxy-phenyl)-3-(4-trifluoromethyl-phenyl)-propylamino]-N-methyl-acetamide, (R)-2-[(S)-1-(3,4-dimethoxy-phenyl)-3-(4-trifluoromethyl-phenyl)-propylamino]-2-(4-fluoro-phenyl)-N-methyl-acetamide, (R)-2-[(S)-1-(2-chloro-3,4-dimethoxy-phenyl)-3-(4-chloro-phenyl)-propylamino]-N-methyl-2-phenyl-acetamide, and (R)-2-[(S)-1-(2-fluoro-5-methyl-phenyl)-3-(4-trifluoromethyl-phenyl)-propylamino]-N-methyl-2-phenyl-acetamide.

8. A compound of claim 1, selected from the group consisting of (R)-2-[(S)-1-(2-fluoro-5-methyl-phenyl)-3-(4-trifluoromethyl-phenyl)-propylamino]-2-(4-fluoro-phenyl)-N-methyl-acetamide, (S,R)-2-[(R,S)-3-(4-chloro-phenyl)-1-(3,4-dimethoxy-phenyl)-propylamino]-N-methyl-2-phenyl-acetamide, (S,R)-2-[(S,R)-1-(3,4-dimethoxy-phenyl)-3-(4-trifluoromethyl-phenyl)-propylamino]-N-methyl-2-phenyl-acetamide, (S,R)-2-[(R,S)-1-(3,4-dimethoxy-phenyl)-3-(4-trifluoromethyl-phenyl)-propylamino]-N-methyl-2-phenyl-acetamide, (S,R)-2-[(R,S)-1-(3,4-dimethoxy-phenyl)-3-(4-fluoro-phenyl)-propylamino]-N-methyl-2-phenyl-acetamide, (S,R)-2-[(R,S)-1-(3,4-dimethoxy-phenyl)-3-(4-methoxy-phenyl)-propylamino]-N-methyl-2-phenyl-acetamide, (R)-2-[(S)-3-(4-chloro-phenyl)-1-(3,4-dimethoxy-phenyl)-propylamino]-N-methyl-2-phenyl-acetamide, (S,R)-2-[(S,R)-1-(4-chloro-3-methoxy-phenyl)-3-(4-trifluoromethyl-phenyl)-propylamino]-N-methyl-2-phenyl-acetamide, (S,R)-2-[(R,S)-1-(4-chloro-3-methoxy-phenyl)-3-(4-trifluoromethyl-phenyl)-propylamino]-N-methyl-2-phenyl-acetamide, (R)-2-[(S)-1-(3,4-dimethoxy-phenyl)-3-(6-trifluoromethyl-pyridin-3-yl)-propylamino]-N-methyl-2-phenyl-acetamide hydrochloride, (S,R)-2-[(R,S)-1-(3,4-dimethoxy-phenyl)-3-p-tolyl-propylamino]-N-methyl-2-phenyl-acetamide, and (R)-2-[(S)-1-(3-methoxy-phenyl)-3-(4-trifluoromethyl-phenyl)-propylamino]-N-methyl-2-phenyl-acetamide hydrochloride.

9. A compound of claim 1, selected from the group consisting of (S)-2-[(R)-1-(3-methoxy-phenyl)-3-(4-trifluoromethyl-phenyl)-propylamino]-N-methyl-2-phenyl-acetamide hydrochloride, (S,R)-2-[(R,S)-1-(3,4-bis-difluoromethoxy-phenyl)-3-(4-trifluoromethyl-phenyl)-propylamino]-N-methyl-2-phenyl-acetamide, (R)-2-[(S)-1-(3,4-dimethoxy-phenyl)-3-phenyl-propylamino]-N-methyl-2-phenyl-acetamide, (R,S)-2-(4-chloro-phenyl)-2-[(S,R)-3-(4-chloro-phenyl)-1-(3,4-dimethoxy-phenyl)-propylamino]-N-methyl-acetamide, (R,S)-2-[(R,S)-1-(3,4-dimethoxy-phenyl)-3-(3-trifluoromethyl-phenyl)-propylamino]-N-methyl-2-phenyl-acetamide, (R,S)-2-[(S,R)-1-(3,4-dimethoxy-phenyl)-3-(3-trifluoromethyl-phenyl)-propylamino]-N-methyl-2-phenyl-acetamide, (R,S)-2-[(S,R)-1-(4-fluoro-3-methyl-phenyl)-3-p-tolyl-propylamino]-N-methyl-2-phenyl-acetamide,
(R)-2-[(S)-1-(3-difluoromethoxy-phenyl)-3-(4-trifluoromethyl-phenyl)-propylamino]-N-methyl-2-phenyl-acetamide,
(R)-2-[(S)-1-(3-difluoromethoxy-phenyl)-3-(4-trifluoromethyl-phenyl)-propylamino]-N-methyl-2-p-tolyl-acetamide,
(R)-2-[(S)-3-(4-chloro-phenyl)-1-(4-fluoro-3-methyl-phenyl)-propylamino]-N-methyl-2-phenyl-acetamide, and
(R)-2-[(S)-1-(4-fluoro-3-methyl-phenyl)-3-p-tolyl-propylamino]-N-methyl-2-phenyl-acetamide.

10. A compound of claim 5, wherein one of $R^1$ or $R^2$ is hydrogen and the other is $(CH_2)_p$-cycloalkyl.

11. A compound claim 1, wherein the compound is (R)—N-cyclopropylmethyl-2-[(R or S)-1-(3,4-dimethoxy-phenyl)-3-(4-trifluoromethyl-phenyl)-propylamino]-2-phenyl-acetamide.

12. A compound of claim 1 having formula I-3,

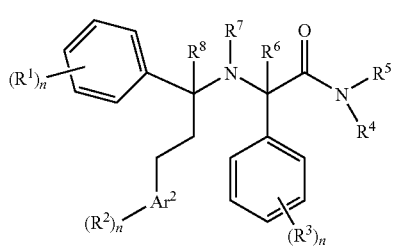

wherein
Ar² is heteroaryl;
$R^1$, $R^2$ and $R^3$ are each independently hydroxy, halogen, lower alkyl substituted by hydroxy lower alkyl, lower alkyl substituted by halogen, lower alkoxy, lower alkoxy substituted by halogen, cyano, 3-hydroxy-oxetan-3-yl, $SO_2$-lower alkyl or di-lower alkyl amino;
$R^4$ and $R^5$ are each independently hydrogen, lower alkyl, lower alkyl substituted by halogen, lower alkyl substituted by hydroxy, —$(CH_2)_o$—O-lower alkyl, —$(CH_2)_o$N-(lower alkyl)$_2$, $(CH_2)_p$-cycloalkyl, $(CH_2)_p$-aryl, which aryl ring is optionally substituted by halogen, or
$R^4$ and $R^5$ together with the N-atom to which they are attached form a heterocyclic ring, optionally containing further ring-heteroatoms selected from N, O and S;
$R^6$ is hydrogen or lower alkyl;
$R^8$ is hydrogen or cyano;
n is 0, 1, 2 or 3;
o is 1, 2 or 3; and
p is 0, 1 or 2;
or a pharmaceutically suitable acid addition salt, an optically pure enantiomer, racemate or a diastereomeric mixture thereof.

13. A compound of claim 12, wherein one of $R^1$ or $R^2$ is hydrogen and the other is lower alkyl.

14. A compound of claim 1, selected from the group consisting of
(R)-2-[(S)-1-(5-chloro-2-methoxy-phenyl)-3-(6-trifluoromethyl-pyridin-3-yl)-propylamino]-2-(4-fluoro-phenyl)-N-methyl-acetamide,
(R)-2-[(S)-1-(2-fluoro-5-methyl-phenyl)-3-(6-trifluoromethyl-pyridin-3-yl)-propylamino]-2-(4-fluoro-phenyl)-N-methyl-acetamide,
(S,R)-2-[(R,S)-1-(3,4-dimethoxy-phenyl)-3-(6-trifluoromethyl-pyridin-3-yl)-propylamino]-N-methyl-2-phenyl-acetamide,
(S,R)-2-[(S,R)-1-(4-chloro-3-methoxy-phenyl)-3-(6-trifluoromethyl-pyridin-3-yl)-propylamino]-N-methyl-2-phenyl-acetamide,
(S,R)-2-[(R,S)-1-(4-chloro-3-methoxy-phenyl)-3-(6-trifluoromethyl-pyridin-3-yl)-propylamino]-N-methyl-2-phenyl-acetamide,
(S,R)-2-[(R,S)-1-(4-chloro-3-methoxy-phenyl)-3-(6-trifluoromethyl-pyridin-3-yl)-propylamino]-2-(4-chloro-phenyl)-N-methyl-acetamide,
(S,R)-2-[(S,R)-1-(4-chloro-3-methoxy-phenyl)-3-(6-trifluoromethyl-pyridin-3-yl)-propylamino]-2-(4-fluoro-phenyl)-N-methyl-acetamide,
(S,R)-2-[(R,S)-1-(4-chloro-3-methoxy-phenyl)-3-(6-trifluoromethyl-pyridin-3-yl)-propylamino]-2-(4-fluoro-phenyl)-N-methyl-acetamide,
(S,R)-2-[(R,S)-1-(3-difluoromethoxy-phenyl)-3-(6-trifluoromethyl-pyridin-3-yl)-propylamino]-N-methyl-2-phenyl-acetamide,
(S,R)—N-methyl-2-phenyl-2-[(S,R)-1-(3-trifluoromethoxy-phenyl)-3-(6-trifluoromethyl-pyridin-3-yl)-propylamino]-acetamide, and
(S,R)-2-[(R,S)-1-(4-Fluoro-3-methyl-phenyl)-3-(6-trifluoromethyl-pyridin-3-yl)-propylamino]-N-methyl-2-phenyl-acetamide.

15. A compound of claim 1, selected from the group consisting of
(S,R)-2-(4-chloro-phenyl)-2-[(R,S)-1-(4-fluoro-3-methoxy-phenyl)-3-(6-trifluoromethyl-pyridin-3-yl)-propylamino]-N-methyl-acetamide,
(S,R)-2-[(R,S)-1-(4-fluoro-3-methoxy-phenyl)-3-(6-trifluoromethyl-pyridin-3-yl)-propylamino]-N-methyl-2-phenyl-acetamide,
(S,R)-2-(4-chloro-phenyl)-2-[(R,S)-1-(4-difluoromethoxy-3-methoxy-phenyl)-3-(6-trifluoromethyl-pyridin-3-yl)-propylamino]-N-methyl-acetamide,
(S,R)-2-[(R,S)-1-(3-chloro-4-methyl-phenyl)-3-(6-trifluoromethyl-pyridin-3-yl)-propylamino]-N-methyl-2-phenyl-acetamide,
(S,R)-2-[(R,S)-1-(4-fluoro-3-methoxy-phenyl)-3-(6-trifluoromethyl-pyridin-3-yl)-propylamino]-2-(4-fluoro-phenyl)-N-methyl-acetamide,
(S,R)-2-[(S,R)-1-(4-chloro-3-methyl-phenyl)-3-(6-trifluoromethyl-pyridin-3-yl)-propylamino]-N-methyl-2-phenyl-acetamide,
(S,R)-2-[(R,S)-1-(4-chloro-3-methyl-phenyl)-3-(6-trifluoromethyl-pyridin-3-yl)-propylamino]-N-methyl-2-phenyl-acetamide,
(S,R)-2-[(R,S)-1-(3,4-dimethyl-phenyl)-3-(6-trifluoromethyl-pyridin-3-yl)-propylamino]-N-methyl-2-phenyl-acetamide,
(S,R)-2-[(S,R)-1-(3-methoxy-4-methyl-phenyl)-3-(6-trifluoromethyl-pyridin-3-yl)-propylamino]-N-methyl-2-phenyl-acetamide,
(S,R)-2-[(R,S)-1-(3-methoxy-4-methyl-phenyl)-3-(6-trifluoromethyl-pyridin-3-yl)-propylamino]-N-methyl-2-phenyl-acetamide, and
2-[1-(4-fluoro-3-methyl-phenyl)-3-(6-methyl-pyridin-3-yl)-propylamino]-N-methyl-2-phenyl-acetamide.

16. A compound of claim 1, selected from the group consisting of
(R)-2-[(S)-1-(4-Fluoro-3-methyl-phenyl)-3-(6-methyl-pyridin-3-yl)-propylamino]-N-methyl-2-phenyl-acetamide, 2-[1-(3,4-bis-difluoromethoxy-phenyl)-3-(6-trifluoromethyl-pyridin-3-yl)-propylamino]-N-methyl-2-phenyl-acetamide, (S,R)-2-[(R,S)-3-(6-chloro-pyridin-3-yl)-1-(4-fluoro-3-methyl-phenyl)-propylamino]-N-methyl-2-phenyl-acetamide, (S,R)-2-[(R,S)-1-(3,4-bis-difluoromethoxy-phenyl)-3-(6-chloro-pyridin-3-yl)-propylamino]-N-methyl-2-phenyl-acetamide, (S,R)-2-[(R,S)-1-(3,4-bis-difluoromethoxy-phenyl)-3-(5-chloro-pyrazin-2-yl)-propylamino]-N-methyl-2-phenyl-acetamide, (S,R)-2-[(R,S)-1-(3,4-bis-difluoromethoxy-phenyl)-3-(5-chloro-pyridin-2-yl)-propylamino]-N-methyl-2-phenyl-acetamide, (R,S)-2-[(S,R)-1-(4-fluoro-3-methyl-phenyl)-3-(6-trifluoromethyl-pyridin-3-yl)-propylamino]-N-methyl-2-p-tolyl-acetamide, (R,S)—N-ethyl-2-[(S,R)-1-(4-fluoro-3-methyl-phenyl)-3-(6-trifluoromethyl-pyridin-3-yl)-propylamino]-2-phenyl-acetamide, (R,S)-2-[(S,R)-1-(4-fluoro-3-methyl-phenyl)-3-(6-trifluoromethyl-pyridin-3-yl)-propylamino]-2-(4-methoxy-phenyl)-N-methyl-acetamide, and (R)-2-[(S)-1-(4-fluoro-3-methyl-phenyl)-3-(6-trifluoromethyl-pyridin-3-yl)-propylamino]-2-phenyl-acetamide.

17. A compound of claim 12, wherein one of $R^1$ or $R^2$ is hydrogen and the other is lower alkyl substituted by hydroxy.

18. A compound of claim 1, wherein the compound is
(R,S)-2-[(S,R)-1-(4-fluoro-3-methyl-phenyl)-3-(6-trifluoromethyl-pyridin-3-yl)-propylamino]-N-(2-hydroxy-ethyl)-2-phenyl-acetamide.

19. A compound of claim 1 having formula I-4,

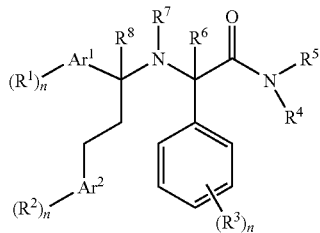

wherein
$Ar^1$ and $Ar^2$ are heteroaryl;
$R^1$, $R^2$ and $R^3$ are each independently hydroxy, halogen, lower alkyl, lower alkyl substituted by halogen, lower alkoxy, lower alkoxy substituted by halogen, cyano, 3-hydroxy-oxetan-3-yl, $SO_2$-lower alkyl or di-lower alkyl amino;
$R^4$ and $R^5$ are each independently hydrogen, lower alkyl, lower alkyl substituted by halogen, lower alkyl substituted by hydroxy, —$(CH_2)_o$—O-lower alkyl, —$(CH_2)_o$—N-(lower alkyl)$_2$, $(CH_2)_p$-cycloalkyl, $(CH_2)_p$-aryl, which aryl ring is optionally substituted by halogen, or
$R^4$ and $R^5$ together with the N-atom to which they are attached form a heterocyclic ring, optionally containing further ring-heteroatoms selected from N, O and S;
$R^6$ is hydrogen or lower alkyl;
$R^7$ is hydrogen or lower alkyl;
$R^8$ is hydrogen or cyano;
n is 0, 1, 2 or 3;

o is 1, 2 or 3; and
p is 0, 1 or 2;
or a pharmaceutically suitable acid addition salt, an optically pure enantiomer, racemate or a diastereomeric mixture thereof.

20. A compound of claim 19, wherein one of $R^1$ or $R^2$ is hydrogen and the other is lower alkyl.

21. A compound of claim 1, wherein the compound is selected from the group consisting of
(S,R)-2-(4-fluoro-phenyl)-N-methyl-2-[R,S]-1-(5,6,7,8-tetrahydro-naphthalen-2-yl)-3-(6-trifluoromethyl-pyridin-3-yl)-propylamino]-acetamide and
(R)-2-(4-fluoro-phenyl)-N-methyl-2-[(S)-1-(5,6,7,8-tetrahydro-naphthalen-2-yl)-3-(6-trifluoromethyl-pyridin-3-yl)-propylamino]-acetamide.

22. A compound of formula I-A

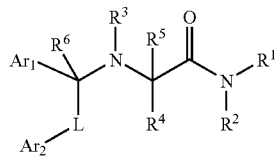

wherein
$R^1$ and $R^2$ are each independently hydrogen, lower alkyl, lower alkyl substituted by halogen, —$(CH_2)_o$—O-lower alkyl, —$(CH_2)_o$—N-(lower alkyl)$_2$, $(CH_2)_p$-cycloalkyl, $(CH_2)_p$-heterocycloalkyl, $(CH_2)_p$-aryl, $(CH_2)_p$-heteroaryl, which rings is optionally substituted by R, or
$R^1$ and $R^2$ together with the N-atom to which they are attached form a heterocyclic ring, optionally containing further ring-heteroatoms selected from N, O and S;
R is lower alkyl, lower alkoxy, halogen or lower alkyl substituted by halogen;
$R^3$ is hydrogen, lower alkyl or cycloalkyl;
$Ar^1$ and $Ar^2$ are unsubstituted or substituted aryl or heteroaryl and wherein the aryl and the heteroaryl groups are optionally substituted by one or more substituents selected from the group consisting of hydroxy, halogen, lower alkyl, lower alkyl substituted by halogen, lower alkoxy, lower alkoxy substituted with halogen, nitro, cyano, $SO_2$-lower alkyl and —$NR^1R^2$;
$R^4$ is lower alkyl, lower alkyl substituted by halogen, cycloalkyl, heterocycloalkyl, unsubstituted or substituted aryl or heteroaryl and wherein the aryl and the heteroaryl groups are optionally substituted by one or more substituents selected from the group consisting of hydroxy, halogen, lower alkyl, lower alkyl substituted by halogen, lower alkoxy, lower alkoxy substituted with halogen, nitro, cyano, $SO_2$-lower alkyl and —$NR^1R^2$;
L is —$(CR^7R^8)_n$—;
$R^5$ and $R^6$ are each independently hydrogen, lower alkyl;
$R^7$ and $R^8$ are each independently hydrogen, lower alkyl;
n is 2 or 3;
o is 2 or 3; and
p is 0, 1 or 2;
or pharmaceutically suitable acid addition salts, optically pure enantiomers, racemates or diastereomeric mixtures thereof.

23. A pharmaceutical composition comprising a therapeutically effective amount of a compound of formula I

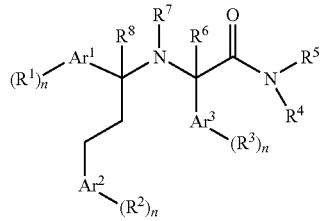

wherein
- $Ar^1$, $Ar^2$ and $Ar^3$ are each independently unsubstituted or substituted aryl or heteroaryl;
- $R^1$, $R^2$ and $R^3$ are each independently hydroxy, halogen, lower alkyl, lower alkyl substituted by halogen, lower alkoxy, lower alkoxy substituted by halogen, cyano, 3-hydroxy-oxetan-3-yl, $SO_2$-lower alkyl or di-lower alkyl amino;
- $R^4$ and $R^5$ are each independently hydrogen, lower alkyl, lower alkyl substituted by halogen, lower alkyl substituted by hydroxy, $-(CH_2)_o-$O-lower alkyl, $-(CH_2)_o-$N-(lower alkyl)$_2$, $(CH_2)_p$-cycloalkyl, $(CH_2)_p$-aryl, which aryl ring may be substituted by halogen, or
- $R^4$ and $R^5$ together with the N-atom to which they are attached form a heterocyclic ring, optionally containing further ring-heteroatoms selected from N, O and S;
- $R^6$ is hydrogen or lower alkyl;
- $R^7$ is hydrogen or lower alkyl;
- $R^8$ is hydrogen or cyano;
- n is 0, 1, 2 or 3;
- o is 1, 2 or 3; and
- p is 0, 1 or 2;

or a pharmaceutically suitable acid addition salt, an optically pure enantiomer, racemate or a diastereomeric mixture thereof.

24. The pharmaceutical composition of claim 23, wherein the compound of formula I comprises a compound of formula I-1

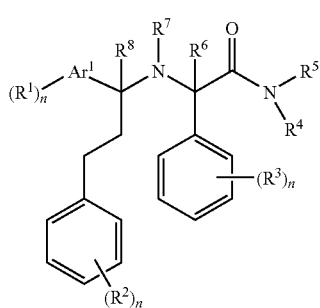

wherein
- $Ar^1$ is heteroaryl;
- $R^1$, $R^2$ and $R^3$ are each independently hydroxy, halogen, lower alkyl, lower alkyl substituted by halogen, lower alkoxy, lower alkoxy substituted by halogen, cyano, 3-hydroxy-oxetan-3-yl, $SO_2$-lower alkyl or di-lower alkyl amino;
- $R^4$ and $R^5$ are each independently hydrogen, lower alkyl, lower alkyl substituted by halogen, lower alkyl substituted by hydroxy, $-(CH_2)_o-$O-lower alkyl, $-(CH_2)_o-$N-(lower alkyl)$_2$, $(CH_2)_p$-cycloalkyl, $(CH_2)_p$-aryl, which aryl ring is optionally substituted by halogen, or
- $R^4$ and $R^5$ together with the N-atom to which they are attached form a heterocyclic ring, optionally containing further ring-heteroatoms selected from N, O and S;
- $R^6$ is hydrogen or lower alkyl;
- $R^7$ is hydrogen or lower alkyl;
- $R^8$ is hydrogen or cyano;
- n is 0, 1, 2 or 3;
- o is 1, 2 or 3; and
- p is 0, 1 or 2.

25. The pharmaceutical composition of claim 23 wherein the compound of formula I comprises a compound of formula I-2

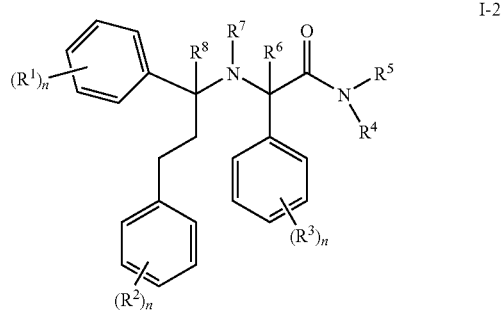

wherein
- $R^1$, $R^2$ and $R^3$ are each independently hydroxy, halogen, lower alkyl, lower alkyl substituted by halogen, lower alkoxy, lower alkoxy substituted by halogen, cyano, 3-hydroxy-oxetan-3-yl, $SO_2$-lower alkyl or di-lower alkyl amino;
- $R^4$ and $R^5$ are each independently hydrogen, lower alkyl, lower alkyl substituted by halogen, lower alkyl substituted by hydroxy, $-(CH_2)_o-$O-lower alkyl, $-(CH_2)_o-$N-(lower alkyl)$_2$, $(CH_2)_p$-cycloalkyl, $(CH_2)_p$-aryl, which aryl ring is optionally substituted by halogen, or
- $R^4$ and $R^5$ together with the N-atom to which they are attached form a heterocyclic ring, optionally containing further ring-heteroatoms selected from N, O and S;
- $R^6$ is hydrogen or lower alkyl;
- $R^7$ is hydrogen or lower alkyl;
- $R^8$ is hydrogen or cyano;
- n is 0, 1, 2 or 3;
- o is 1, 2 or 3; and
- p is 0, 1 or 2.

26. The pharmaceutical composition of claim 23, wherein the compound of formula I comprises a compound of formula I-3

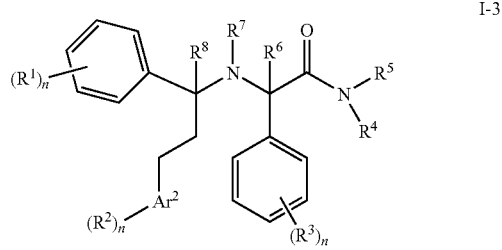

wherein
- $Ar^2$ is heteroaryl;
- $R^1$, $R^2$ and $R^3$ are each independently hydroxy, halogen, lower alkyl, lower alkyl substituted by halogen, lower alkoxy, lower alkoxy substituted by halogen, cyano, 3-hydroxy-oxetan-3-yl, $SO_2$-lower alkyl or di-lower alkyl amino;
- $R^4$ and $R^5$ are each independently hydrogen, lower alkyl, lower alkyl substituted by halogen, lower alkyl substituted by hydroxy, —$(CH_2)_o$—O-lower alkyl, —$(CH_2)_o$—N-(lower alkyl)$_2$, $(CH_2)_p$-cycloalkyl, $(CH_2)_p$-aryl, which aryl ring is optionally substituted by halogen, or
- $R^4$ and $R^5$ together with the N-atom to which they are attached form a heterocyclic ring, optionally containing further ring-heteroatoms selected from N, O and S;
- $R^6$ is hydrogen or lower alkyl;
- $R^8$ is hydrogen or cyano;
- n is 0, 1, 2 or 3;
- o is 1, 2 or 3; and
- p is 0, 1 or 2.

27. The pharmaceutical composition of claim 23, wherein the compound of formula I comprises a compound of formula I-4

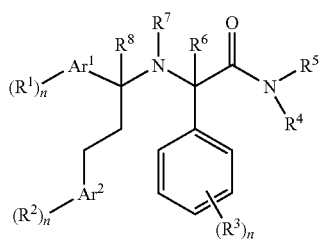

wherein
- $Ar^1$ and $Ar^2$ are heteroaryl;
- $R^1$, $R^2$ and $R^3$ are each independently hydroxy, halogen, lower alkyl, lower alkyl substituted by halogen, lower alkoxy, lower alkoxy substituted by halogen, cyano, 3-hydroxy-oxetan-3-yl, $SO_2$-lower alkyl or di-lower alkyl amino;
- $R^4$ and $R^5$ are each independently hydrogen, lower alkyl, lower alkyl substituted by halogen, lower alkyl substituted by hydroxy, —$(CH_2)_o$—O-lower alkyl, —$(CH_2)_o$—N-(lower alkyl)$_2$, $(CH_2)_p$-cycloalkyl, $(CH_2)_p$-aryl, which aryl ring is optionally substituted by halogen, or
- $R^4$ and $R^5$ together with the N-atom to which they are attached form a heterocyclic ring, optionally containing further ring-heteroatoms selected from N, O and S;
- $R^6$ is hydrogen or lower alkyl;
- $R^7$ is hydrogen or lower alkyl;
- $R^8$ is hydrogen or cyano;
- n is 0, 1, 2 or 3;
- o is 1, 2 or 3; and
- p is 0, 1 or 2.

28. The pharmaceutical composition comprising a compound of formula I-A

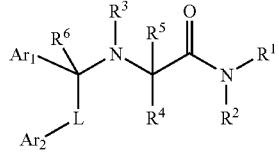

wherein
- $R^1$ and $R^2$ are each independently hydrogen, lower alkyl, lower alkyl substituted by halogen, —$(CH_2)_o$—O-lower alkyl, —$(CH_2)_o$—N-(lower alkyl)$_2$, $(CH_2)_p$-cycloalkyl, $(CH_2)_p$-heterocycloalkyl, $(CH_2)_p$-aryl, $(CH_2)_p$-heteroaryl, which rings is optionally substituted by R, or
- $R^1$ and $R^2$ together with the N-atom to which they are attached form a heterocyclic ring, optionally containing further ring-heteroatoms selected from N, O and S;
- R is lower alkyl, lower alkoxy, halogen or lower alkyl substituted by halogen;
- $R^3$ is hydrogen, lower alkyl or cycloalkyl;
- $Ar^1$ and $Ar^2$ are unsubstituted or substituted aryl or heteroaryl and wherein the aryl and the heteroaryl groups are optionally substituted by one or more substituents selected from the group consisting of hydroxy, halogen, lower alkyl, lower alkyl substituted by halogen, lower alkoxy, lower alkoxy substituted with halogen, nitro, cyano, $SO_2$-lower alkyl and —$NR^1R^2$;
- $R^4$ is lower alkyl, lower alkyl substituted by halogen, cycloalkyl, heterocycloalkyl, unsubstituted or substituted aryl or heteroaryl and wherein the aryl and the heteroaryl groups are optionally substituted by one or more substituents selected from the group consisting of hydroxy, halogen, lower alkyl, lower alkyl substituted by halogen, lower alkoxy, lower alkoxy substituted with halogen, nitro, cyano, $SO_2$-lower alkyl and —$NR^1R^2$;
- L is —$(CR^7R^8)_n$—;
- $R^5$ and $R^6$ are each independently hydrogen, lower alkyl;
- $R^7$ and $R^8$ are each independently hydrogen, lower alkyl;
- n is 2 or 3;
- o is 2 or 3; and
- p is 0, 1 or 2.

* * * * *